US012564695B2

(12) United States Patent
Sullivan et al.

(10) Patent No.: US 12,564,695 B2
(45) Date of Patent: Mar. 3, 2026

(54) DIRECTIONAL ADJUSTMENT MECHANISM FOR HEADGEAR OF A RESPIRATORY THERAPY MASK OR INTERFACE

(71) Applicant: Fisher & Paykel Healthcare Limited, Auckland (NZ)

(72) Inventors: Nick Sullivan, Auckland (NZ); Christopher Michael Wong, Auckland (NZ); Vitaly Kapelevich, Auckland (NZ); Matthew Robert Geoff Slight, Auckland (NZ); David Monroy Felix, Auckland (NZ); Fadi Karim Moh'd Mashal, Auckland (NZ); Christopher Gareth Sims, Auckland (NZ); Jonathan Tong Lok Sng, Auckland (NZ); Steve Thomas, Auckland (NZ); Jeroen Hammer, Auckland (NZ); Mark Arvind McLaren, Auckland (NZ); Yi-Jen Lin, Auckland (NZ); Silas Sao Jin Siew, Auckland (NZ); Arvin San Jose Gardiola, Auckland (NZ); Chris Onin Limpin Hipolito, Auckland (NZ); Janine Elizabeth Collins, Auckland (NZ); Blair Raymund Dadson Murphy, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1134 days.

(21) Appl. No.: 17/309,191

(22) PCT Filed: Nov. 5, 2019

(86) PCT No.: PCT/NZ2019/050147

§ 371 (c)(1),
(2) Date: May 5, 2021

(87) PCT Pub. No.: WO2020/096467

PCT Pub. Date: May 14, 2020

(65) Prior Publication Data

US 2022/0023574 A1     Jan. 27, 2022

Related U.S. Application Data

(60) Provisional application No. 62/842,982, filed on May 3, 2019, provisional application No. 62/755,777, filed (Continued)

(51) Int. Cl.
| | |
|---|---|
| *A61M 16/06* | (2006.01) |
| *A61M 16/08* | (2006.01) |
| *A61M 16/16* | (2006.01) |

(52) U.S. Cl.
CPC .... *A61M 16/0683* (2013.01); *A61M 16/0605* (2014.02); *A61M 16/0816* (2013.01); *A61M 16/16* (2013.01)

(58) Field of Classification Search
CPC ......... A44B 11/18; A44B 11/02; A44B 11/06; A44B 11/065; A44B 11/12; A44B 11/125;
(Continued)

(56) References Cited

U.S. PATENT DOCUMENTS

| | | | | | |
|---|---|---|---|---|---|
| 764,065 | A | * | 7/1904 | Mitchell | ............... A44B 11/18 |
| | | | | | 24/DIG. 28 |
| 1,646,545 | A | * | 10/1927 | Laier | ..................... A44B 11/18 |
| | | | | | 24/193 |

(Continued)

FOREIGN PATENT DOCUMENTS

| | | |
|---|---|---|
| JP | A 2016-516527 | 6/2016 |
| JP | A 2017-531464 | 10/2017 |

(Continued)

OTHER PUBLICATIONS

International Search Report for International Application No. PCT/NZ2019/050147 dated Feb. 6, 2020.

*Primary Examiner* — Annette Dixon
(74) *Attorney, Agent, or Firm* — VIA LLP

(57) ABSTRACT

According to this disclosure there is provided various embodiments of directional adjustment unit for a headgear for a respiratory mask, comprising
(Continued)

a housing, at least one frictional engagement member arranged to be movable with respect to the housing, the at least one frictional engagement member having an aperture extending therethrough for receiving a filament of a strap of the headgear therethrough, wherein the at least one frictional engagement member in a first movable configuration provides a disengaged configuration with respect to the filament, and in a second movable configuration provides an engaged configuration with respect to the filament.

Also disclosed herein are various headgear, yoke assemblies, mask assemblies, mask frames and headgear filaments, some of which are for use with such a directional adjustment unit.

21 Claims, 79 Drawing Sheets

Related U.S. Application Data on Nov. 5, 2018, provisional application No. 62/755,766, filed on Nov. 5, 2018.

(58) Field of Classification Search

CPC ....... A44B 11/14; A44B 11/25; A44B 11/258; A44B 11/2592; A61M 16/06; A61M 16/0666; A61M 16/0672; A61M 16/0683; A61M 16/0816; A61M 16/0825; A61M 2205/0216; A61M 2205/0222; A61M 2205/0238; A62B 18/084; A62B 18/08; F16G 11/101; F16G 11/105; Y10S 24/28; Y10T 24/4077; Y10T 24/1408; Y10T 24/1412; Y10T 24/1427; Y10T 24/1498; Y10T 24/21; Y10T 24/2147; Y10T 24/2153; Y10T 24/2183; Y10T 24/3938; Y10T 24/3944; Y10T 24/40; Y10T 24/4016; Y10T 24/4047; Y10T 24/4072; Y10T 24/4093; Y10T 24/44538; Y10T 24/45581; Y10T 70/404; A41D 13/1161; A61B 17/12009; A61B 17/1325; A61B 17/1327; A61B 17/82; A61B 17/823; A61B 17/8861; A61B 2017/00084; A61B 2017/00115; A61B 2017/00407; A61B 2017/00853; A61B 2017/00862; A61B 2017/00955; A61B 2090/034; A61B 2090/064; A61B 2090/0807; A61B 2562/0247; A61B 5/01; A61B 5/02055; A61B 5/024; A61B 5/03; A61B 5/1112; A61B 5/14521; A61B 5/14532; A61B 5/14542; A61B 5/7405; A63C 10/04; A63C 10/06; A63C 10/24; B60R 22/19; B65D 63/14; E05B 15/0046; E05B 35/008; E05B 75/00; F16L 33/08

See application file for complete search history.

(56) References Cited

U.S. PATENT DOCUMENTS

| | | | | |
|---|---|---|---|---|
| 5,372,146 | A * | 12/1994 | Branch | .................. A61B 17/08 |
| | | | | 606/328 |
| 2016/0082217 | A1 | 3/2016 | Mclaren et al. | |
| 2016/0144146 | A1* | 5/2016 | Huddart | ............ A61M 16/0672 |
| | | | | 128/206.21 |
| 2017/0281894 | A1 | 10/2017 | Walls et al. | |
| 2022/0362502 | A1* | 11/2022 | Kapelevich | ....... A61M 16/0683 |

FOREIGN PATENT DOCUMENTS

| | | |
|---|---|---|
| WO | WO 2014/175752 | 10/2014 |
| WO | WO 2016/043603 | 3/2016 |
| WO | WO 2017/158544 | 9/2017 |
| WO | WO 2017/160166 | 9/2017 |
| WO | WO 2018/063009 A1 | 4/2018 |
| WO | WO 2019/175814 A1 | 9/2019 |

* cited by examiner

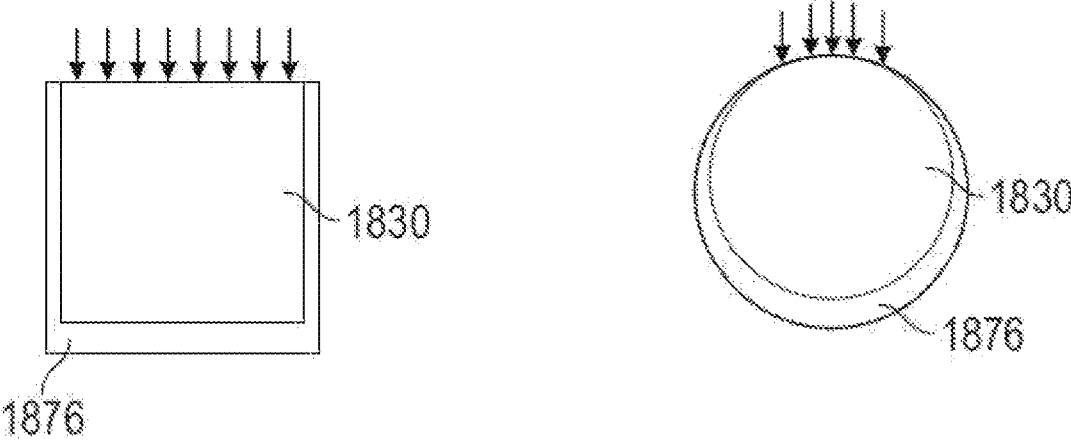
FIG. 5A          FIG. 5B
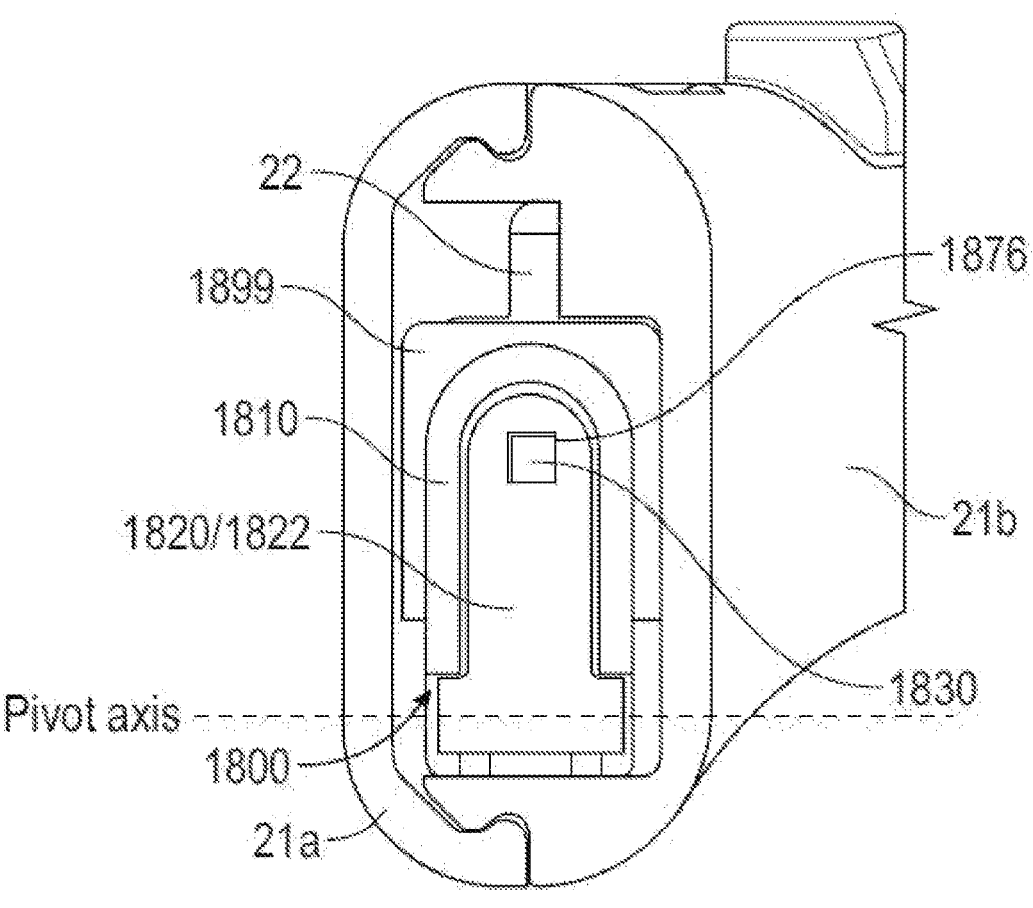
FIG. 6

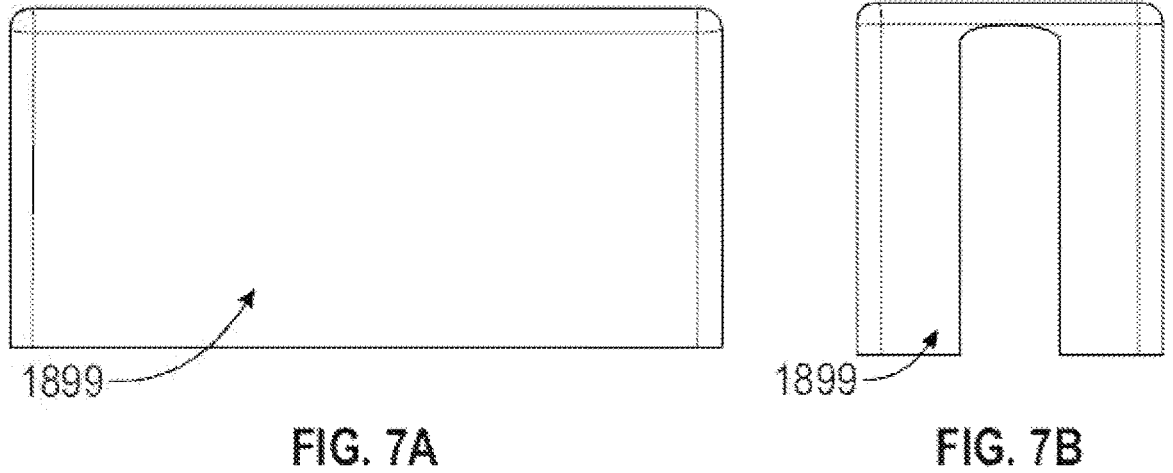
1899
FIG. 7A
1899
FIG. 7B
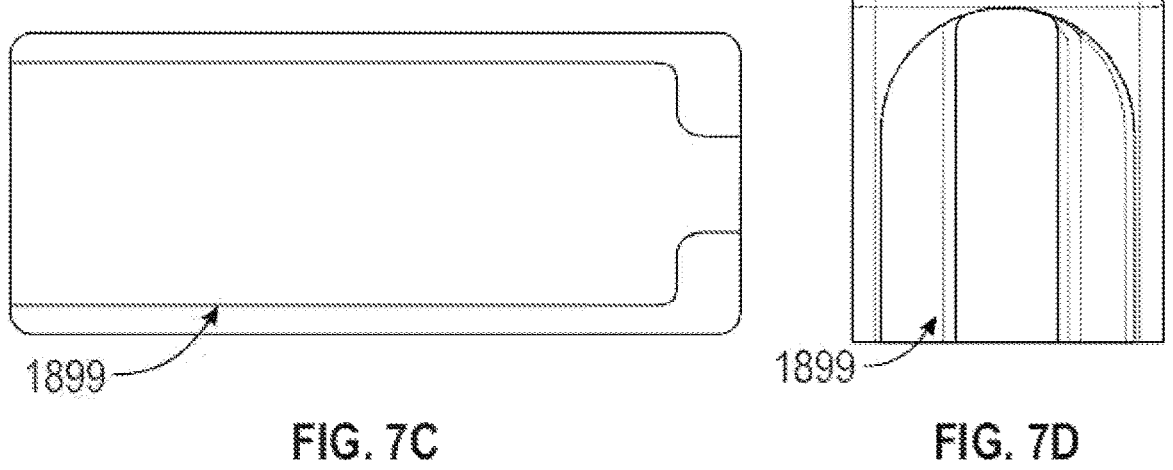
1899
FIG. 7C
1899
FIG. 7D

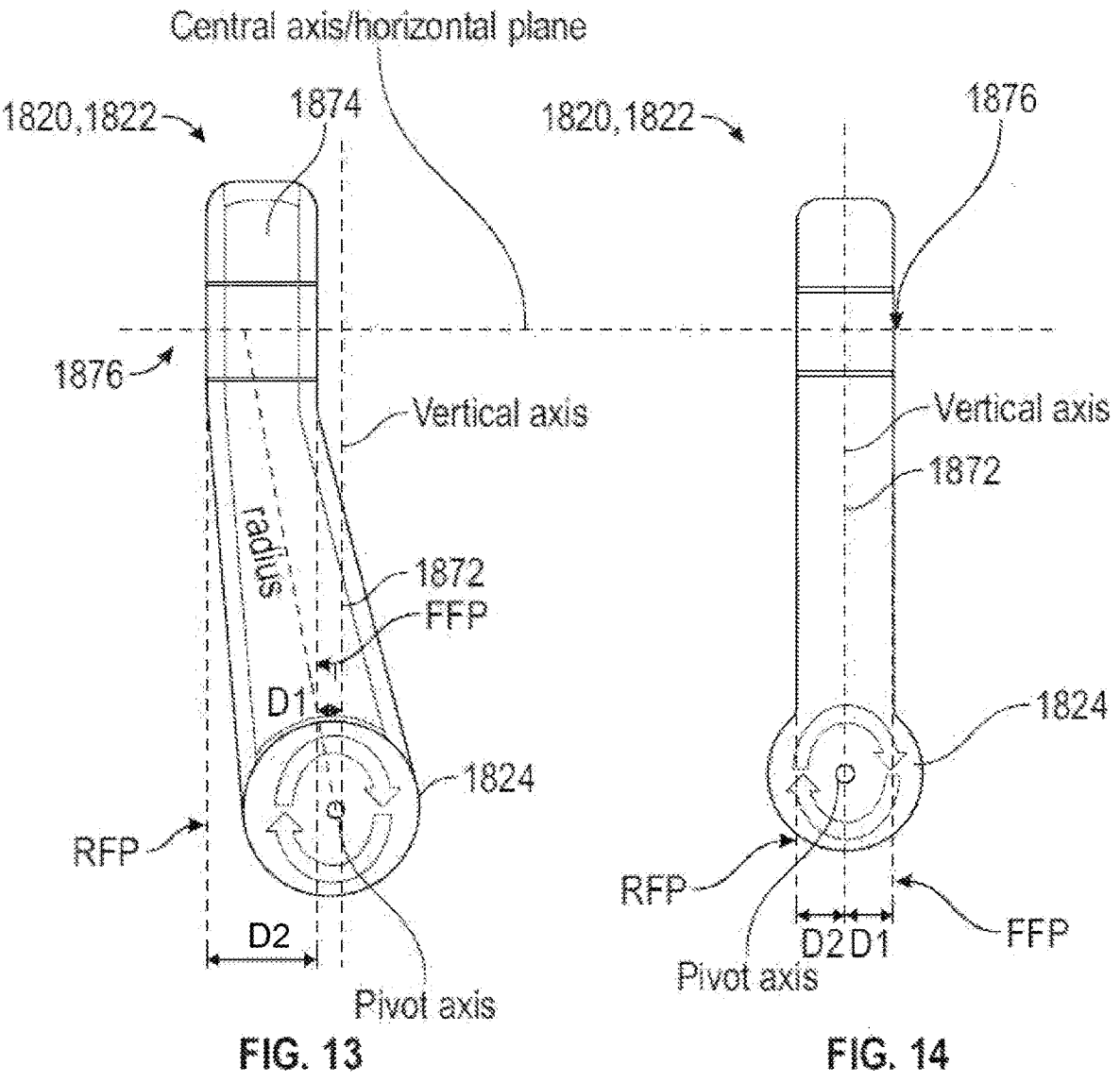
FIG. 13                    FIG. 14

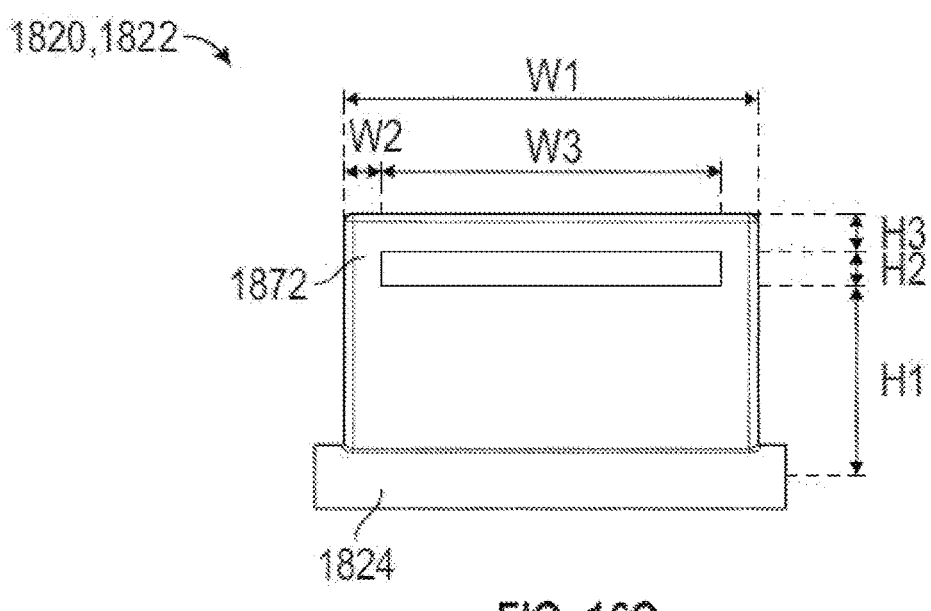
FIG. 16C
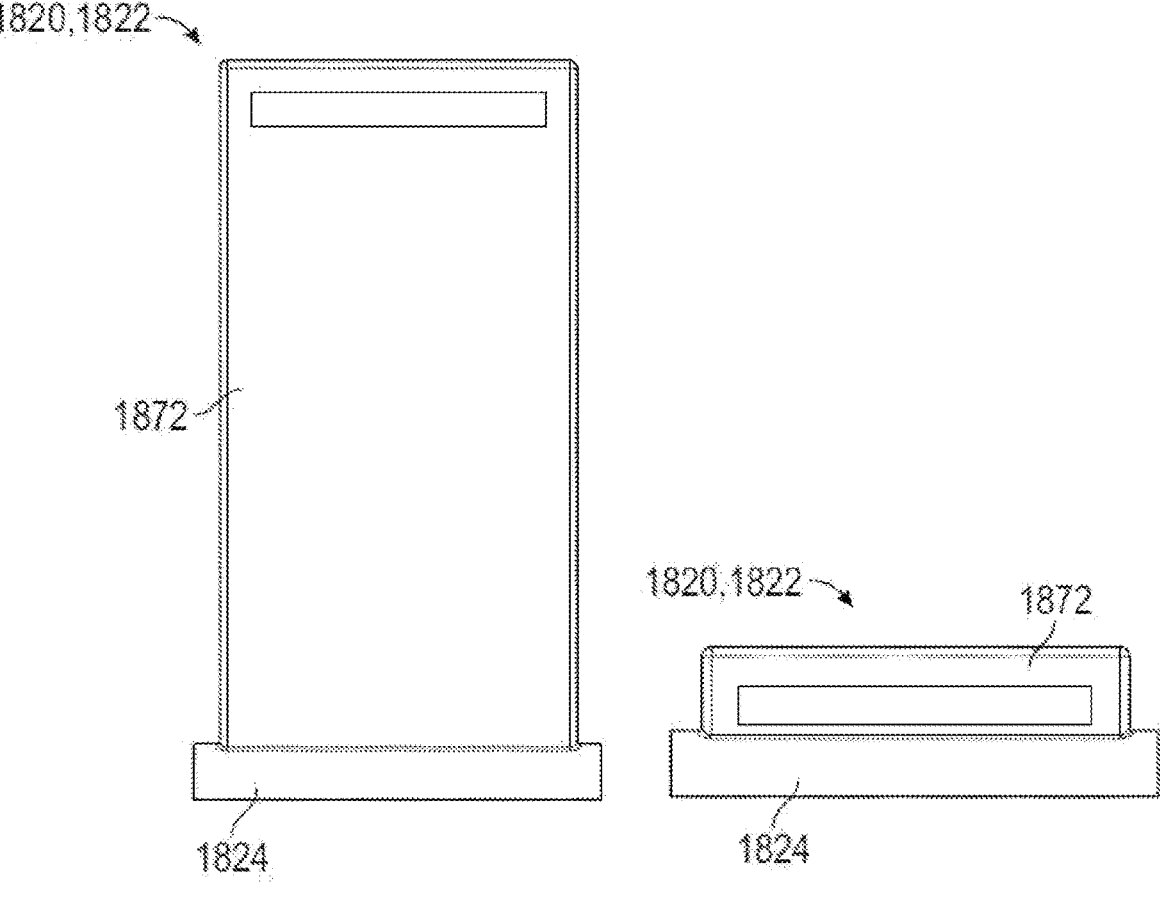
FIG. 16D                    FIG. 16E

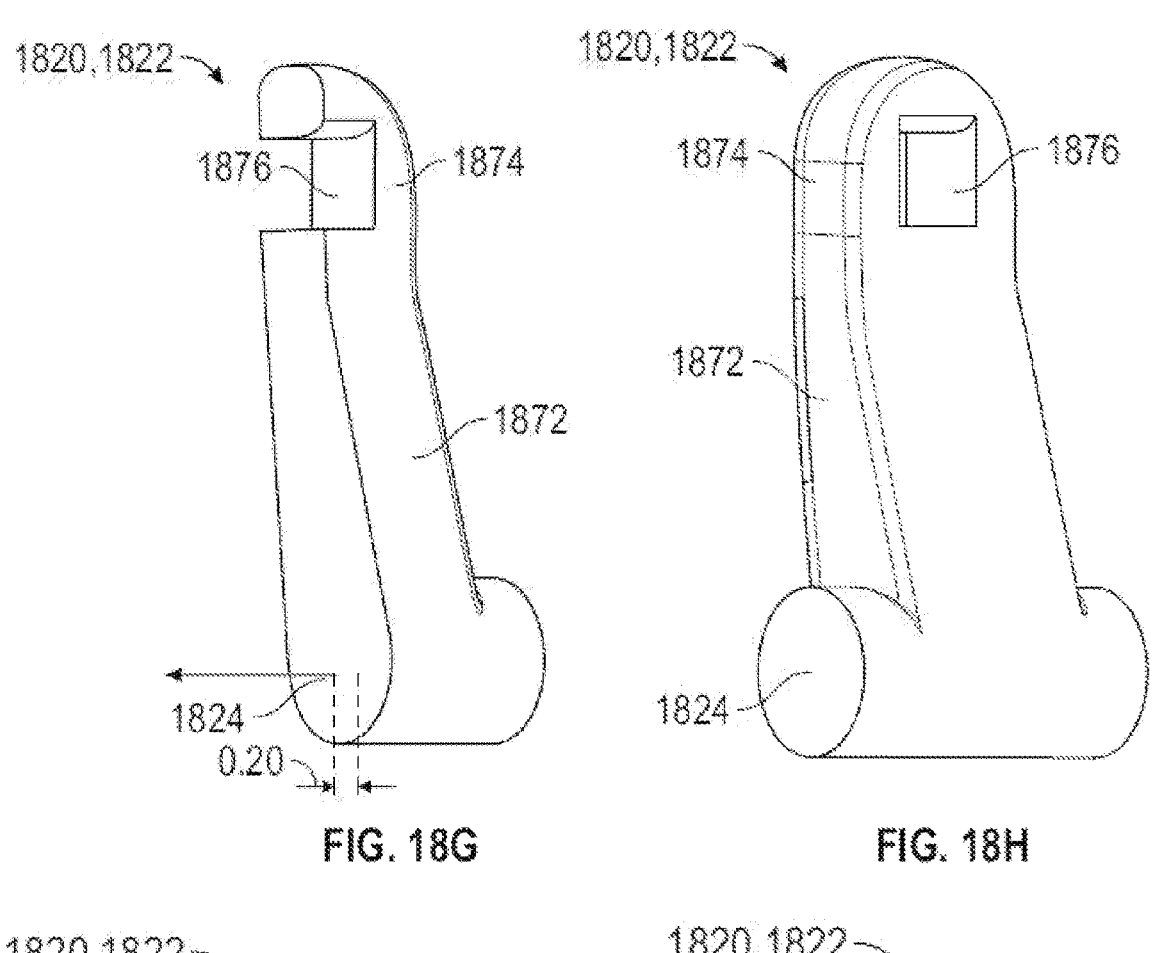
FIG. 18G                    FIG. 18H
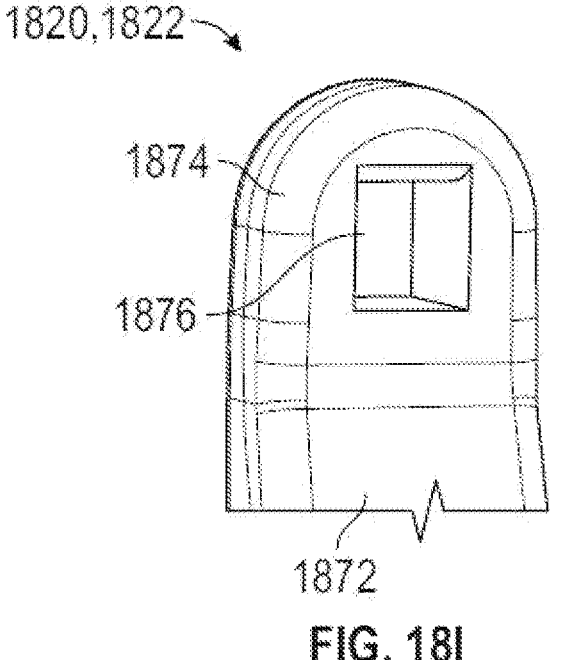
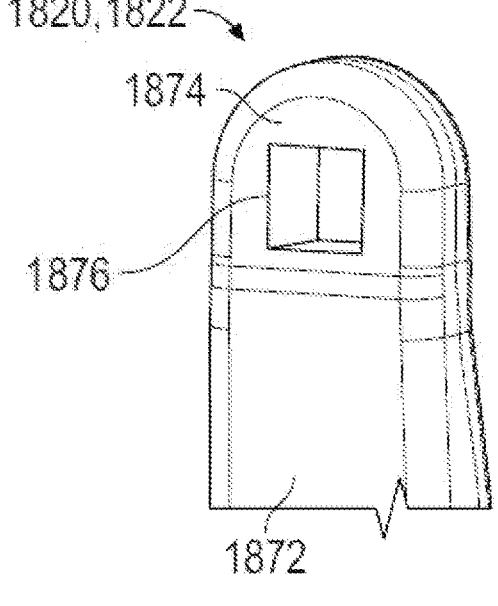
FIG. 18I                    FIG. 18J Extension (mm)

——— Braid    ~~~~ Mechanical Hardstop

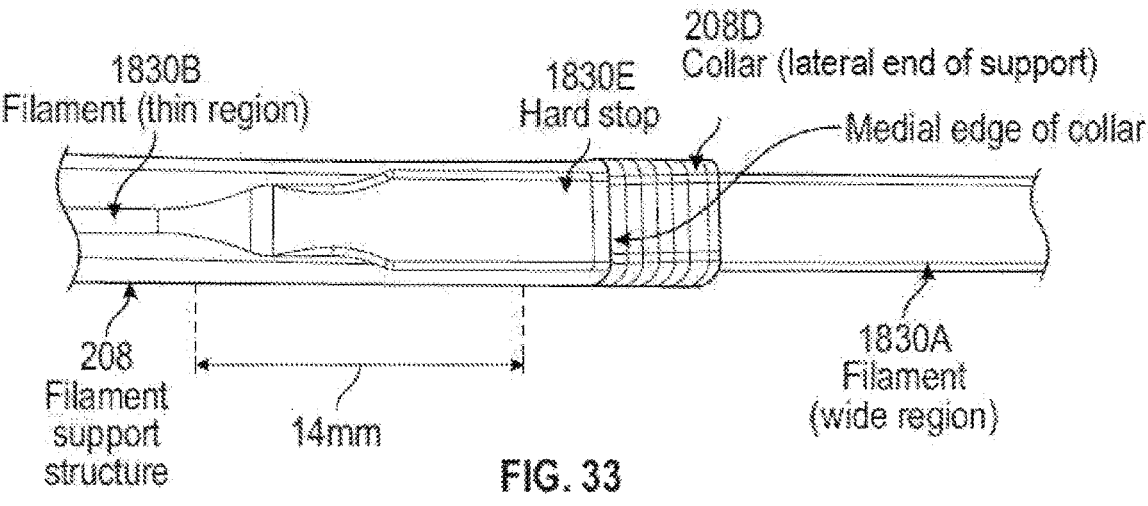

1830B
Filament (thin region)

1830E
Hard stop

208D
Collar (lateral end of support)

Medial edge of collar

208
Filament
support
structure

14mm

1830A
Filament
(wide region)

FIG. 33

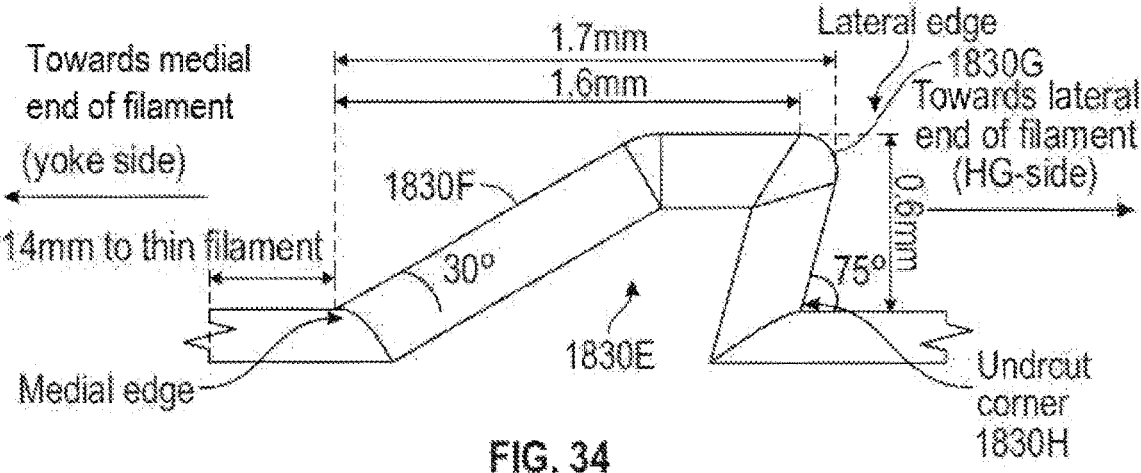

Towards medial
end of filament
(yoke side)

1.7mm 1.6mm

Lateral edge

1830G
Towards lateral
end of filament
(HG-side)

1830F

14mm to thin filament

30°

0.6mm

75°

Medial edge

1830E

Undercut
corner
1830H

FIG. 34

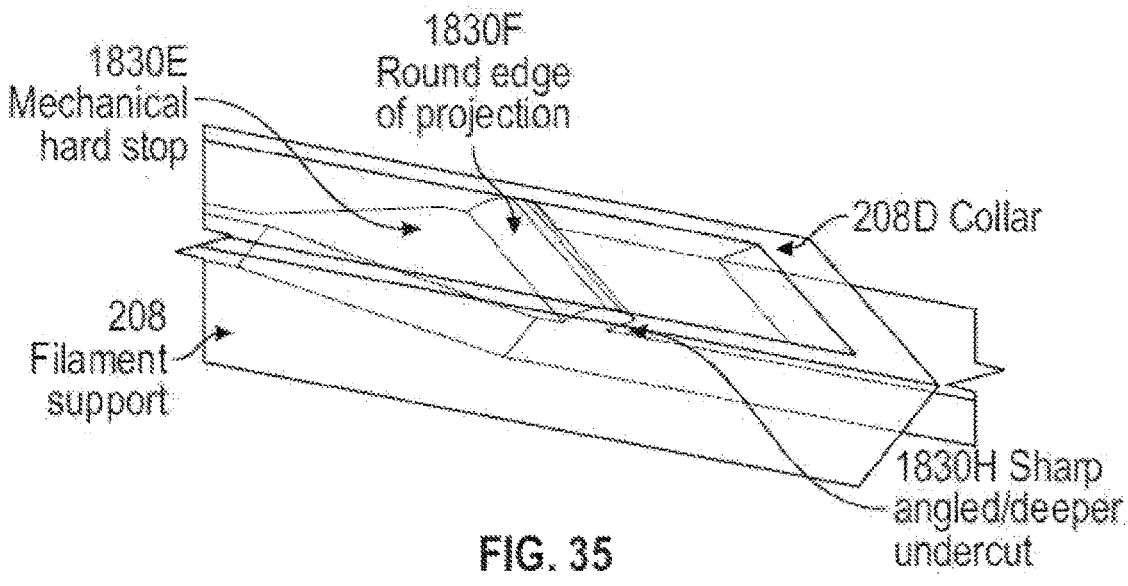

1830E
Mechanical
hard stop

1830F
Round edge
of projection

208D Collar

208
Filament
support

1830H Sharp
angled/deeper
undercut

FIG. 35

Channel divider
(0.2mm thickness)
208M

Interior

Exterior

208N

Wide
channel
208K

Small channel
208I

Small channel
208I

Channel divider
208M

Medial Collar
208C

208N  Wide channel
(exposed)
208K

Wide channel
(exposed)
208K

Small channel
208I

208N

Medial
Collar
208C

208C

Exterior

Interior

208I

208N

208K

1830A

1830C

1830E

1830B

1830I 1830J
locating/alignment
features

1830K
Barbs that catch and retain the lateral
end of the elastic (knitted/braided tube)

1830K

1830A
Thick region of filament

1830L

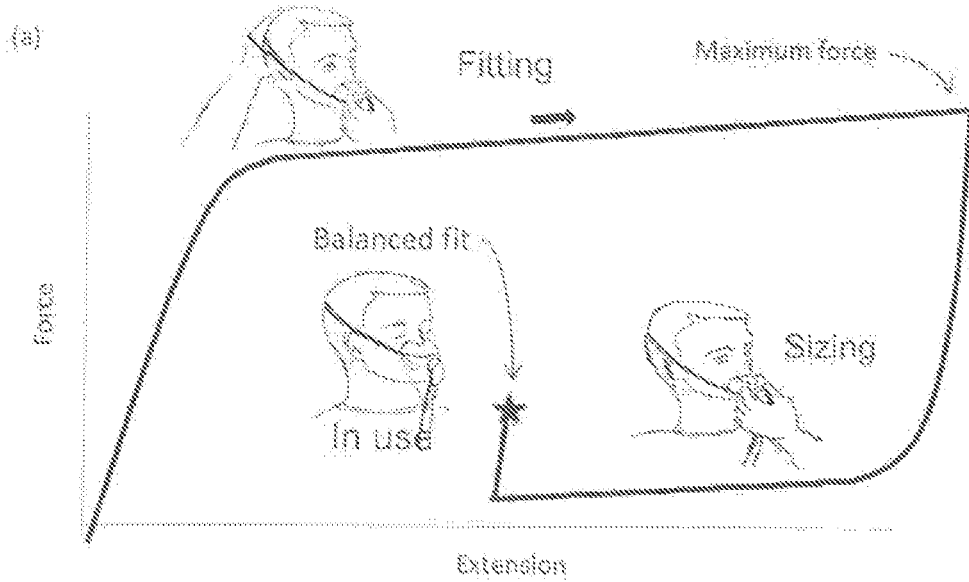
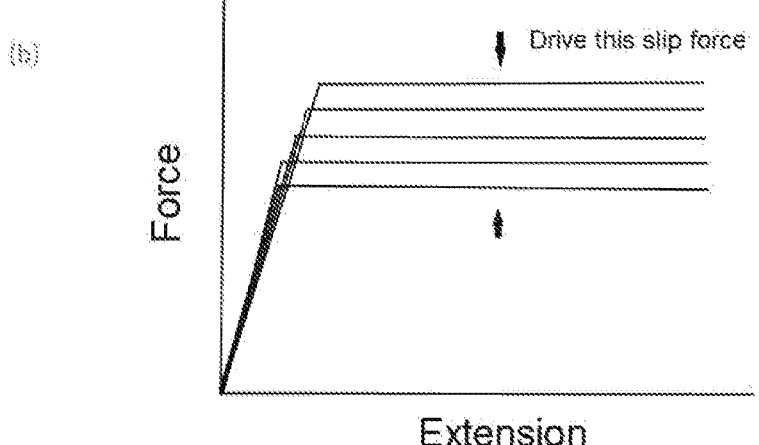
Fig. 58

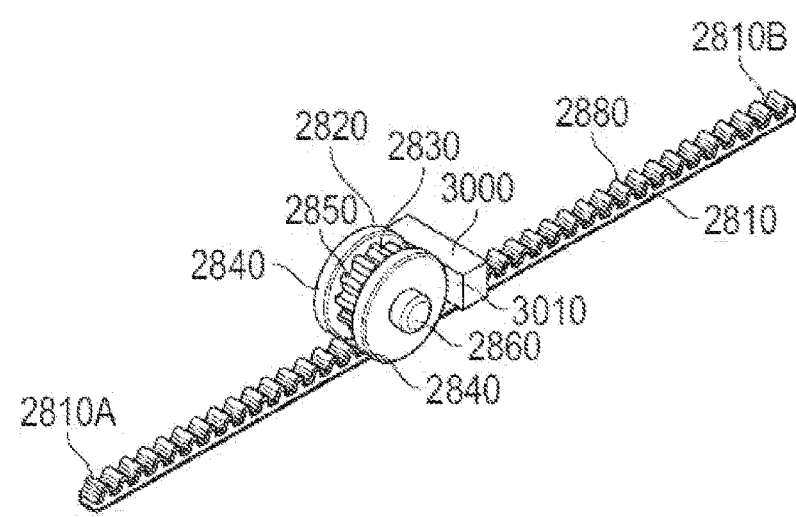
FIG. 65A
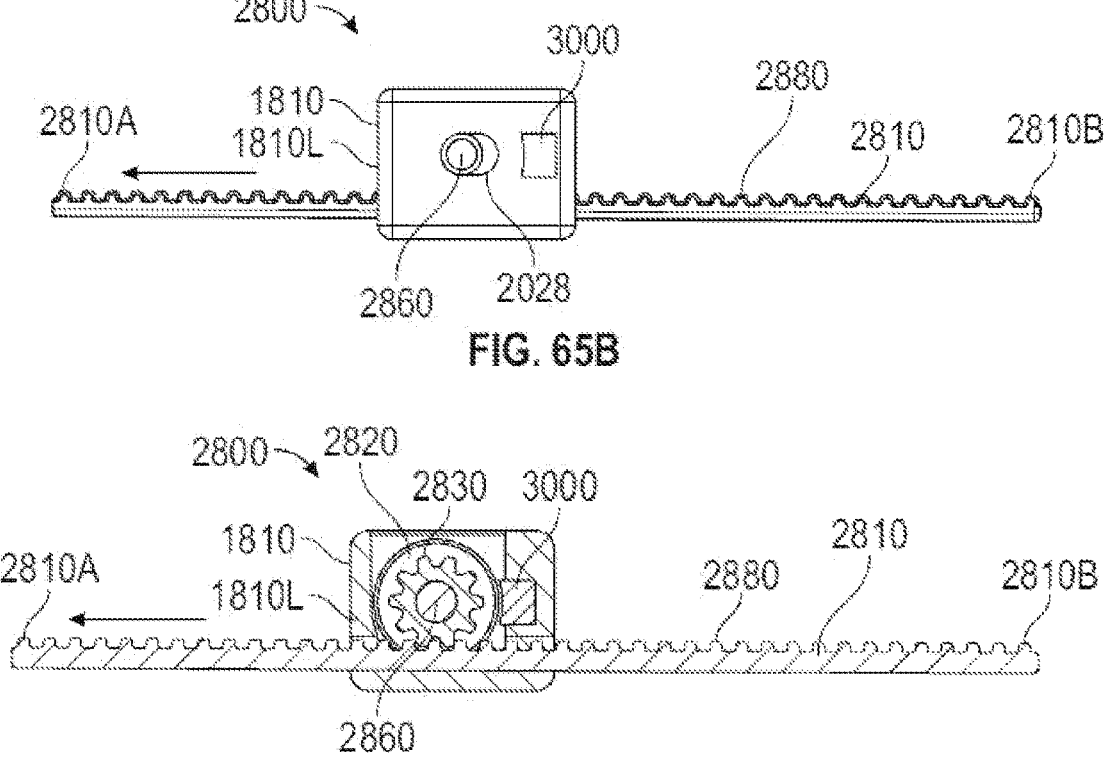
FIG. 65B
FIG. 65C (a)
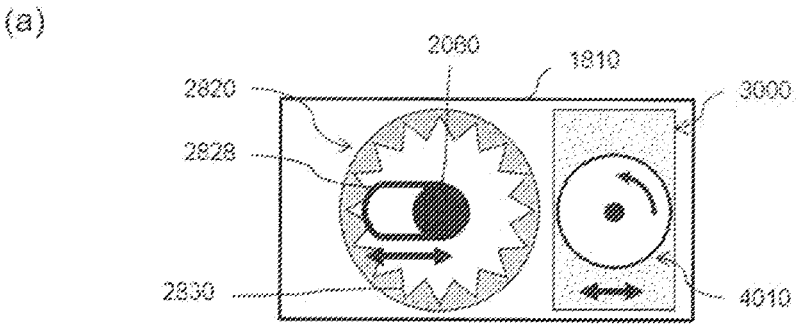
(b)
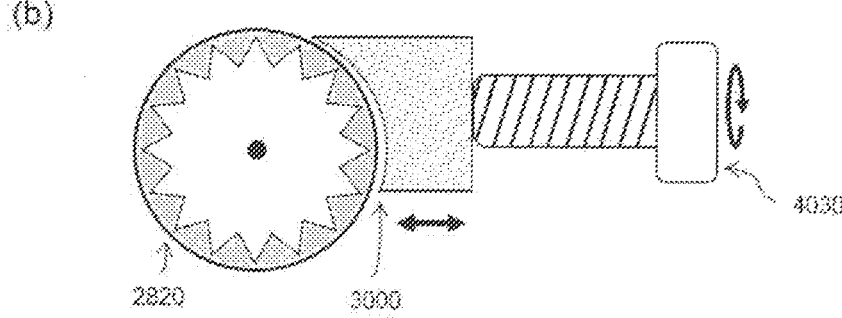
FIG. 66
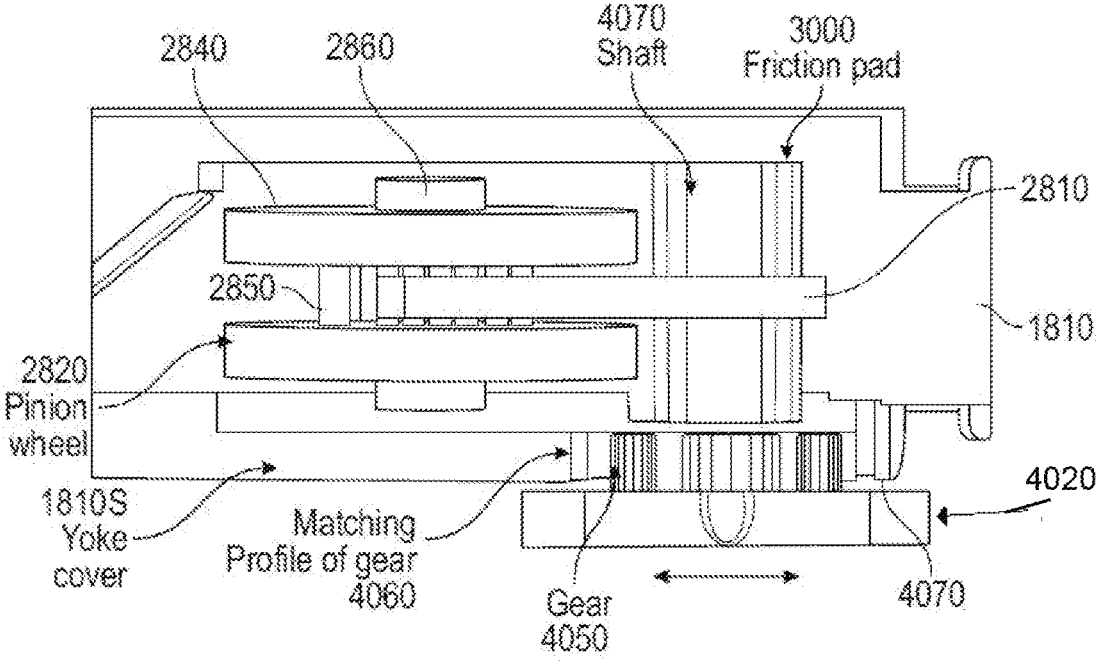
FIG. 67

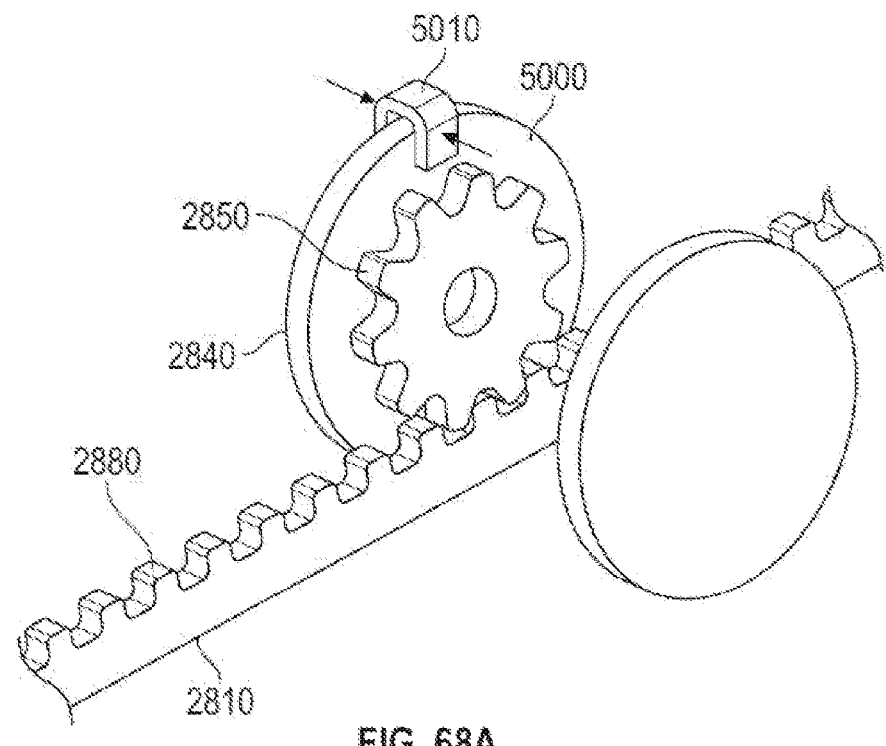
FIG. 68A
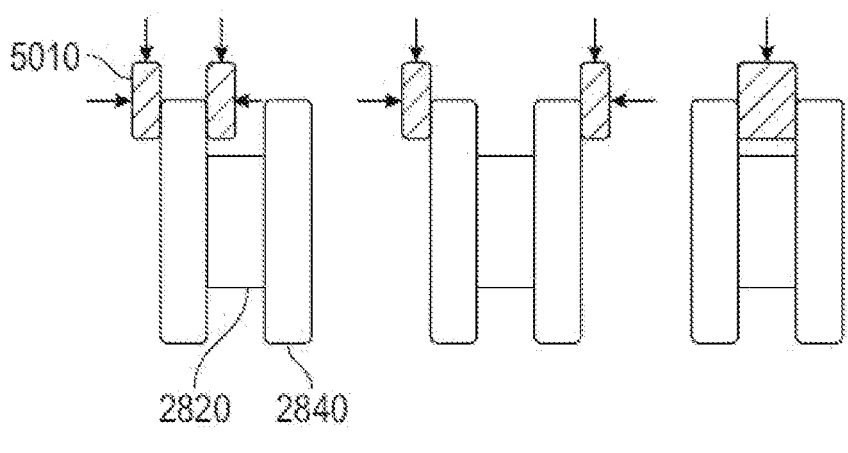
FIG. 68B   FIG. 68C   FIG. 68D

3108

2108B

2106E

2106G

OW

2106C

2106B

2140

2106G

2106C

2106D

2106D

2106A

2108B

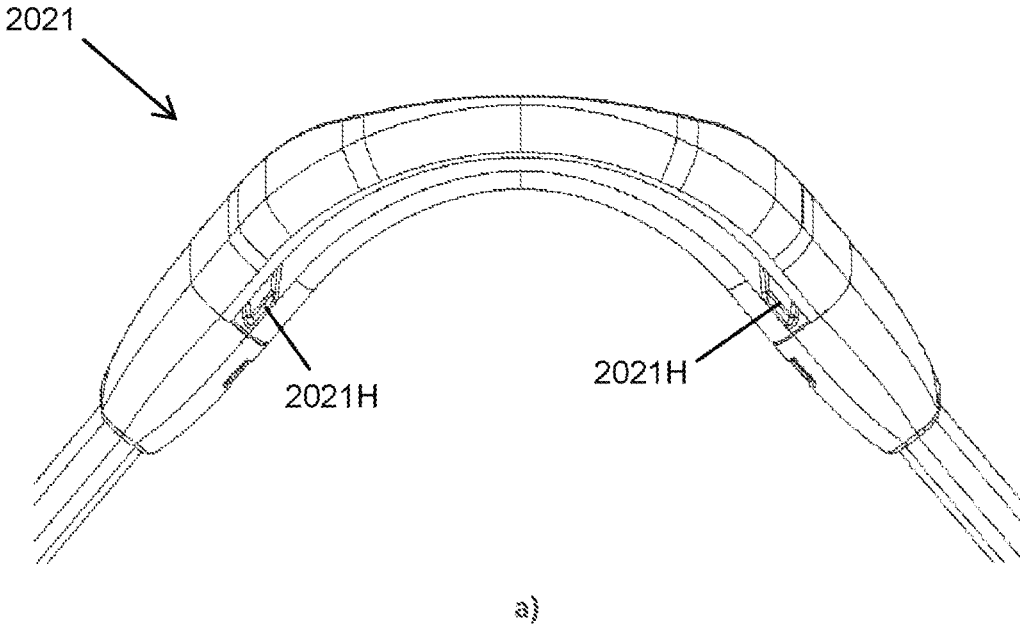
a)
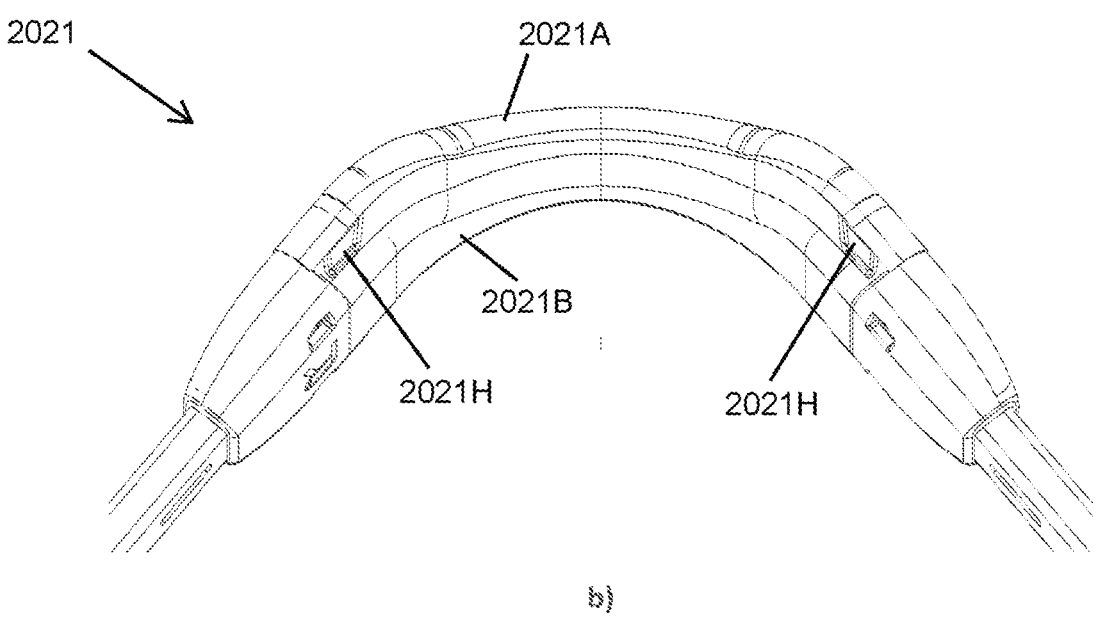
b)
Figure 104

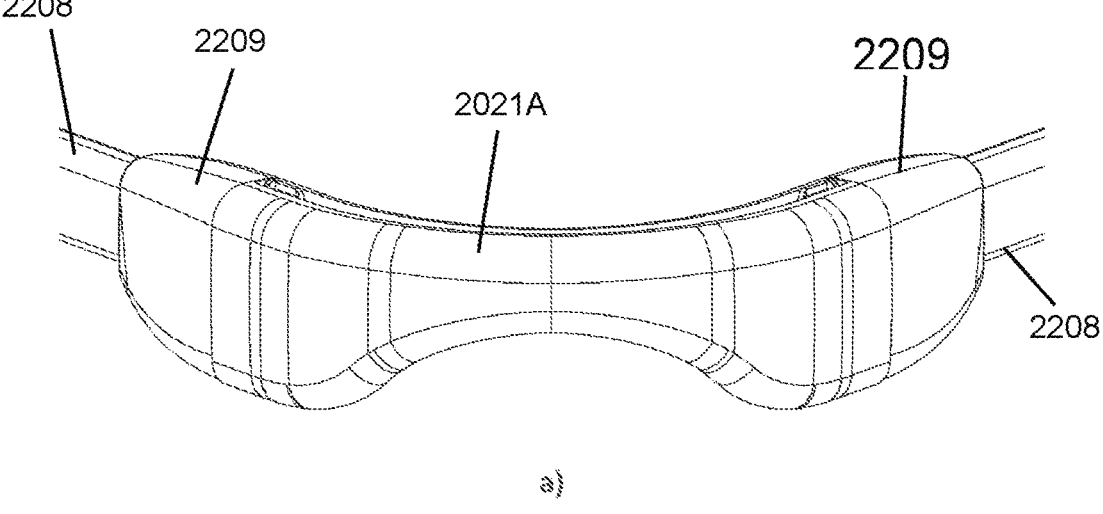
2208
2209
2021A
2209
2208
a)
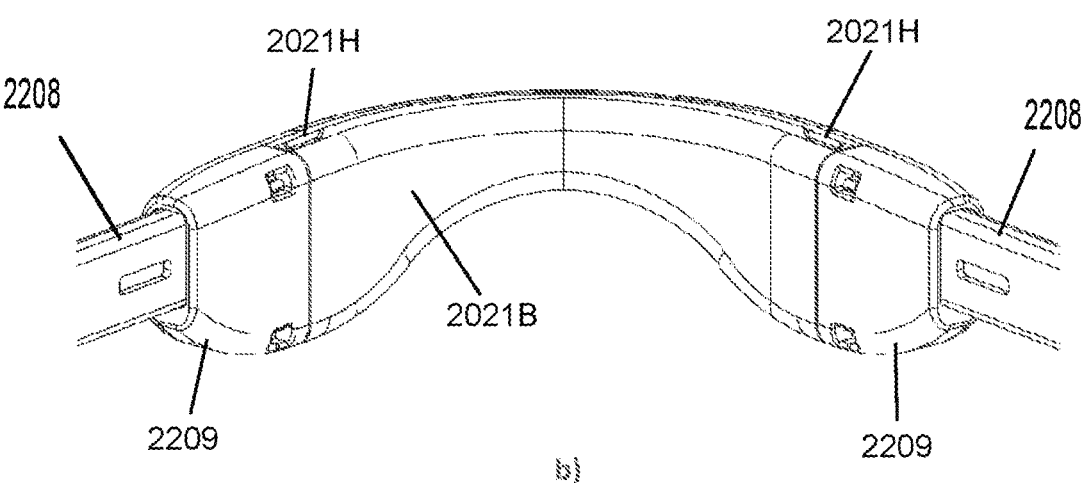
2021H
2021H
2208
2208
2021B
2209
2209
b)
Figure 105 a)

b)

1830B                    1830A

1830C 1830B                1830E         1830A

DIRECTIONAL ADJUSTMENT MECHANISM FOR HEADGEAR OF A RESPIRATORY THERAPY MASK OR INTERFACE

FIELD OF THE DISCLOSURE

The present disclosure relates to a directional adjustment mechanism for headgear of a respiratory therapy mask or interface of a respiratory therapy systems.

This disclosure relates to the disclosure of the following earlier patent applications, the entire contents of which are hereby incorporated by reference: WO2014/175752 filed 24 Apr. 2014, WO2016/043603 filed 16 Sep. 2015, WO2017/158544 filed 16 Mar. 2017, WO2017/160166 filed 15 Mar. 2016, and U.S. 62/644,002 filed 16 Mar. 2018. This application claims priority to provisional applications U.S. 62/755,766 filed 5 Nov. 2018, U.S. 62/755,777 filed 5 Nov. 2018, and U.S. 62/842,982 filed 3 May 2019, the entire contents of each of which are hereby incorporated by reference.

DESCRIPTION OF THE RELATED ART

Masks providing a substantially air-tight seal between a wearer and the mask are used in a variety of fields (e.g. gasmasks, diving masks, respiratory therapy masks). Some of these masks use headgear including one or more straps to secure the mask against the face of the wearer.

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnea (OSA), a condition in which a patient's airway intermittently collapses, during sleep, preventing the patient from breathing for a period of time. The cessation of breathing, or apnea, results in the patient awakening. Repetitive and frequent apneas may result in the patient rarely achieving a full and restorative night's sleep.

CPAP therapy involves the delivery of a supply of continuous positive air pressure to the airway of the patient via a respiratory mask. The continuous positive pressure acts as a splint within the patient's airway, which secures the airway in an open position such that the patient's breathing and sleep are not interrupted.

Respiratory masks typically comprise a patient interface and a headgear, wherein the patient interface is configured to deliver the supply of continuous positive air pressure to the patient's airway via a seal or cushion that forms an airtight seal in or around the patient's nose and/or mouth. Respiratory masks are available in a range of styles including full-face, nasal, direct nasal, pillows and oral masks, which create an airtight seal with one or more of the nares, nose and/or mouth. The seal or cushion is held in place on the patient's face by the headgear.

In order to maintain an airtight seal, the headgear should provide support to the patient interface such that it is held in a stable position relative to the patient's face during use. Such respiratory masks may also be used to deliver NIV and other therapies.

We have previously proposed a headgear for a respiratory mask comprising at least one strap having a filament, and a directional adjustment unit which has an engaged configuration and a disengaged configuration with respect to the filament. The directional adjustment unit allows the filament to be pulled through the unit in one direction, to tighten the headgear, but resists movement of the filament through the unit in an opposite direction, until the filament is released. the directional adjustment unit therefore functions as a headgear tensioning arrangement.

We have also previously proposed a filament or elongate flexible member that is received in, and can be moved through, the directional adjustment unit. We have proposed a filament comprising a core member and a wider diameter outer braided sheath. The wider diameter outer sheath functions as a stop, limiting the amount by which the filament can be pulled through the directional adjustment unit.

We have also proposed alternative directional adjustment units configured to produce a force profile similar to that of FIG. 6a. Such directional adjustment units comprise one or more movable frictional engagement members which each comprise an aperture through which the filament is fed, and which tilt/engage when the filament that is fed through them is drawn out of the unit. This provides the system with resistance, hence increases the slip/pull force that the user needs to overcome when elongating the headgear.

When the filament is retracted/recoiled and the headgear returns to its resting or neutral (e.g. balanced on face) configuration, the frictional engagement member tilts back, releasing the filament. This reduces resistance, allowing for the mask or patient interface to appear to the user to spring back onto the face.

One or more desirable features of such a directional adjustment unit include that the unit should:

Stretch far enough to be able to be pulled over the user's head;

Retract freely and be further adjustable to a point where the user feels they can achieve a secure fit;

Once CPAP pressure is applied, the system transforms into an inelastic headgear;

provide sufficient holding force to be able to comfortably hold the same seal position overnight;

During removal be able to be stretched over the user's head;

The force generated by the elastic braid must be low enough that the directional adjustment unit functions as an inelastic headgear even at the lowest CPAP pressure;

Have a sufficient activation length that it does not over tighten during normal bed use.

SUMMARY OF THE DISCLOSURE

Aspects of this disclosure may provide improved components associated with such a headgear, for example any one or more of a yoke assembly, a directional adjustment unit, a filament, one or more straps.

Aspects of this disclosure may provide an improved directional adjustment unit and associated filament design for reducing the shear stress on the filament, in use, thereby reducing the wear on the associated components during use. Such an improved directional adjustment unit may form part of a respiratory mask.

In some configurations, this is achieved by providing a frictional engagement member of the directional adjustment unit with an aperture having a transverse cross sectional shape forming at least one linear or substantially linear portion of the frictional engagement member for engaging a corresponding flat or substantially flat portion of the filament when the at least one frictional engagement member is in an engaged configuration.

According to an aspect of this disclosure, there is provided a directional adjustment unit for a headgear for a respiratory mask. The directional adjustment unit comprises a housing, and at least one frictional engagement member movable with respect to the housing, the at least one frictional engagement member having an aperture forming a cavity extending through the at least one frictional engagement member. The aperture is arranged to receive a filament of a strap of the headgear therethrough. The at least one frictional engagement member in a first configuration provides a disengaged configuration with respect to the filament, and in a second configuration provides an engaged configuration with respect to the filament. The cavity forms an engagement surface region that is linear or substantially linear in transverse cross-section, the engagement surface region for engaging a flat or substantially flat portion of the filament when the at least one frictional engagement member is in the engaged configuration.

The at least one frictional engagement member may be movable around a pivot axis. and wherein the first movably attained configuration relates to a first pivoted configuration, and the second movably attained configuration relates to a second pivoted configuration.

The engagement surface region may be linear or substantially linear along a lateral axis parallel or substantially parallel to the pivot axis.

The aperture, at a face of the at least one frictional engagement member, may be non-round, non-circular, non-elliptic, or non-oval.

The aperture may be provided offset to the pivot axis and extends through the at least one frictional engagement member along an axis having a component perpendicular to the pivot axis.

The aperture, at a face of the at least one frictional engagement member, may be quadrilateral, and preferably rectangular.

A side of the aperture may be parallel or substantially parallel to the pivot axis.

The aperture may have a quadrilateral cross section in a plane parallel to the pivot axis and an axis normal to the pivot axis.

The aperture, at the face of the at least one frictional engagement member, may triangular.

A side of the triangular aperture may be parallel or substantially parallel to the pivot axis.

The triangular aperture may have a vertex arranged closer to the pivot axis than the side being parallel or substantially parallel to the pivot axis.

The aperture may have a triangular cross section in a plane parallel to the pivot axis and an axis normal to the pivot axis.

The aperture may extend through the at least one frictional engagement member perpendicular or substantially perpendicular to the pivot axis.

The aperture or cavity may extend through the at least one frictional engagement member symmetrically around a central axis.

The engagement surface region may form part of at least one interior cavity wall surface of the at least one frictional engagement member.

The engagement surface region may comprise at least one interior cavity wall surface of the at least one frictional engagement member.

The cavity may have the shape of a rectangular elongated body or prism.

The cavity may have the shape of a triangular elongated body or prism.

At least one interior cavity sidewall surface may have a flat or substantially flat profile in one or more frontal planes, wherein each frontal plane intersects the central axis at a distinct position and comprises the normal vector of the central plane said distinct position.

At least one interior cavity sidewall surface may have a flat or substantially flat profile along one or more central plane normal vectors, each intersecting the central axis at different longitudinal positions thereof.

At least one interior cavity sidewall surface may maintain said flat or substantially flat profile along a portion of the central axis.

The central axis may follow a straight line in space.

The central axis may have a curvature.

The at least one frictional engagement member may have a base member through which the pivot axis extends, and at least a first section extending from the base member in a direction perpendicular to the pivot axis.

The at least one frictional engagement member may comprise a second section extending from an end of the first section in a direction away from the pivot axis, wherein the second section is arranged at an angle in relation to the first section.

The at least first section may have a tapered cross section in plane perpendicular to the pivot axis.

The at least first section may have a rectangular cross section in plane perpendicular to the pivot axis.

The engagement surface region may provide, in the engaged configuration, a frictional engagement against the filament, in use.

The housing may comprise an external opening for slidably receiving and/or accommodating the filament and/or part of the strap, in use.

The external opening may have a size smaller than that of at least one portion of a transitional region of the filament, in use.

At least one portion of the transitional region of the filament may be received by the external opening of the housing.

At least one portion of the transitional region of the filament may be received by a yoke assembly configured to connect the headgear to the respiratory mask.

The aperture may form a rounded edge at a face of the at least one frictional engagement member.

The rounded edge may have a curvature with reference to an axis parallel to the pivot axis.

The aperture may have a polygonal transverse cross section having three or more sides.

The central axis may be formed in a central plane having a normal vector parallel or substantially parallel to the pivot axis.

The at least one transverse cross section may be perpendicular to the central axis.

According to a further aspect of this disclosure, a filament of a headgear for a respiratory interface or mask is provided. The filament may a filament body extending along a longitudinal axis thereof, the filament body having a core region having a first geometrical shape, an end region having a second geometrical shape, wherein the filament body in the end region may have at least one flat or substantially flat exterior surface extending along a longitudinal axis thereof, and a transitional region provided along the longitudinal axis between the core region and the end region, wherein the transitional region may have a shape transitioning from the first geometrical shape of the core to the second geometrical shape of the end region over a longitudinal distance along the longitudinal axis of the filament body.

The transitional region in at least a portion thereof may have a dimension, transverse cross section, being larger than the corresponding dimension of an external opening of a housing of a frictional engagement member of a directional adjustment unit, in use.

The transitional region may be offset from the longitudinal axis of the filament.

The filament may comprise upper and lower elongate margins extending along the longitudinal axis of the filament, wherein the margins taper toward one another at least in the transitional region. Both margins may taper toward one another. Only one margin may taper toward the other, the other margin being substantially straight along its length. One margin may comprise a continuous substantially flat surface formed by the end region and the core region.

According to a yet another aspect of this disclosure, a headgear for a respiratory mask is provided. The headgear may comprise the directional adjustment unit disclosed herein, and at least one filament comprising a filament body having at least one flat or substantially flat exterior surface extending along a longitudinal axis thereof, so that in the engaged configuration the substantially flat or flat exterior surface of the filament body is brought into contact with engagement surface region of the directional adjustment unit.

The filament may further comprise a core region having a first geometrical shape, an end region having a second geometrical shape, and a transitional region provided longitudinally between the core region and the end region, wherein the transitional region may have a shape transitioning from the first geometrical shape of the core region to the second geometrical shape of the end region over a longitudinal distance along the longitudinal axis of the filament body.

The headgear may further comprise a yoke assembly configured to connect the headgear to the respiratory mask.

The directional adjustment unit may be arranged in the yoke assembly.

The yoke assembly may comprise a central portion and at least one section extending from the central portion, wherein the at least one section may be configured to connect to the at least one strap of the headgear.

According to another aspect, a respiratory mask is provided. The respiratory mask may comprise a directional adjustment unit and headgears as disclosed herein.

According to yet another aspect of this disclosure, a respiratory therapy system comprising the respiratory mask is provided.

In yet another aspect a headgear for a respiratory mask is provided. The headgear comprises a strap, and a filament located at least partially within the strap. The headgear further comprises a directional adjustment unit having at least one movable frictional engagement member. The frictional engagement member has an aperture forming a cavity extending through the at least one frictional engagement member, wherein the aperture is arranged to receive the filament therethrough. The at least one frictional engagement member in a first configuration may provide a disengaged configuration with respect to the filament, and in a second configuration may provide an engaged configuration with respect to the filament. The at least one frictional engagement member may be movable between engaged and disengaged configurations. The filament may further comprise a filament body having a substantially flat exterior surface portion extending along a longitudinal axis thereof, so that in the engaged configuration the substantially flat exterior surface portion of the filament body is brought into contact with the at least one frictional engagement member.

According to another aspect of this disclosure, there is provided a directional adjustment unit for a headgear for a respiratory mask. The directional adjustment unit comprises a housing, and at least one frictional engagement member movably arranged to the housing. The at least one frictional engagement member has an aperture extending therethrough for receiving a filament of a strap of the headgear. At least one frictional engagement member in a first movably attained configuration provides a disengaged configuration with respect to the filament, and in a second movably attained configuration provides an engaged configuration with respect to the filament. The aperture forms an engagement surface of the frictional engagement member which in transverse cross section has a linear or substantially linear portion for engaging a corresponding linear or substantially linear portion of the filament when the at least one frictional engagement member is in the engaged configuration.

According to an aspect of this disclosure, there is provided a directional adjustment unit for a headgear for a respiratory mask. The directional adjustment unit comprises a housing, and at least one frictional engagement member movable with respect to the housing, the at least one frictional engagement member having an aperture forming a cavity extending through the at least one frictional engagement member. The aperture is arranged to receive a filament of a strap of the headgear therethrough. The at least one frictional engagement member in a first configuration provides a disengaged configuration with respect to the filament, and in a second configuration provides an engaged configuration with respect to the filament. The cavity forms at least one engagement surface region of the frictional engagement member. The at least one engagement surface region, in at least one transverse cross-section, comprises at least one linear or substantially linear portion for engaging a corresponding transverse cross sectional linear or substantially linear portion of the filament when the at least one frictional engagement member is in the engaged configuration.

According to an aspect of this disclosure, there is provided a directional adjustment unit for a headgear for a respiratory mask. The directional adjustment unit comprises a housing, and at least one frictional engagement member movable with respect to the housing, the at least one frictional engagement member having an aperture forming a cavity extending through the at least one frictional engagement member. The aperture is arranged to receive a filament of a strap of the headgear therethrough. The at least one frictional engagement member in a first configuration provides a disengaged configuration with respect to the filament, and in a second configuration provides an engaged configuration with respect to the filament. The cavity forms at least one engagement surface region of the frictional engagement member. The at least one engagement surface region, in at least one transverse cross-section, comprises at least one straight or substantially straight portion for engaging a corresponding transverse cross sectional straight or substantially straight portion of the filament when the at least one frictional engagement member is in the engaged configuration.

According to yet another aspect, a filament of a headgear for a respiratory interface or mask is provided. The filament comprises a filament body having at least one flat or substantially flat exterior surface extending along a longitudinal axis thereof.

The flat exterior surface of the filament may be arranged to engage with an engagement surface region of the frictional engagement member of a directional adjustment unit.

The engagement surface region may comprise a linear portion in a transverse cross section.

The transverse cross sectional linear portion of the engagement surface region may correspond to a transverse cross sectional linear portion of the flat exterior surface of the filament. The linear or substantially linear portion at the transverse cross section of the engagement surface region may refer to portion being linear or substantially linear at least along one dimension of said transverse cross section.

In some configurations, the expression "linear" may be interchangeably be referred to as "straight".

The systems, methods and devices described herein have innovative aspects, no single one of which is indispensable or solely responsible for their desirable attributes. Without limiting the scope of the claims, some of the advantageous features will now be summarized.

In some configurations, a headgear for a respiratory mask comprises at least one strap having a filament, a directional adjustment unit having an engaged configuration and a disengaged configuration with respect to the filament.

In some configurations, a headgear for a respiratory mask comprises at least one strap comprising a filament, a directional adjustment unit configured to limit movement of the filament in a direction until a minimum force in said direction is applied to the filament.

In some configurations, the headgear further comprises at least one strap that does not include a filament.

In some configurations, a mask comprises any of the above described headgear. The mask assembly further comprises a patient interface. The patient interface comprises a frame and a cushion module having a housing and a seal. The patient interface further comprises a connection arrangement configured to connect the cushion module to the frame. The connection arrangement comprises at least one protrusion located on one of the cushion module and the frame and at least one recess located on the other of the cushion module and the frame. The at least one protrusion is configured to engage the at least one recess to secure the cushion module to the frame.

In some configurations, the headgear comprises a yoke assembly configured to connect the headgear to the patient interface.

In some configurations, the directional adjustment unit is arranged on the frame.

In some configurations, the directional adjustment unit is arranged in the yoke assembly.

In some configurations, the yoke comprises a central portion and at least one section extending from the central portion. The at least one section is configured to connect to the at least one strap of the headgear.

Aspects of this disclosure may provide improved components associated with such a headgear, for example any one or more of a yoke assembly, a directional adjustment unit, a filament, one or more straps.

Aspects of this disclosure may provide an improved directional adjustment unit and associated filament for providing a more defined and/or reliable and/or effective stop between the filament and the directional adjustment unit. Such an improved directional adjustment unit may form part of a respiratory mask or headgear.

The systems, methods and devices described herein have innovative aspects, no single one of which is indispensable or solely responsible for their desirable attributes. Without limiting the scope of the claims, some of the advantageous features will now be summarized.

In some configurations, a headgear for a respiratory mask comprises at least one strap having a filament, a directional adjustment unit having an engaged configuration and a disengaged configuration with respect to the filament.

In some configurations, a headgear for a respiratory mask comprises at least one strap comprising a filament, a directional adjustment unit configured to limit movement of the filament in a direction until a minimum force in said direction is applied to the filament.

In some configurations, the headgear further comprises at least one strap that does not include a filament.

In some configurations, a mask comprises any of the above described headgear. The mask assembly further comprises a patient interface. The patient interface comprises a frame and a cushion module having a housing and a seal. The patient interface further comprises a connection arrangement configured to connect the cushion module to the frame. The connection arrangement comprises at least one protrusion located on one of the cushion module and the frame and at least one recess located on the other of cushion module and the frame. The at least one protrusion is configured to engage the at least one recess to secure the cushion module to the frame.

In some configurations, the headgear comprises a yoke configured to connect the headgear to the patient interface. In some configurations the frame of the patient interface comprises a yoke.

In some configurations, the yoke comprises a central portion and at least one section extending from the central portion. The at least one section is configured to connect to the at least one strap of the headgear.

According to an aspect of this disclosure, there is provided a directional adjustment unit for a headgear for a respiratory mask, comprising a housing, at least one frictional engagement member arranged to be movable with respect to the housing, the at least one frictional engagement member having an aperture extending therethrough for receiving a filament of a strap of the headgear therethrough, wherein the at least one frictional engagement member in a first movable/movably attained configuration provides a disengaged configuration with respect to the filament, and in a second movable/movably attained configuration provides an engaged configuration with respect to the filament, and wherein the directional adjustment unit comprises an abutment feature configured to abut a stop provided on the filament, to limit the extent of movement of the filament relative to the directional adjustment unit.

The aperture forms a cavity or bore or passage extending through the at least one frictional engagement member.

In some embodiments, the at least one frictional engagement member is pivotally arranged to the housing around a pivot axis, wherein the at least one frictional engagement member in a first pivoted configuration provides a disengaged configuration with respect to the filament, and in a second pivoted configuration provides an engaged configuration with respect to the filament.

The directional adjustment unit may further comprise the filament.

The abutment of the abutment feature and the stop may be configured to generate a sudden increase in force, while any increase in extension of the filament is relatively low such that the abutment feature abuts the stop before the extension of the filament is sufficient to yield. The stop and the filament may be configured such that the start of the elastic region of deformation of the filament occurs at a force that is lower than the start of the elastic region of deformation of the stop of the filament.

The filament may comprise a length comprising a larger region and a length comprising a smaller region. The ratio of thickness of the larger region to the smaller region may be in the range of: 2:1, preferably 1.5:1 and most preferably 1.4:1. The ratio of cross sectional area of the larger region to the smaller region may be in the range of: 10:1, preferably 7.5:1, and most preferably about 5:1. The ratio of the length of larger region to the length of the smaller region may be in the range of 10:1, preferably 5:1, and most preferably about 4:1. The ratio of the width of the larger region to the width of the smaller region may be in the range of 0.5:1, preferably 0.75:1, and most preferably about 1:1.

A filament support structure may be provided located between the housing and the headgear and which comprises an elongate support body which extends along, and constrains, at least part of the filament.

The filament support structure may comprise opposed ends, each end comprising an abutment feature configured to abut the stop of the filament, such that the abutment features between them limit the extent of movement of the filament through the lock unit.

At least one abutment feature may comprise a collar defining a slot through which the filament extends, and an abutment surface or face configured to abut the stop of the filament. Each abutment feature may comprise a respective collar. The collar may taper inwardly, when viewed from the side, towards an end of the filament support structure. The abutment surface or face may comprise a protrusion which protrudes from a main body of the collar. The protrusion may comprise a protruding bar or strip which extends transversely across at least part of the collar and which comprises a forward face against which the filament stop abuts when the filament is fully retracted into the directional adjustment unit. The abutment surface or face of the protrusion may be supported by upper and lower inclined walls extending from the collar. The abutment surface or face is planar and occupies a plane which is substantially, but not perfectly, perpendicular, that is within 0-15°, to the longitudinal axis of the flexible support structure.

The filament support structure may comprise at least one elongate guide surface that extends along the filament support structure parallel to the longitudinal axis of the filament support structure, and which constrains the filament relative to the filament support structure in a direction perpendicular to the longitudinal axis. A pair of elongate guide surfaces may be provided on opposed margins of the filament support structure. The elongate guide surface ramps upwardly from a main body of the support structure to the collar.

The filament support structure may comprise a length, along at least part of which the filament is exposed. At least part of the length of the filament support structure may comprise a guide feature, extending along the support structure which constrains movement of the filament in at least one direction. The filament support structure may comprise multiple guide features such that movement of the filament is constrained in multiple directions.

The filament support structure, at one end, may comprise engagement features configured to engage with the housing, to mount the filament support structure on the housing. The or each engagement feature may comprise at least one rib. The or each engagement feature may comprise at least one aperture.

The filament support structure may comprise at least one channel configured to receive the filament. The filament support structure may comprise multiple channels, each channel being configured to receive a respective filament. A feature of one channel may be different from that of the other channel, the feature being selected from any one of:
- a) width;
- b) height;
- c) cross sectional area;
- d) cross sectional shape.

The or each channel may have any one of more the following properties, characteristics of configurations:
- a) the width of one channel may be between 1.1 and 2.5 times greater than the width of the other channel, preferably between 1.1 and 1.5 times greater and most preferably between 1.1 and 1.3 times greater.
- b) the height of one channel may be between 2 and 10 times greater than the height of the other channel, preferably between 4 and 9 times greater and most preferably between 6 and 8 times greater.
- c) one channel may be stacked above the other, when viewed along the longitudinal axis of the filament support structure.
- d) one channel may be adjacent the other, so as to be side by side when viewed along the longitudinal axis of the filament support structure.

The filament support structure may comprise an interior surface configured to contact the face of the user, and an exterior surface configured to face away from the user, one of the surfaces comprising at least one modified or strengthened or weakened region as compared to the other surface. The modified or strengthened or weakened region comprises any one or more of:
- a) a rib;
- b) a castellation;
- c) a tooth;
- d) a recess.

A plurality of modified or strengthened or weakened regions may be provided.

The filament may comprise a length comprising a larger region and a length comprising a smaller region, and a length comprising a transitional region between the larger and smaller regions, wherein when the filament stop abuts the collar, the transitional region has passed through the collar.

In some configurations, the directional adjustment unit is arranged on the frame.

In some configurations, the directional adjustment unit is arranged in the yoke assembly.

According to another aspect of this disclosure there is provided a filament of a headgear for a respiratory interface or mask, comprising a filament body comprising a plurality of regions including:
- a. a length comprising a larger region;
- b. a length comprising a smaller region, and
- c. a length comprising a transitional region between the larger and smaller regions;
- wherein the length comprising one of the regions comprises a stop.

The stop, and the filament, may be configured such that the start of the elastic region of deformation of the filament occurs at a force that is lower than the start of the elastic region of deformation of the stop of the filament.

The stop may comprise a protrusion, which protrudes from the filament, orthogonal to the longitudinal axis of the filament. The protrusion may be elongate and extend transversely across at least part of the larger region of the filament. The stop may be adjacent the transitional region.

The stop may comprise an abutment surface or face which is inclined relative to the longitudinal axis of the filament. The sloped or inclined abutment surface or face may be inclined at an angle between 5 and 90° to the longitudinal axis of the filament, preferably 15 and 70°, and most preferably 20 and 45°. The stop may comprise an abutment surface or face which is undercut relative to the longitudinal axis of the filament. The abutment surface or face may be undercut at an angle between 5 and 90° to the longitudinal axis of the filament, preferably 30 and 85°, and most preferably 60 and 80°.

The stop may comprise any one or more of:

a) an obtuse trapezoid shape when viewed from the side.

b) a pair of opposed abutment surfaces or faces.

c) an abutment surface or face which is planar or comprises a planar portion.

d) an abutment surface or face which is arcuate or comprises an arcuate portion.

The stop may be formed integrally with the filament.

The filament may comprise a filament anchor comprising a location and/or alignment feature configured to locate and/or align the filament with the headgear to enable mating/connection between the filament anchor and headgear.

The location and/or alignment feature may:

a) comprise any one or more of a lugs and/or recess and/or slot and/or aperture.

b) be provided on a widened end of the filament that forms the filament anchor.

The widened end may be substantially planar and extends transversely outwardly from the longitudinal axis of the filament. The location and/or alignment feature may also be generally planar and extends transversely away from the longitudinal axis of the filament. The distal end of the filament anchor may comprise an elongate slot whose distal margin is open such that the distal end of the filament anchor is generally 'U' shaped or forked when viewed from above. The filament anchor may comprise a single oblong aperture. The filament may comprise an outer sheath or tube or cover, wherein the filament anchor also comprises at least one barb to retain the lateral end of the outer sheath or tube or cover.

According to another aspect of this disclosure there is provided a headgear for a respiratory interface or mask, comprising, a) the directional adjustment unit of any one of the above statements; and b) the filament of any one of the above statements.

The headgear may comprise a yoke configured to connect the headgear to the respiratory interface or mask. The directional adjustment unit may be arranged in the yoke. The yoke may comprise a central portion and at least one section extending from the central portion, wherein the at least one section is configured to connect to the at least one strap of the headgear.

According to another aspect of this disclosure there is provided a headgear for a respiratory mask, comprising the filament of any one of the above statements.

According to another aspect of this disclosure there is provided a headgear for a respiratory mask or interface, comprising:

a strap;

a filament located at least partially within the strap;

a directional adjustment unit comprising at least one movable frictional engagement member, the at least one frictional engagement member having an aperture forming a cavity or bore or passage extending therethrough for receiving the filament therethrough, wherein the at least one frictional engagement member in a first configuration provides a disengaged configuration with respect to the filament, and in a second configuration provides an engaged configuration with respect to the filament, the at least one frictional engagement member being movable between engaged and disengaged configurations; and wherein the directional adjustment unit comprises an abutment feature configured to abut a stop provided on the filament, to limit the extent of movement of the filament relative to the directional adjustment unit.

According to another aspect of this disclosure there is provided a respiratory mask or interface, comprising the headgear of any one of the above statements.

According to another aspect of this disclosure there is provided a respiratory therapy system, comprising the respiratory mask or interface of any one of the above statements.

The respiratory therapy system may comprise any one or more of:

a flow generator;

a humidifier;

a breathing gas delivery conduit.

According to an aspect of this disclosure, there is provided a directional adjustment unit for a headgear for a respiratory mask, comprising a housing, at least one frictional engagement member arranged to be movable with respect to the housing, the at least one frictional engagement member having an aperture forming a cavity extending therethrough for receiving a filament of a strap of the headgear therethrough, wherein the at least one frictional engagement member in a first movable configuration provides a disengaged configuration with respect to the filament, and in a second movable configuration provides an engaged configuration with respect to the filament in which the frictional engagement member frictionally engages the filament to resist movement of the filament through the aperture, and wherein the directional adjustment unit comprises frictional adjustment arrangement configured to adjust the degree of frictional engagement of the frictional engagement member with the filament when in the engaged configuration.

The directional adjustment unit may further comprise the filament.

The frictional adjustment arrangement may be configured to adjust the actual or effective aperture size of the frictional engagement member.

The frictional adjustment arrangement may be configured to adjust a characteristic of the movement of the frictional engagement member with respect to the housing. The characteristic of the movement includes any one or more of:

a) the position of the frictional engagement member when in the first movable configuration;

b) the position of the frictional engagement member when in the second movable configuration;

c) the extent or range or magnitude of movement of the frictional engagement member between the first and second movable configurations.

The frictional adjustment arrangement may be configured to adjust the position of the frictional engagement member in the housing.

The frictional adjustment arrangement may be configured to adjust a minimum or maximum angle of inclination of the frictional engagement member with respect to the housing.

The frictional engagement member may be pivotally mounted in the housing, for movement about a pivot axis, the aperture being spaced from the pivot axis.

The frictional adjustment arrangement may be configured to adjust the position of the pivot axis relative to the housing.

The frictional engagement member may comprise a contact surface or face, distal from the pivot axis, the frictional adjustment arrangement being configured to contact the contact surface or face when the frictional engagement member is in the engaged configuration, the position of at least part of the frictional adjustment arrangement being adjustable relative to the contact surface or face.

The position of at least part of the frictional adjustment arrangement may be adjustable relative to the contact surface or face in a direction perpendicular to the pivot axis. The position of at least part of the frictional adjustment arrangement may be adjustable relative to the contact surface or face in a direction parallel to a longitudinal axis of the filament.

The frictional adjustment arrangement may comprise an engagement formation configured to abut the frictional engagement member when in the engaged configuration to limit movement of the frictional engagement member, the relative position between the abutment member and the frictional engagement member being adjustable.

The engagement formation may be movable relative to the frictional engagement member. The frictional engagement member may be movable relative to the engagement formation.

The housing may comprise at least one side wall and at least one end wall, the engagement formation comprising one of the side or end walls of the housing.

The frictional adjustment arrangement may comprise a movable part of the housing, movement of the movable part of the housing adjusting the minimum or maximum extent of movement of the frictional engagement member relative to the housing.

The movable part may comprise an upper or lower sub-housing, the frictional engagement member being mounted on one of the sub-housings, the other sub-housing being configured to engage the frictional engagement member.

The frictional engagement member may be mounted on, or comprises part of, the lower sub-housing.

The movable part of the housing may be slidably movable relative to the other housing part.

The frictional adjustment arrangement may comprise an actuator configured to enable adjustment of the degree of frictional engagement of the frictional engagement member with the filament.

The actuator may comprise any one or more of:
d) a screw threadably mounted in the housing;
e) a slider, slidably movable along a channel or slot or elongate opening in the housing;
f) a movable button or contact pad;
g) a rotatable dial or wheel;
h) a switch or rocker.

The actuator may be directly connected to the engagement formation. The actuator may be integral with the engagement formation. The actuator may be configured to be a user actuator.

The engagement formation may comprise a cam configured to engage the frictional engagement member, the relative position between the cam and the frictional engagement member being adjustable. The cam may comprise a rotary cam comprising a rotatable contact surface which engages the frictional engagement member. The cam may comprise a linear cam configured for linear movement in or on the housing, and comprising a camming surface which engages the frictional engagement member. The camming surface may comprise any one or more of:
i) a planar portion;
j) a curved portion;
k) a curvi-linear portion.

The cam may be movable toward and away from the frictional engagement member to adjust the frictional force.

A plurality of frictional engagement members may be provided.

The frictional adjustment arrangement may be configured to adjust the degree of frictional engagement of two or more of the frictional engagement members with the filament.

The frictional adjustment arrangement may be configured to adjust the adjust the degree of frictional engagement of all but one of the frictional engagement members with the filament.

According to another aspect of this disclosure there is provided a headgear for a respiratory interface or mask, comprising,
    the directional adjustment unit of any one of the above statements; and a filament.

The headgear may further comprise a yoke configured to connect the headgear to the respiratory interface or mask. The directional adjustment unit may be arranged in the yoke. The yoke may comprise a central portion and at least one section extending from the central portion, wherein the at least one section is configured to connect to the at least one strap of the headgear.

According to another aspect of this disclosure, there is provided a headgear for a respiratory mask or interface, comprising:
    a strap;
    a filament located at least partially within the strap;
    a directional adjustment unit comprising
        at least one movable frictional engagement member, the at least one frictional engagement member having an aperture forming a cavity extending therethrough for receiving the filament therethrough, wherein
        the at least one frictional engagement member in a first configuration provides a disengaged configuration with respect to the filament, and in a second configuration provides an engaged configuration with respect to the filament, the at least one frictional engagement member being movable between engaged and disengaged configurations; and
    wherein the directional adjustment unit comprises frictional adjustment arrangement configured to adjust the degree of frictional engagement of the frictional engagement member with the filament when in the engaged configuration.

According to a further aspect of this disclosure, there is provided a headgear for a respiratory interface, comprising:
    a housing defining an interior space, a first opening and a second opening, wherein each of the first and second openings communicates with the interior space;
    a brake element defined by or supported by the housing;
    at least one rotary element disposed within the housing and comprising a rotational axis;
    a core element that passes through one or both of the first and second openings of the housing and engages the rotary element such that movement of the core element relative to the housing causes rotation of the rotary element;

wherein the rotational axis of the rotary element is movable relative to the housing between a first position, which provides a first level of resistance to rotation of the rotary element, and a second position, which provides a second level of resistance to rotation of the rotary element, wherein the second level of resistance is higher than the first level;

wherein the second level of resistance is caused at least in part by frictional engagement between the rotary element and the brake element;

the directional adjustment unit further comprising a frictional adjustment arrangement configured to adjust the frictional engagement between the rotary element and the brake element when the rotary element is in the second position.

The rotary element may be a pinion. The core element may comprise a rack. The core element may comprise a filament.

According to another aspect of this disclosure, there is provided a directional adjustment unit for a headgear for a respiratory interface, comprising:

a housing defining an interior space, a first opening and a second opening, wherein each of the first and second openings communicates with the interior space;

a rack and pinion mechanism comprising:

a pinion positioned within the interior space and rotatable relative to the housing, the pinion also configured to move between a first displacement position and a second displacement position; and a rack engaged with the pinion and configured to move through the first and second openings of the housing; and a brake mounted in or on or comprising part of the housing, wherein the pinion is rotatable in a first pinion direction when in the first displacement position by moving the rack through the housing in a first rack direction, and wherein the pinion frictionally engages the brake when the pinion is in the second displacement position such that the brake inhibits rotation of the pinion in a second pinion direction which inhibits movement of the rack through the housing in a second rack direction;

the directional adjustment unit further comprising a frictional adjustment arrangement configured to adjust the frictional engagement between the pinion and the brake when the pinion is in the second displacement position.

The frictional adjustment arrangement may be configured to adjust the position of the brake relative to the housing.

The frictional adjustment arrangement may be configured to adjust the position of the pinion relative to the housing.

The frictional adjustment arrangement may be configured to adjust the position of the brake or the pinion relative to the housing by moving the brake or pinion toward or away from the other of the pinion or brake.

An actuator may be configured to control the brake adjuster. The actuator may comprise a user actuator. The actuator may comprise a rotary actuator configured to be rotatable relative to the housing. The rotary actuator may comprise an adjustment dial or wheel. The rotary actuator may comprise a threaded portion and an engaging portion, rotation of the threaded portion adjusting the position of the engaging portion relative to the housing, the engaging portion engaging the brake.

The brake adjuster may comprise a toothed portion on the housing and a toothed portion on the brake, rotation of the rotary actuator rotating one of the toothed portions to move that one toothed portion along the other toothed portion, relative movement between the toothed portions adjusting the relative position between the pinion and the brake.

The toothed portion on the housing may be linear and the toothed portion on the brake is rotary.

The actuator may comprise a linear actuator configured to be linearly movable relative to the housing. The linear actuator may comprise a slider, slidably mounted on the housing.

The actuator may comprise a cam configured to engage the brake or the pinion, movement of the cam adjusting the position of the brake or pinion.

According to a further aspect of this disclosure, there is provided a directional adjustment unit for a headgear for a respiratory interface, comprising a housing defining an interior space, a first opening and a second opening, wherein each of the first and second openings communicates with the interior space; a rack and pinion mechanism comprising:

a pinion positioned within the interior space and rotatable relative to the housing; and a rack engaged with the pinion and configured to move through the first and second openings of the housing;

and a brake mounted in or on the housing, wherein the pinion is rotatable in a first pinion direction such that the rack moves in a first rack direction through the housing, the pinion also being rotatable in a second pinion direction such that the rack moves in an opposite rack direction through the housing; and wherein the directional adjustment unit further comprises a selective engagement unit configured to selectively engage the pinion with the brake and configured such that the pinion engages the brake via the selective engagement unit when rotated in the first pinion direction such that the brake inhibits rotation of the pinion which inhibits movement of the rack in the first rack direction; and wherein the pinion does not engage, or has reduced engagement with, the brake, when rotated in the second pinion direction.

The brake may comprise a rotary brake member, and a frictional brake member configured to frictionally engage the rotary brake member.

The rotary brake member may comprise a brake wheel or drum, the frictional brake member being configured to frictionally engage a surface of the wheel or drum that is coaxial with the axis of rotation of the brake wheel or drum.

The rotary brake member may comprise a brake disc, the frictional brake member being configured to frictionally engage a surface of the wheel or drum that is perpendicular to the axis of rotation of the brake wheel or drum.

The selective engagement unit may comprise a one way mechanism configured to engage the pinion with the rotary member when the pinion is rotated in the first pinion direction, and to disengage, or reduce the engagement of, the pinion from the rotary member to allow relative rotation therebetween, when the pinion is rotated in the second pinion direction.

The selective engagement unit may comprise, for example, a ratchet mechanism, a clutch mechanism, or a slipper clutch mechanism.

The selective engagement unit may comprise an electro mechanical actuator configured to selectively engage the pinion with the brake, in response to a control signal.

According to a further aspect of this disclosure, there is provided a directional adjustment unit for a headgear for a respiratory mask, comprising a housing, at least one frictional engagement member arranged to be movable with respect to the housing, the at least one frictional engagement member having an aperture extending therethrough for receiving a filament of a strap of the headgear therethrough, wherein the at least one frictional engagement member in a first movable configuration provides a disengaged configuration with respect to the filament, and in a second movable configuration provides an engaged configuration with respect to the filament, and wherein the directional adjustment unit comprises an abutment feature configured to abut a stop provided on the filament, to limit the extent of movement of the filament relative to the directional adjustment unit.

A filament support structure may be located between the housing and the headgear and which comprises an elongate support body which extends along, and constrains, at least part of the filament, the elongate support body having a longitudinal axis extending substantially parallel to the user's face, a lateral or transverse axis extending away from the user's face, and a vertical axis extending substantially parallel to the user's face;

wherein at least a portion of the elongate support body has a bending control structure configured to provide the elongate support body with a bending stiffness which is greater in a direction along the lateral or transverse axis than in a direction along the vertical axis.

The bending control structure may comprise an apertured structure comprising a plurality of apertures spaced apart along the elongate support body. The bending control structure may comprise a honeycomb structure. At least one aperture may be of any one of the following shapes:

a) circular;
b) elliptical;
c) triangular;
d) quadrilateral;
e) pentagonal;
f) hexagonal.

The bending control formation of the elongate support body may extend over 50% of the length of the elongate support body, preferably over 75% of the length, and more preferably over 90% of the length.

The elongate support member may be hollow and comprises a laterally inner elongate support wall arranged to contact a user's face, a laterally outer wall, laterally spaced from the elongate support wall, and upper and lower walls connecting the inner and outer walls, the walls between them defining a hollow space in which the elongate filament is received, the bending control formation further comprising the hollow space.

The laterally outer wall may comprise upper and lower laterally outer sub walls spaced apart so as to define a slot therebetween. At least one of the laterally outer, upper and lower walls may comprise at least one cut-out being a portion of the wall where there is no, or reduced, wall material. A plurality of cut-outs may be provided. Each of the laterally outer, upper and lower walls may comprise a cut-out. Each cut-out may be of geometric shape, comprising regular lines and shapes. At least one of the outer, upper and lower walls may comprise cut-outs arranged such that the at least one wall is castellated or toothed and comprises a plurality of castellations or teeth each pair of which is separated by a respective cut-out, the bending control formation further comprising the castellations or teeth.

According to a further aspect of this disclosure, there is provided a headgear for a respiratory interface or mask, comprising, the directional adjustment unit of any one of the above statements; and a filament.

According to a further aspect of this disclosure, there is provided a respiratory mask or interface, comprising the headgear of any one of the above statements.

According to a further aspect of this disclosure, there is provided a respiratory therapy system, comprising the respiratory mask or interface of any one of the above statements.

The respiratory therapy system may comprise any one or more of:

a. a flow generator;
b. a humidifier;
c. a breathing gas delivery conduit;
d. an expiratory circuit.

According to another aspect of this disclosure there is provided a respiratory mask or interface for use with a respiratory therapy system; comprising:

a mask frame;

a cushion configured to be mounted on the frame and configured to seal with the user's face;

the mask frame comprising:

a gases inlet configured to receive breathable gases from a gases supply;

the mask frame further comprising a vent for venting exhaled gases from the mask;

wherein the vent is positioned above and behind the gases inlet when the mask or interface is viewed from the front and one side.

The respiratory mask or interface mat further comprise a mount, above the gases inlet when the mask is viewed from the front in a direction along a central axis of the gases inlet; wherein the mount is configured to mount a yoke assembly of headgear to the mask frame, the yoke assembly being connected to, or being configured to be connected to, side straps of the headgear, the yoke assembly connecting the headgear to the mask frame when the yoke assembly is mounted on the mount.

According to another aspect of this disclosure there is provided a respiratory mask or interface for use with a respiratory therapy system; comprising:

a mask frame;

a cushion mounted on the frame and configured to seal with the user's face;

the mask frame comprising:

a gases inlet configured to receive breathable gases from a gases supply;

the mask frame further comprising:

a vent for venting exhaled gases from the mask;

a mount, above the gases inlet when the mask is viewed from the front in a direction along a central axis of the gases inlet; wherein the mount is configured to mount a yoke assembly of headgear to the mask frame, the yoke assembly being connected to, or being configured to be connected to, side straps of the headgear, the yoke assembly connecting the headgear to the mask frame when the yoke assembly is mounted on the mount;

wherein the vent is positioned above and behind the mount when the mask or interface is viewed from the front and one side.

The mount may comprise a recess into which the yoke assembly is at least partially received.

The recess may be defined by a lower surface which bounds the top of the gases inlet, and at least one upper surface vertically spaced from the gases inlet.

The upper surface may comprise a plurality of upper surfaces laterally spaced apart when the mask is viewed from the front, and provided on a plurality of outwardly protruding portions of the frame.

The frame may comprise at least one yoke retention feature configured to engage the yoke assembly to retain the yoke assembly on the mount.

The yoke retention feature may comprise at least one snap fit connector.

The vent may comprise at least one vent aperture that is inclined upwardly away from the axis of the inlet.

The vent may comprise at least one vent aperture that is inclined laterally outwardly away from the axis of the inlet.

The vent may comprise an array of vent apertures.

The or each vent aperture may be laser drilled.

The vent may be provided on a vent surface of the mask frame, the vent surface being arcuate when viewed from the front of the mask.

The vent may be provided on a vent surface of the mask frame, the vent surface being arcuate when viewed from the top of the mask.

The vent surface may be elongate, with the width of the vent surface being longer than the height of the vent surface, when viewed from the front.

The vent surface may be elliptical, when viewed from the front.

The vent surface may be configured such that exhaled gases are dispersed radially outwardly away from the mask.

The vent surface may be convex when viewed from the front of the mask.

The vent surface may be curved about a plurality of axes so that the vent surface is curved in a plurality of dimensions.

The width of the vent surface may be substantially equal to the width of the gases inlet.

The gases inlet may be provided on a boss which projects outwardly from the front of the mask frame.

The boss may be inclined downwardly, when the mask is viewed from the side.

The gases inlet may be any one of:

elliptical;

circular;

non-circular.

The respiratory mask or interface may comprise a gases inlet conduit connector configured to connect the frame to a gases delivery conduit.

The gases inlet conduit connector may be integral with the boss, and projects outwardly therefrom.

The gases inlet conduit connector may be removably mounted on the boss, and projects outwardly therefrom.

The respiratory mask or interface may comprise at least one user grip portion on the mask frame adjacent the inlet.

The user grip portion may comprise an indented portion.

The respiratory mask or interface may comprise a pair of user grip portions, one each side of the inlet.

The or each user grip portion may be substantially below the central axis of the inlet.

The respiratory mask or interface may comprise the yoke assembly.

The yoke assembly may comprise a central portion and a pair of opposed lateral portions extending laterally outwardly from the central portion, wherein each lateral portion is configured to connect to a respective side strap of the headgear, and the central portion is configured to be mounted on the mount of the mask frame.

At least one of the mount and the yoke assembly may comprise a connector formation configured to engage the other of the mount and the yoke assembly to mount the yoke assembly on the mount.

The connector formation may comprise a snap-fit connector formation.

The width of the yoke assembly, from one lateral margin to the other lateral margin when viewed from the front, is less than 80 mm, preferably less than 75 mm, more preferably less than 70 mm, and in one example is 67 mm.

The thickness of the yoke assembly from front to back as measured in a central portion of the yoke assembly may be less than 8 mm, preferably less than 7 mm, and in one example is 6.7 mm.

The yoke assembly may comprise a front yoke member and a rear yoke member, the yoke members defining a filament guide path through the yoke assembly.

The yoke assembly may comprise a pair of filament guide paths extending through the yoke assembly, each guide path being configured to guide a respective filament.

One guide path may cross over the other guide path, inside the yoke assembly, when the yoke assembly is viewed from the front.

One guide path may cross over the other guide path, inside the yoke assembly, when the yoke assembly is viewed from the top.

One guide path may extend from a first vertical position at one lateral end of the yoke assembly, to a different vertical position at the opposed lateral end of the yoke assembly, the other guide path extending from a first vertical position at the opposed lateral end of the yoke assembly to a different vertical position at the one lateral end of the yoke assembly.

The yoke assembly may comprise a pair of laterally spaced filament inlets, and a pair of laterally spaced filament outlets.

The yoke assembly may comprise a pair of spaced apart lateral ends, a filament inlet and a filament outlet being positioned at each lateral end of the yoke assembly.

The filament inlet may be vertically spaced from the filament outlet.

The filament inlet may be positioned below the filament outlet.

The may be filament inlets may be positioned at the same height, such that the filament inlet at one lateral end of the yoke assembly is at the same height as the filament inlet at the other lateral end of the yoke assembly.

The filament outlets may be positioned at the same height, such that the filament outlet at one lateral end of the yoke assembly is at the same height as the filament outlet at the other lateral end of the yoke assembly.

The guide paths, inlets and outlets may be configured such that the filaments are force balanced across the yoke, meaning that the force required to move one filament through the yoke assembly is substantially equal to the force required to move the other filament through the yoke assembly.

The yoke assembly may be of two piece construction, comprising a front yoke member and a rear yoke member.

The yoke assembly may comprise a snap fit connection to mount the front yoke member to the rear yoke member.

The front yoke member and the rear yoke member may together define the filament guide paths through the yoke assembly. The rear yoke member may comprise an integral part of a mask frame.

The respiratory mask or interface may comprise a pair of filament support structures, each filament support structure being configured to be mounted on a respective lateral end of the yoke assembly, each filament support structure comprising a pair of filament passages, each configured to receive a respective filament.

The cushion may comprise an outlet through which breathable gases are delivered to the patient and having a central axis extending through the centre of the outlet in the direction of gases flow, wherein the outlet aperture is of inversely trapezoidal shape, when viewed along the central axis of the outlet, wherein the outlet comprises an upper portion above the central axis, and a lower portion below the central axis, the upper portion having a maximum width which is greater than the maximum width of the lower portion, when viewed along the central axis of the outlet.

The respiratory mask or interface may comprise a directional adjustment unit for a headgear of the respiratory mask assembly, the directional adjustment unit comprising:

a housing configured to be mounted on the mask frame, at least one frictional engagement member arranged to be movable with respect to the housing, the at least one frictional engagement member having an aperture forming a cavity extending therethrough for receiving a filament of a strap of the headgear therethrough, wherein the at least one frictional engagement member in a first movable configuration provides a disengaged configuration with respect to the filament, and in a second movable configuration provides an engaged configuration with respect to the filament in which the frictional engagement member frictionally engages the filament to resist movement of the filament through the aperture.

The directional adjustment unit may comprise a yoke assembly configured to be mounted on the respiratory mask, and to retain the housing, the yoke assembly comprising a pair of laterally extending opposed arms each of which terminates in a respective lateral end of the yoke assembly.

According to another aspect of this disclosure there is provided a respiratory mask or interface for use with a respiratory therapy system; comprising:

a mask frame;

a cushion mounted on the frame and configured to seal with the user's face;

the mask frame comprising:

a gases inlet configured to receive breathable gases from a gases supply;

wherein the cushion comprises an outlet through which breathable gases are delivered to the patient and having a central axis extending through the centre of the outlet in the direction of gases flow, wherein the outlet aperture comprises an upper portion above the central axis, and a lower portion below the central axis, the upper portion having a maximum width which is greater than the maximum width of the lower portion, when viewed along the central axis of the outlet.

The outlet aperture may be of inversely trapezoidal shape, when viewed along the central axis of the outlet.

The outlet may be elongate, with the width of the outlet when viewed along the central axis of the outlet being longer than the height of the outlet.

The outlet may be elliptical.

The outlet may comprise at least one arcuate portion.

The arcuate portion may bow outwardly away from the central axis of the outlet.

The outlet may comprise a plurality of arcuate portions.

The respiratory mask or interface may comprise a directional adjustment unit for a headgear of the respiratory mask assembly, the directional adjustment unit comprising:

a housing configured to be mounted on the mask frame, at least one frictional engagement member arranged to be movable with respect to the housing, the at least one frictional engagement member having an aperture forming a cavity extending therethrough for receiving a filament of a strap of the headgear therethrough, wherein the at least one frictional engagement member in a first movable configuration provides a disengaged configuration with respect to the filament, and in a second movable configuration provides an engaged configuration with respect to the filament in which the frictional engagement member frictionally engages the filament to resist movement of the filament through the aperture.

The directional adjustment unit may comprise a yoke assembly configured to be mounted on the respiratory mask, and to retain the housing, the yoke assembly comprising a pair of laterally extending opposed arms each of which terminates in a respective lateral end of the yoke assembly.

According to another aspect of this disclosure there is provided a directional adjustment unit for a headgear for a respiratory mask, comprising a housing, at least one frictional engagement member arranged to be movable with respect to the housing, the at least one frictional engagement member having an aperture forming a cavity extending therethrough for receiving a filament of a strap of the headgear therethrough, wherein the at least one frictional engagement member in a first movable configuration provides a disengaged configuration with respect to the filament, and in a second movable configuration provides an engaged configuration with respect to the filament in which the frictional engagement member frictionally engages the filament to resist movement of the filament through the aperture;

the directional adjustment unit further comprising a yoke assembly configured to be mounted on the respiratory mask, and to retain the housing, the yoke assembly comprising a pair of laterally extending opposed arms each of which terminates in a respective lateral end of the yoke assembly, wherein the width of the yoke assembly, extending from one lateral end to the other lateral end when viewed from the front, is in the range of 60 to 85 mm, preferably 60 to 80 mm, more preferably 65 to 70 mm.

The width of the yoke assembly may be less than 80 mm.

The thickness of the yoke assembly from front to back as measured in a central portion of the yoke assembly may be in the range of 5 to 7 mm, preferably 6 to 6.8 mm.

The thickness of the yoke assembly may be less than 7 mm.

At least a portion of the at least one frictional engagement member may be within the width of the yoke assembly.

The depth of the yoke assembly, when viewed from above, from the frontmost exterior surface to the rearmost exterior surface of the yoke assembly may be between 25 and 35 mm.

The depth of the yoke assembly, when viewed from above, from the frontmost exterior surface to the rearmost exterior surface of the yoke assembly may be less than 30 mm.

The ratio of the width of the yoke assembly to the depth of the yoke assembly, when viewed from above, from the frontmost exterior surface to the rearmost exterior surface of the yoke assembly may be less than 2.5:1, preferably less than 2:1, and more preferably less than 1.8:1.

The housing of any of the above directional adjustment units may be formed by the yoke assembly. The yoke assembly of any of the above embodiments may be formed as part of a mask frame.

The yoke assembly may comprise a front yoke member and a rear yoke member, the yoke members defining a filament guide path through the yoke assembly.

The yoke assembly may comprise a pair of filament guide paths extending through the yoke assembly, each guide path being configured to guide a respective filament.

One guide path may cross over the other guide path, inside the yoke assembly, when the yoke assembly is viewed from the front.

One guide path may cross over the other guide path, inside the yoke assembly, when the yoke assembly is viewed from the top.

One guide path may extend from a first vertical position at one lateral end of the yoke assembly, to a lower vertical position at the opposed lateral end of the yoke assembly, the other guide path extending from a first vertical position at the opposed lateral end of the yoke assembly to a lower vertical position at the one lateral end of the yoke assembly.

The yoke assembly may comprise a pair of laterally spaced filament inlets, and a pair of laterally spaced filament outlets.

The yoke assembly may comprise a pair of spaced apart lateral ends, a filament inlet and a filament outlet being positioned at each lateral end of the yoke assembly.

The filament inlet may be vertically spaced from the filament outlet.

The filament inlet may be positioned below the filament outlet.

The filament inlets may be positioned at the same height, such that the filament inlet at one lateral end of the yoke assembly is at the same height as the filament inlet at the other lateral end of the yoke assembly.

The filament outlets may be positioned at the same height, such that the filament outlet at one lateral end of the yoke assembly is at the same height as the filament outlet at the other lateral end of the yoke assembly.

The guide paths, inlets and outlets may be configured such that the filaments are force balanced across the yoke, meaning that the force required to move one filament through the yoke assembly is substantially equal to the force required to move the other filament through the yoke assembly.

The yoke assembly may be of two piece construction, comprising a front yoke member and a rear yoke member.

The yoke assembly may comprise a snap fit connection to mount the front yoke member to the rear yoke member.

The front yoke member and the rear yoke member may together define the filament guide paths through the yoke assembly.

The directional adjustment unit may comprise a pair of filament support structures, each filament support structure being configured to be mounted on a respective lateral end of the yoke assembly, each filament support structure comprising a pair of filament passages, each configured to receive a respective filament.

The yoke assembly may comprise a pair of spaced apart lateral ends, a filament inlet and a filament outlet being positioned at each lateral end of the yoke assembly.

The directional adjustment unit may comprise a pair of filament support member, each filament support member being configured to be mounted on a respective lateral end of the yoke assembly, each filament support member comprising a pair of filament passages, each configured to receive a respective filament.

The yoke assembly may comprise a pair of laterally extending opposed arms each of which terminates in a respective lateral end of the yoke assembly, wherein the width of the yoke assembly, extending from one lateral end to the other lateral end when viewed from the front, is in the range of 60 to 85 mm, preferably 60 to 80 mm, more preferably 65 to 70 mm, and in some cases less than 80 mm.

According to another aspect of this disclosure there is provided a yoke assembly for use with a directional adjustment unit for a headgear for a respiratory mask, the directional adjustment unit being configured to allow adjustment of a filament of the headgear;

the yoke assembly being configured to be mounted on the respiratory mask, and to retain a housing of the directional adjustment unit, the yoke assembly comprising a pair of laterally extending opposed arms each of which terminates in a respective lateral end of the yoke assembly, wherein the width of the yoke assembly, extending from one lateral end to the other lateral end when viewed from the front, is less than 80 mm.

The yoke assembly may further comprise the directional adjustment unit, the directional adjustment unit comprising a housing, at least one frictional engagement member arranged to be movable with respect to the housing, the at least one frictional engagement member having an aperture forming a cavity extending therethrough for receiving a filament of a strap of the headgear therethrough, wherein the at least one frictional engagement member in a first movable configuration provides a disengaged configuration with respect to the filament, and in a second movable configuration provides an engaged configuration with respect to the filament in which the frictional engagement member frictionally engages the filament to resist movement of the filament through the aperture.

According to another aspect of this disclosure there is provided a directional adjustment unit for a headgear for a respiratory mask, comprising at least one movable frictional engagement member, the at least one frictional engagement member having an aperture forming a cavity extending therethrough for receiving a filament of a strap of the headgear therethrough, wherein the at least one frictional engagement member in a first movable configuration provides a disengaged configuration with respect to the filament, and in a second movable configuration provides an engaged configuration with respect to the filament in which the frictional engagement member frictionally engages the filament to resist movement of the filament through the aperture;

the directional adjustment unit further comprising a yoke assembly configured to be mounted on the respiratory mask, and to engage the housing; wherein the yoke assembly defining a filament guide path through the yoke assembly and configured to receive the filament, the filament having a filament operative length being the length by which the filament can be moved through the at least one frictional engagement member, the filament operative length being greater than the length of the filament guide path.

The yoke assembly may comprise a front yoke member and a rear yoke member, the yoke members defining the filament guide path through the yoke assembly.

The yoke assembly may comprise a pair of filament guide paths extending through the yoke assembly, each guide path being configured to guide a respective filament.

One guide path may cross over the other guide path, inside the yoke assembly, when the yoke assembly is viewed from the front.

One guide path may cross over the other guide path, inside the yoke assembly, when the yoke assembly is viewed from the top.

One guide path may extend from a first vertical position at one lateral end of the yoke assembly, to a lower vertical position at the opposed lateral end of the yoke assembly, the other guide path extending from a first vertical position at the opposed lateral end of the yoke assembly to a lower vertical position at the one lateral end of the yoke assembly.

The yoke assembly may comprise a pair of laterally spaced filament inlets, and a pair of laterally spaced filament outlets.

The yoke assembly may comprise a pair of spaced apart lateral ends, a filament inlet and a filament outlet being positioned at each lateral end of the yoke assembly.

At least a portion of the at least one frictional engagement member may be within the width of the yoke assembly.

The depth of the yoke assembly, when viewed from above, from the frontmost exterior surface to the rearmost exterior surface of the yoke assembly may be between 25 and 35 mm.

The depth of the yoke assembly, when viewed from above, from the frontmost exterior surface to the rearmost exterior surface of the yoke assembly may be less than 30 mm.

The ratio of the width of the yoke assembly to the depth of the yoke assembly, when viewed from above, from the frontmost exterior surface to the rearmost exterior surface of the yoke assembly may be less than 2.5:1.

The ratio of the width of the yoke assembly to the depth of the yoke assembly, when viewed from above, from the frontmost exterior surface to the rearmost exterior surface of the yoke assembly may be less than 2:1.

The ratio of the width of the yoke assembly to the depth of the yoke assembly, when viewed from above, from the frontmost exterior surface to the rearmost exterior surface of the yoke assembly may be less than 1.8:1.

The filament inlet may be vertically spaced from the filament outlet.

The filament inlet may be positioned below the filament outlet.

The filament inlets may be positioned at the same height, such that the filament inlet at one lateral end of the yoke assembly is at the same height as the filament inlet at the other lateral end of the yoke assembly.

The filament outlets may be positioned at the same height, such that the filament outlet at one lateral end of the yoke assembly is at the same height as the filament outlet at the other lateral end of the yoke assembly.

The guide paths, inlets and outlets may be configured such that the filaments are force balanced across the yoke, meaning that the force required to move one filament through the yoke assembly is substantially equal to the force required to move the other filament through the yoke assembly.

The yoke assembly may be of two piece construction, comprising a front yoke member and a rear yoke member.

The yoke assembly may comprise a snap fit connection to mount the front yoke member to the rear yoke member.

The front yoke member and the rear yoke member may together define the filament guide paths through the yoke assembly.

The directional adjustment unit may comprise a pair of filament support structures, each filament support structure being configured to be mounted on a respective lateral end of the yoke assembly, each filament support structure comprising a pair of filament passages, each configured to receive a respective filament.

The yoke assembly may comprise a pair of laterally extending opposed arms each of which terminates in a respective lateral end of the yoke assembly, wherein the width of the yoke assembly, extending from one lateral end to the other lateral end when viewed from the front, is less than 75 mm.

The width of the yoke assembly may be in the range of 60 to 85 mm, preferably 60 to 80 mm, more preferably 65 to 70 mm, and in some cases less than 80 mm The thickness of the yoke assembly from front to back as measured in a central portion of the yoke assembly may be less than 7 mm.

The directional adjustment unit may comprise at least one filament.

The directional adjustment unit may comprise a pair of filaments.

According to another aspect of this disclosure there is provided a yoke assembly for use with a directional adjustment unit for a headgear for a respiratory mask, the directional adjustment unit being configured to allow adjustment of a filament of the headgear;

the yoke assembly being configured to be mounted on the respiratory mask, and to retain a housing of the directional adjustment unit, the yoke assembly defining a filament guide path through the yoke assembly and configured to receive the filament, the filament having an operative length being the length by which the filament can be moved through the housing, the filament operative length being greater than the length of the filament guide path.

The yoke assembly may comprise the directional adjustment unit, the directional adjustment unit comprising:

a housing, at least one frictional engagement member arranged to be movable with respect to the housing, the at least one frictional engagement member having an aperture forming a cavity extending therethrough for receiving a filament of a strap of the headgear therethrough, wherein the at least one frictional engagement member in a first movable configuration provides a disengaged configuration with respect to the filament, and in a second movable configuration provides an engaged configuration with respect to the filament in which the frictional engagement member frictionally engages the filament to resist movement of the filament through the aperture.

The housing may be formed at least partially by the yoke assembly.

The yoke assembly may be formed as part of a mask frame. The yoke assembly may comprise front and rear yoke members, where the yoke member comprises the, or part of the, mask frame.

According to another aspect of this invention there is provided a headgear for a respiratory mask or interface, comprising, the directional adjustment unit of any one of the above statements; and the filament of any one of the above statements.

According to another aspect of this invention there is provided a headgear for a respiratory mask or interface, comprising, the directional adjustment unit of any one of the above statements; and a filament.

The headgear may comprise a yoke assembly configured to connect the headgear to the respiratory mask or interface.

The directional adjustment unit may be retained at least partially in the yoke assembly.

The yoke assembly may comprise a central portion and at least one lateral portion extending laterally outwardly from the central portion, wherein the at least one lateral portion is configured to connect to the at least one strap of the headgear.

According to another aspect of this invention there is provided a headgear for a respiratory mask or interface, comprising the filament of any one of the above statements.

According to another aspect of this invention there is provided a respiratory mask or interface, comprising the headgear of any one of the above statements.

According to another aspect of this invention there is provided a respiratory therapy system, comprising the respiratory mask or interface of any one of the above statements.

According to another aspect of this invention there is provided a respiratory therapy system, comprising the yoke assembly of any one of the above statements.

According to another aspect of this invention there is provided a respiratory therapy system according to any one of the above statements, and also comprising any one or more of:

a flow generator;

a humidifier;

a breathing gas delivery conduit;

an expiratory circuit.

Further aspects of the disclosure, which should be considered in all its novel aspects, will become apparent from the following description.

BRIEF DESCRIPTION OF THE DRAWINGS

Throughout the drawings, reference numbers can be reused to indicate general correspondence between reference elements. A number of embodiments of the disclosure will now be described by way of example with reference to the drawings in which:

FIGS. 4b and 4c are cutaway views of the yoke assembly of FIG. 4a;

FIGS. 5a to 5b respectively show a cross sectional front view illustrating the associated contact surfaces between a filament and a sidewall of the frictional engagement member aperture;

FIG. 6 is a cross sectional view showing a directional adjustment unit having a rectangular aperture according to an embodiment assembled in a yoke assembly;

FIGS. 7a to 7d respectively show different views of a housing sleeve allowing a housing of a directional adjustment unit according to an embodiment to be mounted securely within the yoke assembly;

FIG. 12b is a cross sectional perspective view of the directional adjustment unit of FIG. 11a;

FIG. 13 is a side view of a frictional engagement member of a directional adjustment unit according to an embodiment, where the frictional engagement member comprises two sections arranged at an angle in relation to each other;

FIG. 14 is a cross sectional side view of a frictional engagement member of a directional adjustment unit according to an embodiment, where the frictional engagement member comprises a single section;

FIG. 16c shows a front view of a single section frictional engagement member identifying a number of adjustable dimensions;

FIG. 16d shows a front view of a single section frictional engagement member having a first set of dimensions of an embodiment;

FIG. 16e shows a front view of a single section having a second set of dimensions of an embodiment;

FIG. 17b is a cutaway top view of the directional adjustment unit of FIG. 17a;

FIG. 18g shows a perspective cross sectional view of the double section frictional engagement member of FIGS. 18a to 18f;

FIG. 18h shows a perspective view of the double section frictional engagement member of FIGS. 18a to 18g;

FIG. 18i shows a perspective contour front view of the double section frictional engagement member of FIGS. 18a to 18h;

FIG. 18j shows a perspective contour rear view of the double section frictional engagement member of FIGS. 18a to 18i;

FIG. 19a shows a perspective view of a filament according to an embodiment;

FIG. 19b shows a side view of the filament of FIG. 19a;

FIG. 19c shows a top view of a filament according to an embodiment;

FIG. 33 is an enlarged view of FIG. 32;

FIG. 34 is an enlarged side view of a stop of a directional adjustment unit in accordance with an embodiment;

FIG. 35 is a perspective view of a filament having a modified stop;

FIG. 58*a* shows a force profile of a directional adjustment unit without a frictional adjustment mechanism;

FIG. 58*b* shows a number of force profiles of a directional adjustment unit having a frictional adjustment arrangement in accordance with the present disclosure;

FIGS. 65*a* to 65*e* show a seventh embodiment of a frictional adjustment arrangement in accordance with the present disclosure;

FIGS. 66*a*) and *b*) show alternative adjustment mechanisms for the frictional adjustment arrangement of FIG. 65;

FIG. 67 is a plan view of the frictional adjustment arrangement of FIG. 65;

FIGS. 68*a*) to *d*) show an eighth embodiment of a frictional adjustment arrangement in accordance with the present disclosure.

FIG. 91 is an enlarged cross-sectional side view of the frame assembly of FIG. 75;

FIG. 92 is an enlarged bottom view of the frame assembly of FIG. 75;

FIG. 93 is an enlarged top view of the frame assembly of FIG. 75;

FIG. 94 is an enlarged perspective view from the rear of the frame assembly of FIG. 75;

FIG. 95 is an enlarged front view of another embodiment of the frame assembly of FIG. 75;

FIG. 96 is an enlarged perspective view from the front of the frame assembly of FIG. 95;

FIG. 97 is an enlarged side view of the frame assembly of FIG. 95;

FIG. 98 is an exploded perspective from the front of the seal assembly of FIG. 75;

FIG. 99 is a cross sectional side view of the seal assembly of FIG. 98, taken through the sagittal (mid) plane;

FIG. 100 is a cross sectional side view of the seal assembly of FIG. 98, taken through the parasagittal (offset from the midline) plane;

FIG. 101 is perspective rear view of the seal assembly of FIG. 98, with a section of the seal assembly removed;

FIG. 102 is a comparison view from the front of a) the yoke assembly of the mask assembly of FIG. 2 and b) the yoke assembly of FIG. 75;

Figures 2A, 2B:
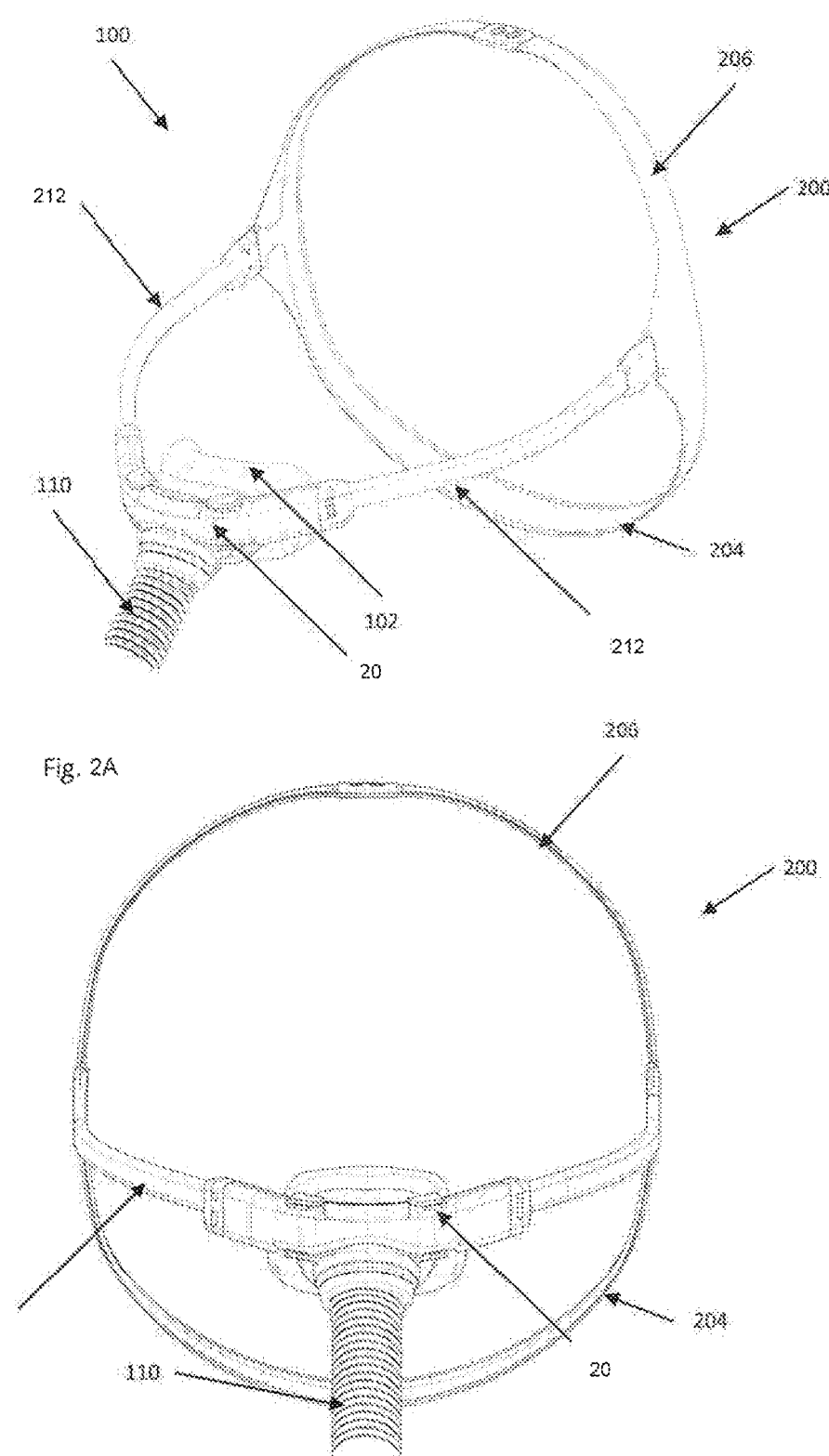
FIG. 2a-2d are perspective, front, side and rear perspective views of a mask assembly, including a headgear, a seal assembly, and a frame assembly according to an embodiment.
Figures 2C, 2D:
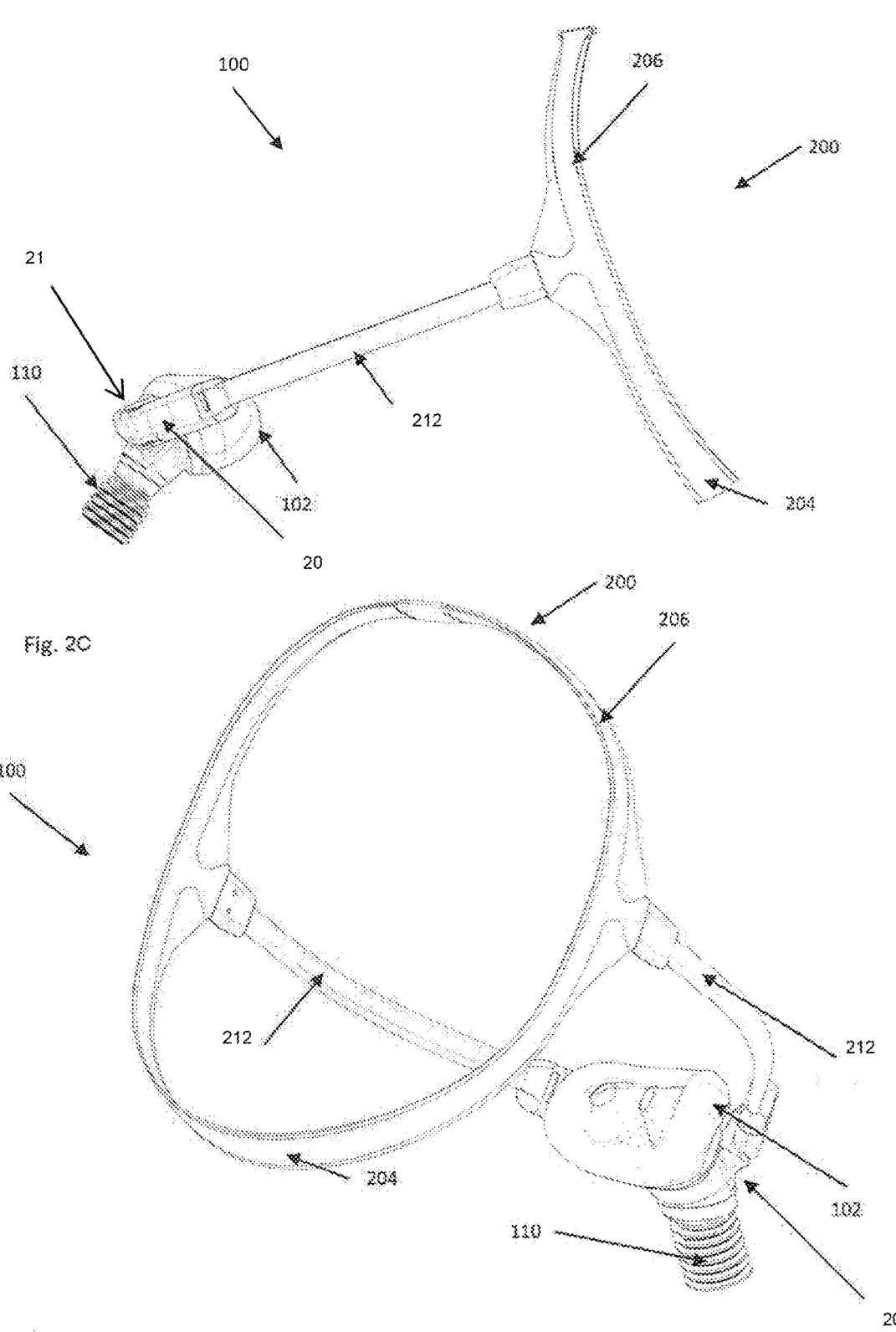
Figure 75:
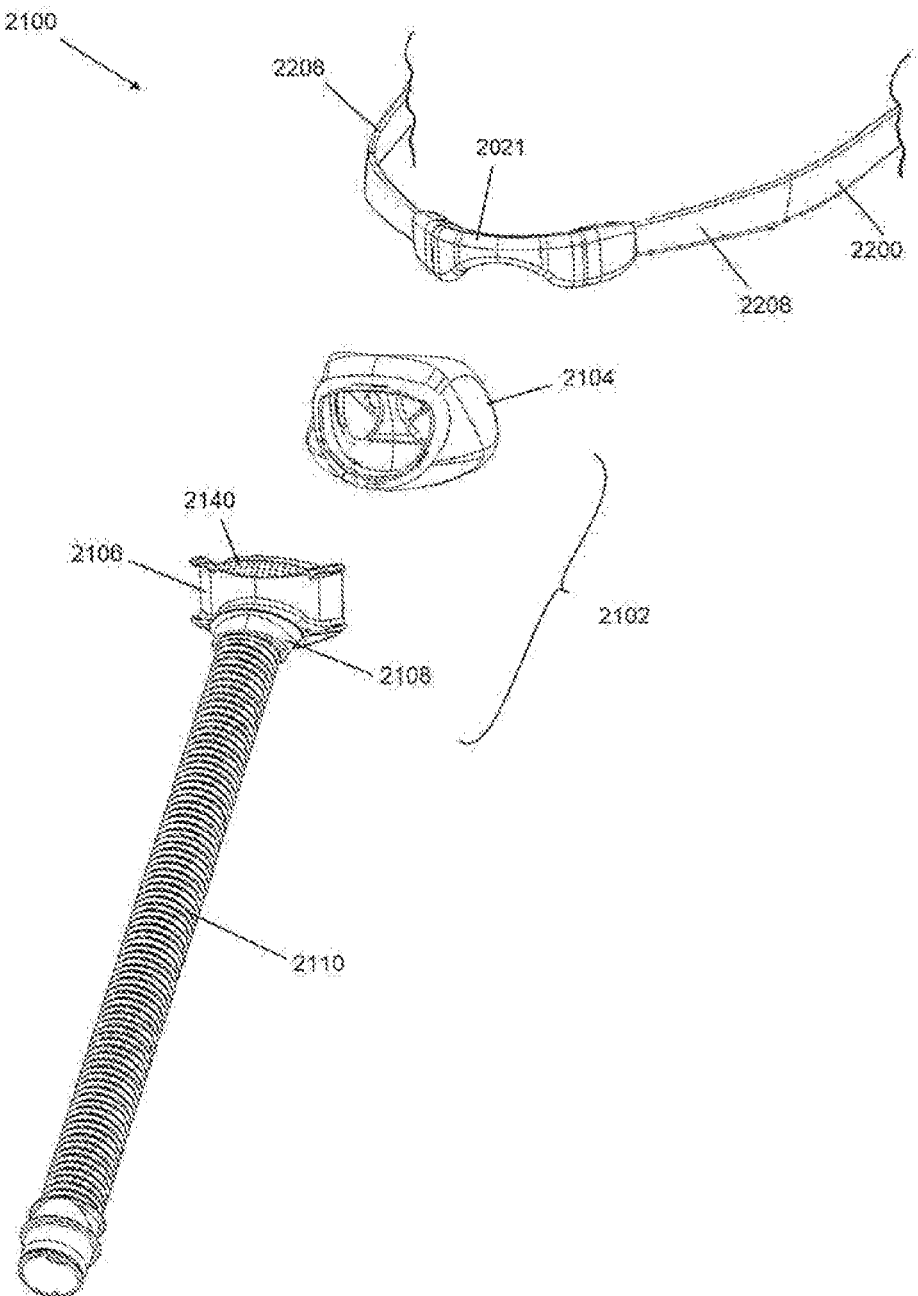
FIG. 75 is an exploded perspective view of a mask assembly, including the front portion of a headgear, a seal assembly, and a frame assembly according to an embodiment.
Figures 76, 77:
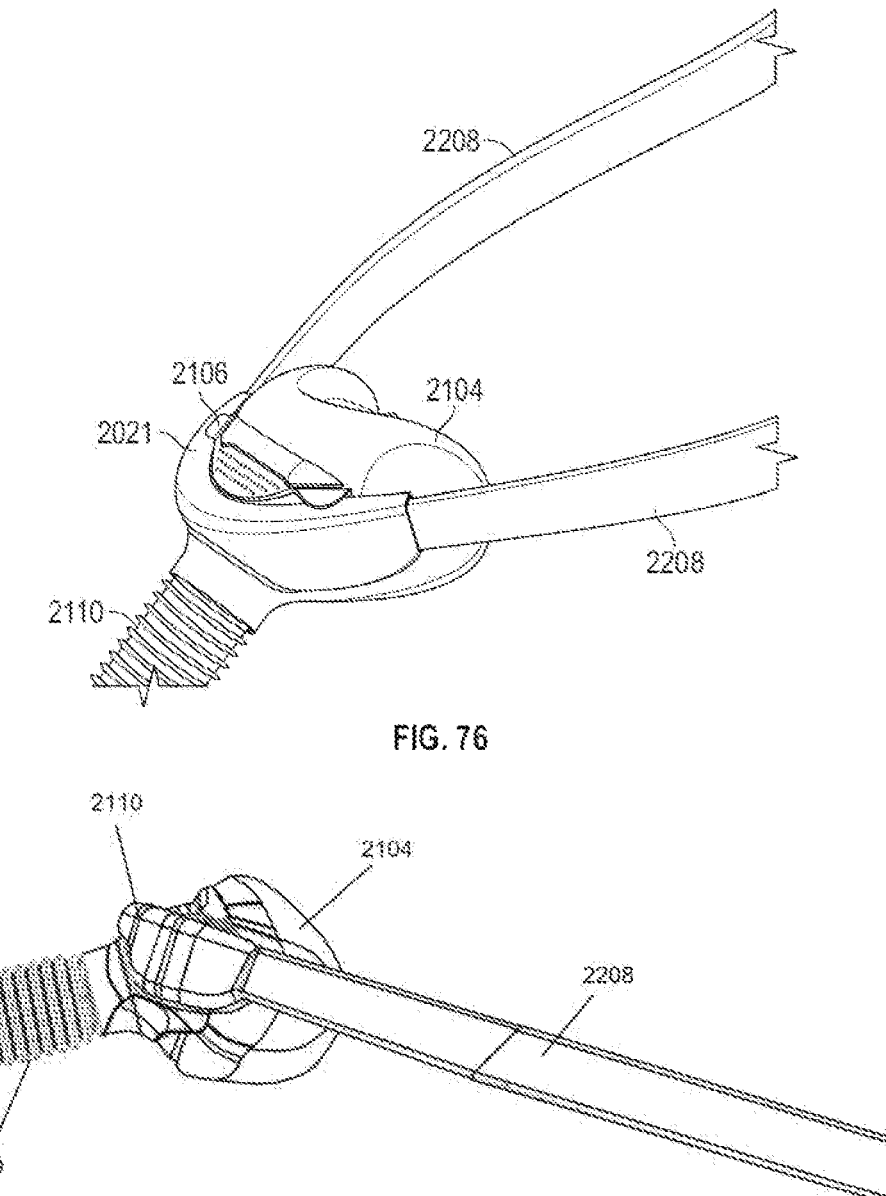
FIG. 76 is a perspective view of the mask assembly of FIG. 75.
FIG. 77 is a side view of the mask assembly of FIG. 75
Figure 78:
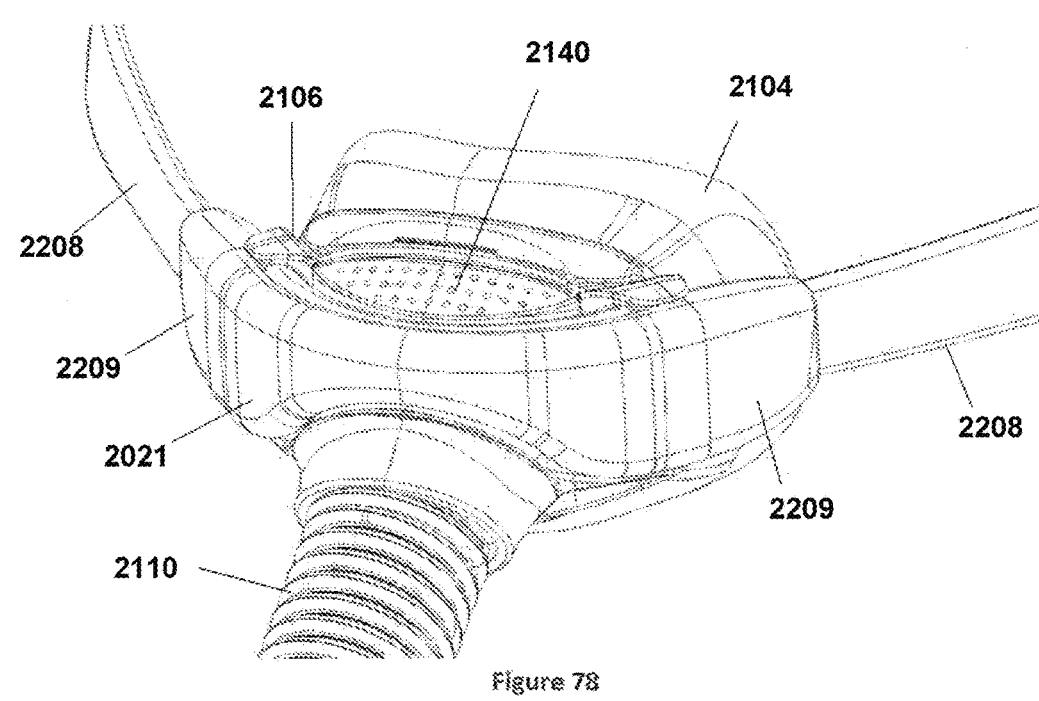
FIG. 78 is an enlarged perspective view of the seal assembly and front part of the headgear of the mask assembly of FIG. 75.
Figure 79:
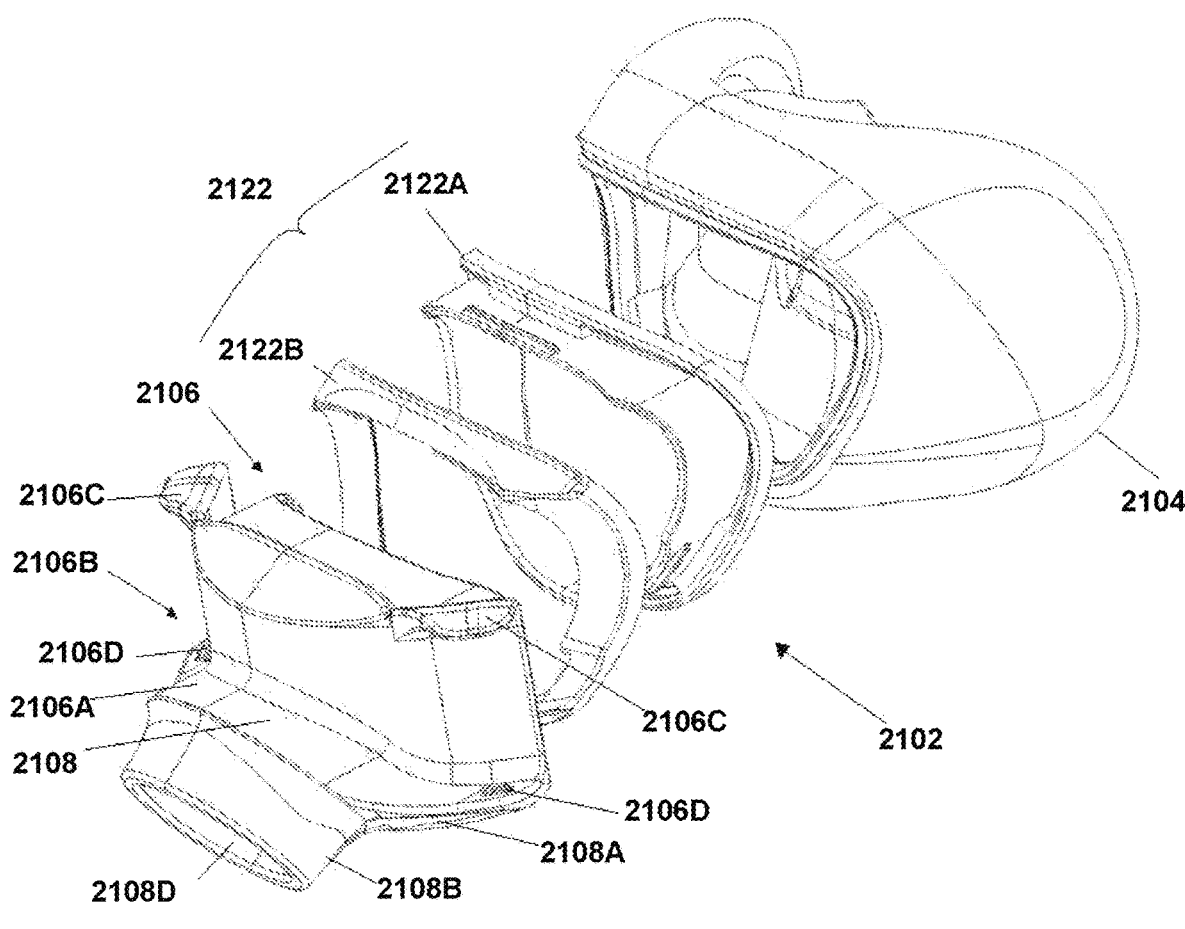
FIG. 79 is an exploded perspective view of the seal assembly of the mask assembly of FIG. 75.
Figure 80:
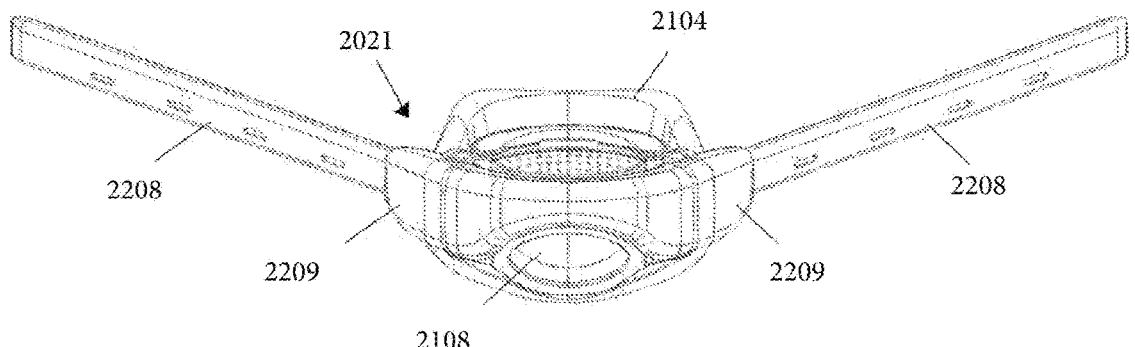
FIG. 80 is a front view of the seal assembly of FIG. 75, with a filament support structure.
Figure 81:
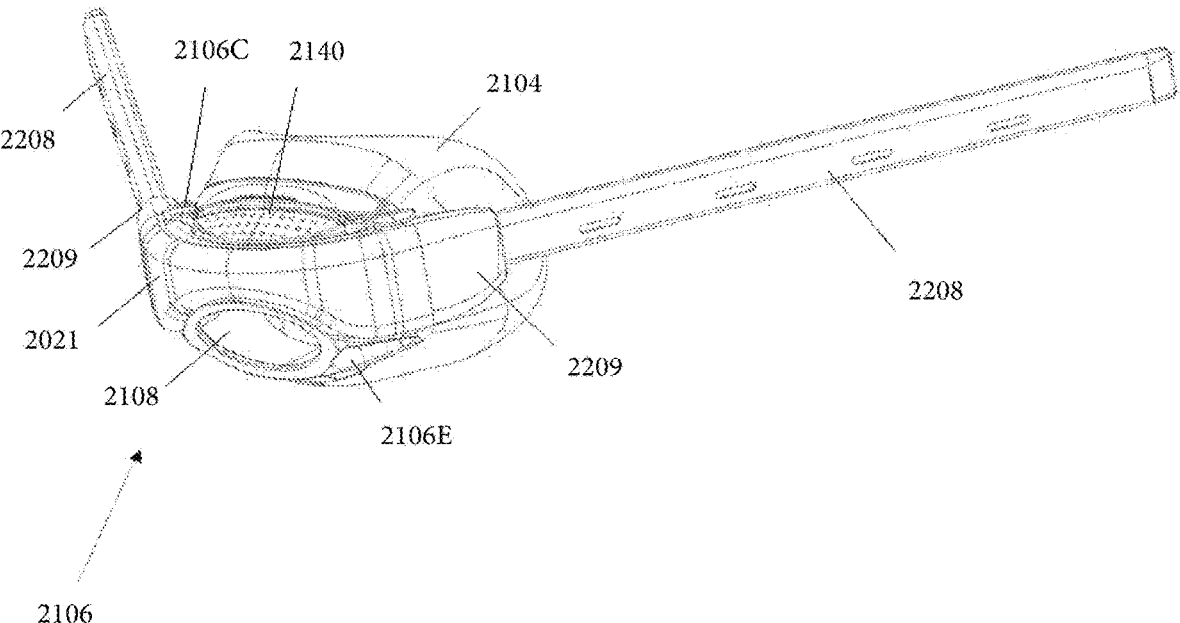
FIG. 81 is a perspective view of the seal assembly and filament support structure of FIG. 80.
Figure 103:
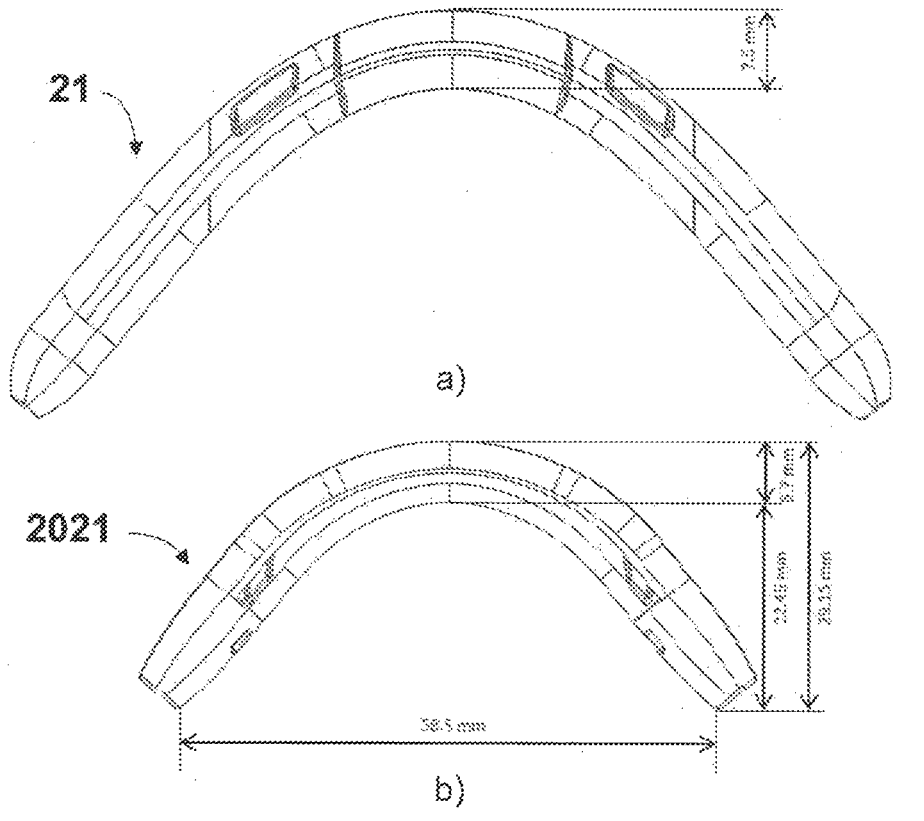
Figure 106:
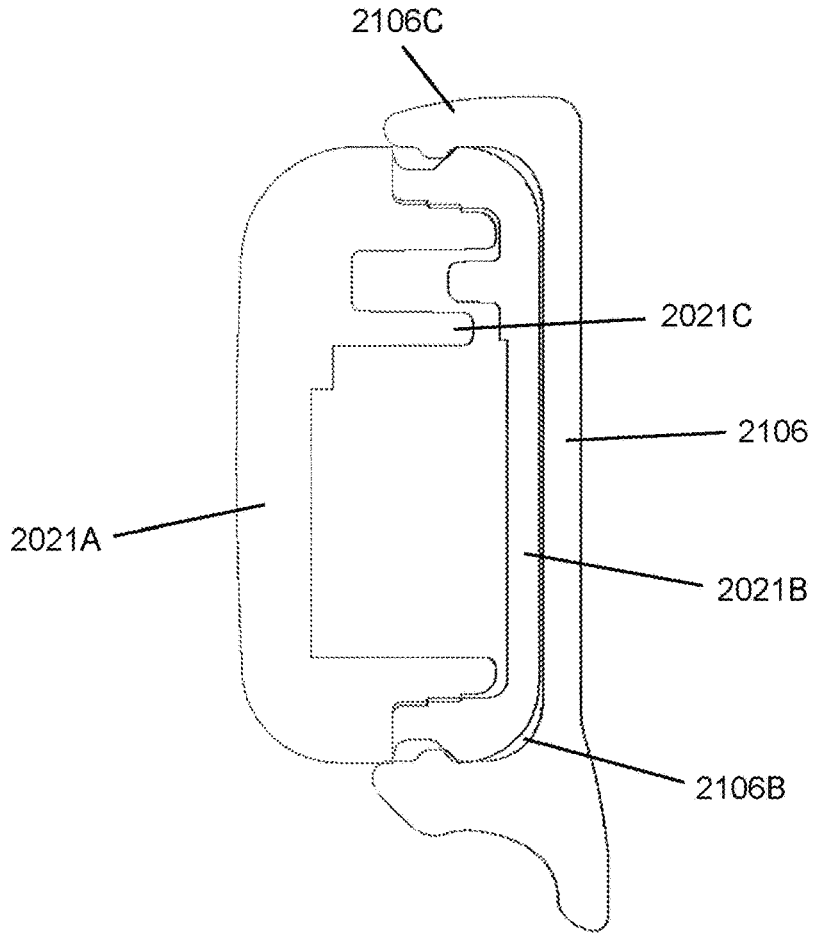
Figure 107:
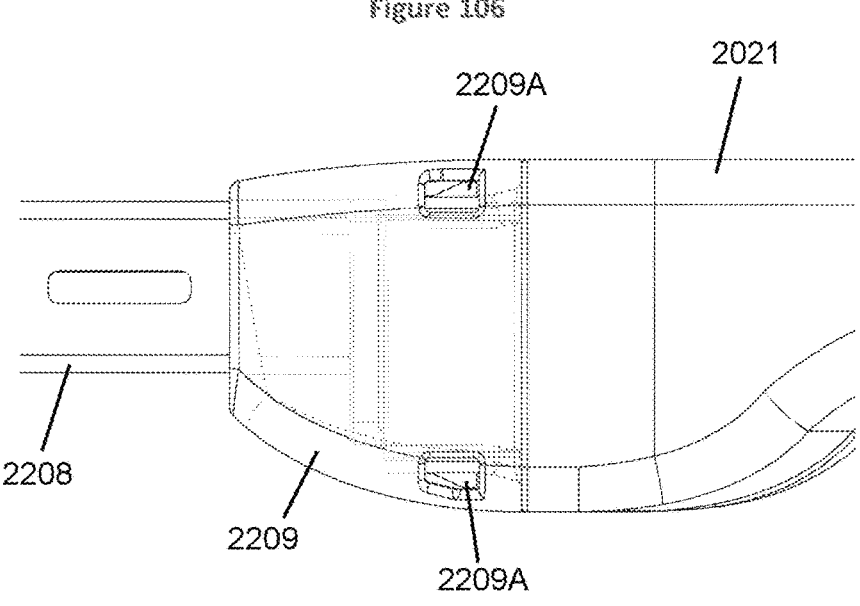
Figure 108:
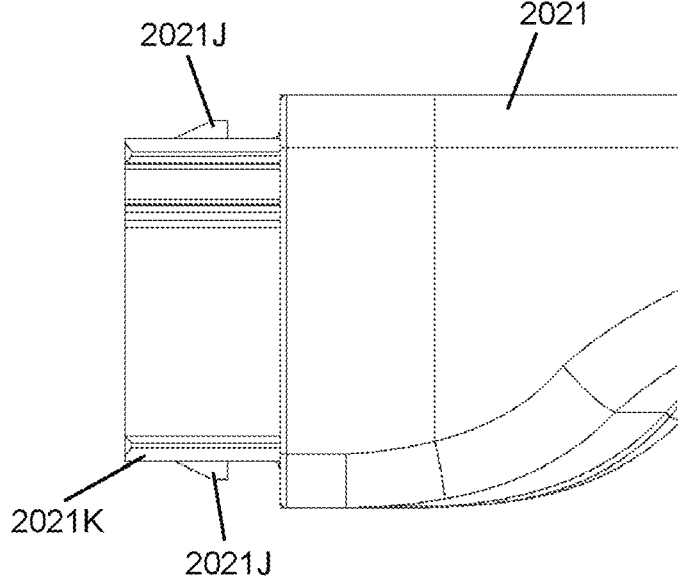
Figure 109:
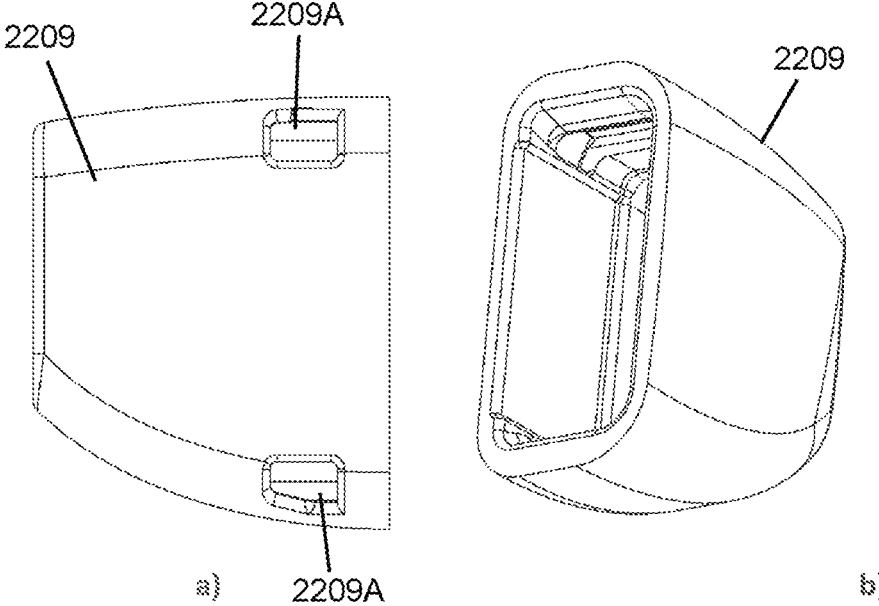
Figure 110:
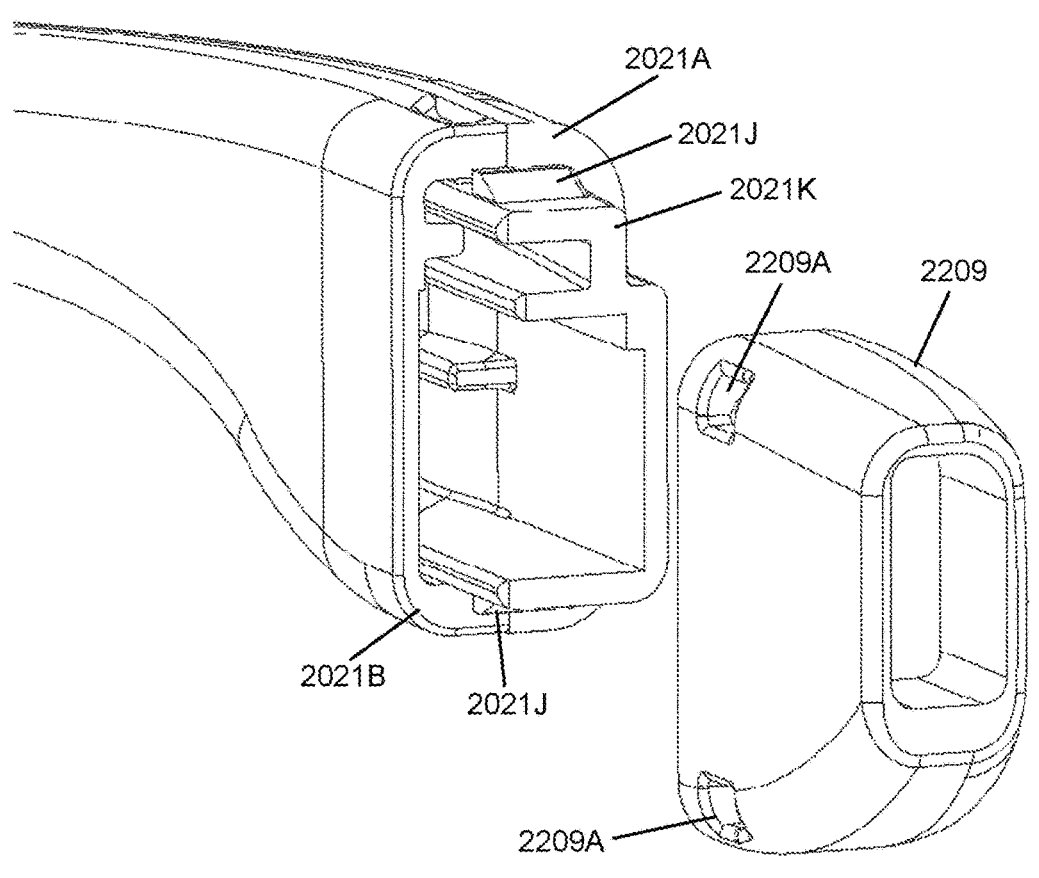
Figure 111:
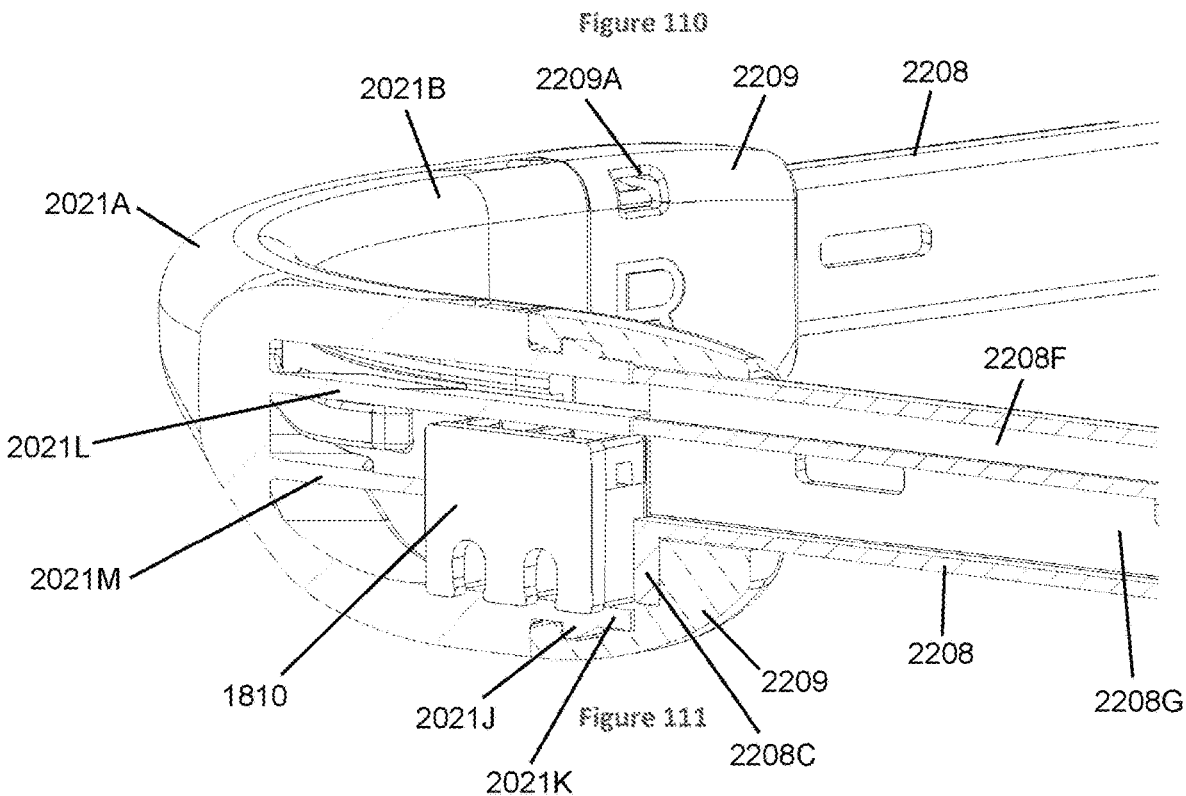
Figure 112:
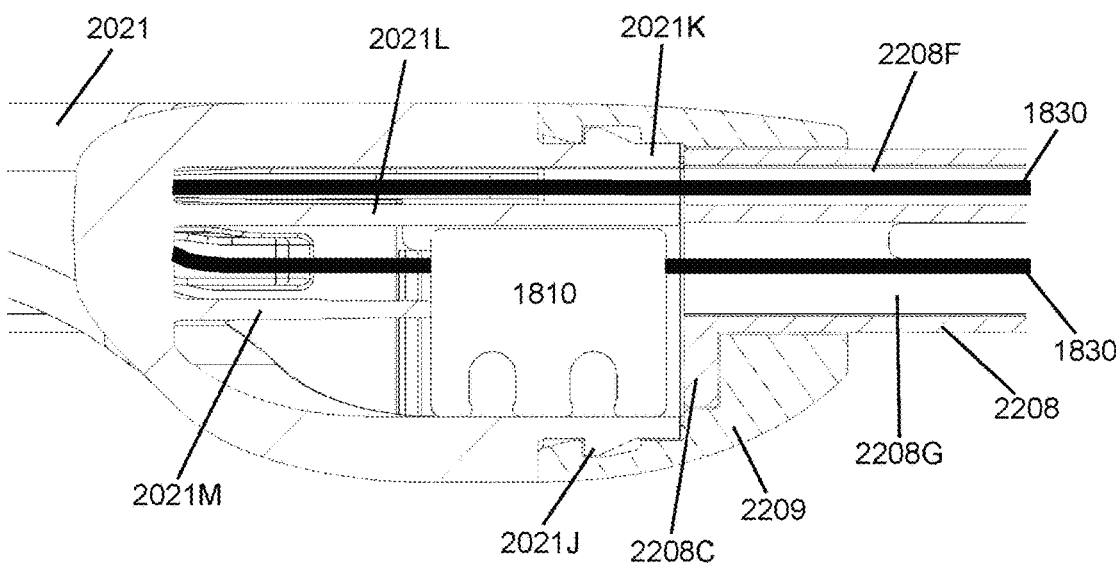
Figure 113:
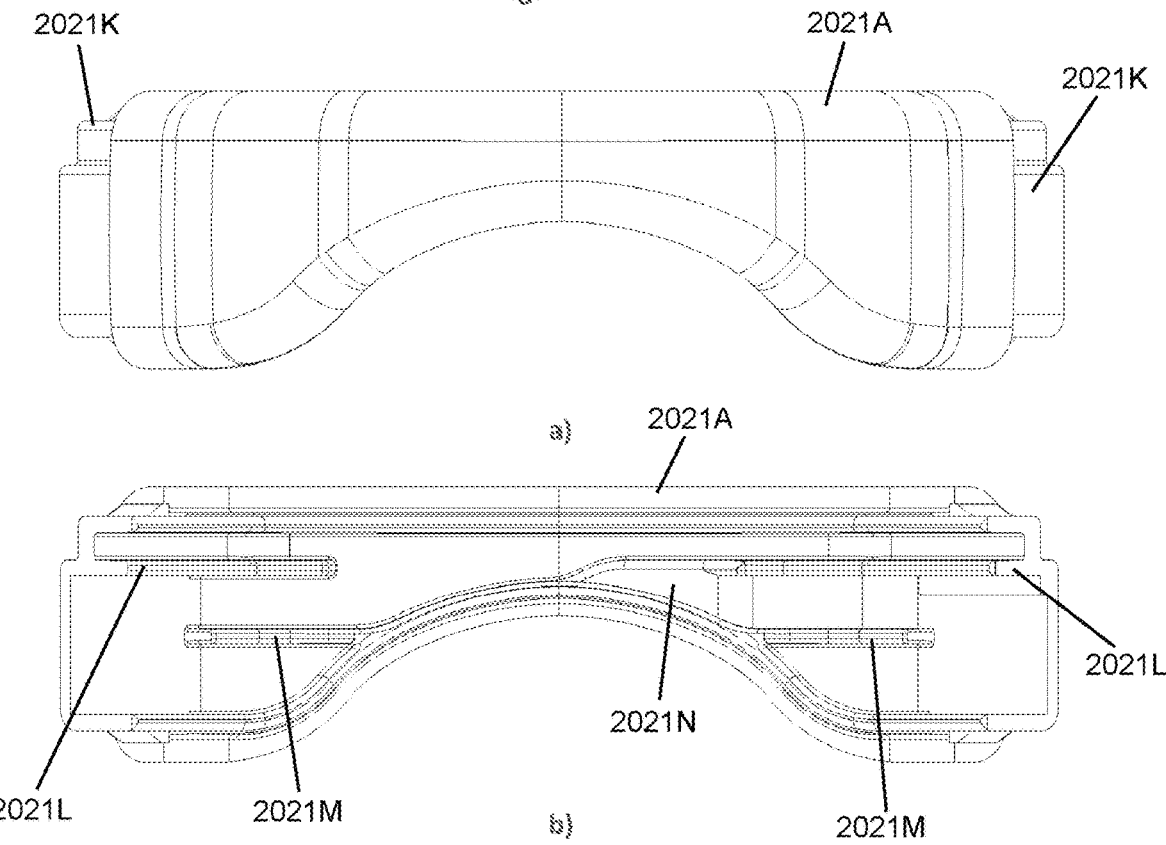
Figure 115:
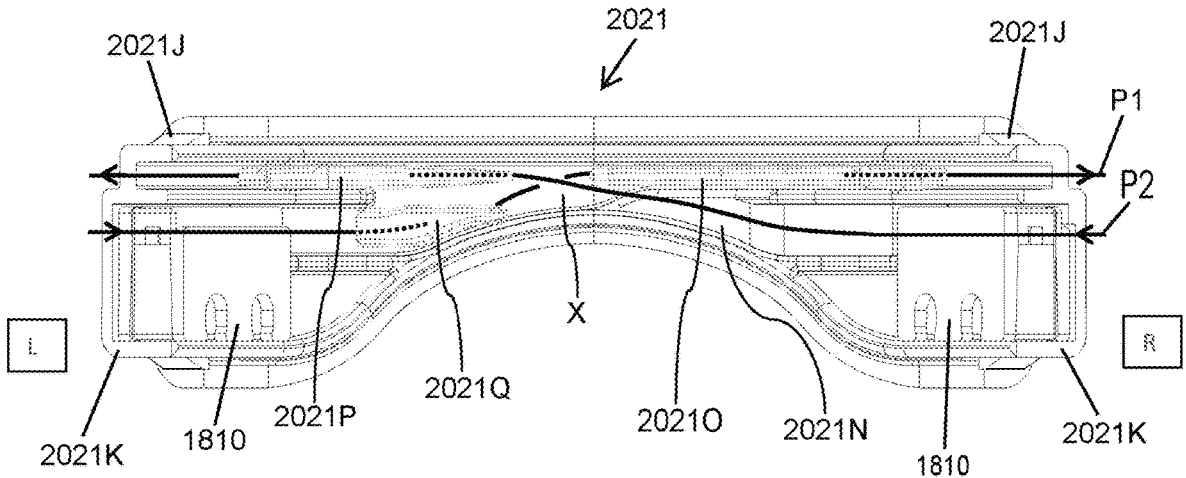
Figure 116:
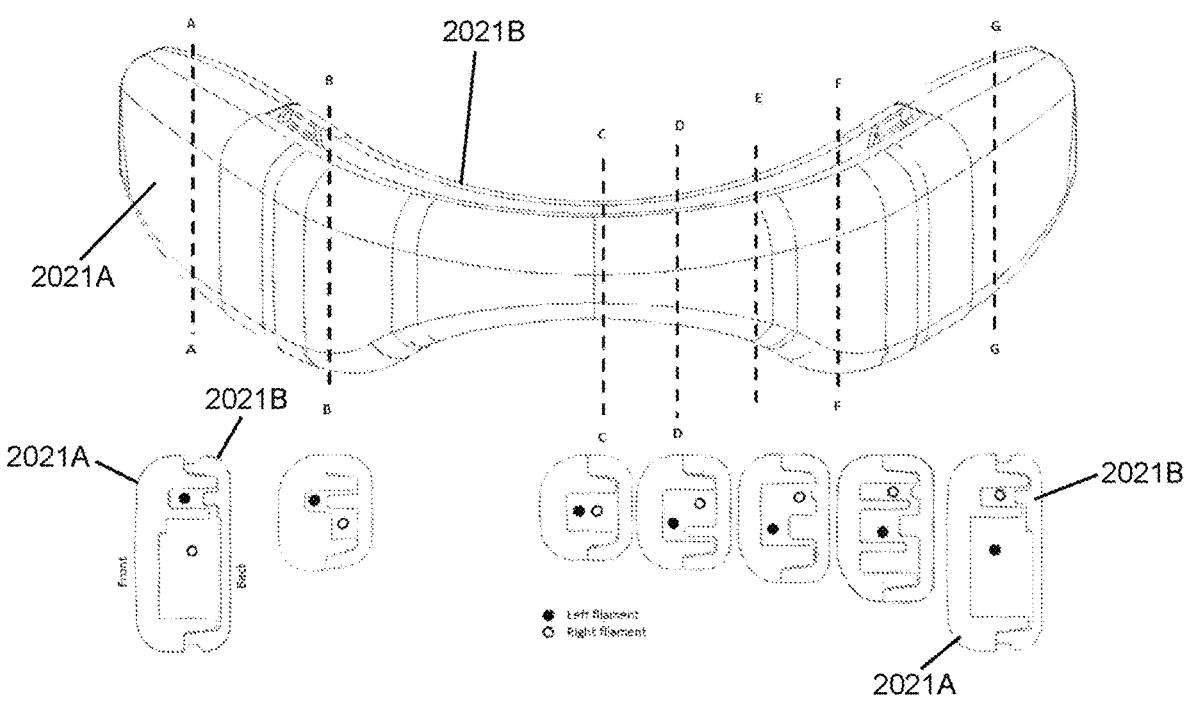
Figure 117:
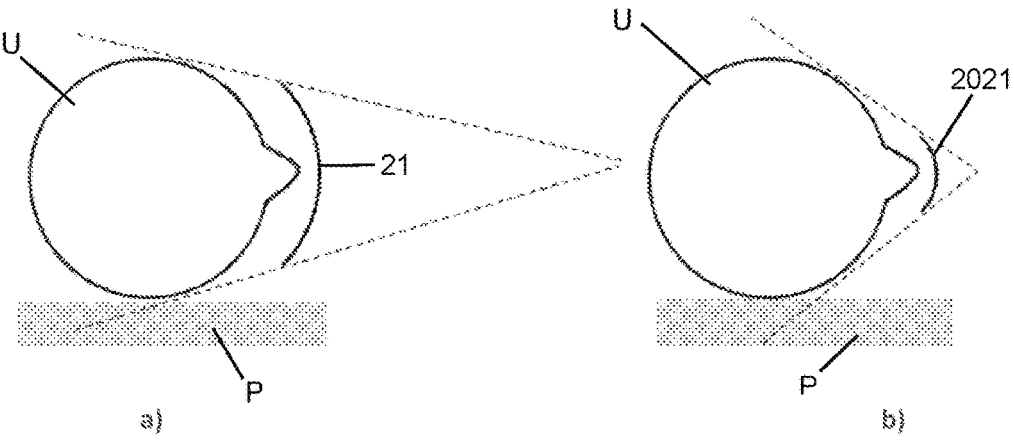
Figure 118:
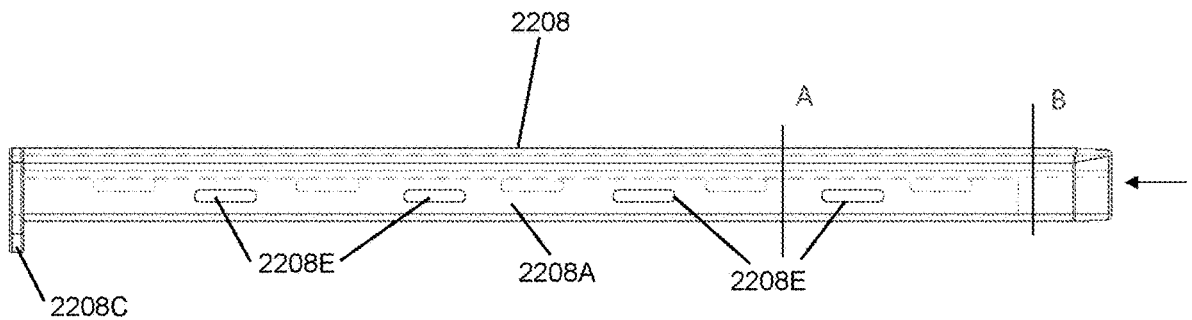
Figure 119:
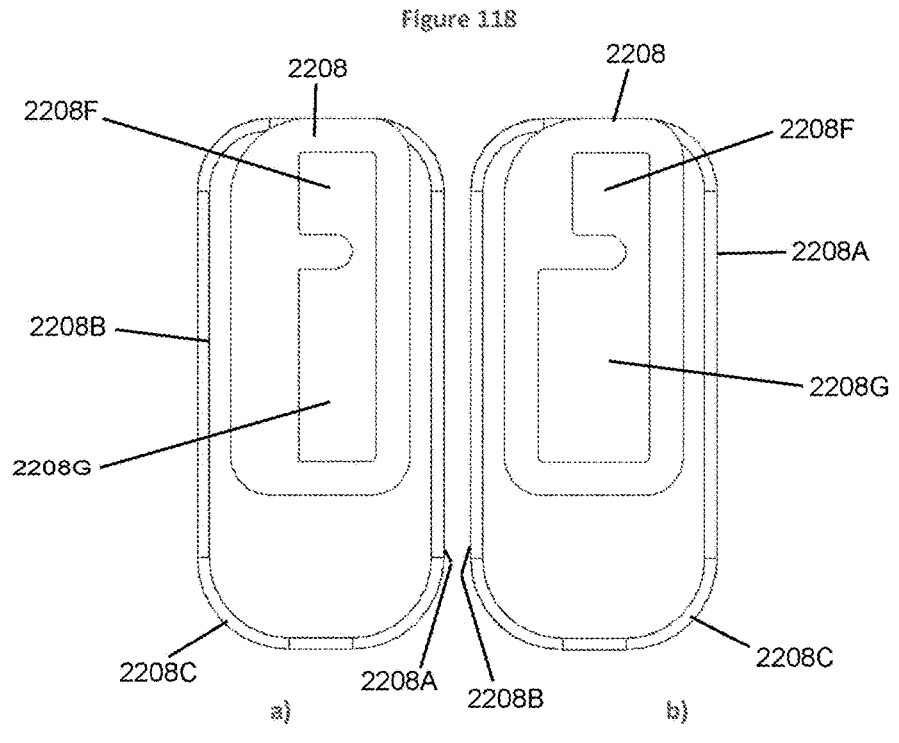
Figure 120:
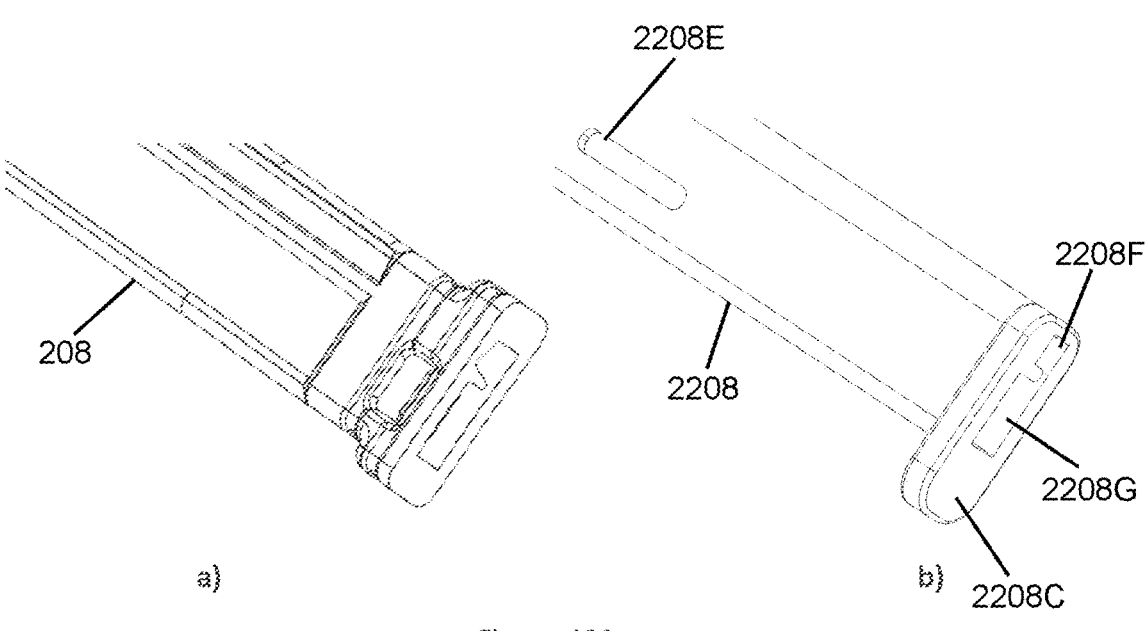
Figure 121:
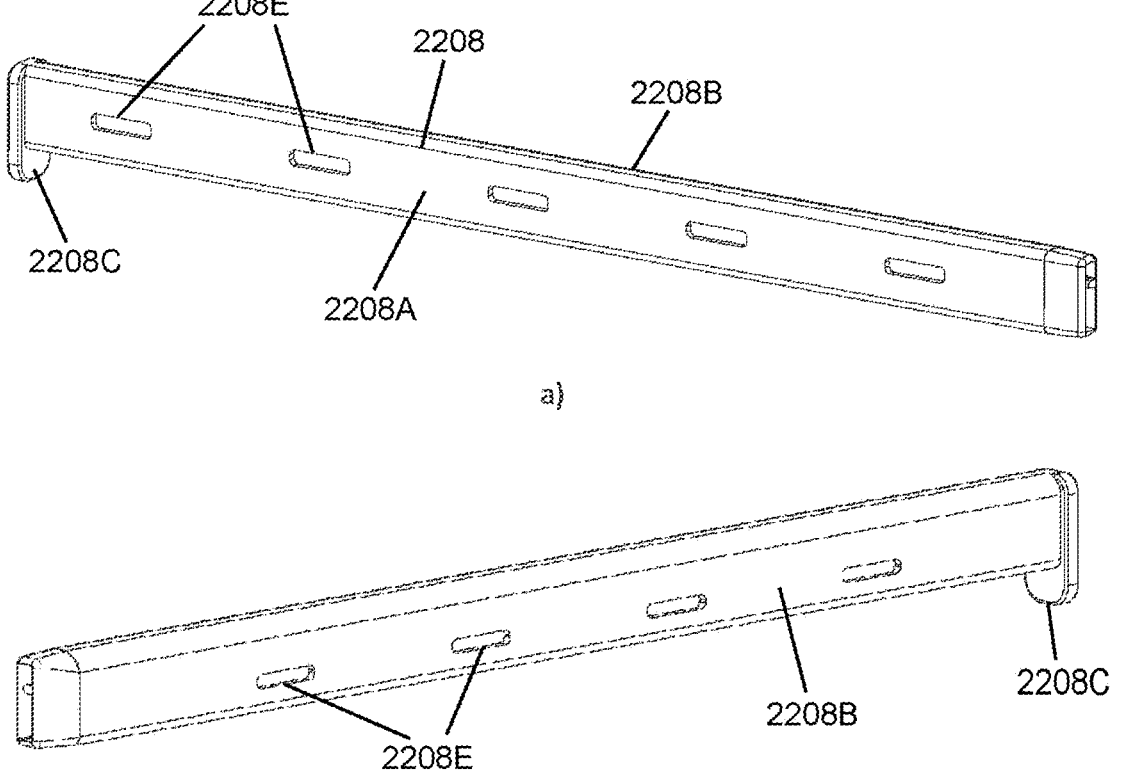
Figure 122:
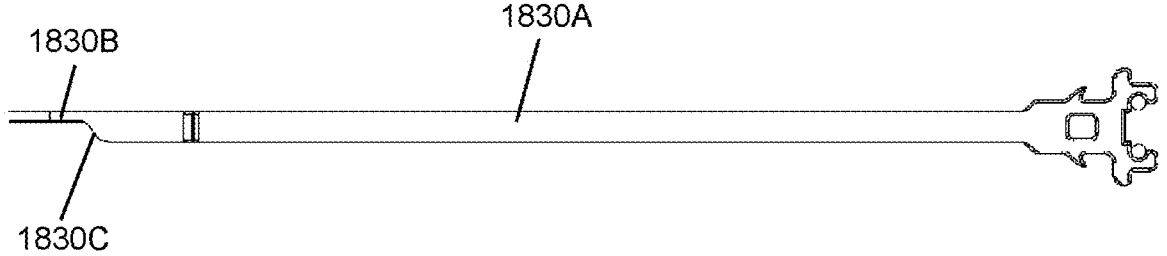
Figure 123:
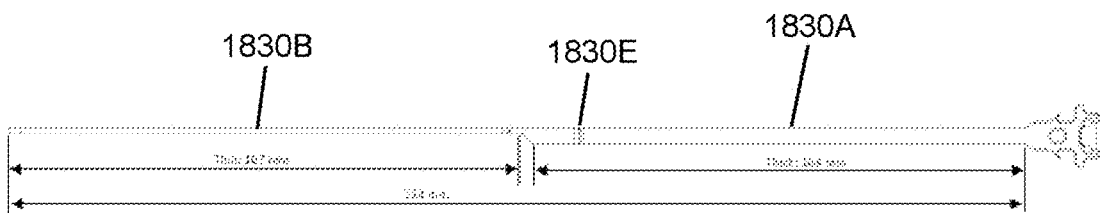

FIG. 103 is a comparison view from the top of a) the yoke assembly of the mask assembly of FIG. 2 and b) the yoke assembly of FIG. 75;

FIG. 104 is a comparison view from the front of a) the yoke assembly of FIG. 2 and b) the yoke assembly of FIG. 75, each attached to the elongate support bodies;

FIG. 105*a*) and b) are front and rear views of the yoke assembly of FIG. 75 and attached elongate support bodies;

FIG. 106 is a cross sectional view of the yoke assembly and mask frame of the mask assembly of FIG. 75;

FIG. 107 is an interior side view of a lateral end of the yoke assembly of FIG. 75, with an end cap mounted on the lateral end, being the side of the yoke assembly that is closest to the user's face;

FIG. 108 is an interior side view of a lateral end of the yoke assembly of FIG. 75, with the end cap removed;

FIGS. 109*a* and *b* are interior side and perspective views of the end cap of FIG. 107;

FIG. 110 is an exploded view corresponding to FIG. 107;

FIG. 111 is a part cross sectional perspective view of the yoke assembly and elongate support bodies of the mask assembly of FIG. 75, showing a directional adjustment unit;

FIG. 112 is an enlarged cross sectional view of the yoke assembly and elongate support bodies of the mask assembly of FIG. 75, showing a directional adjustment unit;

FIGS. 113*a* and *b* are front and rear views of a front member of the yoke assembly of FIG. 75;

FIGS. 114*a* and *b* are front and rear views of a rear member of the yoke assembly of FIG. 75;

FIG. 115 is a rear view of a front member of the yoke assembly of FIG. 75, showing a pair of directional adjustment units mounted in the yoke assembly, and also showing a pair of filaments routed through the front member;

FIG. 116 is a view corresponding to FIG. 105*a*, additionally showing the change in internal cross section of the yoke assembly, at various different positions along the length of the yoke assembly;

FIGS. 117*a* and *b* are schematic views of the yoke assembly of FIG. 3 and the yoke assembly of FIG. 75 respectively, in use with a patient on a bed or pillow;

FIG. 118 is a side view of an elongate support body of the mask assembly of FIG. 75;

FIGS. 119*a* and *b* are cross sectional views taken on lines A-A and B-B of FIG. 116;

FIG. 120 is a comparison perspective view of a) the elongate support body of FIG. 7 and b) the elongate support body of FIG. 75;

FIGS. 121*a* and *b* are perspective views of the interior and exterior sides of the elongate support body of FIG. 75; and FIGS. 122 and 123 are side views of another embodiment of a filament.

DETAILED DESCRIPTION

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "horizontal," "vertical," "front," "back," "left," "right," "rear," and "side" describe the orientation and/or location of portions of the components or elements within a consistent but arbitrary frame of reference which is made clear by reference to the text and the associated drawings describing the components or elements under discussion, which in the context of a patient interface is often in an as-worn orientation with the user's head in an upright orientation. Moreover, terms such as "first," "second," "third," and so on may be used to describe separate components. Such terminology may include the words specifically mentioned above, derivatives thereof, and words of similar import.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

The term "alternatively" refers to selection of one of two or more alternatives, and is not intended to limit the selection to only those listed alternatives or to only one of the listed alternatives at a time, unless the context clearly indicates otherwise.

The disclosure may also be said broadly to consist in the parts, elements and features referred to or indicated in the specification of the application, individually or collectively, in any or all combinations of two or more of said parts, elements or features.

In this disclosure, the term 'exterior side' refers to the side facing away from the user's face while the 'interior side' refers to that facing towards to user's face.

The present disclosure relates to different components of a headgear for a respiratory mask. In particular, the associated components may relate to a directional adjustment unit for a headgear for a respiratory mask, a strap containing, comprising or being secured to a filament operatively coupled to the directional adjustment unit, or a combination between the two, optionally in combination with other components associated with a headgear for a respiratory mask.

More particularly, the present disclosure relates to various components of a respiratory mask or interface system.

Directional Adjustment Unit

FIGS. 1a to 1d show an embodiment of the directional adjustment unit 1800 of our earlier application U.S. 62/644, 002, comprising a housing 1810, a first and a second lock element (e.g., frictional engagement member 1820, 1822) and a filament 1830 of a headgear strap. The directional adjustment unit 1800, which can be referred to herein as a directional lock unit, a directional control unit, a frictional adjustment unit, or a directional resistance unit, allows the position of the headgear relative to the housing to be adjusted. The frictional engagement member in some embodiments may be referred to as a lock or adjustment washer comprising an aperture through which the filament extends. The frictional engagement members 1820, 1822 apply a significantly higher resistance to movement on the filament in the direction of elongation of the headgear relative to the direction of retraction of the headgear. The headgear strap includes an elastic portion that is configured to provide a bias in the direction of retraction when the headgear is elongated. As such the headgear requires the application of a sufficient force to overcome the resistance to elongation including the bias of the elastic portion and frictional force applied by the directional adjustment units to the filament. Once extended, the bias of the elastic portion applies a retraction force that is greater than any frictional force applied to the filament by the directional adjustment unit. Thus, the extended headgear will automatically retract under the bias force until any counter force is equal to the bias force provided by the elastic portion. This counter force may include the reaction force of the mask pressing against a user's face.

The housing 1810 comprises a first and a second chamber 1840, 1842 wherein the first and second chambers 1840, 1842 are configured to house the first and second frictional engagement members 1820, 1822, respectively. Frictional engagement members 1820 may be made out of a material that provides at least some resistance to wear from friction (e.g. polypropylene, high density polyethylene, aluminium, steel). In the illustrated arrangement, the first and second chambers 1840, 1842 are separated by an internal wall 1812 of the housing 1810. However, in other arrangements, the first and second chambers 1840, 1842 are not necessarily physically separate spaces, but can, for example, be portions of a chamber. The housing 1810 has two end walls 1814, which along with the internal wall 1812, have an elongate external opening 1860 for accommodating the filament 1830, or in other words allow the filament to pass through. The filament 1830 may be an elongate thread, fibre, string, wire, or filament, e.g. a nylon, polyethylene, polypropylene fibre, or a metal (e.g. aluminium, copper, silver) wire. Advantageously, a material may be chosen that provides at least some resistance to friction, abrasion, fraying and splaying. Other shapes or geometries may be used, including a rectangular cross section (e.g. a ribbon, band or belt) or multiple threads, fibres, strings, wires or filaments (e.g. a cable or braided or twisted wires). All of these may be referred to as the filament 1830.

The material or materials of the filament may be chosen to be substantially non-elastic, thus allowing the filament 1830 to remain substantially the same length under elongative tensile force. The external housing openings 1860 may be substantially aligned with each other. The external opening 1860 of the end wall 1814 of the housing shown on the right side of the figures may be larger than one or both of the external opening 1860 of the internal wall 1812 and the end wall 1814 shown on the left of the figures. This allows for manipulation or deflection of the path of the filament 1830 through the housing 1810. The first and second chambers 1840, 1842 are each delimited by the internal wall 1812, one of the end walls 1814 and a pair of side walls 1816; wherein the side walls 1816 extend between the end walls 1814 of the housing 1810. The first and second chambers 1840, 1842 are configured to be open at one or both of a top and a bottom of the housing 1810.

Each of the first and second chambers 1840, 1842 has a pair of frictional engagement member retainers 1850 that are aligned on opposing side walls 1816 of the housing 1810. Each pair of frictional engagement member retainers 1850 is configured to pivotally retain one of the first or second frictional engagement members 1820, 1822 within the respective first or second chamber 1840, 1842. The frictional engagement member retainers comprise a circular bush 1852 and an elongate slot 1854, wherein circular bushes 1852 intersect with the bottom of the housing such that an entrance is formed. The entrance is configured to allow the first and/or second frictional engagement members 1820, 1822 to be received into the frictional engagement member retainers 1850. The slot 1854 may extend radially from the circular bush 1852 towards the top of the housing 1810.

With reference to FIGS. 1a to 1d, the first and second frictional engagement members 1820, 1822 each comprise a base 1824, forming cylindrical shaft, and an arm that extends from their respective base 1824. The cylindrical base 1824 is substantially the same width W, as the housing 1810 and the arm is narrower to fit within the first and second chambers 1840, 1842. In the illustrated arrangement, the arm comprises a first section 1872 and a second section 1874, wherein the first section 1872 extends radially or perpendicularly from the cylindrical base 1824 and the second section 1874 extends at an obtuse angle from the end of the first section 1872. Hence, the first section 1872 and the second section 1874, in general extend in two respectively different directions. Such an obtuse angled double or two section frictional engagement member may be referred to as a double section frictional engagement member throughout the present specification.

In this particular illustrated embodiment, the first section 1872 of the arm of the first frictional engagement member 1820 is shorter than the first section 1872 of the arm 1826 of the second frictional engagement member 1822. The angle between the first and second sections 1872, 1874 of the arm of the first frictional engagement member 1820 is greater than the corresponding angle of the second frictional engagement member 1822. The angles can be selected such that the second section 1874 of one or both of the first and second frictional engagement members 1820, 1822 lies substantially flat against the corresponding wall (e.g., internal wall 1812 and end wall 1814, respectively) of the housing 1810 in one position of the frictional engagement members 1820, 1822. The second section 1874 of the arm comprises an aperture 1876 configured to receive the fila- ment 1830. The first and second chambers 1840, 1842 differ in size according to the size of the frictional engagement member that is to be housed within it, i.e. the first chamber 1840 is smaller than the second chamber 1842 because the first frictional engagement member 1820 is smaller than the second frictional engagement member 1822. Hence, in some configurations, the frictional engagement members of the directional adjustment unit are different. In an alternative embodiment, each frictional engagement member 1820 is identical, or has at least one identical property or character- istic, for example the first section 1872 of each member 1820 can be of identical length.

The cylindrical base 1824 of the first and second frictional engagement members 1820, 1822 have a diameter substan- tially the same as that of the circular bushes 1852 of the frictional engagement member retainer 1850, and are con- figured to be received and retained by the circular bush 1852 in a snap-fit configuration. The snap-fit configuration is provided by the entrance of the circular bush 1852 being narrower than the diameter of the cylindrical base 1824. The slots 1854 of the frictional engagement member retainers 1850 are configured to allow the entrance to be flexed open to increase the ease with which the first and second frictional engagement members 1820, 1822 can be pushed through the entrances and assembled to the housing 1810. Once assembled within the first and second chambers 1840, 1842 of the housing 1810, the first and second frictional engage- ment members 1820, 1822 can pivot back and forward around a pivot axis that runs through the cylindrical base 1824.

The filament 1830 may be configured to pass through the external openings 1860 of the housing 1810 and the aper- tures 1876 of the first and second frictional engagement members 1820, 1822.

The general operation of the directional adjustment unit according to each of the embodiments disclosed herein will now be described, with reference to the particular embodi- ment shown in FIGS. 1a to 1d.

Figure 1A:
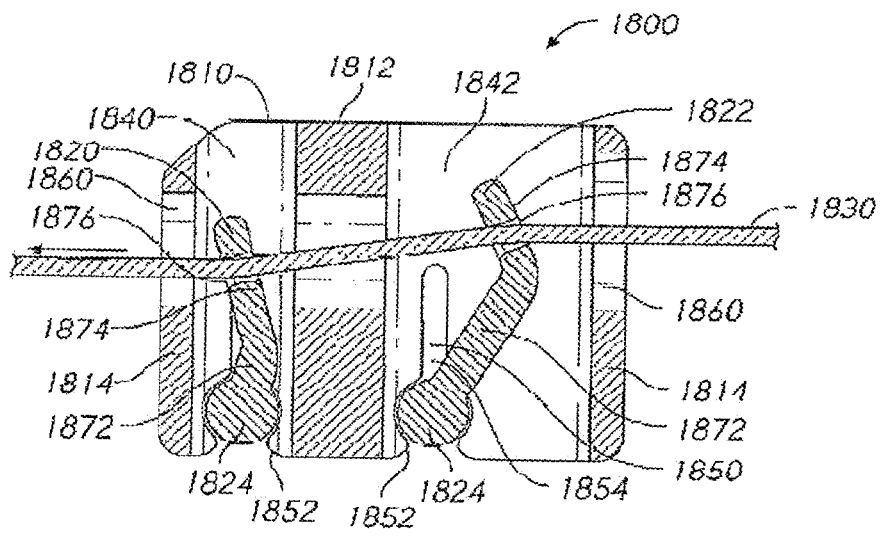
FIG. 1a is a cross-sectional view of a directional adjustment unit in an engaged configuration.
Figure 1B:
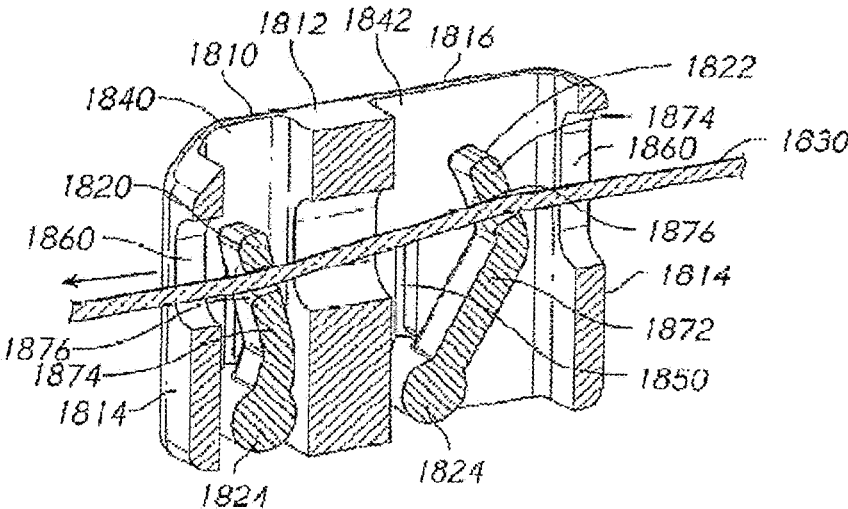
FIG. 1b is a perspective cross-sectional of the directional adjustment unit in FIG. 1a in the engaged configuration.

Application of a tension force to the filament 1830 causes the first and second frictional engagement members 1820, 1822 to move back and/or forward between a locked or engaged position or configuration and/or an open or unlocked or disengaged position or configuration. In this example, the movement back and/or forward is a pivotal movement. Other forms of movement are envisaged. FIGS. 1a and 1b show the directional adjustment in a locked or engaged configuration in which a force is applied to the filament 1830 in a direction towards the left side of the figure (as indicated by the arrow). In some embodiments, the force applied to the filament 1830 in this configuration causes the first and second frictional engagement members 1820, 1822 to pivot in an anti-clockwise direction, such that the path of the filament 1830 through the directional adjustment unit 1800 is non-linear or tortuous and/or an increased frictional force is applied to resist movement of the filament 1830, e.g. due to an increase of the area in contact between filament 1830 and first and second frictional engagement members 1820, 1822 and an increase in contact pressure.

Figure 1C:
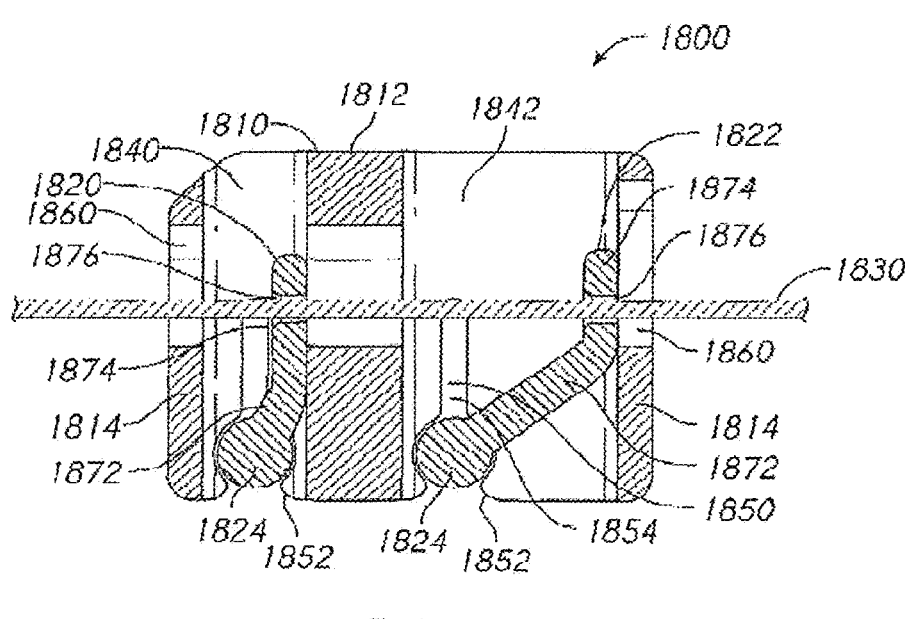
FIG. 1c is a cross-sectional view of the directional adjustment unit in FIG. 1a in the disengaged configuration.
Figure 1D:
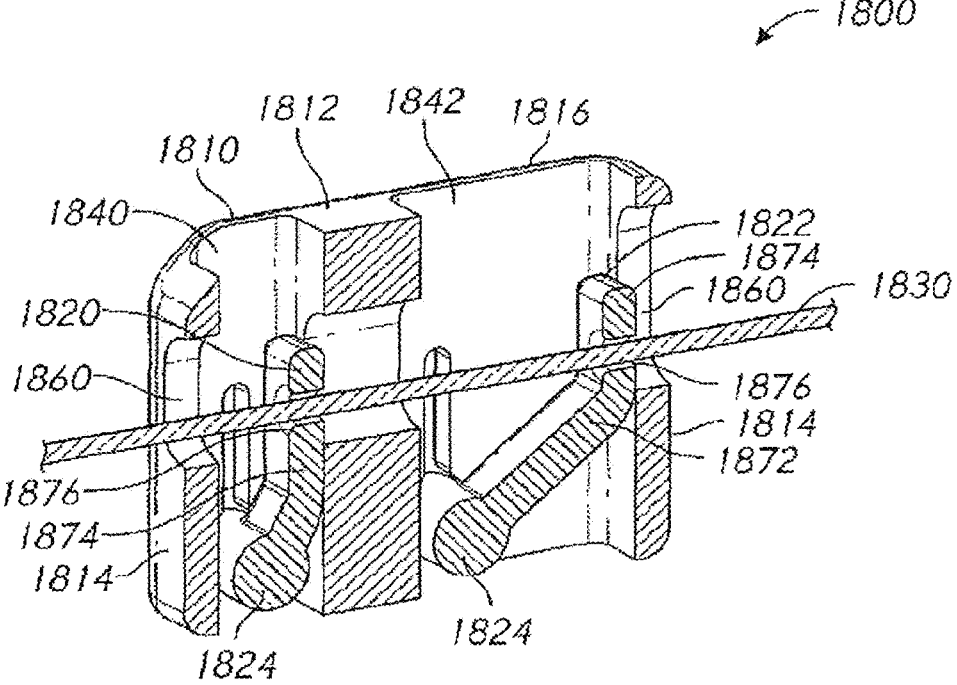
FIG. 1d is a perspective cross-sectional of the directional adjustment unit in FIG. 1a in the disengaged configuration.

FIGS. 1c and 1d show the directional adjustment in an open or unlocked or disengaged configuration in which a force is applied to the filament 1830 in a direction towards the right side of the figure (as indicated by the arrow). In this configuration, the first and second frictional engagement members 1820, 1822 may be pivoted in a clockwise direc- tion such that the apertures 1876 and external openings 1860 are aligned in a substantially straight line. This provides a smooth and low-friction path and/or reduced contact pres- sure for the filament 1830 to be pulled substantially freely through the directional adjustment unit 1800. Based on the different amount of frictional force exerted on filament 1830 in the closed position and the open position, the amount of force required to move filament 1830 through the directional adjustment unit 1800 may be varied.

While the illustrated embodiment of directional adjust- ment unit 1800 utilizes first and second frictional engage- ment members 1820, 1822, fewer or more frictional engage- ment members could be used. The number of frictional engagement members, the type, length and thickness of filament 1830, and the geometry of frictional engagement members 1820 are design parameters that can be varied to achieve a pre-determined amount of force necessary to overcome directional adjustment unit 1800 while in the engaged, closed or locked configuration ("yield force") and a second pre-determined force necessary to open, release or move the directional adjustment member into the disen- gaged position ("opening force").

The frictional engagement members 1820 are permitted to move between a disengaged configuration (FIGS. 1c and 1d) and an engaged configuration (FIGS. 1a and 1b) in response to an outward movement of the yoke in use.

When the frictional engagement members 1820 are per- mitted to move or pivot, the movement of filament 1830 in the elongation direction may be restricted (e.g., inhibited or prevented) by friction between filament 1830 and frictional engagement members 1820, as shown in FIGS. 1a to 1b. Conversely, if the frictional engagement members 1820 are oriented in the disengaged configuration, as shown in FIGS. 1c to 1d, the friction between filament 1830 and frictional engagement members 1820 is reduced and movement of filament 1830 in the elongation direction becomes easier relative to the engaged configuration.

Additional particulars of the operation of the directional adjustment units 1800 are described above and in Appli- cant's earlier patent applications as referenced in the first paragraph of this specification.

In some configurations, the minimum force of the direc- tional adjustment unit 1800 is between about 2 Newtons and 8 Newtons. In some configurations, two or more directional adjustments with a minimum force between 2 Newtons and 8 Newtons may be combined to yield an overall minimum force between 4 and 16 Newtons, or between 16 and 32 Newtons.

In some configurations, the minimum force of the direc- tional adjustment unit 1800 is between about 4 Newtons and 6 Newtons. In some configurations, two or more directional adjustments with a minimum force between 4 Newtons and 6 Newtons may be combined to yield an overall minimum force between 8 and 12 Newtons, or between 16 and 32 Newtons.

For the purpose of facilitating understanding of the pres- ent disclosure, the following definitions are used throughout the present specification:

A plane having a normal vector parallel to the pivot axis may also be referred to as a side plane throughout this specification.

A plane having a normal vector parallel to the pivot axis and intersecting a central line of the frictional engage- ment member may also be referred to as a central plane throughout this specification.

The central plane may intersect the centre of mass of the frictional engagement member or could be provided laterally offset to the centre of mass of the frictional engagement member.

A central line is a line extending through the frictional engagement member along which the aperture is at least partly symmetrical.

Headgear

With reference to FIGS. 2 and 3, in an embodiment, a headgear 200 for a respiratory mask is provided. The headgear 200 comprises at least one strap 212, at least one yoke assembly 20, and at least one filament 1830 which extends within the at least one strap 212 and enters the yoke assembly 20. The headgear 200 also comprises the directional adjustment unit 1800 according to any of the embodiments disclosed herein. The filament 1830 has at least one flat or substantially flat exterior surface extending along a longitudinal axis thereof, so that in the engaged configuration the substantially flat or flat exterior surface of the filament 1830 is brought into contact with the substantially flat or flat region of the at least one frictional engagement member 1820, 1822 of the directional adjustment unit 1800.

In some configurations, the at least one strap 212 is flexible, elastic, and/or spring elastic, allowing it to be extended from an idle length when the yoke assembly 20 is pulled outwards by the hand of the user, while allowing it to attempt to return to its idle length when the yoke assembly 20 is released. The filament 1830 may extend through the at least one strap 212. The at least one filament 1830 of the headgear further comprises a core region 181 having a first geometrical shape. The filament 1830 further comprises an end region 183 having a second geometrical shape. The filament 1830 further comprises a transitional region 182 provided longitudinally between the core region 181 and the end region 183. The transitional region 182 has a shape transitioning from the first geometrical shape of the core region 181 to the second geometrical shape of the end region 183 over a longitudinal distance along the longitudinal axis of the filament 1830.

In some configurations, the yoke assembly 20 is arranged to connect the headgear to the respiratory mask.

In some configurations, the at least one strap 212 forms a cavity therein for accommodating the filament 1830. At least one part of the cavity of the strap may have a shape conforming with that of the filament 1830. For example, for a filament 1830 with a transverse rectangular cross section, at least part of the strap cavity may be transversely rectangular with slightly larger dimension to fit the rectangular filament 1830.

For a filament 1830 with a transverse triangular cross section, at least part of the strap cavity may be transversely triangular with slightly larger dimension to fit the triangular filament 1830. The directional adjustment unit 1800 may be arranged within the yoke assembly 20, when assembled. The housing 1810 of the directional adjustment unit 1800 may comprise an external opening 1860 for slidably accommodate at least part of the filament 1830, e.g. a part of the transitional region 182 and/or the end region 183, in use. In some configurations, the external opening 1860 has a size, i.e. at least one cross sectional dimension, smaller than that of a portion of a transitional region 182 of the filament 1830, in use, so as to prevent the transitional region 182 to fully enter the directional adjustment unit 1800.

In some configurations, the yoke assembly 20 comprises a central portion and at least one section extending from the central portion, wherein the at least one section is configured to connect to the at least one strap 212 of the headgear.

Respiratory Interface System

FIGS. 2 and 3 illustrate an example of a respiratory interface system 100 or respiratory mask system 100 for the delivery of respiratory therapy to a patient according to an embodiment. The mask system 100 may comprise an interface, such as a mask 102. In the illustrated arrangement, the mask 102 comprises a seal, or seal module, and a frame, as described in further detail herein. The illustrated mask system 100 also includes a headgear 200 (which may also be referred to as a "headgear assembly" herein). The mask 102 and headgear 200 may comprise a connection system to attach the headgear 200 to the mask 102. Various forms of connection systems may be used to attach the headgear 200 to the mask 102. Similarly, the mask 102 may be coupled to at least one and possibly multiple different types of headgear.

Figures 3A, 3B:
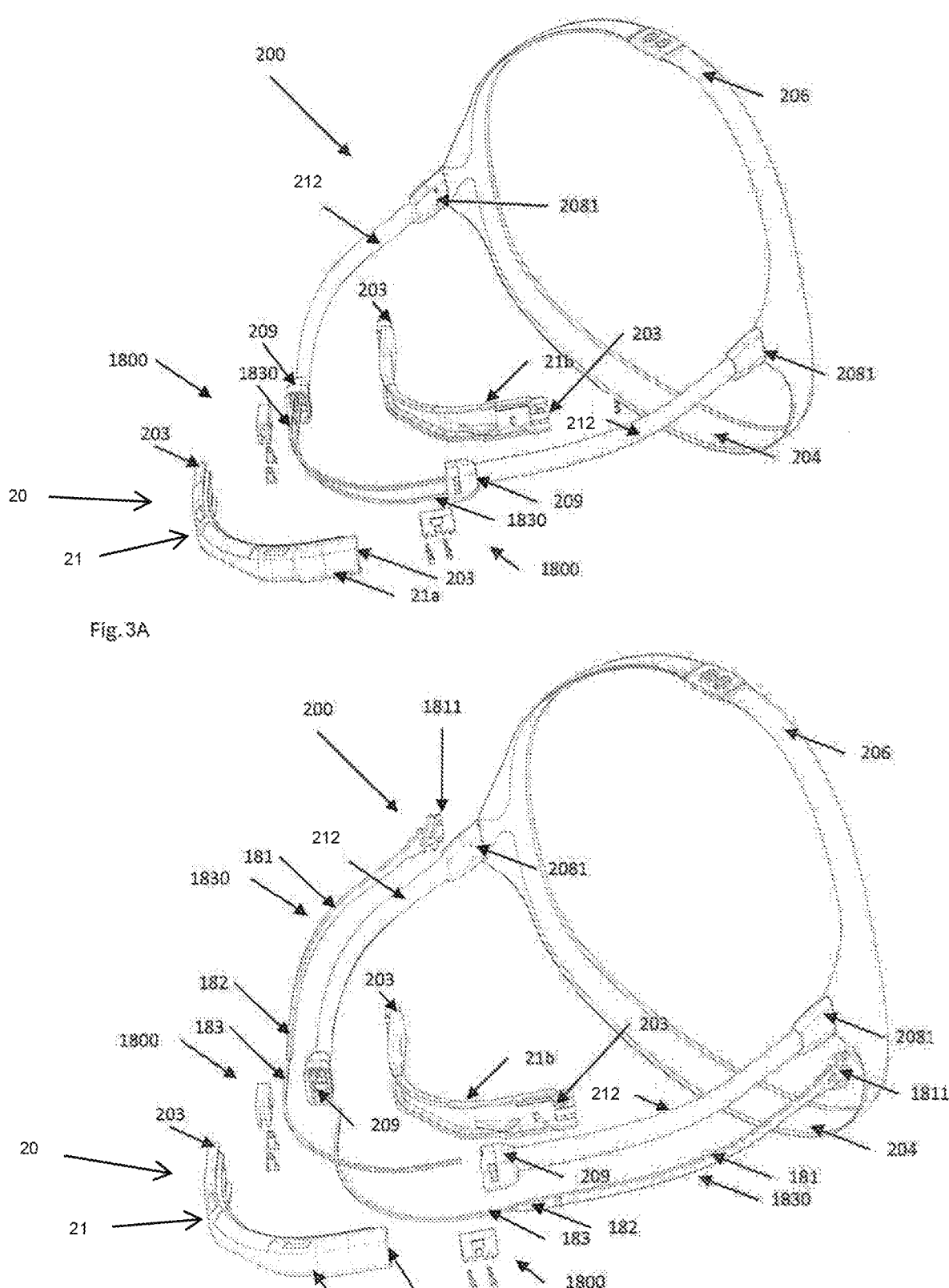
FIG. 3a is an exploded view of the seal assembly, frame assembly, and a front portion of the headgear.
FIG. 3b is an exploded view of one form of headgear according to an embodiment.
Figure 3C:
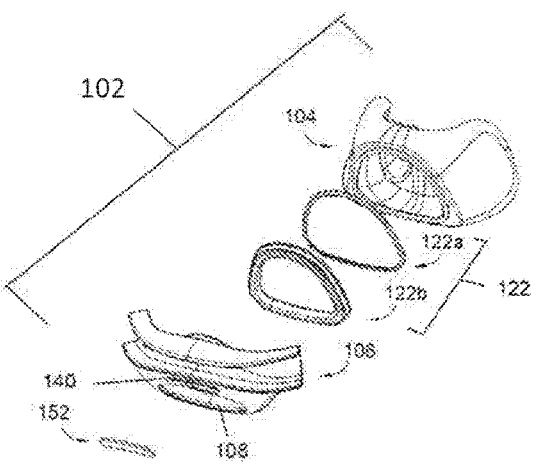
FIG. 3c shows a cross sectional front view illustrating the associated contact surfaces between a filament and a sidewall of the frictional engagement member aperture.

Referring to FIG. 3c, the mask 102 may comprise a seal 104 and a frame 106. The seal 104 can be configured for sealing around and/or underneath a patient's mouth and/or nose. In the illustrated arrangement, the seal 104 is a nasal seal configured to deliver the flow of breathing gases only to the user's nose. In particular, the illustrated seal 104 includes a pair of nasal pillows configured to create a seal with the user's nares and a secondary sealing portion that surrounds the nasal pillows and is configured to create a secondary seal with one or more of an underside of the user's nose, side portions of the user's nose and the user's upper lip.

However, features of the present disclosure can be implemented with other mask systems having other types of mask seals, such as full-face seals, for example and without limitation.

Figure 25:
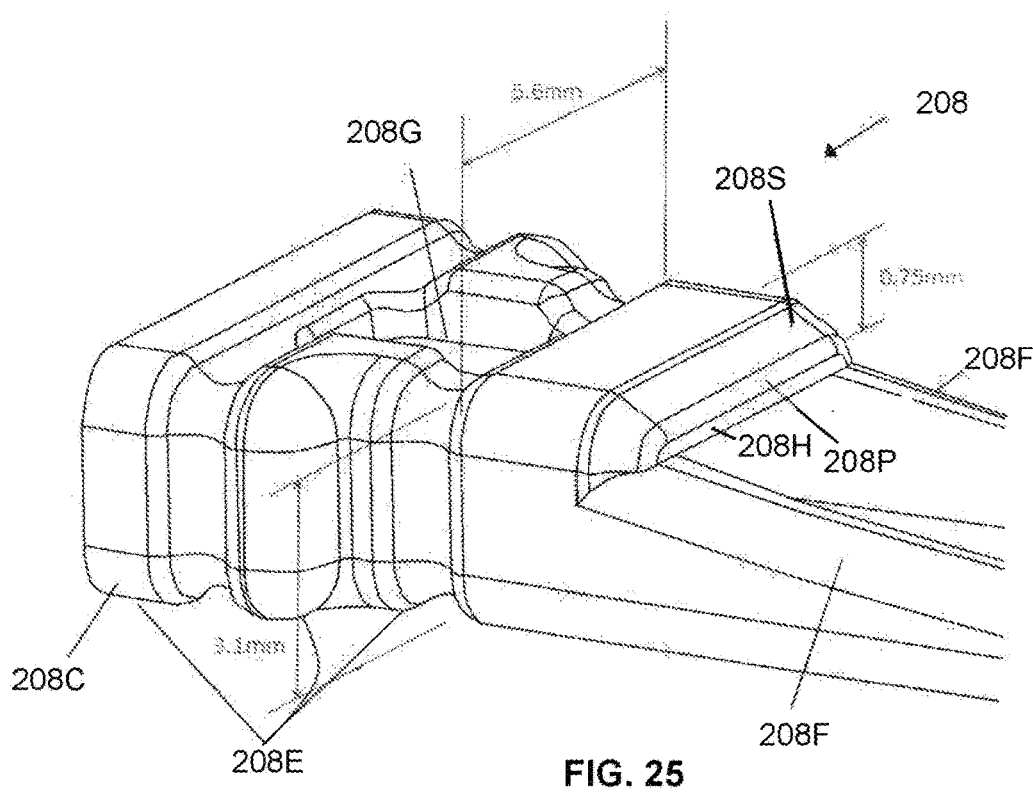
FIGS. 25 and 26 are perspective views of a medial end of the support structure of FIG. 24.
Figure 26:
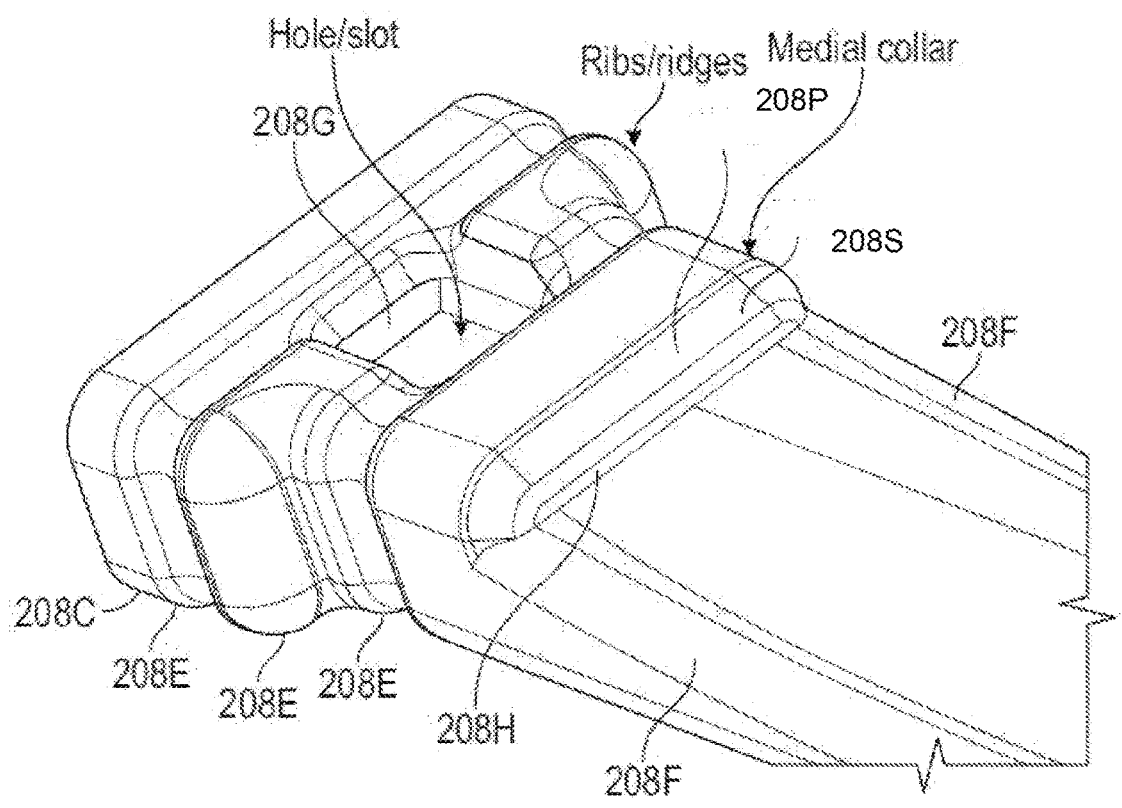

The frame 106 is configured for supporting the seal 104 and attaching the seal 104 to the headgear 200. The frame 106 may also comprise a gas inlet 108, see FIG. 25, configured to attach to a gas conduit 110 for delivering a flow of breathing gas to the patient via the mask 102.

The seal 104 can include an attachment frame or clip 122, which in some arrangements can include a first portion 122a and a second portion 122b that capture a rim of the seal 104 between them. The clip 122 is configured to selectively connect to the frame 106, such as by a snap-fit, friction fit or other suitable arrangement. The frame 106 can include a vent 140, which is configured to exhaust gases from an interior of the seal 104. Optionally, the mask 102 can include a vent insert or diffuser 152 that covers the vent 140 to control the exhaust flow.

The headgear 200 of the respiratory mask system 100 is used to hold the mask 102 to the patient's face. The headgear 200 is typically attached to the mask 102 and wraps around the rear of the patient's head to hold the mask 102 in sealed contact with the patient's face.

In one form, the headgear 200 may comprise a yoke assembly 20 or collector, which is configured to attach to the mask 102, as described in greater detail herein.

The yoke assembly 20 may be configured to attach to straps of the headgear 200 such that the straps and yoke assembly 20 cooperate to form a closed loop that surrounds the head of the user. In the illustrated embodiment, the headgear 200 comprises an assembly of straps, including a rear strap 204 configured to wrap behind a patient's head, an upper strap 206 configured to wrap over the top of a patient's head, and a pair of front straps 212, see FIG. 25, configured to extend along the patient's cheeks during use.

In some configurations, for example as shown in FIGS. 3a and 3c, the at least one filament 1830 comprises the core region 181, transitional region 182, and end region 183 as described above.

In some configurations, each front strap 212 is attached to the rear strap 204 of the headgear assembly 200, e.g., to a free end 207 of the rear strap 204 or a connector coupled to the free end 207, by a rear connector 205. In another form, the rear strap 204 comprises side extensions that form front straps to extend along the patient's cheeks during use.

In one form, the headgear 200 can be adjustable (e.g. manually adjustable, automatically adjustable) and/or can incorporate one or more locks (e.g. the directional adjustment unit 1800 as described above) that allow the headgear 200 to reduce in length with a relatively low amount of resistance and resist an increase in length of the headgear 200. In some configurations, a locking force of the directional adjustment units 1800 may be overcome to allow lengthening of the headgear 200 for donning of the mask system 100. In some forms, the yoke assembly 20 may form a collector for filaments used in an automatically adjustable headgear system. In this form, the yoke assembly 20 may incorporate one or more directional adjustment units 1800, each of which can comprise one or more lock elements, which can be referred to herein as frictional engagement members or frictional engagement members. The frictional engagement members are configured to frictionally engage with the filament during elongation of the headgear 200, but allow relatively friction-free movement during retraction of the headgear 200.

The frictional engagement members 1820, 1822 and/or filaments 1830 may have at least one flat or substantially flat region as described above.

In some configurations, the headgear 200, or mask system 100, includes a release mechanism or arrangement that is configured to release or hold open the directional adjustment units 1800 to allow for low-friction movement while a control or other actuator is operated by a user, and provide high-friction resistance if the control or actuator is not engaged.

The directional adjustment units 1800 may be incorporated into the ends of the yoke assembly or collector 20 and the body or yoke housing 21 of the yoke assembly 20 may be substantially hollow to receive the filaments within the body. The headgear 200 or any portion thereof can be configured in accordance with any of the embodiments disclosed in Applicant's U.S. Publication No. 2016/0082217, U.S. application Ser. No. 14/856,193, filed Sep. 16, 2015, and PCT Publication No. WO2016/043603, the entireties of which are incorporated by reference herein.

As perhaps best shown in FIGS. 3a and 3b the headgear 200 comprises two filaments 1830, one for each front strap 212. However, any number of filaments could be used.

With reference to FIGS. 3a and 3b each front strap 212 may comprise a free end to which may be attached an end cap or a connector 209. Each connector 209 may engage with a complementary strap connector 203 located on the yoke assembly 20. Preferably, the yoke assembly 20 is substantially elongate and comprises a strap connector 203 located at or near each end of the front member 21a and rear member 21b of the yoke housing 21.

The connection between the front straps 212 and yoke assembly 20 may be any suitable form of connection, such as a snap-fit connection, a screw and thread type connection, an overmould connection, or a hooked connection. In one configuration, each strap connector 203 comprises a cap 210 (not shown in FIGS. 3a to 3c) located at each end of the yoke assembly 20. Each cap 210 may comprise an opening, such as an aperture or recess, configured to receive the connector 209 of the front strap 212 in a snap-fit arrangement to attach the yoke assembly to the front straps 212 of the headgear assembly 200.

With reference to FIG. 3b, the filament 1830 may be connected to the upper strap 206 and or rear strap 204, via a front strap connector 2081, thereby securing one end 1811 of the core region 181 of the filament 1830 to the front strap connector 2081.

This means that as the front strap 212 is extended, e.g. as a result of pulling the yoke assembly to which the strap 212 is connected in use, the extending parts of the front strap 212 will move, e.g. slide, in relation to the filament 1830, as both the front strap 212 and the core region end 1811 are connected to together in or adjacent to front strap connector 2081. This in turn leads to the free end of the end region 183 of the filament 1830 to move closer to the connector 209 of the strap 212 in which said filament is provided. This in turn leads to a relative motion between the end region 183 of the filament 1830 and the directional adjustment unit 1800 through which the filament 1830 is arranged. As the yoke assembly 20, and indirectly also the directional adjustment unit 1800, are connected to connector 209, the filament 1830 will move relative the directional adjustment unit 1800. This relative motion, activates the associated frictional engagement members 1820, 1822, by means of friction between the filament the and the frictional engagement member cavities, in which the filament is provided, so as to move from their disengaged position towards their engaged position.

The opposite phenomenon occurs when the strap is allowed to return from its extended state to its non-extended state, for example upon the user releasing the yoke assembly 20 with his/her hand. The spring elasticity in the strap 212 acts to retract the strap 212 from its extended state to its idle state. In this scenario, the distance between the free end of the end region 183 of the filament 1830 to move further apart from the connector 209 of the strap 212 in which said filament is provided. This in turn leads to a relative motion between the end region 183 of the filament 1830 and the directional adjustment unit 1800 through which the filament 1830 is arranged. This relative motion, forces the frictional engagement members 1820, 1822, by means of friction between the filament the and the frictional engagement member cavities, in which the filament is provided, to move from their engaged position towards their disengaged position.

With reference to FIG. 3b, the rightmost front strap 212 is connected to the leftmost directional adjustment unit 1800, whereas the leftmost front strap 212 is connected to the rightmost directional adjustment unit 1800. It should appreciated that the directional adjustment unit 1800 having at least one frictional engagement member 1820, 1822 having an aperture forming a flat or substantially flat region for engaging a corresponding flat or substantially flat region of the filament 1830, may be provided in any headgear design, i.e. also designs other than those disclosed herein. In such designs the respective directional adjustment unit 1800 and filament 1830 may be oriented, arranged or connected in different manners in relation to the other components of the headgear, while still allowing for the relative motion therebetween, which triggers the movement between the disengaged state and engaged state.

As mentioned above, the yoke assembly 20 may also be configured to attach to the frame 106 of the mask 102. In one form, the frame 106 may comprise a recessed region configured to receive at least a portion of the yoke assembly 20 therein when the yoke assembly 20 and frame 106 are attached together. A cover sleeve, or front portion, can be configured to facilitate the removable connection of the yoke assembly 20 with the frame 106.

FIGS. 4a to 4d show different views of a yoke assembly 20 of a headgear for a respiratory mask according to an embodiment of this disclosure.

Figure 4A:
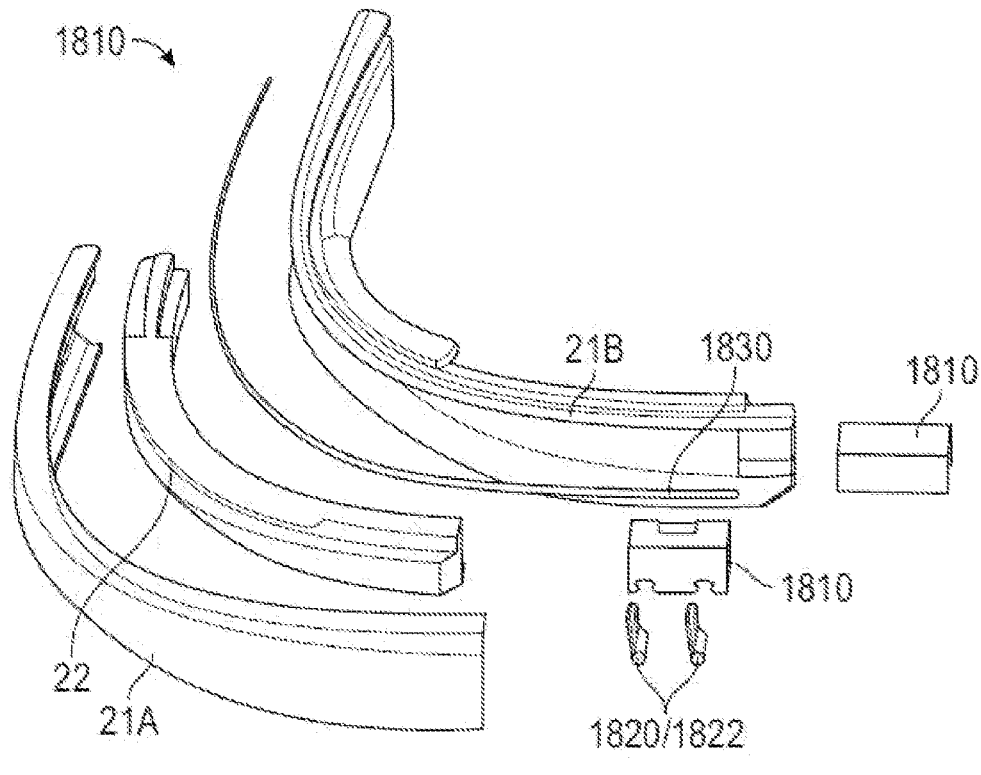
FIG. 4a is an exploded view of different components of a yoke assembly (end caps not shown) of a headgear for a respiratory mask comprising a directional adjustment unit and a filament.

FIG. 4a is an exploded view of different components of the yoke assembly 20 (end caps not shown) of a headgear for a respiratory mask. The yoke assembly 20 comprises a yoke housing 21 comprising a front member 21a and a rear member 21b. The front member 21a and rear member 21b permanently connect together with an interference fit to secure the directional adjustment unit within the yoke housing 21. A filament divider insert 22 is arranged within the yoke housing 21.

A purpose of the filament divider insert 22 is to guide the filament in position for a directional adjustment unit of the yoke assembly 20.

The filament divider insert 22 comprises a first guide channel 221 for slidably accommodating a first filament 1830. The first guide channel 221 has a first opening arranged at a first end of the filament divider insert 22. The first opening of the first guide channel 221 is arranged at a first vertical level of the filament divider insert 22. The first guide channel 221 further comprises a second opening arranged at a second end of the filament divider insert 22. The second opening of the first guide channel 221 may be arranged at a second vertical level of the filament divider insert 22. The first vertical level and the second vertical level may relate to the same vertical level. Optionally, the first vertical level may differ from the second vertical level. In some configurations, the first vertical level may be above or below the second vertical level, in use.

The yoke assembly 20 further comprises a directional adjustment unit 1800, such as that shown with reference to FIGS. 1a to 1d. The directional adjustment unit 1800 comprises a housing 1810 and at least one frictional engagement member 1820, 1822 pivotally arranged to the housing 1810 around a pivot axis. The at least one frictional engagement member 1820, 1822 has an aperture 1876 extending therethrough for accommodating the filament 1830, in use. The at least one frictional engagement member 1820, 1822 provides for a disengaged configuration in a first pivoted configuration with respect to the filament 1830. The at least one frictional engagement member 1820, 1822 further provides for an engaged configuration in a second pivoted configuration with respect to the filament 1830.

Figure 4B:
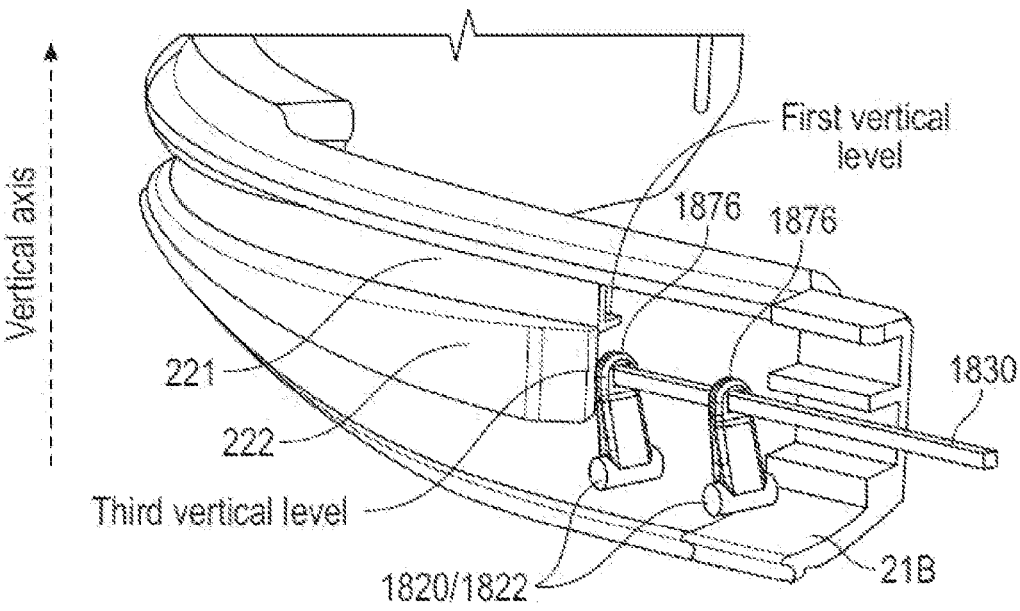
Figure 4C:
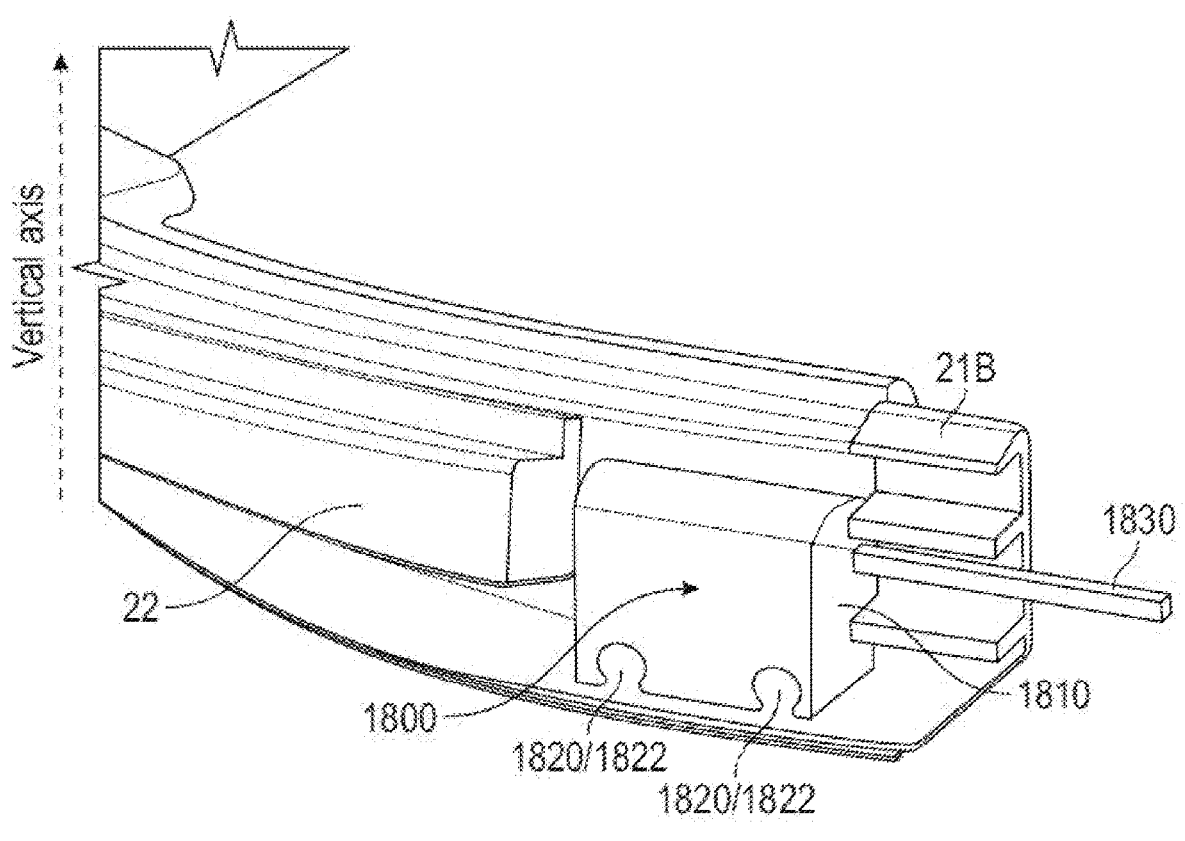
Figure 4D:
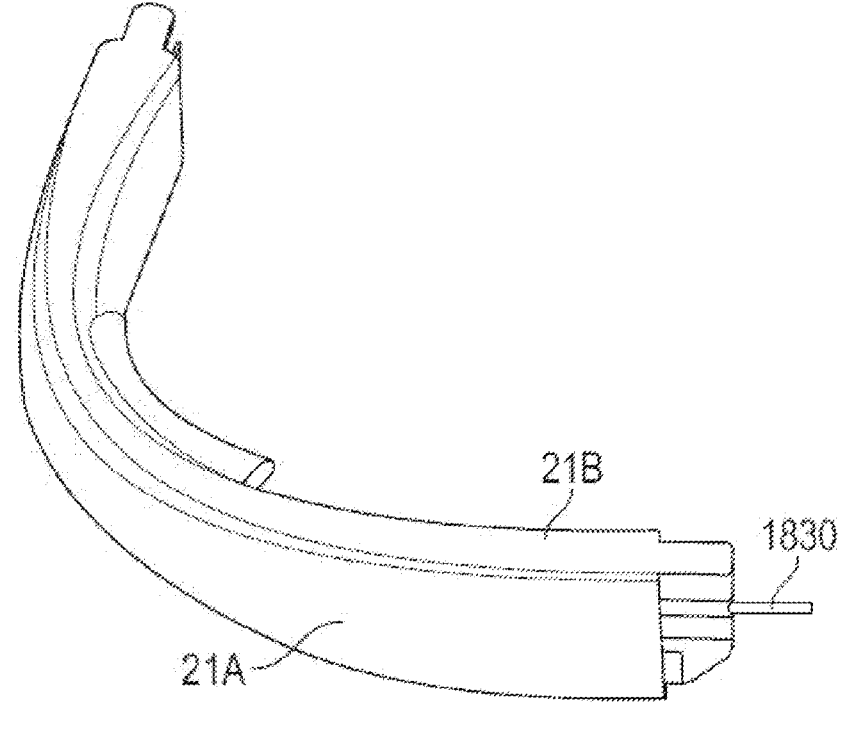
FIG. 4d is a view of the yoke assembly of FIG. 4a in a partly assembled state (with end caps and optional second directional adjustment unit not shown)

FIGS. 4b and 4c are cutaway views of a yoke assembly 20 of FIG. 4a. In FIG. 4b the directional adjustment unit housing 1810 has been removed for showing how the apertures of the at least one frictional engagement member 1820, 1822 is operatively associated with the filament 1830 and the second channel 222 of the filament divider insert 22, whereas FIG. 4c shows the housing 1810 to which the frictional engagement members 1820, 1822 are pivotably arranged, in use. FIG. 4d is a view of the yoke assembly 20 of FIG. 4a in a partly assembled state (with end caps and optional second directional adjustment unit not shown).

With reference to FIGS. 4a to 4d, the aperture 1876 or the cavity formed by said aperture forms in a transverse cross section at least one linear or substantially linear portion of the at least one frictional engagement member 1820, 1822 for engaging a corresponding flat or substantially flat portion or exterior surface of the filament 1830 when the at least one frictional engagement member 1820, 1822 is in the engaged configuration. In some configurations, the corresponding flat or substantially flat portion or exterior surface of the filament has in transverse cross section a linear or substantially linear portion corresponding to the linear or substantially linear portion of the engagement surface region.

Here "transverse" cross section means a cross section in which it is possible to observe the entire aperture boundary. The transverse cross section may be parallel to a front view plane.

As will be further elucidated below, the aperture forms a cavity extending through the frictional engagement member. In some configurations the cavity extends along a central axis. Hence, a "transverse cross section" may also mean any cross section that intersects the central axis or the extension of the cavity and/or aperture. In some configurations, the transverse cross section is perpendicular to the central axis. In other configurations, the transverse cross section may be arranged at an angle with reference to the central axis.

It should also be appreciated that the expression "linear" may also be referred to as "straight" throughout this disclosure. It is believed that a filament design and corresponding frictional engagement member aperture having respective mating linear or flat surfaces or regions, reduces the shear forces acting on the filament, in use.

We have discovered that a filament having a round shape, e.g. circular transverse cross section, may not withstand the load created by the natural operation of the mechanism, which causes damage to the filament in the form of a kink, when operatively coupled to a frictional engagement member having a corresponding round aperture of somewhat larger size encompassing the round filament, in use. A reason for this may be that high local stress points cause deformation to the filament at the point of contact between the frictional engagement member and the filament. This may cause the round filament to be permanently deformed by reshaping the cross section into an oval shape, thus prohibiting it from returning freely through the mechanism.

The stress (o) acting on the filament in use may be defined using the following stress formula:

$$\sigma = F/A,$$

where F relates to the associated force and A relates to the contact surface area. It follows that increasing the contact surface area will reduce the stress for any given force.

A contact surface area between a round or circular filament and a slightly larger round or circular aperture is relatively small, leading to a relatively large local stress at the contact surface area.

We have realized that an increased contact surface area may be achieved by altering the shape of the filament and aperture (and/or the associated interior cavity sidewall surfaces of the cavity formed through the frictional engagement member by the aperture) so that a respective flat or substantially flat portion of the filament engages with at least one corresponding transverse cross sectional linear or substantially linear portion of an engagement surface region of the frictional engagement member.

The engagement surface region may comprise the interior wall or surfaces of the aperture or the interior cavity surfaces of the cavity formed by the aperture.

A first transverse cross sectional linear or substantially linear portion of a first transverse cross section of the engagement surface region, and at least one second transverse cross sectional linear or substantially linear portion of a second transverse cross section of the engagement surface region, may together form at least one flat or essentially flat engagement surface or area.

The transverse cross sectional linear or essentially linear portion of the engagement surface region may expand the mutual contact surface area with the filament, whereby the forces are distributed more evenly across the associated contact surfaces.

Such a design may ensure that when the filament engages an interior cavity wall surface of the frictional engagement member, the engagement or contacting surfaces are flat and apply uniform pressure over a significantly larger area. These flat surfaces engaging each other lead to a repeatable and more consistent level of engagement which in turn leads to a more consistent level of friction being supplied by the directional adjustment unit. Further, by increasing the contact surface the stress applied to the filament is minimized and permanent damage to the filament may be prevented during the expected life time cycle.

FIGS. 5a to 5b respectively show a cross sectional front view illustrating the associated contact surfaces between a filament 1830 and a sidewall of the frictional engagement member aperture 1876. In the example of FIG. 5a both the filament and frictional engagement member aperture 1876 are rectangular in transverse cross section, whereas in FIG. 5b the filament and frictional engagement member aperture are circular in transverse cross section, as per our earlier disclosure. The respective contact points are approximately identified by the arrows. As seen from FIG. 5a, by incorporating the rectangular filament a significantly larger percentage of the total surface area of the filament contacts a surface of the frictional engagement member aperture leading a significantly lower stress in the filament as opposed to the circular filament and aperture in which only a small portion of the overlapping radiuses contact each other. This increased contacting area leads to a significantly lower stress being experienced in the filament with the same force being applied.

The contacting surfaces between the filament and frictional engagement member function with the highest mechanical efficiency when they are perpendicular with each other and are able to be fully engaged when the frictional engagement member pivots.

As described previously, with reference to FIGS. 1a to 1d, each filament is configured to contact at least two surfaces, e.g. interior cavity wall surfaces, of each frictional engagement member, in the engaged configuration: the upper front edge of the cavity formed by the frictional engagement member aperture 1876 and a lower rear edge of the cavity formed by the frictional engagement member aperture 1876.

Figures 18A, 18B, 18C:
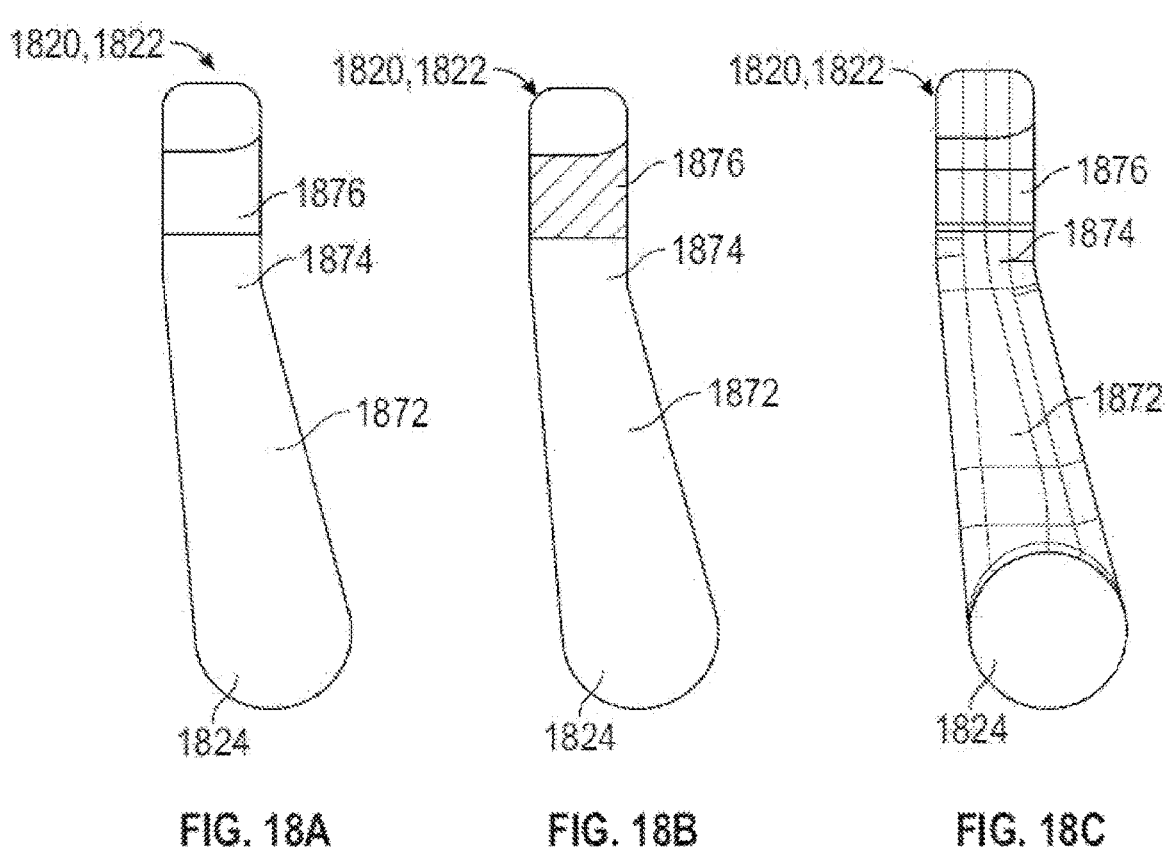
FIG. 18a shows a side view of a double section frictional engagement member of an embodiment, having a rounded edge formed at an upper intersection between the front face, i.e. right face in the Figure, of the frictional engagement member and the aperture.
FIG. 18b shows an alternative side view of the double section frictional engagement member of FIG. 18a, wherein the cross sectional aperture area is filled for improved visualization.
FIG. 18c shows a contour side view of the double section frictional engagement member of FIGS. 18a and 18b.
Figures 18D, 18E, 18F:
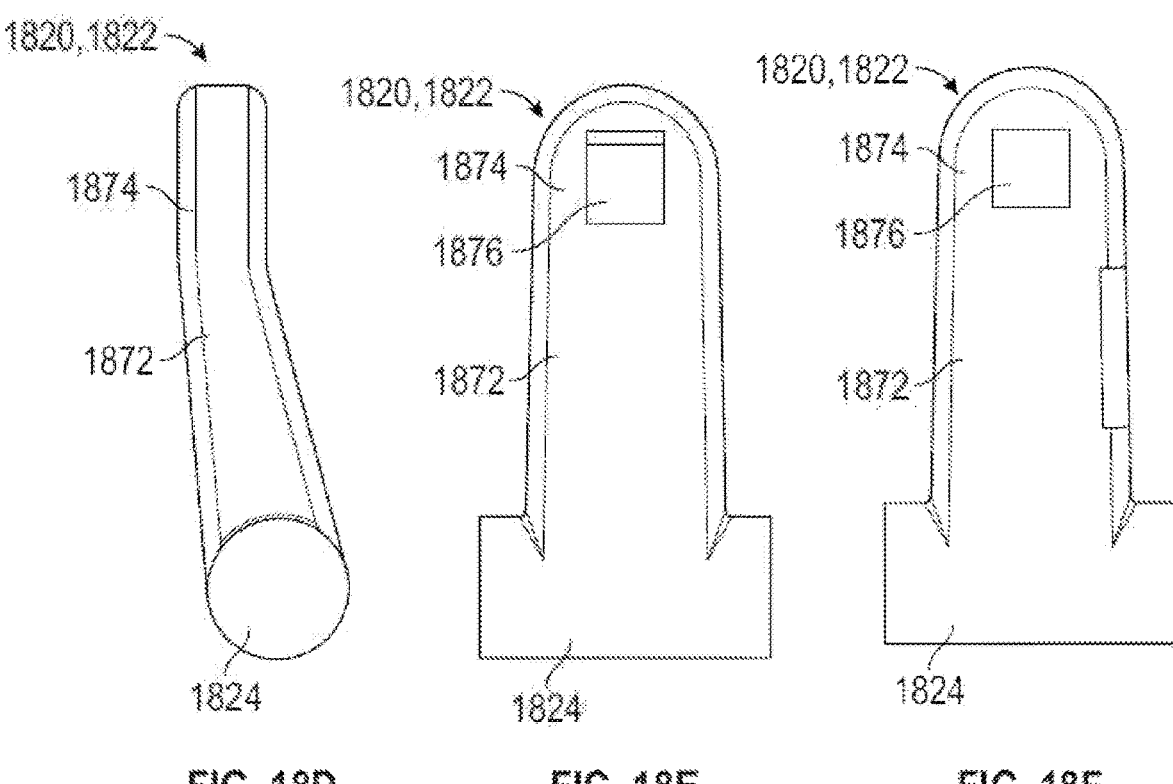
FIG. 18d shows a side design view of the double section frictional engagement member of FIGS. 18a to 18c.
FIG. 18e shows a front view of the double section frictional engagement member of FIGS. 18a to 18d.
FIG. 18f shows a rear view of the double section frictional engagement member of FIGS. 18a to 18e.

In some configurations, for example with reference to FIGS. 18e and 18f, the frictional engagement member aperture 1876, in a front view, i.e. at a face of the at least one frictional engagement member 1820, is non-round, non-circular, non-elliptic, or non-oval.

In some configurations, the at least one transverse cross sectional linear or substantially linear portion of the engagement surface region of the frictional engagement member 1820 is linear along a lateral or transverse axis parallel or substantially parallel to the pivot axis, and/or substantially perpendicular to the longitudinal axis of the filament 1830.

In some configurations, the frictional engagement member aperture 1876 may be provided offset to the pivot axis and extend through the at least one frictional engagement member 1820, 1822 along an axis having a component perpendicular to the pivot axis.

In some configurations, as shown with reference to FIGS. 4a to 4d, 5a to 5b, 6, 8a to 8d, 15a to 15c, 16a to 16b, 18a to 18j, the aperture, at a face, e.g. a front face, of the at least one frictional engagement member 1820, 1822, is rectangular.

In some configurations, the front face of at least one frictional engagement member 1820, 1822 may be formed in a plane parallel to an exterior surface of a first section or second section of the at least one frictional engagement member.

In some configurations, a side margin of the rectangular aperture 1876 may be parallel or substantially parallel to the pivot axis.

In some configurations, the aperture 1876 has a rectangular transverse cross section in a plane parallel to the pivot axis, and a longitudinal axis normal to the pivot axis.

In some configurations, the aperture 1876 has a rectangular transverse cross section in a plane parallel to the front face formed at the surface of a first section or second section of the at least one frictional engagement member.

FIG. 6 is a cross sectional front view showing a directional adjustment unit 1800 having a rectangular aperture 1876, in transverse cross section, according to an embodiment of this disclosure. In this figure the direction adjustment unit 1800 is assembled in the yoke housing 21 comprising the front member 21a and rear member 21b. The filament divider insert 22 is shown behind the directional adjustment unit 1800. In FIG. 6 an optional housing sleeve 1899 is shown to arrange and position the directional adjustment unit 1800 in the yoke housing 21. It should be appreciated that a housing sleeve 1899 may be suitable in some situations, so as to allow for the possibility of using the same type or shape of directional adjustment unit with differently sized or shaped yoke assembly designs. However, in some configurations the directional adjustment unit housing 1810 is shaped to securely fit into the cavity formed by the yoke housing 21, without the need for an optional housing sleeve 1899.

FIGS. 7a to 7c respectively show different views of a housing sleeve 1899 allowing a housing of a directional adjustment unit according to an embodiment to be mounted securely within the yoke assembly 20.

Figures 8A, 8B, 8C, 8D:
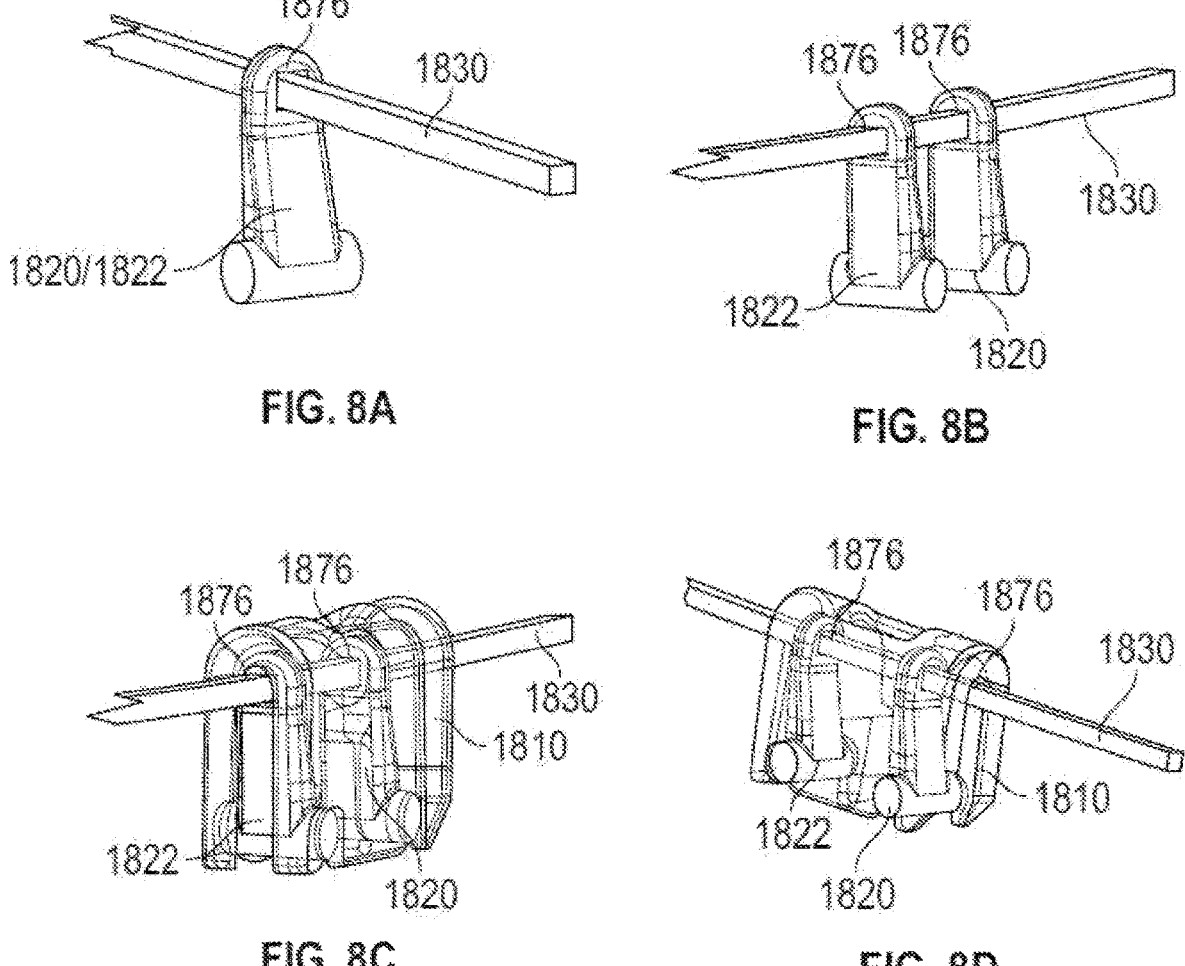
FIG. 8a shows a cutaway perspective view of a filament having a rectangular cross section accommodated through an aperture of a frictional engagement member of the directional adjustment unit, wherein the aperture has a rectangular cross section.
FIG. 8b shows a cutaway perspective view of a filament having a rectangular cross section accommodated through the apertures of a two frictional engagement members of the directional adjustment unit, wherein the aperture has a rectangular cross section.
FIG. 8c shows an alternative cutaway perspective view of the arrangement of FIG. 8b, where the associated housing to which the frictional engagement members are pivotally arranged is semi-transparently shown.
FIG. 8d shows an alternative cutaway perspective view of the arrangement of FIG. 8c.

FIG. 8a shows a cutaway perspective view of a filament 1830 having a rectangular cross section accommodated through an aperture 1876 of a frictional engagement member 1820, 1822 of the directional adjustment unit 1800, wherein the aperture 1876 has a rectangular cross section for slidably receiving the rectangular filament 1830.

FIG. 8b shows a cutaway perspective view of a filament 1830 having a rectangular cross section accommodated through the apertures 1876 of a pair of frictional engagement members 1820, 1822 of the directional adjustment unit 1800, wherein the aperture 1876 has a rectangular cross section.

FIG. 8c shows an alternative cutaway perspective view of the arrangement of FIG. 8b, where the associated directional adjustment unit housing 1810 to which the frictional engagement members 1820, 1822 are pivotally arranged is semi-transparently shown. FIG. 8d shows an alternative cutaway perspective view of the arrangement of FIG. 8c.

FIGS. 9 to 11b show respective cutaway views of the directional adjustment unit 1800 in the engaged position, i.e. when the filament 1830 and the respective frictional engagement members 1820, 1822 are brought in frictional surface contact. As described previously, with reference to FIGS. 1a to 1d, each filament 1830 may contact at least two surfaces, e.g. interior cavity wall surfaces, of each frictional engagement member, in the engaged configuration. These interior cavity wall surfaces are clearly shown in FIGS. 9 to 11b.

Figure 9:
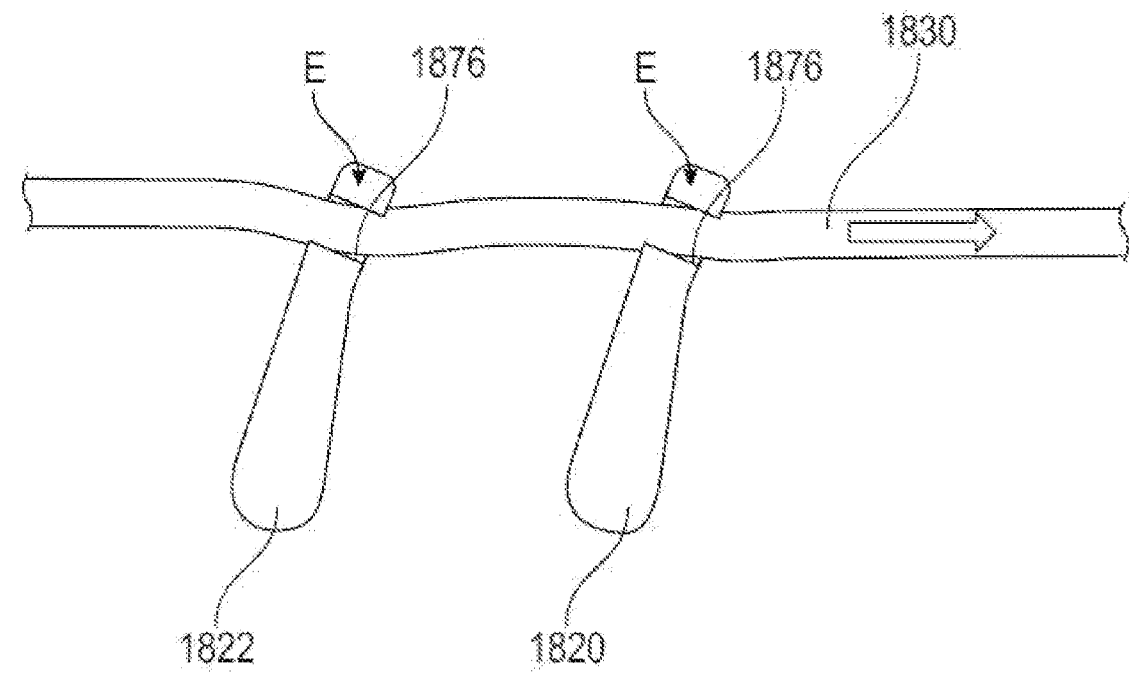
FIG. 9 is a cross sectional cutaway view of the directional adjustment unit according to an embodiment, with two frictional engagement members of the directional adjustment unit and the filament extending through the associated frictional engagement member apertures, in a plane having a normal vector parallel to the pivot axis of each frictional engagement member, wherein sharp edges are formed at an intersection between the face of each frictional engagement member and the aperture.

FIG. 9 is a cross sectional cutaway side view (i.e. in a plane perpendicular to the pivot axis of each frictional engagement member 1820) of the directional adjustment unit 1800 and an associated filament 1830 according to an embodiment of this disclosure. Although not easily perceived from FIG. 9, the aperture has a transverse cross sectional shape forming at least one linear or substantially linear or non-arcuate portion of the at least one frictional engagement member 1820, 1822. Correspondingly, the filament 1830 has a corresponding transverse cross sectional flat or substantially flat portion. Compared to a circular or cylindrical filament and transverse aperture cross section, the contact surface between the filament 1830 and engagement surface region of the frictional engagement member 1820, 1822 is increased thereby decreasing the stresses on the filament 1830, in use as explained above. In this particular embodiment the aperture 1876 forms sharp edges at an intersection between the face of each frictional engagement member 1820, 1822 and the aperture 1876. The cross section of the frictional engagement members 1820, 1822 shows the interaction that occurs between the filament 1830 and the frictional engagement member 1820, 1822 as it is pulled through the path of the formed between the frictional engagement members 1820, 1822 and frictional engagement member housing 1810.

Sharp edges (E) formed at the intersection between the face of the frictional engagement members 1820, 1822 and the rectangular aperture 1876 through the frictional engagement member 1820, 1822 may interfere with the filament 1830 and the contacting points exposed to the high stress may in some situations be permanently damaged, for example by high levels of abrasion occurring due to the contact between the sharp edge and the filament surface.

In order to further alleviate the local stresses on the filament 1830, and in an attempt to further reduce or prevent damage or wear to the filament 1830 and/or frictional engagement member 1820, 1822, in use, in some embodiments at least one aperture edge is rounded or filleted.

Hence, according to some embodiments, the aperture forms a rounded edge at a face of the at least one frictional engagement member 1820, 1822, which may be a forward face.

Figure 10:
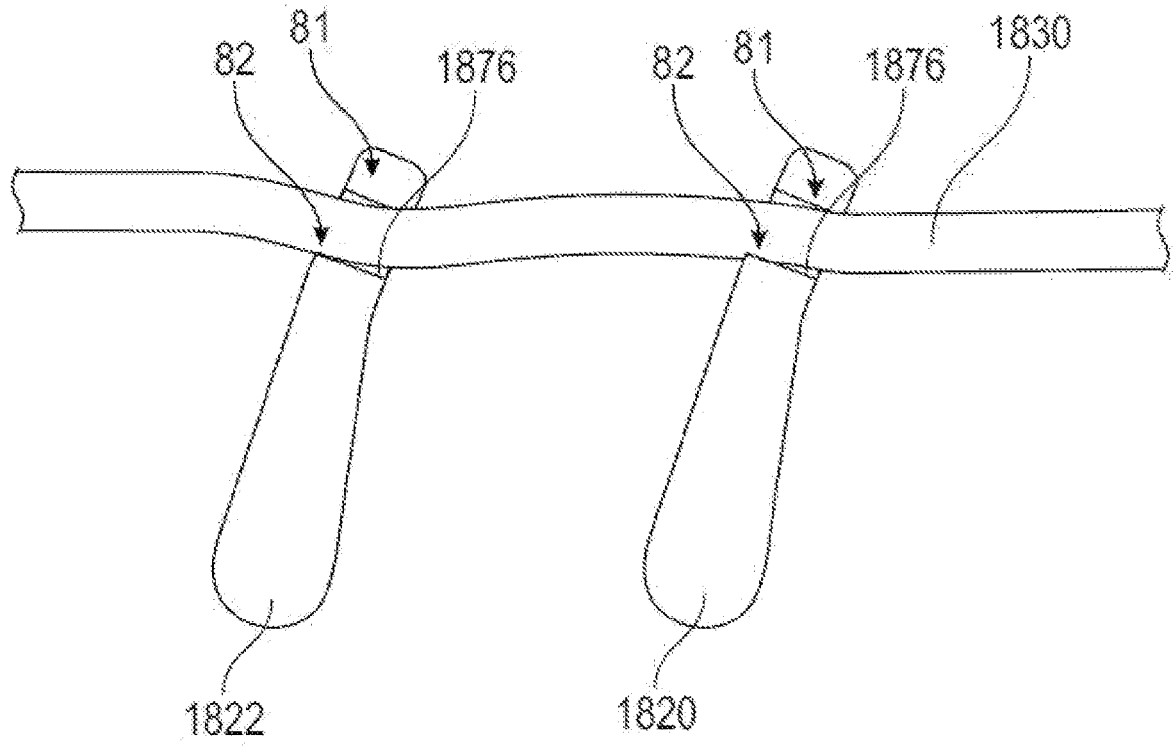
FIG. 10 is a cross sectional cutaway view of the directional adjustment unit according to an embodiment, with two frictional engagement members of the directional adjustment unit and the filament extending through the associated frictional engagement member apertures, in a plane having a normal vector parallel to the pivot axis of each frictional engagement member, wherein rounded edges are provided at an upper intersection between the front face of each frictional engagement member and the aperture.

FIG. 10 is an example of a pair of frictional engagement members 1820, 1822 respectively provided with such rounded aperture edges. FIG. 10 shows a corresponding cross sectional side view as that of FIG. 9, wherein the upper front aperture edge 81, formed at an upper intersection between the front face of each frictional engagement member 1820, 1822 and the aperture 1876, is rounded. Here, the expressions "front" and "rear" are to be interpreted with reference to the front/forward direction of the arrow indicating the filament movement direction when moving from the disengaged configuration to the engaged configuration. FIG. 10 illustrates the effect that rounding the upper front edge 81 of the apertures 1876 of the frictional engagement members 1820, 1822 has on the interaction with the filament 1830. In this particular embodiment, the lower rear edge 82 of each frictional engagement member aperture 1876 maintains a sharp edge that potentially could negatively interfere with the filament 1830. However, during the development stages of the present invention, this lower rear aperture edge 82 has been shown to have a lower effect on the wear and damage of the filament then that of the upper front edge 81.

Hence, only rounding the upper front aperture edges 81 may provide for a more cost effective solution, while still increasing the expected life cycle of the filament 1830.

In some configurations, the rounded edge has a curvature with respect to an axis being parallel to the pivot axis of the frictional engagement member.

However, it is envisaged that both the upper front edges 81 and lower rear edges 82 could be rounded, that is, the edges on diametrically opposed parts of the cavity formed by aperture 1876.

Figure 11A:
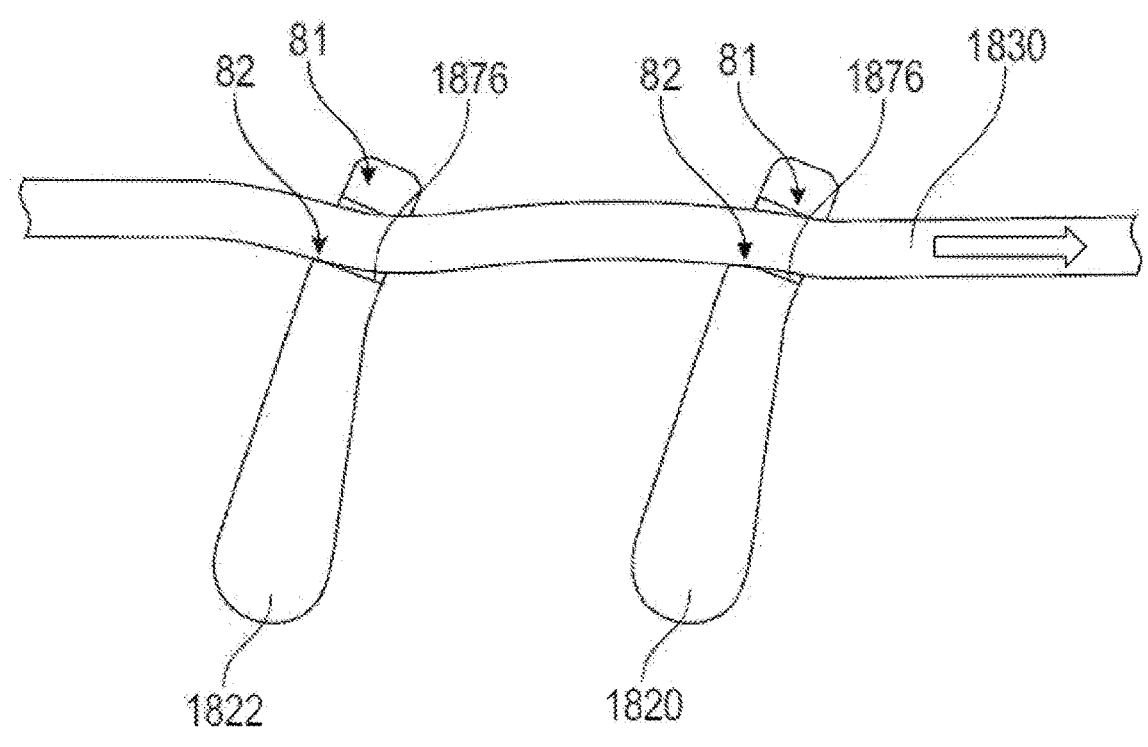
FIG. 11a is a cross sectional cutaway view of the directional adjustment unit according to an embodiment, with two frictional engagement members of the directional adjustment unit and the filament extending through the associated frictional engagement member apertures, in a plane having a normal vector parallel to the pivot axis of each frictional engagement member, wherein rounded edges are provided at an upper intersection between the front face of each frictional engagement member and the aperture and at a lower intersection between the rear face of each frictional engagement member and the aperture.

FIG. 11*a* is a cross sectional cutaway side view of the directional adjustment unit according to an alternative embodiment. FIG. 11*a* shows a corresponding cross sectional side view as that of FIGS. 9 and 10, where both upper front aperture edge(s) 81 and the lower rear aperture edge(s) 82 of each frictional engagement member 1820, 1822 are rounded. FIG. 11*a* may be said to show an ideal cross sectional profile of the frictional engagement member apertures with rounded upper and lower contacting edges to remove any local points of high stress during the interaction between the frictional engagement member 1820, 1822 and filament 1830.

Figure 11B:
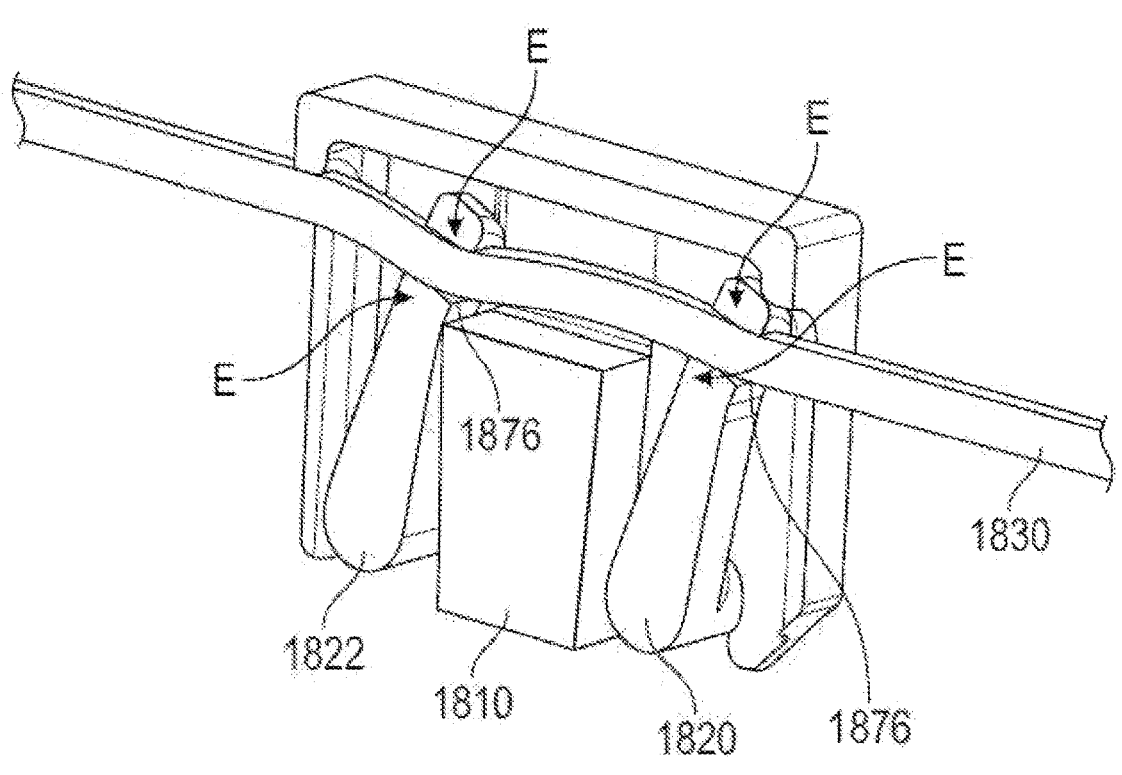
FIG. 11b is a cutaway perspective cross sectional view of the arrangement of FIG. 11a where part of the housing is shown.

FIG. 11*b* is a cutaway perspective cross sectional view of the arrangement of FIG. 11*a* where part of the housing and/or housing 1810 is shown. FIG. 11*b* shows the interaction between the rectangular filament 1830 and the frictional engagement members 1820, 1822, wherein the frictional engagement members 1820, 1822 are in the engaged configuration with the filament 1830 contacting the upper front edges 81 and lower rear edges 82 of each frictional engagement member aperture to create two areas, surfaces, or regions of contact for each frictional engagement member 1820, 1822, resulting in total four areas, surfaces or regions of contact between the filament 1830 and the two frictional engagement members 1820, 1822.

The rounded edges 81, 82 may have a consistent radius along their length.

In an embodiment, the aperture 1876 is triangular at the face of the at least one frictional engagement member 1820, 1822, which means that it is triangular in transverse cross section. The triangular aperture 1876, similarly to a rectangular aperture discussed above, form an engagement surface region of the frictional engagement member that has, in transverse cross section at least one linear or substantially linear portion. More particularly, the triangular aperture 1876 forms in transverse cross section at least three linear or substantially linear or non-arcuate portions, each representing a sidewall of the associated triangle. As such, a triangular aperture 1876 when used together with a triangular (in transverse cross section) filament 1830 provides for the above described increased surface contact area which reduces the stresses on the filament 1830, in use.

Accordingly, the aperture 1876 may have a triangular transverse cross section in a plane parallel to the pivot axis of the frictional engagement member 1820, 1822, and a longitudinal axis normal to the pivot axis.

In some configurations, a side of the triangular aperture is parallel or substantially parallel to the pivot axis of the frictional engagement member 1820, 1822.

Figure 12A:
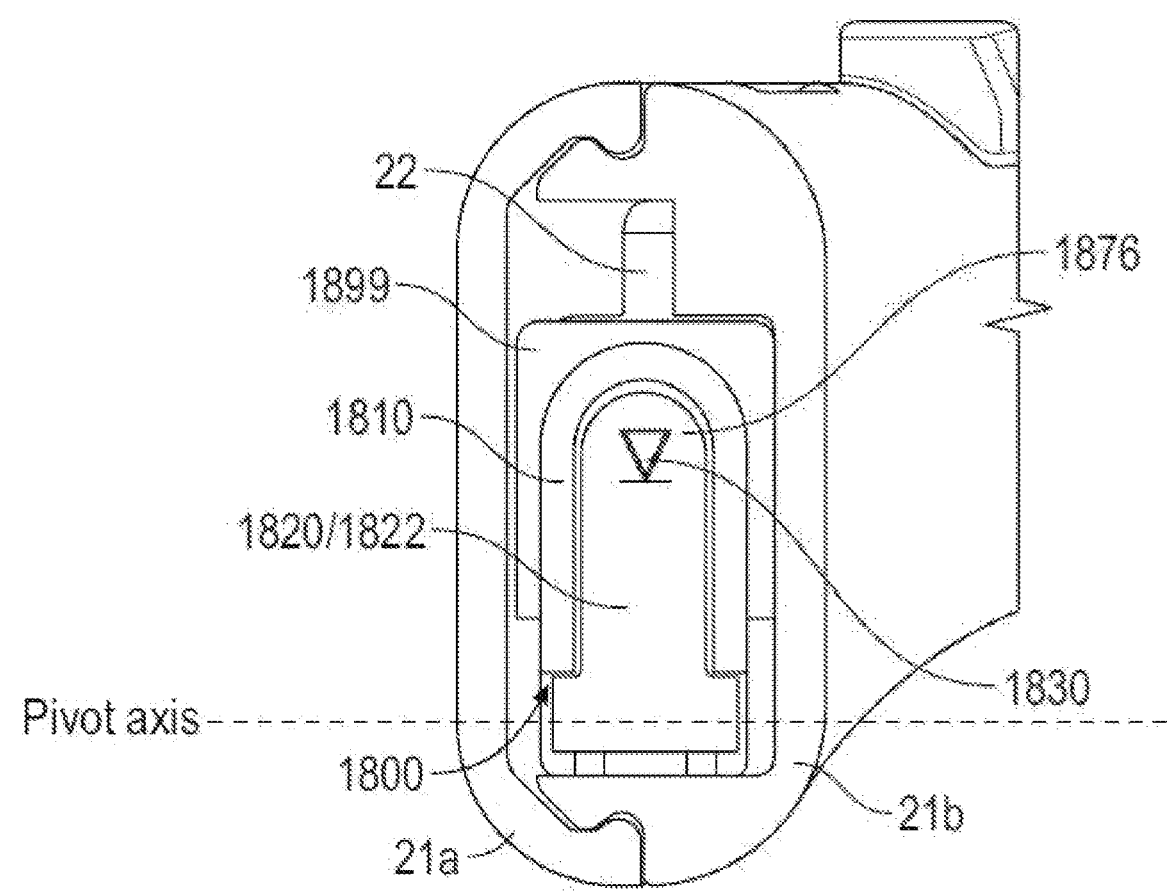
FIG. 12a is a cross sectional view showing a directional adjustment unit having a triangular aperture according to an embodiment assembled in a yoke assembly.
Figure 12B:
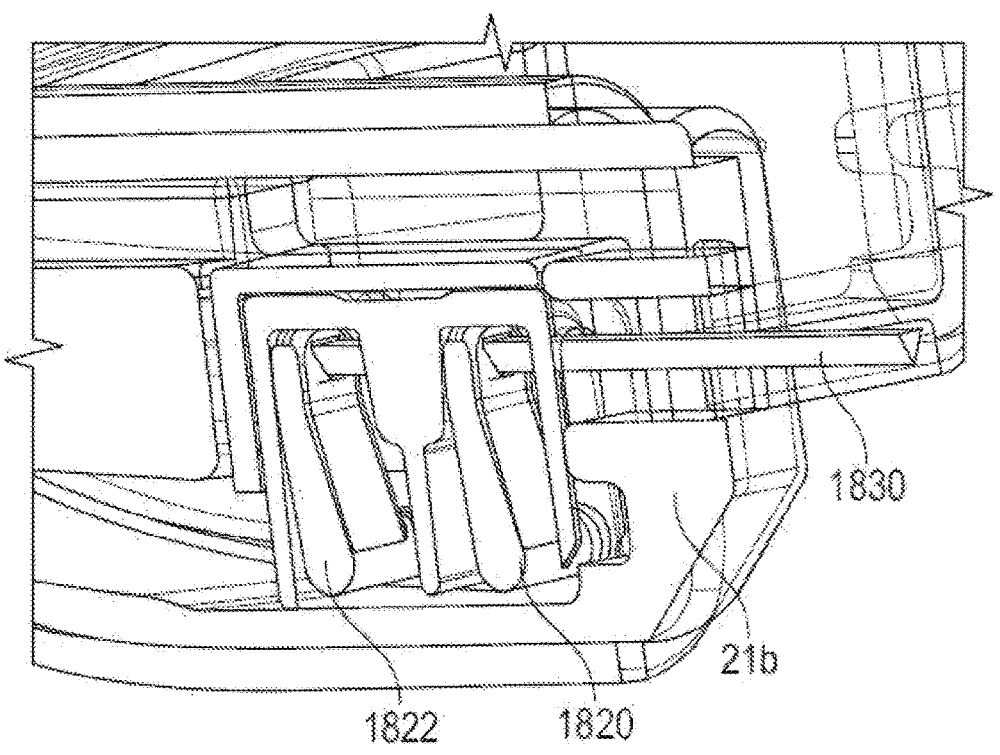
Figure 12C:
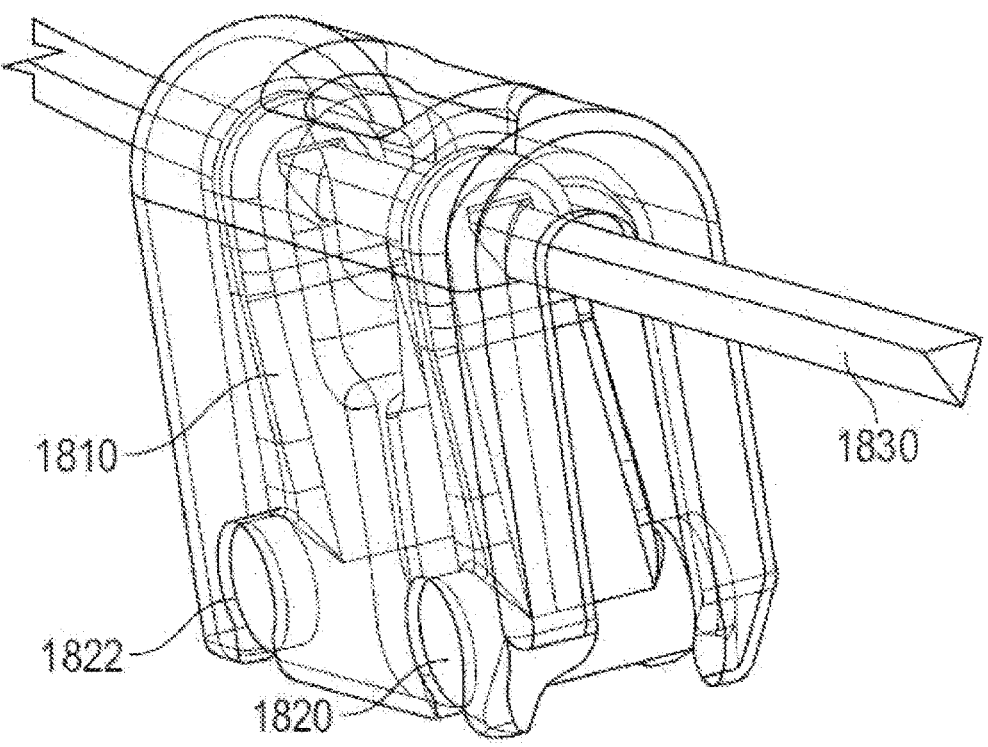
FIG. 12c is a cutaway perspective view of the directional adjustment unit of FIG. 11a where the associated housing to which the frictional engagement members are pivotally arranged is semi-transparently shown.

Such a configuration is shown with reference to FIG. 12*a*. FIG. 12*a* is a transverse cross sectional view, similar to that of FIG. 6, showing a directional adjustment unit having a triangular aperture 1876 according to an embodiment. FIG. 12*b* is a transverse cross sectional exploded perspective view of the directional adjustment unit of FIG. 12*a*. FIG. 12*c* is an alternative cutaway perspective view of the directional adjustment unit of FIG. 11*a* where the associated housing 1810 to which the frictional engagement members 1820, 1822 are pivotally arranged is semi-transparently shown.

As shown with reference to FIGS. 12*a* to 12*c* the triangular aperture has a vertex arranged closer to the pivot axis of the frictional engagement member 1820, 1822 than the side being parallel or substantially parallel to the pivot axis. In other words, a vertex of the triangular aperture points towards the pivot axis.

In some configurations, the triangular aperture may be arranged at any other angular orientation in relation to a central axis around which the cross sectional aperture shape is symmetrically provided. In other words, the triangular aperture may be orientated in any desired orientation rotated about the longitudinal axis of the filament 1830.

In some configurations, the aperture may have a polygonal transverse cross section having more than four sides, for example 5 to 12 sides. Here, the aperture forms a polygon in transverse cross section. The polygonal transverse cross section may be regular (i.e. all sides of the polygon equal length and all internal angles equal), or irregular (i.e. any polygon that is not regular), or concave (i.e. having at least one internal angle greater than 180 degrees), or convex (i.e. having no internal angles greater than 180 degrees).

In an embodiment, aperture 1876 extends through the at least one frictional engagement member 1820, 1822 perpendicular or substantially perpendicular to the pivot axis of the frictional engagement member 1820, 1822.

In some configurations, the aperture 1876 may extend through the at least one frictional engagement member 1820, 1822 symmetrically around a central aperture axis which is substantially perpendicular to the pivot axis, that is, substantially aligned with the longitudinal axis of the filament 1830, and extending from the front face of the frictional engagement member 1820, 1822. The aperture 1876 therefore defines the entrance to a filament engaging cavity or bore which extends through the frictional engagement member 1820, 1822. The cavity or bore may comprise one or more straight or curved segments. In some configurations, the cavity or bore is substantially straight along its length. In some configurations, wherein the central aperture axis has a curvature in space, the cavity or bore is curved or arcuate or has at least one curved or arcuate portion along its length.

In some configurations, the aperture extending through the at least one frictional engagement member 1820, 1822 forms a cavity or bore defined by at least one interior cavity wall surface of the at least one frictional engagement member 1820, 1822.

In some configurations, as shown in FIGS. 6, 12a, 15b, 16c to 16e, 18e, at least one interior cavity wall surface has a linear or substantially linear or no-arcuate profile or portion in one or more frontal planes, wherein each frontal plane intersects the central axis of the bore or cavity at a distinct position thereof and comprises the normal vector of the central plane at said distinct position. This means that such flat profile of at least one interior cavity sidewall surface may be maintained along the length, or part of the length, of the cavity or bore in one or more regions between the front face of the frictional engagement member 1820, 1822 and the rear face of the frictional engagement member 1820, 1822.

In some configurations, the at least one interior cavity or bore wall surface has a linear or flat or substantially linear or flat profile along one or more central plane normal vectors, each central plane normal vector intersecting the central axis at different longitudinal positions thereof. Since the central plane normal vectors are parallel or substantially parallel to the pivot axis, it follows that at least one interior cavity wall surface has a linear or flat or substantially linear or flat profile along one or more lateral axes parallel or substantially parallel to the pivot axis of the frictional engagement member 1820, 1822, wherein each lateral axis intersects the central axis at longitudinal position thereof.

In other words, for any three orthogonal reference axes, the at least one interior cavity wall surface may have a linear or substantially linear portion or profile along one of said reference axes, while being non-linear with reference to the remaining two orthogonal reference axes.

In some configurations, the at least one interior cavity or bore wall surface maintains said transverse cross sectional linear or substantially linear portion or profile along a longitudinal portion of the central axis, i.e. for consecutive transverse cross sections along the central axis.

In some configurations, wherein the aperture 1876 has a rectangular transverse cross section, the cavity or bore is cuboidal.

In some configurations, wherein the aperture 1876 has a triangular transverse cross section, the cavity or bore has the shape of a triangular elongated body or prism.

Further attention is now drawn to the design of the frictional engagement member 1820, 1822.

In some configurations, the at least one frictional engagement member 1820, 1822 has a base member 1824 through which the pivot axis extends, and at least a first section 1872 extending from the base member 1824 in a direction perpendicular to the pivot axis.

In some configurations, the at least one frictional engagement member comprises a second section 1874 extending from an end of the first section 1872 in a direction away from the pivot axis, wherein the second section 1874 is arranged at an angle in relation to the first section. Such a frictional engagement member is shown with reference to FIGS. 1a to 1d, 4a, 8a to 11b, 12b to 12c, 13, 18a to 18f and 19.

Turning to FIG. 13 a cross sectional side view of a frictional engagement member of a directional adjustment unit 1800 according to an embodiment of our earlier disclosure as summarised in the first paragraph of this specification, is shown. As may be observed from FIG. 13, the first section 1872 extends from the base member 1824 in a direction perpendicular to the pivot axis. The second section 1874, optionally having a rectangular cross section, extends from the first section 1872 at an angle with reference to the first section 1872. The frictional engagement member aperture 1876 is provided in and extends though the second section 1874 along the central axis.

The upright frictional engagement member position shown in FIG. 13 shows the frictional engagement member position in the disengaged configuration. In this disengaged configuration the plane FFP comprising the front face is provided at a first perpendicular distance D1 from the pivot axis, and the plane RFP comprising the rear face is provided at a second perpendicular distance D2 from the pivot axis. As may be seen from FIG. 13, the first D1 and second perpendicular distances D2 are not equal, meaning that the second section is not symmetrically provided with reference to the pivot axis. In FIG. 13 the front face and rear face of the second section 1874 are parallel with a plane comprising the vertical axis and pivot axis. Given the configuration of FIG. 13, when the frictional engagement member pivots clockwise from the disengaged configuration towards the engaged configuration, due to the symmetrically offset second section 1874, a fixed point of the aperture 1876 will follow a parabola or radius of curvature shown in FIG. 13. In this configuration the fixed point of the frictional engagement member 1820, 1822 initially travels along an upwardly curved path before then travelling along a downwardly curved path.

FIG. 14 is a cross sectional side view of a frictional engagement member 1820, 1822 where the frictional engagement member comprises only a first section 1872, which can be referred to as a single section 1872. Accordingly, the associated aperture 1876 and cavity or bore is provided through the single section 1872. The frictional engagement member 1820, 1822 of FIG. 14 forms a non-angled or straight frictional engagement member or "flat" frictional engagement member, wherein the single section 1872 extends from the base member 1824 thereof along an axis, e.g. vertical axis, perpendicular to the pivot axis. In other words, the frictional engagement member of FIG. 14 consists of a single section and a base, wherein the single section 1872, in a plane having a normal vector parallel to the pivot axis, extends from the base symmetrically along an axis perpendicular to the pivot axis. Hence, the single section frictional engagement member does not further comprise a second section 1874.

The upright frictional engagement member position shown in FIG. 14 shows the frictional engagement member position in the disengaged configuration. In this disengaged configuration the plane FFP comprising the front face is provided at a first perpendicular distance D1 from the pivot axis, and the plane RFP comprising the rear face is provided at a second perpendicular distance D2 from the pivot axis. As may be seen from FIG. 14, the first D1 and second D2 perpendicular distances are equal. In FIG. 14 the front face and rear face of the first section 1872 are parallel with a plane comprising the vertical axis and pivot axis. Given the configuration of FIG. 14, when the frictional engagement member pivots clockwise from the disengaged configuration towards the engaged configuration, due to the symmetrically aligned first section 1872, a fixed point of the aperture (A) will follow a parabola or curvature with a radius defined with reference to the pivot axis shown in FIG. 14. In this configuration the fixed point of the frictional engagement member 1820, 1822 initially travels only along a downwardly curved path.

As may be seen in the embodiments of FIGS. 13 and 14, in the disengaged configuration, the central axis may align with the horizontal plane. As may be observed from FIG. 13, the center of the aperture is located horizontally rearwardly (i.e. to the left) from the pivot axis. Since the curvature is referenced to the pivot axis, i.e. the curvature follow a radius defined between the pivot axis and the center of the aperture along an axis perpendicular to the pivot axis symmetrically along the first part of the first section 1872. This means that the aperture follows the curvature initially upwards above the horizontal plane before following the radius of curvature downwards. In other words, in FIG. 13, a segment of the radius of curvature is located above the horizontal plane intersecting the central axis at the face of the frictional engagement member in the disengaged configuration. The associated upward and downward movement while following the curvature causes contact between the frictional engagement member and filament to occur at different points throughout this movement. Accordingly, a frictional engagement member having the configuration of FIG. 13 may experience wear at several points or locations along the interior cavity sidewall surfaces of the aperture. The situation is different in FIG. 14. Here, the frictional engagement member locates the center of the aperture vertically in line with and above the pivot axis which means the aperture will only travel on a downward curvature on its way from the disengaged configuration to the engaged configuration. This leads to more consistent contacting points between the frictional engagement member and filament. This may also in turn lead to a more consistent and repeatable friction force to be generated by the frictional engagement member.

In some configurations, as that shown with reference to FIG. 13, the at least first section 1872 has a tapered cross section in plane perpendicular to the pivot axis. It should be appreciated that a tapered cross section may be provided to a single section 1872 frictional engagement member configuration, e.g. that shown in FIG. 14, as well. The tapered section may provide the first section 1872 with increased rigidity.

In some configurations, as that shown with reference to FIG. 14, the at least first section 1872 has a rectangular cross section in plane perpendicular to the pivot axis.

In some configurations, in the engaged configuration the at least one transverse cross sectional linear or substantially linear region of the at least one frictional engagement member is arranged to be in frictional engagement with a corresponding flat or substantially flat region of the filament, in use.

Figures 15A, 15B, 15C, 16A, 16B:
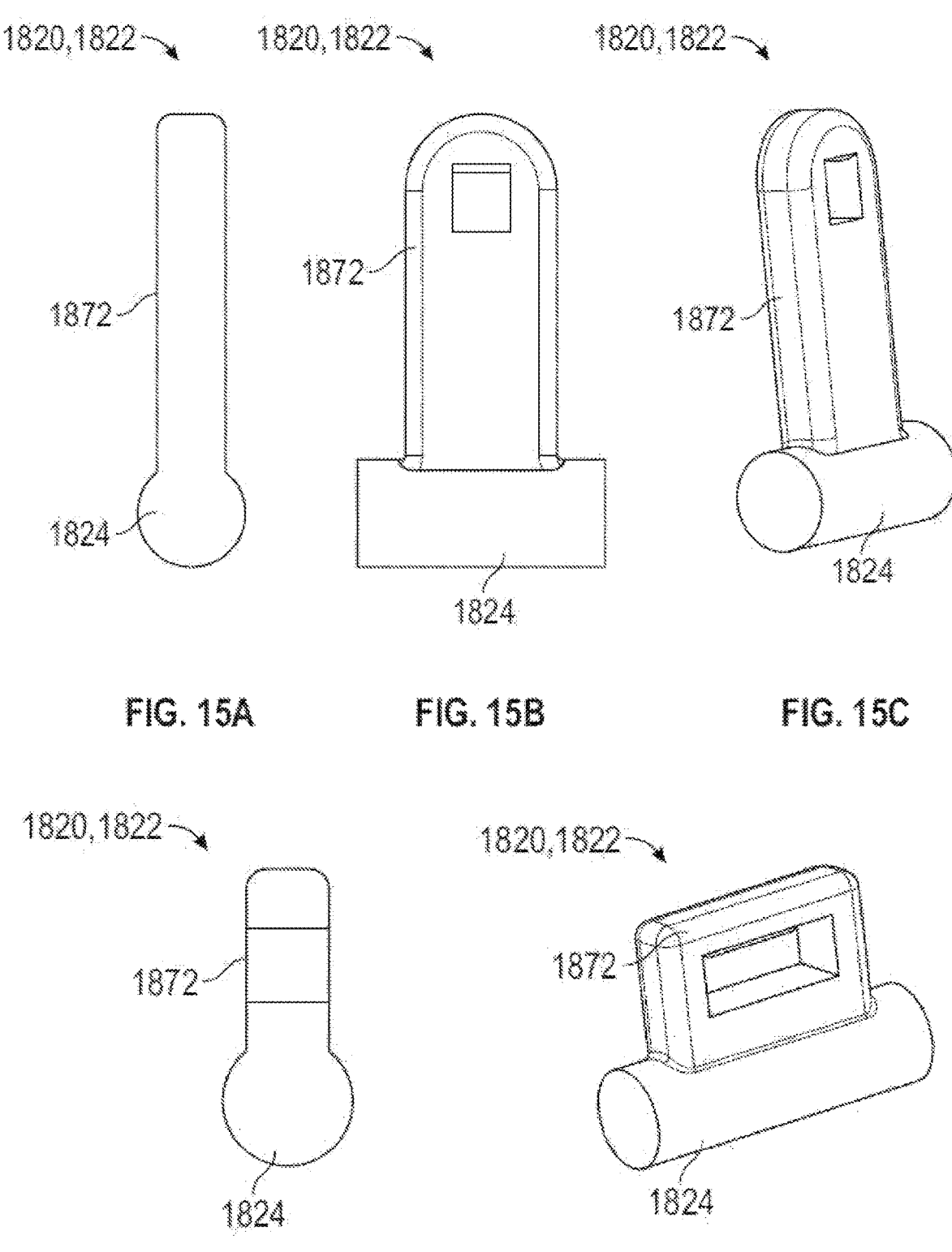
FIGS. 15a to 15c show a respective cross sectional side view, front view, and a perspective view of a single section frictional engagement member.
FIGS. 16a to 16b show a cross sectional side view and perspective view of a single section frictional engagement member.

FIGS. 15a to 15c show a respective side view, front view, and a perspective view of a single section frictional engagement member 1820, 1822. Similar to FIG. 14, the frictional engagement member may be symmetrical about the vertical axis when viewed from the side (see FIG. 15a). This may enable the frictional engagement member 1820, 1822 to be inserted into the frictional engagement member housing 1810 in either orientation during assembly which would minimize any issues with the assembly process.

FIGS. 16a to 16b show a side view and perspective view of a single section frictional engagement member according to another embodiment. As compared to the embodiment shown in FIGS. 15a to 15c, the frictional engagement member of FIGS. 16a and 16b has a shorter first section 1872. Furthermore, the width of the first section is made larger, than that shown in FIGS. 15b and 15c. This provides for a significantly wider aperture than that of the frictional engagement member 1820, 1822 of FIGS. 15a to 15c.

As such the frictional engagement member 1820, 1822 of FIGS. 16a to 16b may employ a significantly wider filament than that of previous embodiments. The wider filament may offer benefits such as improving kink resistance by spreading the force load over a larger contact area. It may also resist twisting which will lead to a reduced occurrence of the headgear becoming twisted in the packaging/storage.

It should be appreciated that in some configurations the frictional engagement member 1820, 1822 may be flipped or rotated 90 degrees so that the widened side of the filament 1830 runs parallel to the face of the patient. Rotating the frictional engagement member 1820, 1822 may also enable the frictional engagement member to fit into a current yoke housing without significant modifications being needed.

In alternate configurations, the entire directional adjustment unit with frictional engagement members and housing may be flipped such that only the internals of the yoke that the frictional engagement member sits in needs modification.

FIG. 16c shows a front view of a single section frictional engagement member 1820, 1822 identifying a number of adjustable dimensions.

Table 1 below identifies a suitable ranges for said adjustable dimensions according to some configurations. However, these dimensions should not be considered limiting. Other dimensions could also be used without departing from the scope of the present invention.

TABLE 1

| | Dimension | | | | | |
| --- | --- | --- | --- | --- | --- | --- |
| | H1 | H2 | H3 | W1 | W2 | W3 |
| As Below | 5.00 mm | 1.00 mm | 1.00 mm | 12.00 mm | 1.00 mm | 10.00 mm |
| Minimum | 1.00 mm | 0.80 mm | 0.50 mm | 3.50 mm | 0.50 mm | 2.50 mm |
| Maximum | 20.00 mm | 2.50 mm | 3.00 mm | 24.50 mm | 3.00 mm | 18.50 mm |

FIG. 16d shows a front view of a single section frictional engagement member having a first set of dimensions of an embodiment, where H1 is 20 mm. FIG. 16e shows a front view of a single section having a second set of dimensions of an embodiment, where H1 is 1 mm. FIGS. 16d and 16e show two examples at each end of an example group of possible range of frictional engagement members 1820, 1822 within the scope of this disclosure.

Figure 17A:
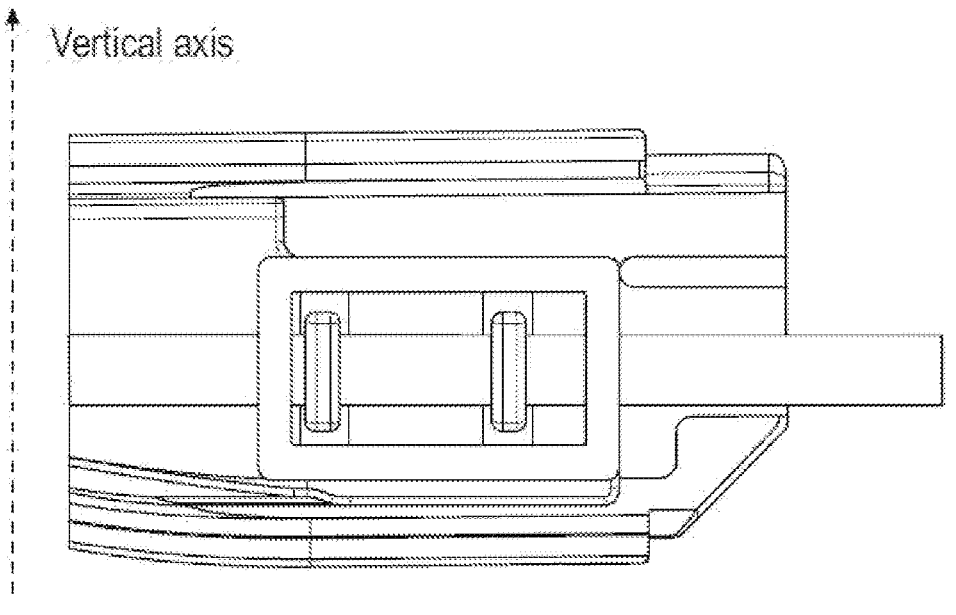
FIG. 17a is a cutaway side view of a directional adjustment unit having two single section frictional engagement members having respective pivot axis extending parallel to the vertical axis.

FIG. 17a is a cutaway side view of the directional adjustment unit 1800 having two single section 1872 frictional engagement members 1820, 1822 having respective pivot axis extending parallel to the vertical axis.

Figure 17B:
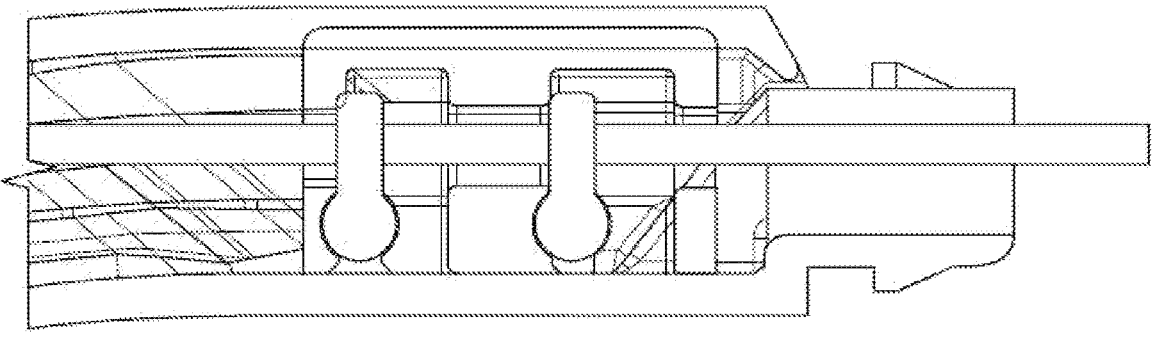

FIG. 17b is a cutaway top view of the directional adjustment unit 1800 of FIG. 17a.

FIGS. 18a to 18j shows respective different view of a double/two section frictional engagement member 1820, 1822 according to an embodiment of this disclosure. FIG. 18a shows a side view of the double section frictional engagement member having a rounded edge formed at an upper intersection between the front face, i.e. right hand face in the Figures, of the frictional engagement member 1820, 1822 and the aperture 1876. FIG. 18b shows an alternative side view of the double section frictional engagement member 1820, 1822 of FIG. 18a, wherein the aperture area is filled for clarity. FIG. 18c shows a contour side view of the double section frictional engagement member of FIGS. 18a and 18b. FIG. 18d shows a side design view of the double section frictional engagement member of FIGS. 18a to 18c. FIG. 18e shows a front view of the double section frictional engagement member of FIGS. 18a to 18d. FIG. 18e shows a rear view of the double section frictional engagement member of FIGS. 18a to 18e. FIG. 18g shows a perspective cross sectional view of the double section frictional engagement member of FIGS. 18a to 18f. FIG. 18h shows a perspective view of the double section frictional engagement member of FIGS. 18a to 18g. FIG. 18i shows a perspective contour front view of the double section frictional engagement member of FIGS. 18a to 18h. FIG. 18j shows a perspective contour rear view of the double section frictional engagement member of FIGS. 18a to 18i.

Figures 19A, 19B, 19C:
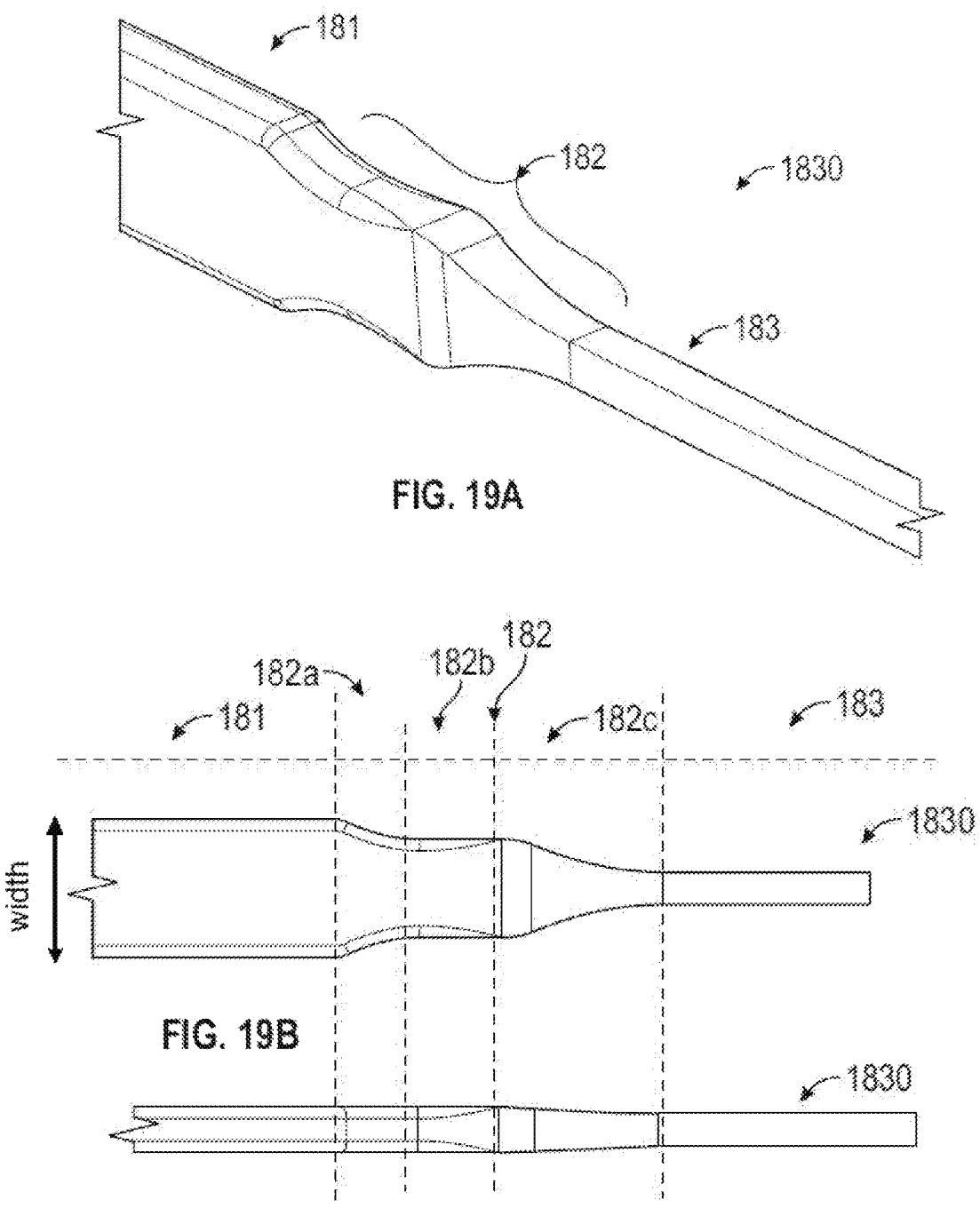

FIGS. 19a to 19c show respective perspective views, side views, and top views of a filament 1830 for a headgear for a respiratory interface or mask according to an embodiment of this disclosure. The filament 1830 comprises a filament body extending along a longitudinal axis thereof. The filament body comprises a core region 181 having a first geometrical shape. The filament body further comprises an end region 183 having a second geometrical shape, wherein the filament 1830 in the end region 183 has at least one flat or substantially flat exterior surface extending along a longitudinal axis thereof. It is this end region 183 of the filament 1830 that engages with the directional adjustment unit 1800, in use. Moreover, the filament body comprises an transitional region 182 provided longitudinally between the core region 181 and the end region 183. The transitional region 182 has a shape transitioning from the first geometrical shape of the core to the second geometrical shape of the end region 183 over a longitudinal distance along the longitudinal axis of the filament body.

In some configurations, the transitional region 182, in at least a portion thereof, has a size, i.e. at least one cross sectional dimension, being larger than that of an external opening 1860 of the frictional engagement member housing 1810, in use. In this way the transitional region 182, or at least core region 181, will be blocked from fully entering the frictional engagement member housing 1810. As shown with reference to FIG. 19b, the transitional region 182 may in a cross sectional side view comprise a first narrowing structure 182a, optionally having a curvature, wherein the width reduces from that of the core region to an intermediate width. The transitional region 182 may further comprise an intermediate region 182b wherein the width is substantially constant following the first narrowing structure 182a. Moreover, a second narrowing structure 182c, following the intermediate region 182b, and optionally having a further curvature, has a width reducing from the that of the intermediate region 182b to that of the end region 183 of the filament 1830.

Figure 20A:
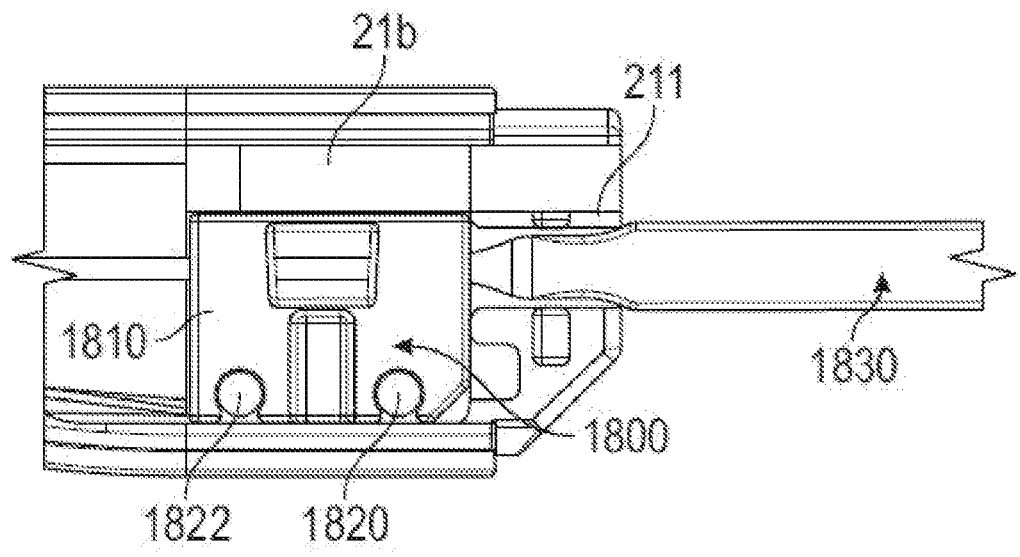
FIG. 20a shows a side cutaway view of a yoke assembly comprising a directional adjustment unit and a filament according to an embodiment.
Figure 20B:
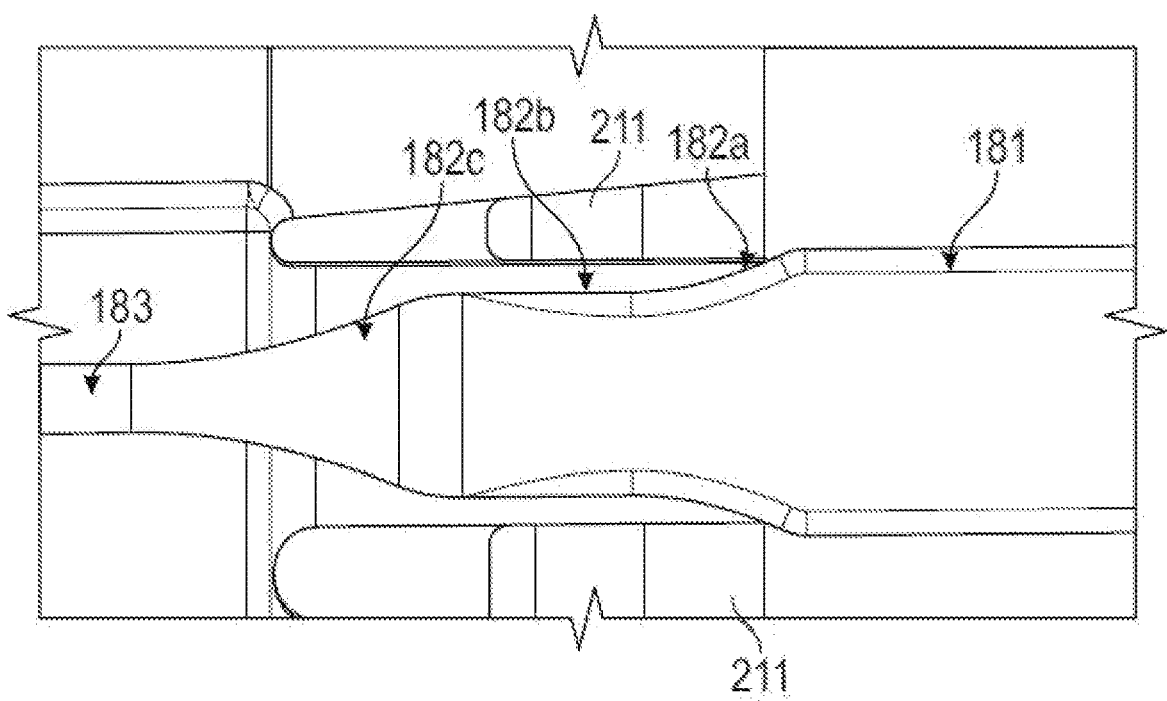
FIG. 20b shows a zoomed in cutaway side view of the arrangement of FIG. 20a highlighting the interaction between the filament and yoke assembly.

FIG. 20a shows a side cutaway view of a yoke assembly 20 comprising a directional adjustment unit 1800 and a filament 1830 of FIGS. 20a and 20b according to an embodiment of this disclosure. A hard stop, formed by the size of at least a portion of the transitional region 182 being larger than a receiving structure of the yoke housing 211 in FIG. 20a, of the yoke assembly 20 restricts the strap from entering too far into the housing 1810. High bending resistance at this point minimizes risk of the associated yoke assembly 20 getting twisted relative to headgear in relaxed state where the transitional region of the strap transitions, tapers or curves towards the smaller sized filament 1830 at the end so that it can be snugly inserted into the yoke housing. This provides high bending resistance which reduces the risk of the strap twisting and kinking when being stored or not in use.

FIG. 20b shows an enlarged cutaway side view of the arrangement of FIG. 20a illustrating the strap with the line track/yoke/frictional engagement member housing 1810 where the transitional region 182 at a longitudinal position thereof provides a hard stop to limit the transitional region 182 from being inserted too far inside the housing 1810 which could damage the directional adjustment unit 1800 and/or inhibit the directional adjustment unit 1800 from functioning correctly.

In an embodiment, the rectangular transverse cross sectional (i.e. perpendicular to the longitudinal axis of the filament) dimensions of the filament 1830 may be 0.85 mm (W) by 0.85 mm (H), meaning 0.85 mm wide and 0.85 mm height in cross section. In such a configuration the rectangular transverse cross section forms an equilateral rectangle, i.e. a square.

In other embodiments, the dimensions may vary, so that each side of the filament 1830 has a size in the range of 0.7 mm to 3 mm. This means that the filament could have a cross section of a square of 0.85 mm×0.85 mm, a rectangle of 0.75 mm×2.5 mm, a square of 3.00 mm by 3.00 mm, a triangular cross section with one 3.00 mm side and two 1.5 mm sides, or any other combination of dimensions.

Experiments have shown that the size, e.g. at least one cross sectional dimension, of the filament 1830 being 30 to 200 microns smaller than that of the aperture of the frictional engagement member 1820, 1822 allows for a proper clearance for the two components to functionality work satisfactory in the disengaged and engaged configuration.

In some configurations, the ratio of the area of the frictional engagement member aperture 1876 transverse cross section (seen at the face of the frictional engagement member) to the filament 1830 transverse cross section can range from 1:1.0201 to 1:1.3061.

Table 2 below identifies a selection of example dimensions, including the example ratios, for an aperture and filament with rectangular transverse cross section. The ratio of A:F can therefore be in the range of 1:1 to 1:1.5.

TABLE 2

| Filament | | | Aperture | | | |
|---|---|---|---|---|---|---|
| Height (mm) | Width (mm) | Area (mm^2) | Height (mm) | Width (mm) | Area (mm^2) | Ratio A/F |
| 0.70 | 0.70 | 0.4900 | 0.73 | 0.73 | 0.5329 | 1.0876 |
| 0.70 | 0.70 | 0.4900 | 0.80 | 0.80 | 0.6400 | 1.3061 |
| 0.85 | 0.85 | 0.7225 | 0.88 | 0.88 | 0.7744 | 1.0718 |
| 0.85 | 0.85 | 0.7225 | 0.95 | 0.95 | 0.9025 | 1.2491 |
| 3.00 | 3.00 | 9.0000 | 3.03 | 3.03 | 9.1809 | 1.0201 |
| 3.00 | 3.00 | 9.0000 | 3.10 | 3.10 | 9.6100 | 1.0678 |

Filament

Figures 23A, 23B:
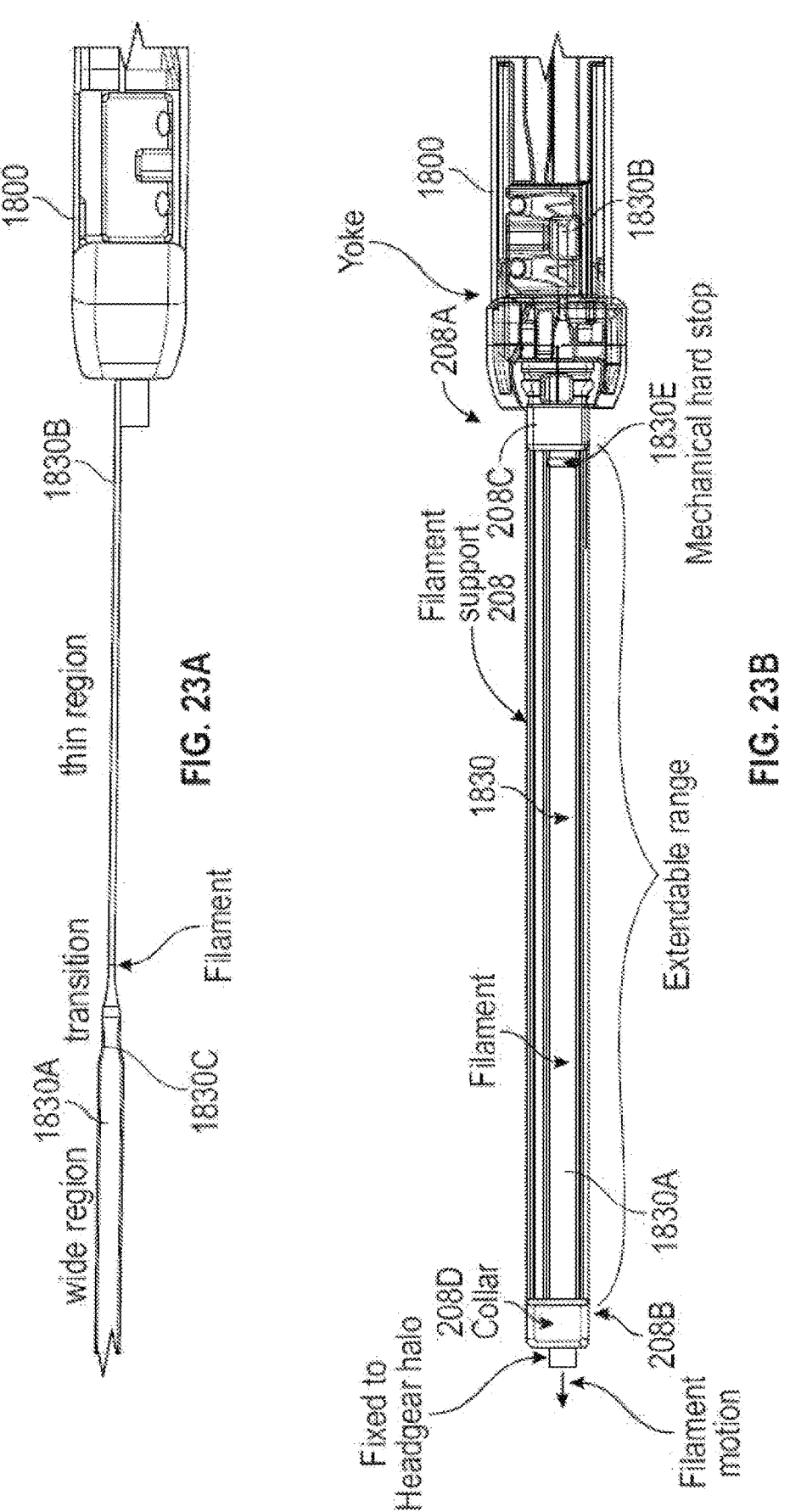
FIG. 23a shows a cutaway view of our prior directional adjustment unit.
FIG. 23b shows a cutaway view of a directional adjustment unit in accordance with this disclosure.

We have proposed, with reference to FIG. 23*a*, a filament 1830 or elongate flexible member, that is received in and engages with the directional adjustment unit 1800, to adjust the tension (the effective length) of the headgear in use.

Our prior filament 1830 comprises a filament body extending along a longitudinal axis thereof. The filament body comprises a core region having a first geometrical shape and being of relative wide transverse cross section. The filament body further comprises an end region having a second geometrical shape, of narrower transverse cross section. It is this end region 183 of the filament 1830 that engages with the directional adjustment unit 1800, in use. Moreover, the filament body comprises a transitional region provided longitudinally between the core region and the end region. The transitional region has a shape transitioning from the first geometrical shape of the core to the second geometrical shape of the end region over a longitudinal distance along the longitudinal axis of the filament body.

The filament in prior designs has been provided with an elastic braided outer sleeve inside which the filament can move. The braided outer sleeve extends as the prior filament moves inside the directional adjustment unit. The elastic limit of the braid provides a stop function which limits the amount by which the filament can slide into the directional adjustment unit 1800. The braided outer sleeve could be knitted or woven for example. The elasticity of the outer sleeve provided some return bias to the headgear when the outer sleeve is elongated.

The filament of the current disclosure is provided with an integral stop, on the filament itself, negating the need to provide the braided outer sleeve of prior designs.

In some configurations, the transitional region, in at least a portion thereof, has a size, i.e. at least one cross sectional dimension, being larger than that of an external opening 1860 of the frictional engagement member housing 1810, in use. In this way the transitional region, or at least core region, will be blocked from fully entering the frictional engagement member housing.

A stop, formed by the size of at least a portion of the transitional region being larger than a receiving structure of the yoke housing of the yoke assembly can assist in restricting the strap from entering too far into the housing.

This stop resists the filament being pulled two far into the directional adjustment unit 1800.

Figure 21A:
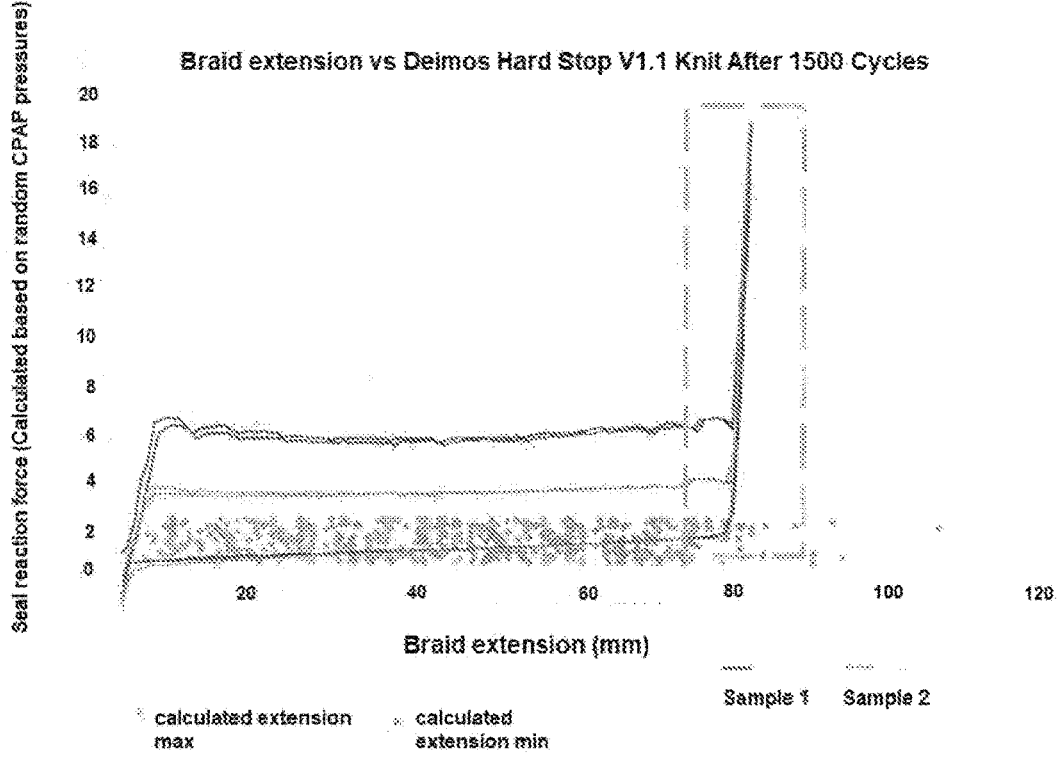
FIG. 21a shows the ideal performance of our prior directional adjustment unit, with the ideal force spike being contained in dashed box.

With reference to FIG. 21*a*, the force spike, contained in the dashed box in FIG. 21*a*, describes the ideal performance of the original mechanical stop in the force profile. There is a resultant sudden increase in force while the increase in braid extension is relatively low.

Figure 21B:
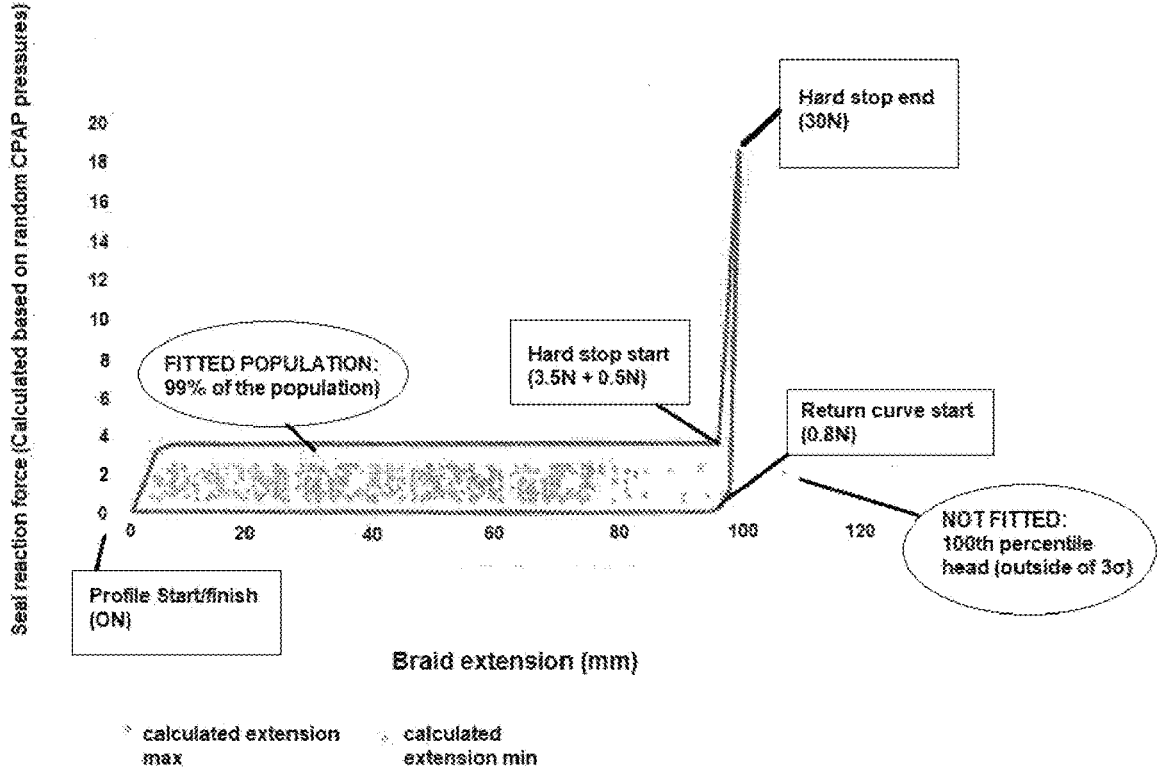
FIG. 21b shows the force profile of an ideal mechanical stop in a directional adjustment unit according to an embodiment.

An improved stop would yield a force profile approximately as shown in FIG. 21*b*. The seal reaction force corresponding to the pull force of the directional adjustment unit (contributed by frictional engagement members and the stretching of the braid of the filament) is constant, until a steep increase when a mechanical stop is activated.

In our earlier design, there is a relatively large increase in elastic force before the braided outer sleeve reaches its maximum (elastic) extension to provide the stop. Although the braided outer sleeve stop performs initially as described in FIG. 21*a*, it gradually stiffens with each cycle as debris builds up within it. Further, users at the large end of the fitting range who require large extensions of the braided outer sleeve for mask fitting will experience a high elastic force. This leads to the mechanism effectively behaving as a simple elastic mechanism.

Force Characteristics and Stop

Aspects of the current disclosure provide a mechanical stop on a filament for a directional adjustment unit, where the mechanical stop is not formed by the braided outer cover. The braid knit or weave will not enter the above described undesirable extension range with the use of a mechanical stop on the filament itself. Therefore, users are able to acquire the balanced fit of the mechanism without a large braid elastic force pulling the headgear into their face (i.e. without causing undesired pressure). Further, users will not be required to exert as much force when extending the headgear to a sufficient length for mask fitting.

This improvement is described in the modified force profile in FIG. 5. The simple elastic mechanism of the braided outer cover (in solid line) is activated around 45 mm extension, in this example, while that of the mechanical stop (in dashed line) on the filament in accordance with the current disclosure is activated at a longer extension length of around 58 mm, in this example. This effectively increases the fitting range of the mechanism with a constant pull force.

Comparison Between Previous Filament and Filament of Current Disclosure

With reference to FIG. 23*a*, our previous filament had a region of relatively smaller cross section 1830B, for example small or thin thickness or width or transverse cross section, that spans along the majority of its length. This smaller region is received in a directional adjustment unit 1800 as described above. The region of larger cross section 1830A, for example larger or wider thickness or width or transverse cross section, extends along a filament support structure, and is secured to the headgear.

With reference to FIGS. 23*b*, 6*c*, a filament in accordance with this disclosure also features a length of relatively smaller cross section filament 1830B which passes through the frictional engagement members of the directional adjustment unit 1800, however, its larger cross section region 1830A extends along a larger portion of the length of the overall filament. With a larger portion of the length of the filament featuring a larger cross section, the filament 1830 as a whole is more durable and stable. In addition to this, due to the reduced length of the smaller region, this smaller region is less likely to buckle.

In one example, the larger region 1830A of the filament has a width of 3.5 mm while the smaller region 1830B has a width of 0.86 mm. There is an inclined transition region 1830C between these two regions in which the thickness or width or transverse cross section of the filament 1830 tapers from the larger region 1830A to the smaller region 1830B. In one example, the length of the larger region 1830A is approximately 100 mm (including transition region) and that of the smaller region 1830B is approximately 95 mm. These lengths however may be variable depending on other features of the directional adjustment unit 1800 such as the yoke, frictional engagement members, and filament support structure 208. For example, the length of the yoke containing the smaller region 1830B of the filament may be reduced, leading to a reduction in the length of the smaller region 1830B of the filament 1830. The length must be short enough to be contained by the yoke, but also long enough that the filament 1830 does not leave the yoke when it is pulled out. This is also dependent on the location of the mechanical stop.

In one example the thickness of the smaller region is approximately 0.86 mm while that of the larger region is approximately 1.20 mm. Thickness is measured between the interior and exterior surfaces of the filament 1830.

Figure 23C:
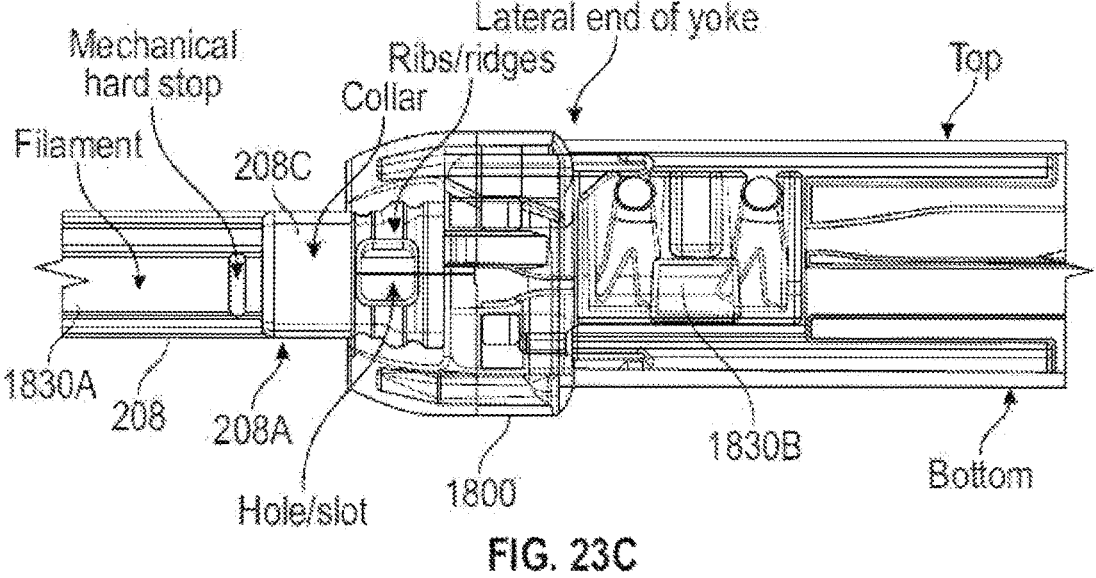
FIG. 23c shows an enlarged cutaway of the directional adjustment of FIG. 23b.
Figure 24:
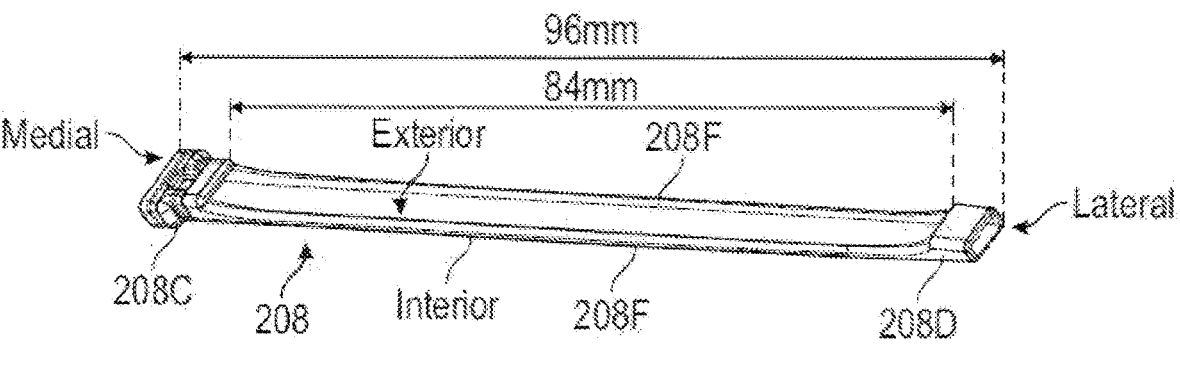
FIG. 24 is a perspective view of a filament support structure of the directional adjustment unit of FIGS. 23b and 23c.

With further reference to FIGS. 23b and 23c, the lock assembly 1 in accordance with this disclosure comprises a directional adjustment unit 1800 as described above, a filament support structure 208 as described above, and a filament 1830. The filament support structure 208, with additional reference to FIG. 24, in accordance with this disclosure is elongate and rigid or semi rigid, and extends between the directional adjustment unit 1800 at a medial end 208A, and the headgear at the other, lateral end 208B. Each end 208A, 208B comprises a hollow collar 208C, 208D, through which the filament 1830 extends. Whilst the filament support structure 208 guides but does not wholly encapsulate the filament 1830 along its length, each collar 208C, 208D extends around the circumference of the filament 1830 to constrain the filament 1830. Each collar 208C, 208D functions as an end stop, limiting the range of movement, or the extendable range, of the filament 1830.

As described above the filament 1830 comprises a larger region 1830A and a smaller region 1830B having a smaller width, thickness and/or cross sectional area. The smaller region 1830B extends into the directional adjustment unit 1800 and the frictional engagement members 1824 thereof. The filament 1830, at a region adjacent a transitional region 1830C of the filament 1830, is provided with a mechanical stop feature 1830E in the form of a rigid formation being a projection or lug or bar or rib that projects radially outwardly from the filament 1830, away from the filament longitudinal axis. The mechanical stop 1830E projects outwardly sufficiently to abut the collars 208C, 208D when the filament 1830 is slid through those collars 208C, 208D. Thus, in the fully retracted configuration shown in FIG. 23b, the filament stop 1830E abuts medial end collar 208C to prevent the filament being further pulled through the directional adjustment unit 1800 in a retracting direction. This abutment forms a non-elastic limit on the amount by which the filament 1830 can extend through the directional adjustment unit 1800, that is, a limit not dependent on any elastic properties of the filament itself. As the filament 1830 is released from the directional adjustment unit 1800, the filament 1830 moves in an extending direction away from the directional adjustment unit 1800 so that stop 1830E abuts the lateral end collar 208D, thus limiting the amount by which the filament 1830 can be pulled from the directional adjustment unit 1800. Advantages of the mechanical stop 1830E and its abutment with collars 208C, 208D, are described above and below.

Filament Support Structure

The filament 1830 is supported by a filament support structure or filament support element 208 in the form of a sheath of a slightly wider width than the larger region 1830B of filament 1830 and with collars 208C, 208D that hold the filament 1830 close to it. The modified filament 1830 feeds through both collars 208C, 208D while being supported by the support structure 208. The support structure 208, with collars 208C, 208D on both ends, otherwise comprises, in this example, a rectangular length of rigid material (e.g. plastic), which supports the filament 1830 on one side only. In terms of orientation, the support structure 208 lays behind the filament 1830 and provides an interface, or intermediate layer, between the user's skin and the filament 1830. The collars 208C, 208D face outwards, away from the user's face.

The lateral-end collar 208D closer to the headgear 200 is a simple rectangular shape while the medial-end collar 208C connected to the yoke of the directional adjustment unit 1800 comprises a rectangular shape (exposed outside of the yoke), but also a further extension which is contained by the yoke (or yoke clip) and increases in width and thickness. This extension also features ribs/ridges 208E surrounding its perimeter and an aperture 208G on the exterior surface (and/or interior surface) to achieve a strong anchorage/bonding of the support structure 208 within the lateral ends of the yoke of the directional adjustment unit 1800. This may be done using an overmoulding process. A sufficient anchor may be achieved in various other ways, specifically any shape that can achieve a mechanical connection between the two components.

The support structure 208 itself is made of a material with sufficient rigidity to support the filament 1830 but whilst preferably being somewhat flexible to be able to curve around and adapt to the contour of the user's face/cheeks. It is preferably constructed of the same material as the filament 1830 (Pebax 7433).

The filament support structure 208 comprises a pair of elongate guide surfaces 208F that extends along the filament support structure parallel to the longitudinal axis of the filament support structure, and which constrains the filament relative to the filament support structure in a direction perpendicular to the longitudinal axis. The elongate guide surfaces ramp upwardly from the main body of the support structure 208 to each collar 208C, 208D.

Medial End Collar

FIGS. 25 to 29, 36 and 37 show some further detail of the medial end 208A of the filament support structure 208, and the medial end collar 208C. The exterior surface of the collar 208C comprises multiple radially outwardly extending ribs 208E which cause the medial end 208A to increase in size and perimeter length away from the main body of the filament support structure 208. These ribs 208E assist in retaining the medial end 208A of the filament support structure in the yoke cap Y of the directional adjustment unit 1800. The medial end 208A is also provided with a centrally located oblong aperture 208G through which the filament 1830 is exposed.

These figures show some possible dimensions of parts of the medial end collar 208C. These dimensions are examples only and not limiting.

Figures 36, 37A, 37B:
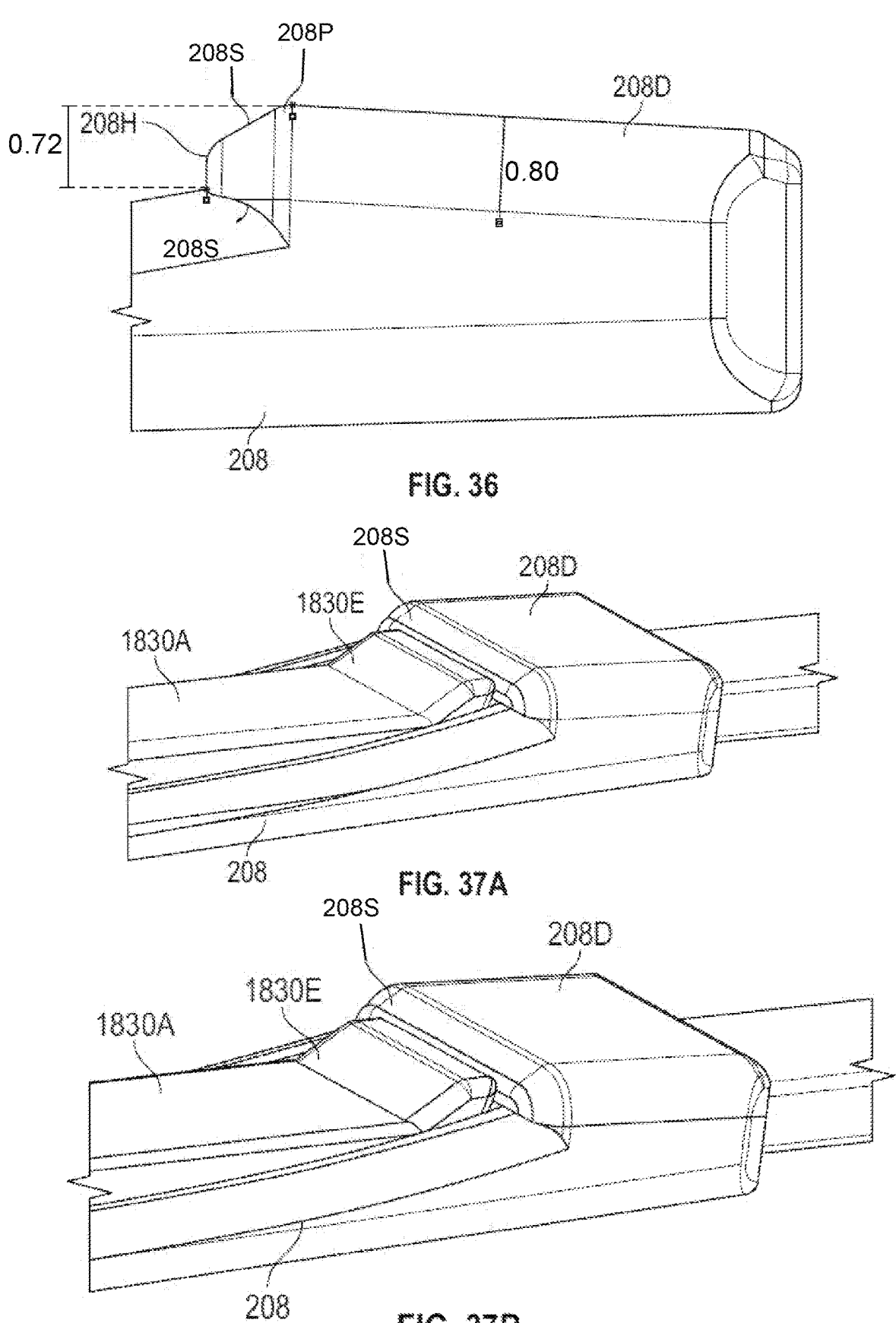
FIG. 36 is an enlarged view of a lateral end of the filament support structure of FIG. 24.
FIGS. 37a to 37c are enlarged perspective views of the lateral end of FIG. 36 with a filament.
Figure 37C:
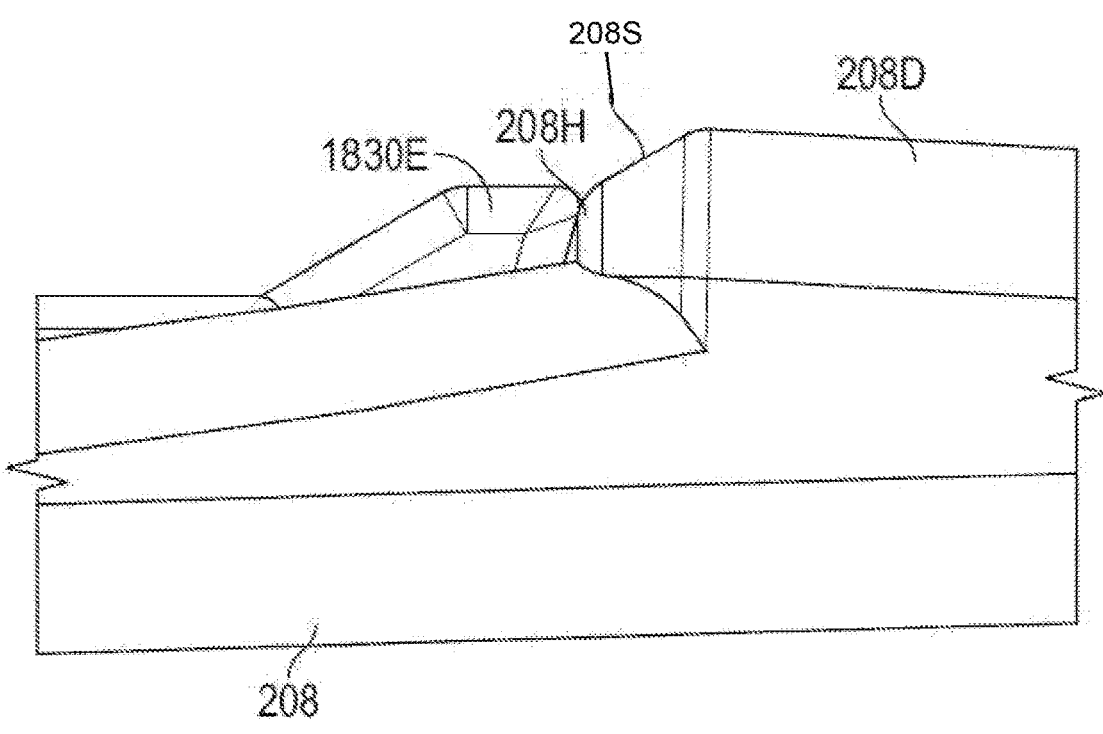
Figure 38:
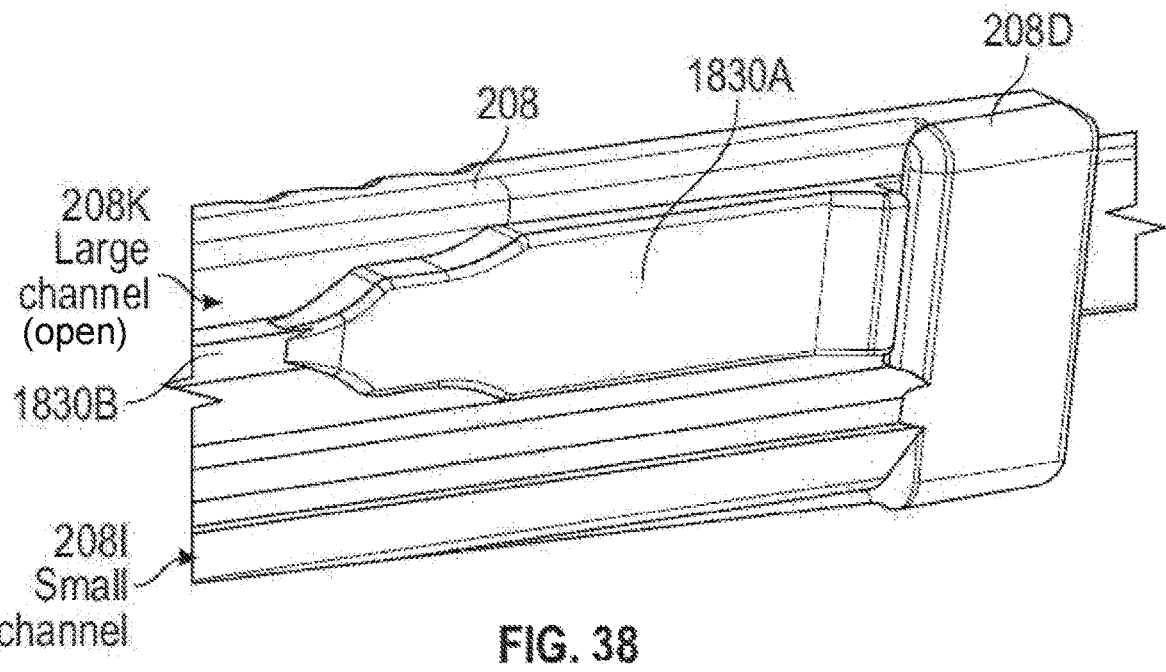
FIG. 38 is a perspective side view of a stop, filament and support structure according to another embodiment.

The shape and features of the medial end collar 208C can be further seen in FIGS. 36 and 37. The collar 208C tapers inwardly, when viewed from the side, towards the medial end of the filament support structure 208. The part of the collar 208C that abuts the filament stop 1830E, comprises a protruding bar or strip 208P which extends across the width of the filament support structure 208 and comprises a forward face 208H against which the filament stop 1830E abuts when the filament 1830 is fully retracted, supported by upper and lower inclined walls 208S. Below the bar or strip 208F, the sides of the filament support structure 208 ramp upwardly from the main body to the medial collar 208C. The forward face 208H is planar and occupies a plane which is substantially, but not perfectly, perpendicular to the longitudinal axis of the filament support structure 208.

Figure 27:
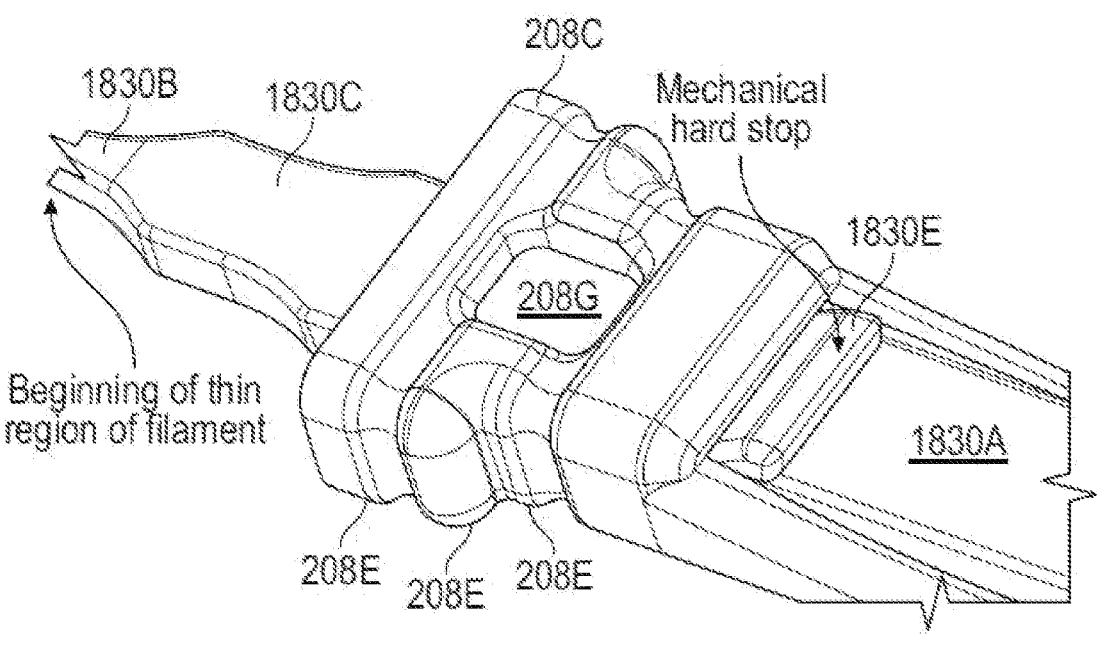
FIG. 27 is an enlarged perspective view of the medial end of FIGS. 25 and 26, with a filament in accordance with an embodiment.
Figure 28:
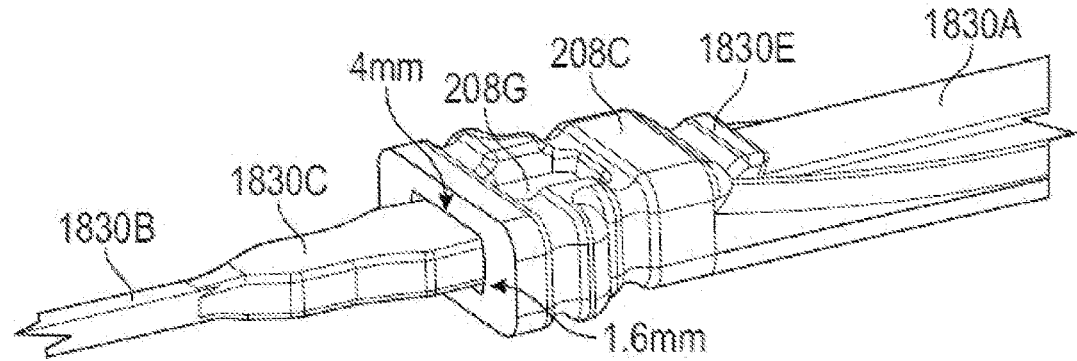
FIG. 28 is a perspective view of the medial end of the support structure with the filament of FIG. 27.
Figure 29:
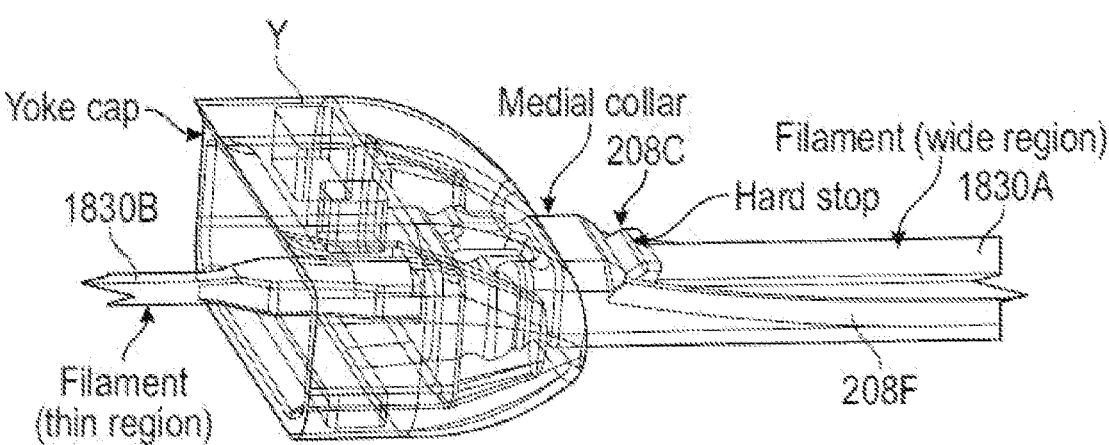
FIG. 29 is a perspective view of the medial end of the support structure with the filament of FIG. 27, showing a yoke cap of the directional adjustment unit.

As can best be seen in FIGS. 27 and 28, when the filament stop 1830E abuts the medial end collar 208C, the transitional region 1830C has passed through the collar 208C and is locate inside the yoke cap of the directional adjustment unit 1800.

Lateral End Collar

FIGS. 30 to 35 show some further detail of the lateral end 208B of the filament support structure 208, and the lateral end collar 208D. Collar 208D has a similar structure to collar 208C except that the ribs 208E are not present, the exterior of the collar 208D being smooth and planar, with the intersections between each face of the collar 208D being chamfered.

Example Dimensions

The channel or slot formed by the collars 208C, 208D through which the filament 1830 passes through has a height (interior/exterior direction) of 1.6 mm and width of 4 mm (top/bottom direction. The filament support structure 208 has a width (top/bottom direction) of 5.6 mm, thickness of 3.1 mm (interior/exterior direction) and overall length of 96 mm (medial/lateral direction) including the anchor region. The distance between the collars 208C, 208D (medial/lateral direction) is 84 mm. The medial collar 208C is approximately 0.75 mm thick (interior/exterior direction). The interior and exterior walls of the medial collar 208C are flat while the exterior wall of the lateral end collar 208D is sloped to taper down in thickness in the interior/exterior direction. This provides a smoother thickness transition from the filament support structure 208 to the lateral end of the filament 1830 and headgear-filament attachment point. The lateral end collar 208D is approximately 0.72 mm thick (interior/exterior direction.

Example Manufacturing Detail

The filament 1830 and filament support structure 208 may be encased by an elastic outer sheath or tube or cover (for example a braided cover of knitted or woven material). The outer cover is attached at the same point as the medial end of the filament support structure 208 (at the lateral end of yoke/yoke cap) and lateral end of the filament 1830 (the attachment point on the headgear halo formed by straps 204, 206).

One, some or all edges and corners are preferably rounded to achieve softer surfaces overall and further reduce the likelihood of any outer sheath or tube or cover (which sheathes filament 1830) catching on components and becoming damaged.

Filament Stop

With reference to FIGS. 32 to 35, the filament stop 1830E can be seen in more detail. The stop 1830E, in this example, comprises a laterally extending protrusion, rib or ridge, which extends laterally across the larger region of the filament 1830A, adjacent transitional region 1830C, transverse to the longitudinal axis of the filament 1830. The stop 1830E projects radially outwardly from the filament 1830, away from the filament longitudinal axis. In this example, the stop 1830E projects away from one surface of the filament 1830, in a directional orthogonal to the filament longitudinal axis.

The medial edge of the stop 1830E is, in one example, approximately 14 mm from the border dividing the transition area 1830C and smaller region 1830A of the filament 1830.

The stop 1830E comprises a sloped or inclined abutment surface or face 1830F on its medial side (towards the yoke Y of the directional adjustment unit 1800) and an abutment surface or face 1830G which is undercut 1830H on the lateral side (towards the headgear). A sloped surface of the stop 1830 aids assembly, specifically insertion of the filament 1830 through the two collars 208C, 208D of the filament support structure 208. The edges and corners of the stop 1830 may be rounded to further aid these aspects and provide smoother surfaces. The stop 1830 may therefore take the form of an obtuse trapezoid, when viewed from the side. Example stop dimensions, and example angles of the sloped surface 1830F and undercut 1830G, are shown in FIG. 34.

The abutment face 1830G may alternatively be perpendicular to the external surface of the filament 1830. However, testing has shown that the maximum pull-out force that the stop can withstand increased with an abutment face, which engages with the collar 208C, comprising an angled undercut. This stop shape acts to bias the stop 1830E so that when it contacts the collar 208C it rises up above the collar 208C instead of trying to wedge itself underneath the collar 208C and pull through.

In one example, the mechanical stop 1830E is approximately 1.7 mm at its longest length (medial edge to lateral edge); the distance between the medial edge and the undercut corner is 1.6 mm. The sloped medial surface of the stop has an angle of 30° relative to the flat exterior surface of the filament. The height (in interior/exterior direction) of the stop is approximately 0.6 mm. The sloped surface of the undercut has an angle of 75° relative to the flat exterior surface of the filament.

The lateral end of the mechanical stop 1830 (i.e. undercut abutment face 1830G) interacts with the medial surface of the lateral end collar 208D of the filament supporting structure 208 while the medial end of the stop 1830 (i.e. sloped surface 1830F) interacts with the medial collar 208C of the filament support structure 208.

The profile of the mechanical stop 1830E may be modified to feature a more rounded edge on the medial side and/or a deeper undercut as illustrated in FIG. 35. A rounder edge reduces the likelihood of the knitted tube, which surrounds the filament 1830, catching on the stop 1830E during return. A deeper undercut refers to a greater distance between the location of the lateral edge and the undercut corner, or a smaller angle between the sloped surface of the undercut and the flat exterior surface of the filament 1830. The former example is illustrated in FIG. 35. These both determine extension limits/ranges of the headgear; the former determines the minimum length while the latter determines the maximum length.

The mechanical filament stop 1830E and collars 208C, 208D are designed so that the stop 1830E rises above the collars to prevent the likelihood of it wedging itself underneath the collars and pulling through. The height of the lateral end collar 208D is preferably approximately 0.72 mm (interior/exterior direction). This corresponds to a pull-out force of 96N (maximum load applied before the stop 1830e and/or collar 208D yields and fails). The larger region 1830B of the filament 1830 yields at a load of 70N. A collar with a height which is too small may lead to a stop 1830E that rises above the exterior wall of the collar and therefore catches the brain/knit tube encasing the system during extension. It may also yield more easily, leading to a lower pull-out force. A stop 1830E with a small height relative to the collar may slip under the collar easily (also leading to low pull-out force).

There are various benefits of introducing a mechanical stop implemented onto the filament:

This increases reliability of the maximum extension length, reducing manufacturing complexity. One benefit is that the braided outer sleeve of prior designs is no longer required to perform a stop function and so more convenient materials can be used. For example the outer sleeve could be of an elastic plastic or rubber or silicone material, or any other material that provides a desired aesthetic or tactile benefit.

This decouples the dual purpose of the braid to be a stop and an elastic returning force. This reduces the constraints on the braid and allows us to experiment with a wider variety of elastic materials.

The parts are relatively simple to manufacture without complex tooling.

The filament has a sheath (support structure) which supports and protects it, which can be particularly advantageous for users who are abusive with the mask.

The filament has more guidance during return.

There is more support to guide the filament when it is returning, this mechanism is difficult to twist, effectively solving a going concern that this could prematurely damage the filament and stop returning when patients twist it.

The size of the yoke of the directional adjustment unit 1800 can therefore be decreased and/or the range of stretch can be increased as the introduced channels and collars protect the free ends of the filament while containing it.

Double Channeled Filament Support

In a further example in accordance with this disclosure, a filament and filament support structure can be provided for each of the left and right sides of the mask. The free ends (i.e. smaller region 1830A) of the opposite filament 1830 feed through a small channel 2081 formed in the filament support structure 208. For example, the free end of the left filament 1830 passes through the small channel 2081 of the filament support structure 208 on the right side of the yoke and vice versa for the right filament and left filament support structure. The larger region 1830b of each filament 1830 feeds through a larger channel 208K of the support structure 208. This means that each filament 1830 will pass through the yoke assembly 20 located in the centre of the mask to reach the opposite filament support structure 208. This can be seen in FIGS. 3a, 3b, and FIGS. 38 to 42.

The channel 208K the larger region 1830B of the filament 1830 passes through is formed between an elongate rim 208L and a channel divider 208M separating the two channels 2081, 208K. The rim 208L located along the top margin of the support structure 208 and the channel divider 208M forming the bottom wall of the larger channel 208K resists vertical movement of the filament 1830. This wider channel 208K is an open channel, not fully enclosed and the exterior surface of the filament 1830 is exposed.

The channel 2081 the smaller region 1830A of the opposing filament 1830 passes through fully encloses/surrounds the filament 1830. The upper wall of the smaller channel 2081 is formed by the same channel divider 208M.

Figure 39:
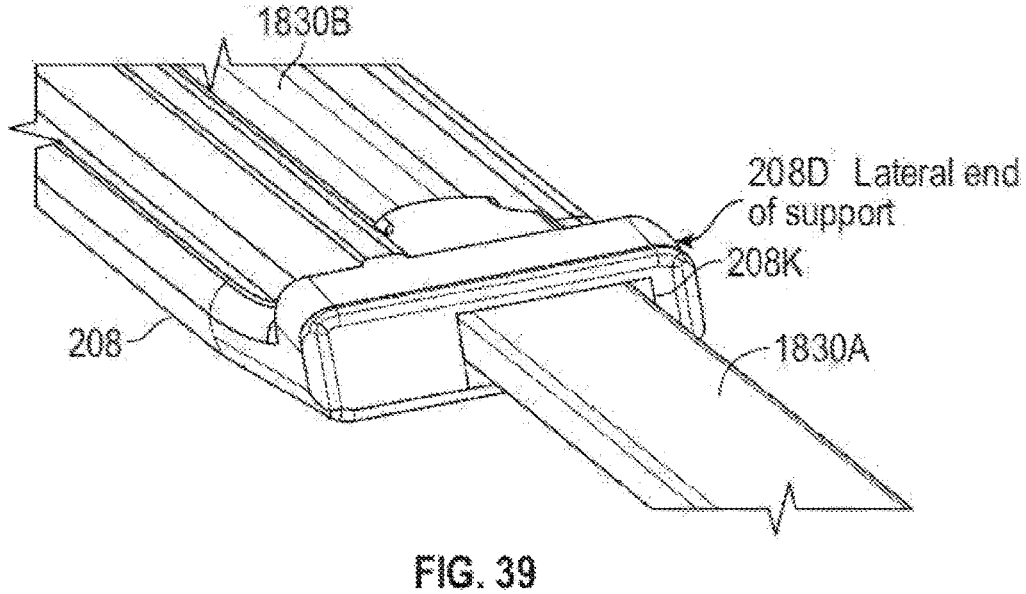
FIG. 39 is a perspective end view according to FIG. 38.
Figure 40:
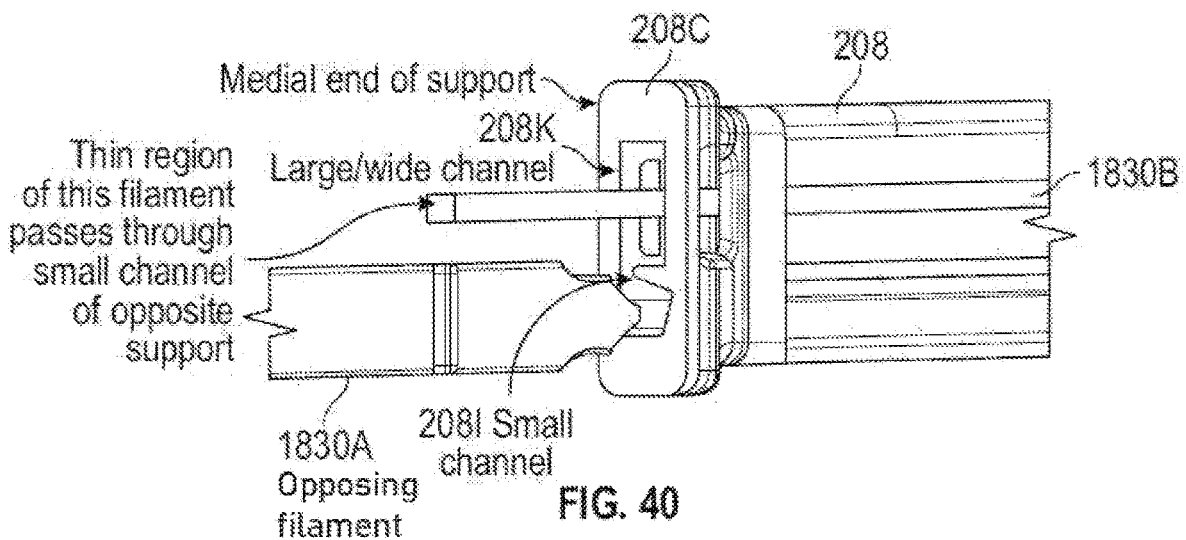
FIG. 40 is an enlarged view of the medial end of the support structure of FIGS. 38 and 39.
Figure 41:
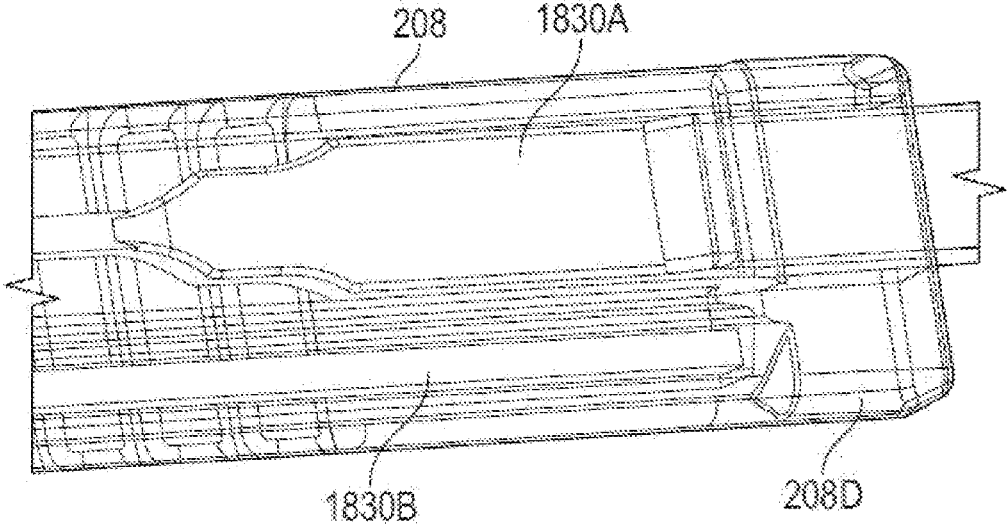
FIG. 41 is an enlarged side view of part of the arrangement of FIG. 38.
Figure 42:
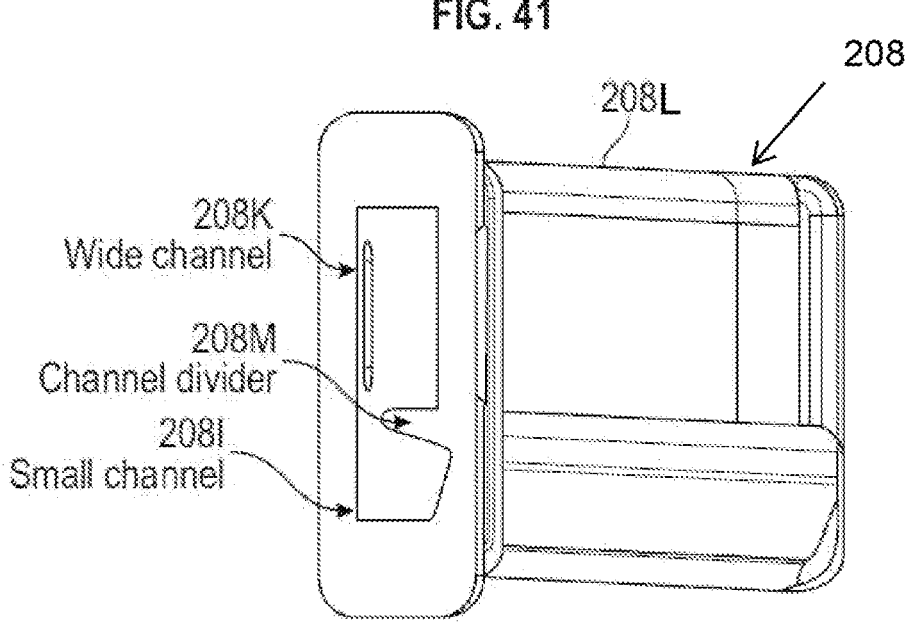
FIG. 42 is an enlarged perspective view of the medial end of the support structure of FIGS. 31 to 41, with the filament omitted.

The medial ends of these channels 2081, 208K are open as shown in FIG. 40. The lateral end of the large/wider channel 208K is open while that of the smaller channel 2081 is closed to limit the range of motion of the opposing filament 1830 along the channel, as can be seen in FIG. 39.

These modified filament support structures 208 can be configured so that the positions of the small and large channels 208K, 2081 alternate between the left and right sides of the mask assembly. For example, one filament 1830 will pass through the large channel 208K positioned above the smaller channel 2081, while its thinner and free end passes through the small channel 2081 of the opposite filament support structure 208 which is positioned above the large channel 208K. In other words, the left side has the smaller channel 2081 on top, and larger channel 208K on the bottom while the right side has the larger channel 208K on top and smaller channel 2081 on the bottom (or vice versa). This would allow the smaller region 1830A of the filament 1830 to pass through the channel on the opposite side without interference from the other filament 1830. This features one channel for each filament with that corresponding to the opposing filament is significantly smaller than the other channel. The blue arrow denotes the movement of the opposing filament and the green arrow denotes that of the other filament. (b) is a view of the internal side of the same component; it shows the rim/lip features that retain the vertical position of the filament. The rim/lip between the two filament channels also act as a channel divider.

Ribbed Filament Support Structure

Figure 43:
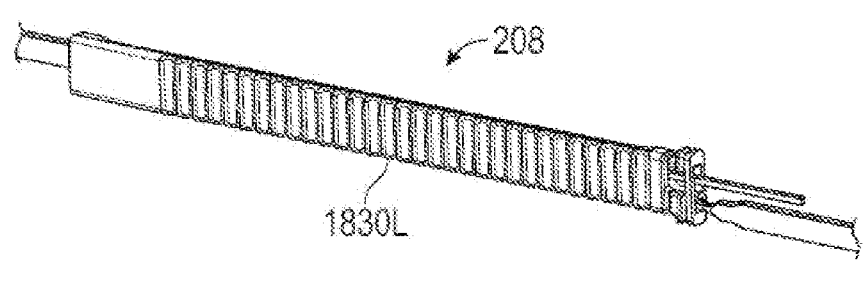
FIG. 43 is a perspective view of a filament support structure in accordance with a further embodiment.
Figure 44:
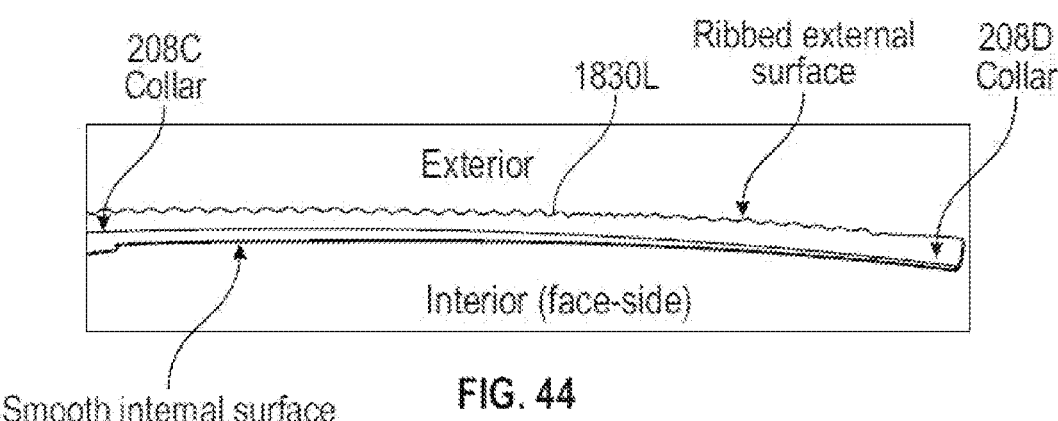
FIG. 44 is photograph from the side of the support structure of FIG. 43.
Figure 45:
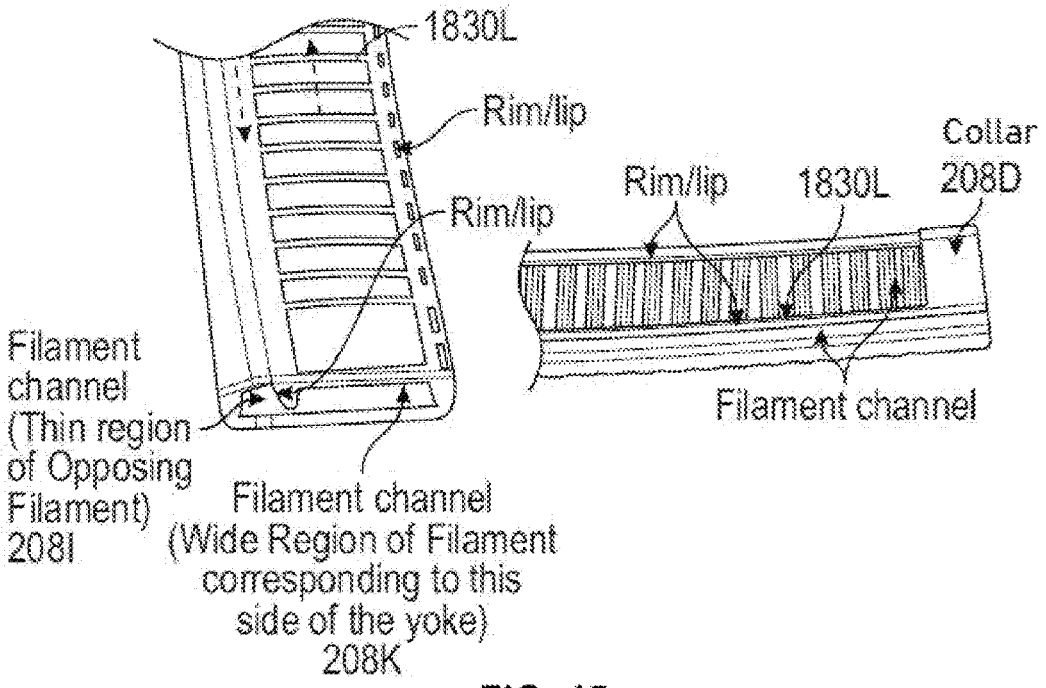
FIGS. 45a and 45b are views showing the cross sectional profile of the support structures of FIGS. 43 and 44.
Figures 46, 47, 48:
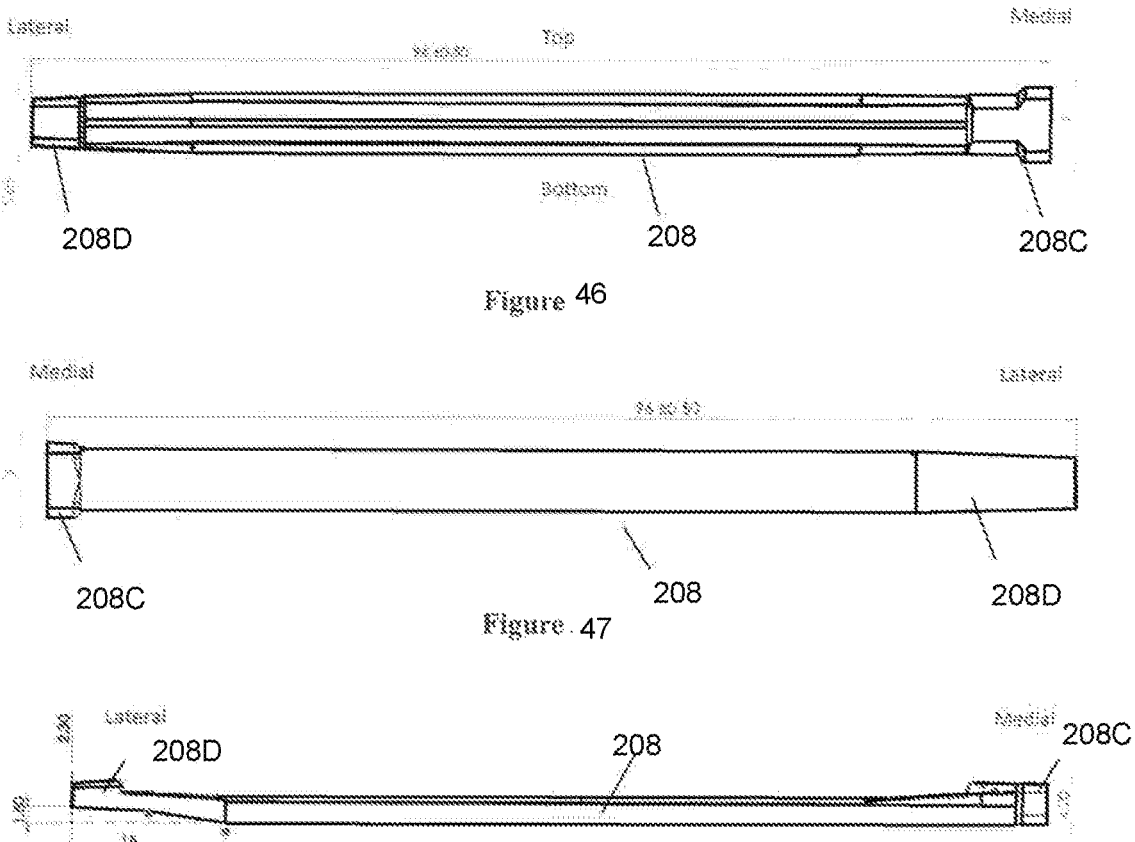
FIGS. 46 to 48 are interior side, exterior side and top views of a filament support structure in accordance with another embodiment.

With reference to FIGS. 43 to 45, the smaller region 1830A of filament 1830, together with its material properties, allow it to be flexible enough to curve around, and adapt to, the contour of the user's cheeks. However, the filament support structure 208 and the thickening/widening of the filament 1830 can result in the system no longer being as flexible. We therefore propose a modified filament 1830 in which one major face or surface of the filament has a modified, strengthened or weakened structure as compared to the opposing major face or surface. Such a structure causes that major face or surface to exhibit different physical properties from the other, for example a stress or strain related property, elasticity, resilience to bending, tensile or compressive strength.

One form of such a modified structure is a plurality of ribs, or castellations, or teeth or recesses 1830L. Having one surface/side/face of the filament support structure 208 ribbed will allow it to curve or bend in one direction. For example, ribs on the exterior surface of the support structure (away from the user's face) will allow the support structure 208 to bend more easily around the contour of the user's face.

Further Double Channeled Filament Support

With reference to FIGS. 46 to 53, a further dual or double filament embodiment is proposed. This embodiment features a different filament support structure 208 with two channels 2081, 208K, one for each opposing filament 1830 as described above. This embodiment differs to the previous in that instead of the two channels 2081, 208K being stacked vertically, they are stacked laterally, in an interior/exterior direction that is, in a direction away from the user's face in use. Due to this, the filament support structure 208 is thicker in an interior/exterior direction. The wide channel 208K is exposed throughout the majority of the length of the filament support structure 208 while the small channel 2081 is enveloped. This can best be seen in FIGS. 51 to 53.

The two channels are not completely separated as with the previous embodiment as the thin channel divider 208M comprises a gap or slot 208N—this allows for easier manufacturing and reduces stiffness throughout the length of the filament support structure 208.

As with the previous double channel embodiment, the filament support structure 208 is stiffer than the single channel embodiments. Stiffness is uniform in the top/bottom direction, that is vertically in use, because channel location is symmetrical unlike the previous double channel embodiment, which may be prone to twisting in one direction due to asymmetrical stiffness.

As with the previous double channel embodiment, this embodiment is also able to flex enough to curve around, and adapt to, the contour of the user's cheek without breaking. The filament support structure must curve around the user's cheeks-one side of the support structure 208 curves with a lower stiffness to form a convex shape, and therefore forms the exterior side of the component, that is, the part of the support structure 208 that faces radially outwardly from the face of the user. This also means that the small channel will be more exterior than the wide channel.

The larger channel 208K as described above is exposed, but is also open on both ends, while the smaller channel 2081 is open on the medial end and closed at the lateral end. This introduces a limit to the length of filament 1830 that may pass through the small channel 2081 of the opposite filament support structure 208. The lateral end of the filament support structure 208 tapers in thickness towards the thickness of the wide region of the filament 1830. As the wall thickness of the exterior side of the filament support structure 208 remains constant, the width of the smaller channel 2081 tapers to zero, closing off one end of the channel. The face contacting side/surface/face of the support structure 208 is unchanged, but the exterior side/surface/face comes, in this example, 1.6 mm closer to the face towards the lateral end over a length of 15 mm, see FIG. 48.

Figure 49:
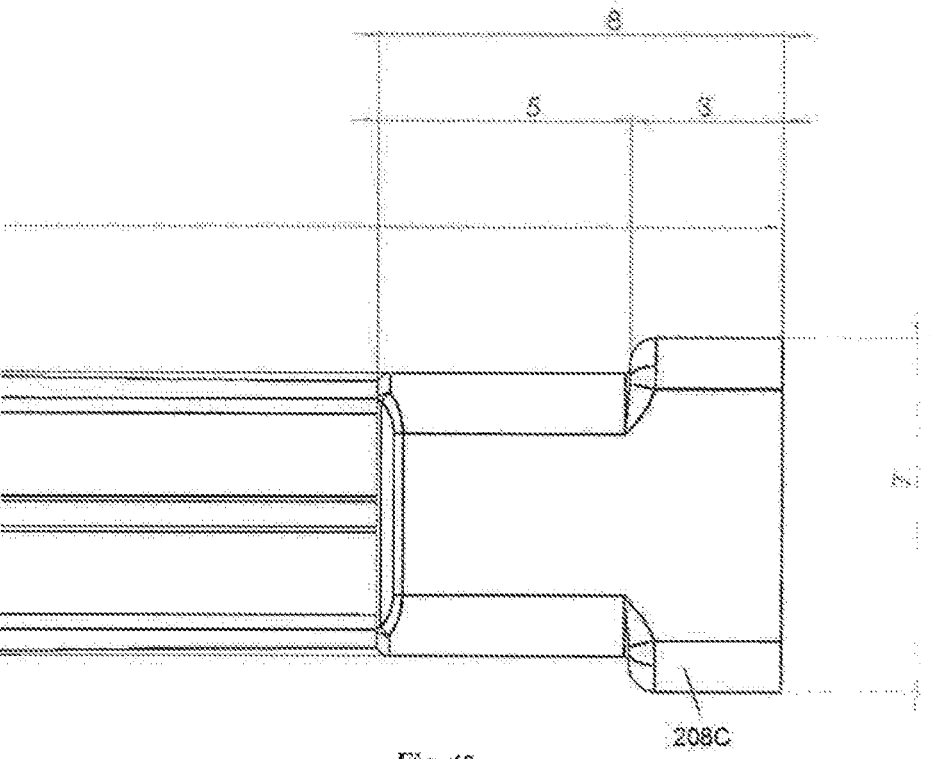
FIG. 49 is an interior view of a medial collar in accordance with an embodiment.

The top and bottom surfaces/faces of the lateral end collar 208C also tapers from the width of the filament support structure 208 along the length of the exposed region of the filament 1830 to a smaller width closer in size to that of the width of the larger region 1830B of the filament 1830, as can be seen in FIG. 49.

Figure 50:
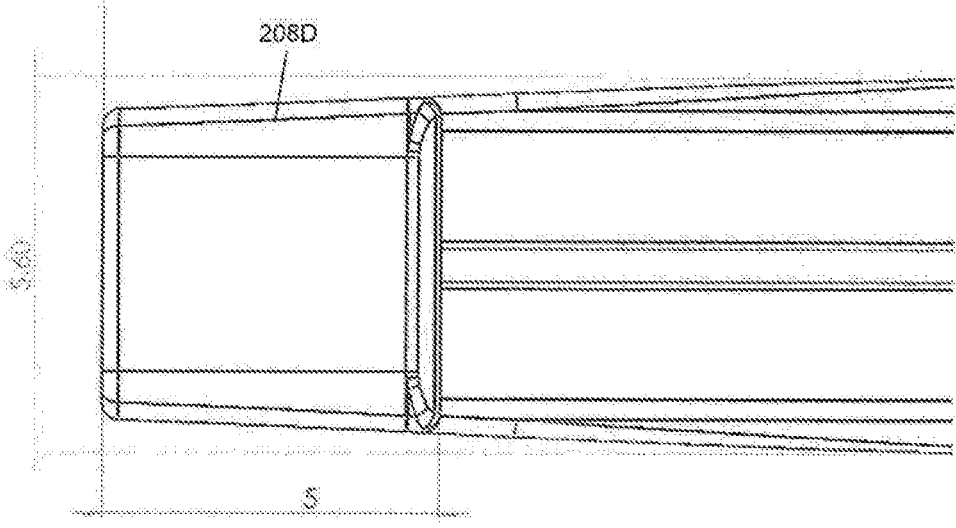
FIG. 50 is an interior view of a lateral collar in accordance with an embodiment.
Figure 51:
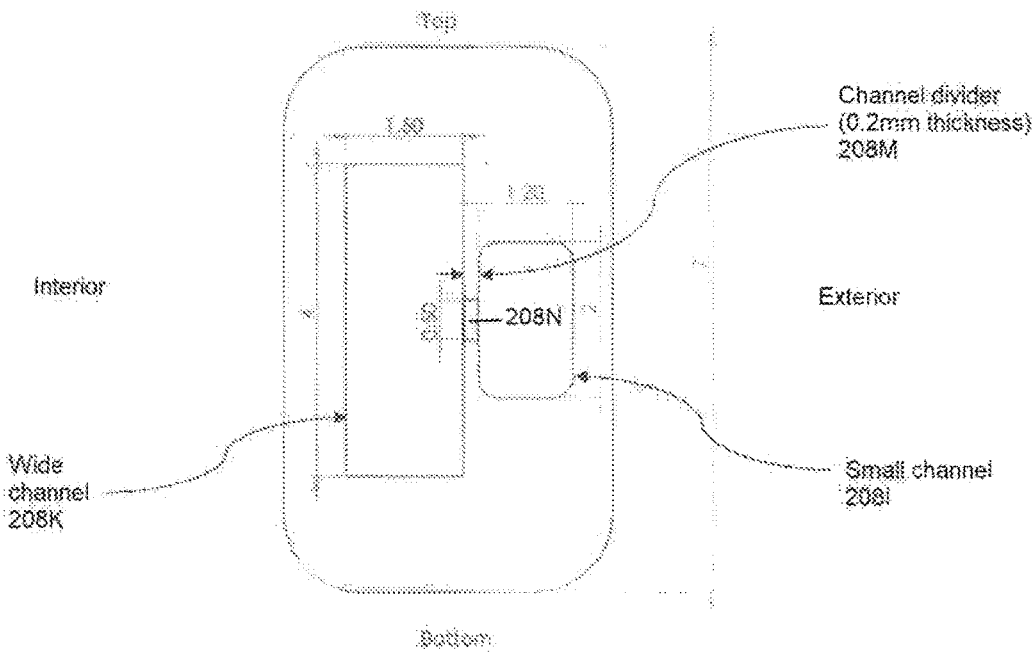
FIG. 51 is a cross sectional view along the length of a filament support structure at the medial collar, in accordance with an embodiment.

Example Filament Support Structure Dimensions of Further Double Channeled Embodiment With reference to FIGS. 49 to 51, the filament support structure 208, in one example, has a total length (medial/lateral direction) of 96 mm with the medial end collar having a width (top/bottom) of 7 mm and the lateral end collar a minimum width of 5.6 mm. The medial end collar has a thickness (interior/exterior) of 4.2 mm and the lateral end collar a thickness of 2.3 mm. The medial end collar has a length of 8.1 mm while the lateral end collar has a length of 5 mm—this provides more space for the attachment of the filament support structure onto the yoke cap, as can be seen in FIGS. 49 and 50. Both face-contacting (interior) sides/surfaces/faces/walls of the collars 208 are about 0.8 mm for both medial and lateral ends of the filament support structure 208.

Figure 52:
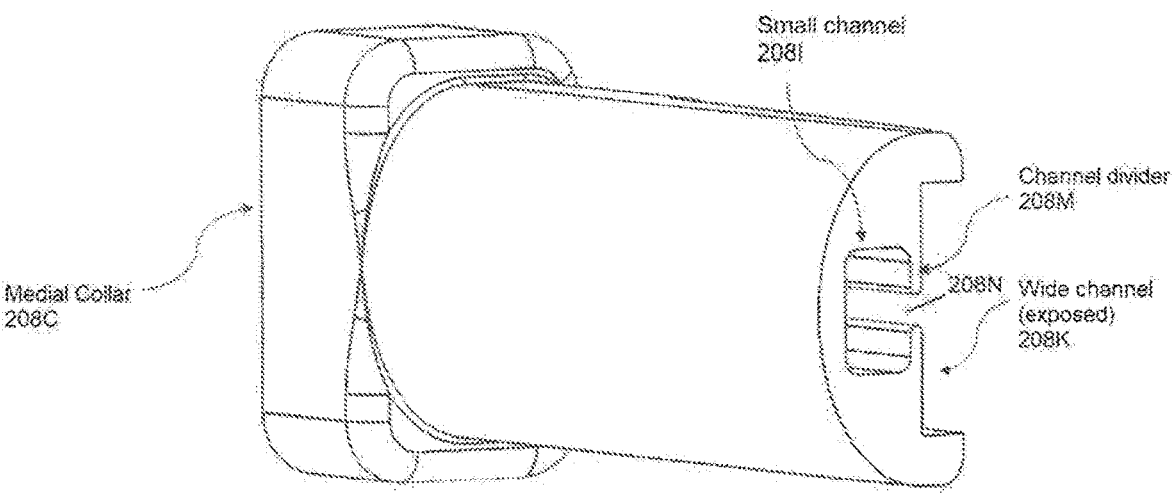
FIG. 52 is an enlarged perspective view of an exterior side of the filament support structure of FIG. 51.
Figure 53A:
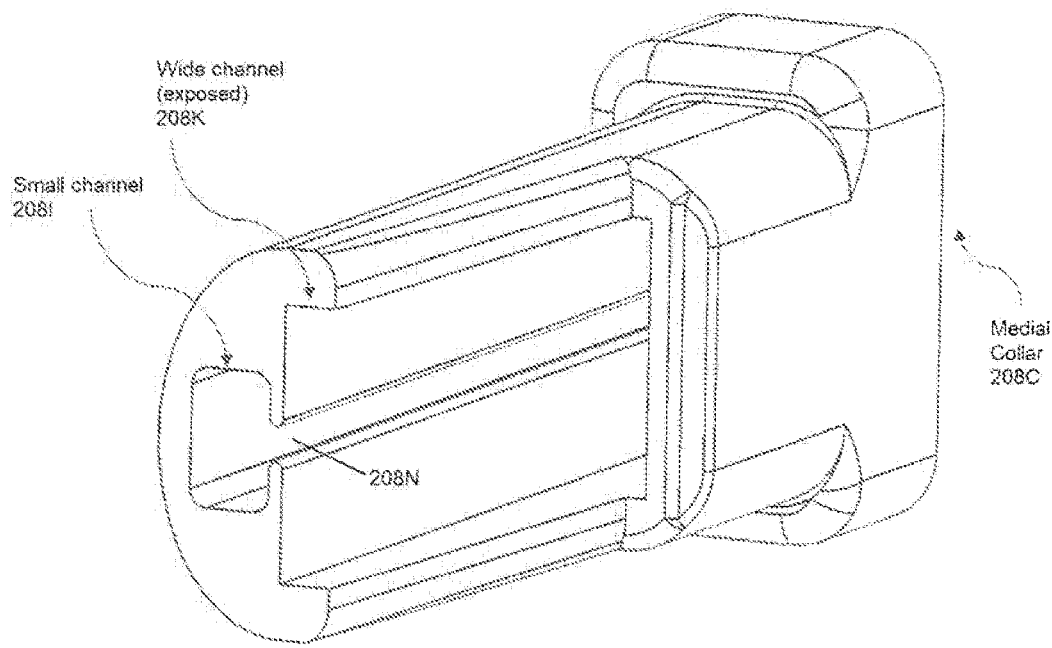
FIGS. 53*a* and 53*b* are enlarged perspective views of an interior side of the filament support structure of FIG. 51.
Figure 53B:
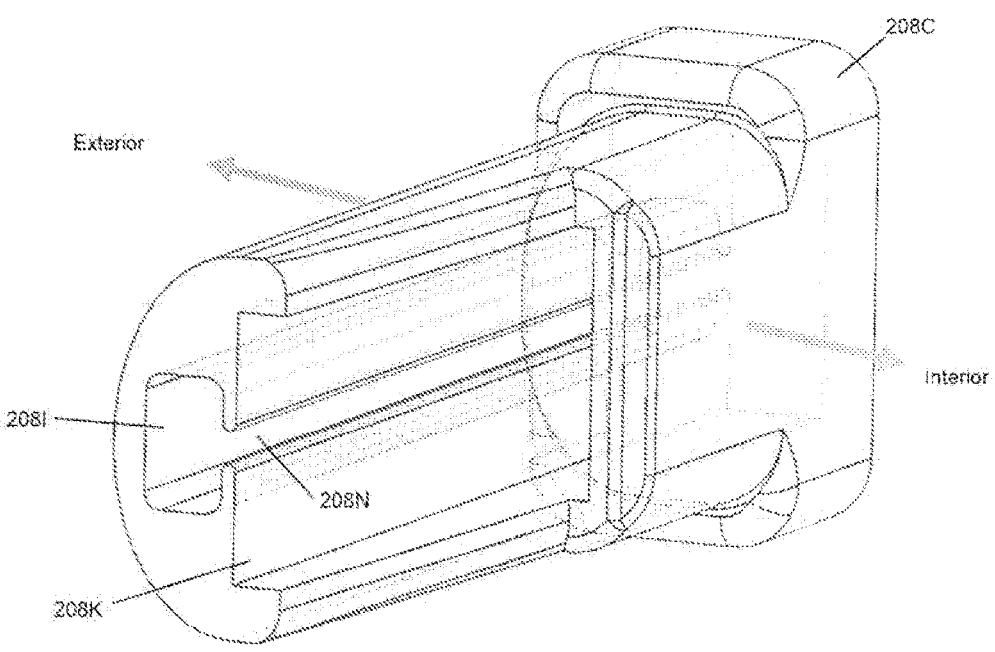

FIGS. 51 to 53 illustrate features visible in the cross-section of the medial end collar 208. In one example, the small channel has a width of 2 mm (top/bottom direction) and depth of 1.2 mm (interior/exterior direction). The wide channel has a width of 4 mm and depth of 1.5 mm. The channel divider has a thickness of 0.2 mm and the gap forming an incomplete separation between the two channels is 0.5 mm wide. The medial end collar 208 itself has a width of 7 mm (top/bottom direction). At the medial end collar 208, the larger channel 208K is not exposed, but is exposed along the majority of the length of the filament support structure 208.

Rounded Stop

Figure 54:
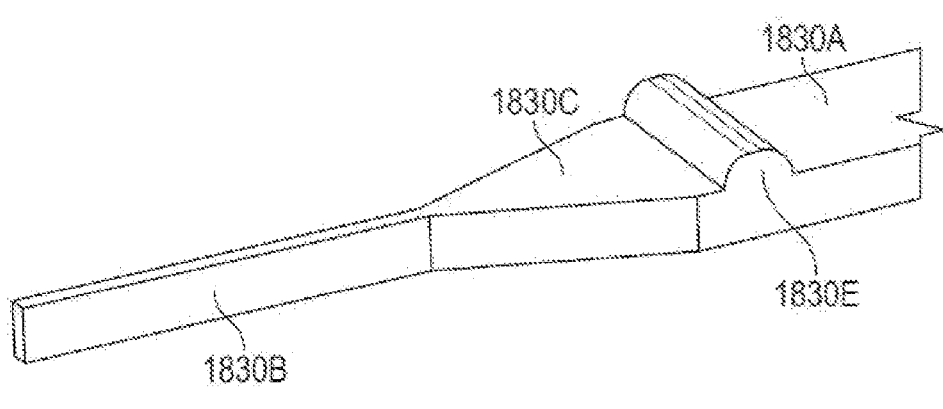
FIG. 54 is a perspective view of a filament having a modified stop.

With reference to FIG. 54, both medial and lateral sides of the stop 1830E may be rounded to further reduce the likelihood of the elastic outer tube getting caught on the stop 1830 (in both extension and contraction direction). This can also lead to less damage to the collars 208 when abutted by the stop 1830.

Filament Locating/Alignment Features

Figure 30:
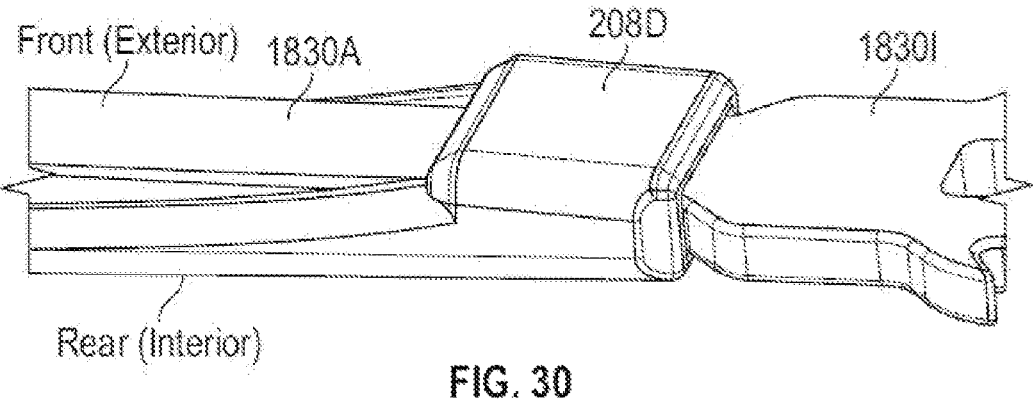
FIGS. 30 and 31 are perspective views of the lateral end of the support structure of FIG. 24.
Figure 31:
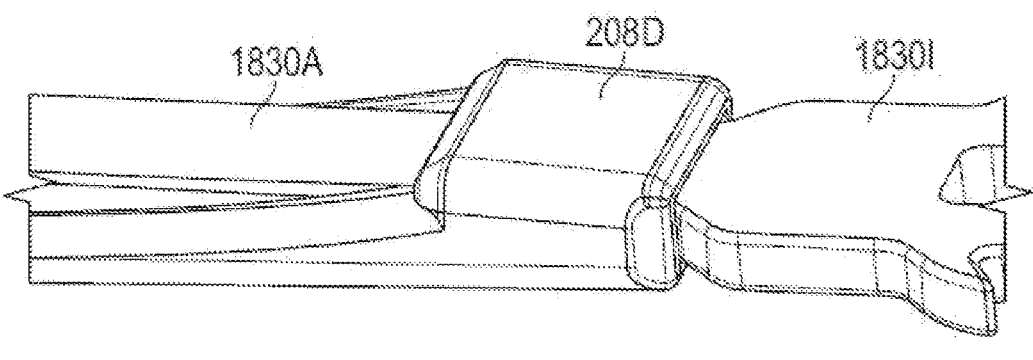
Figure 32:
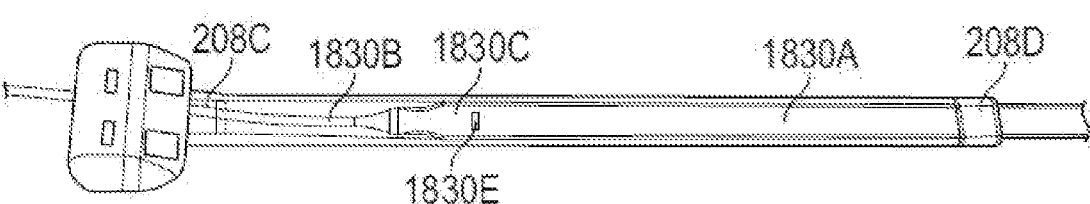
FIG. 32 is a photograph from above of a directional adjustment unit in accordance with an embodiment.
Figure 55:
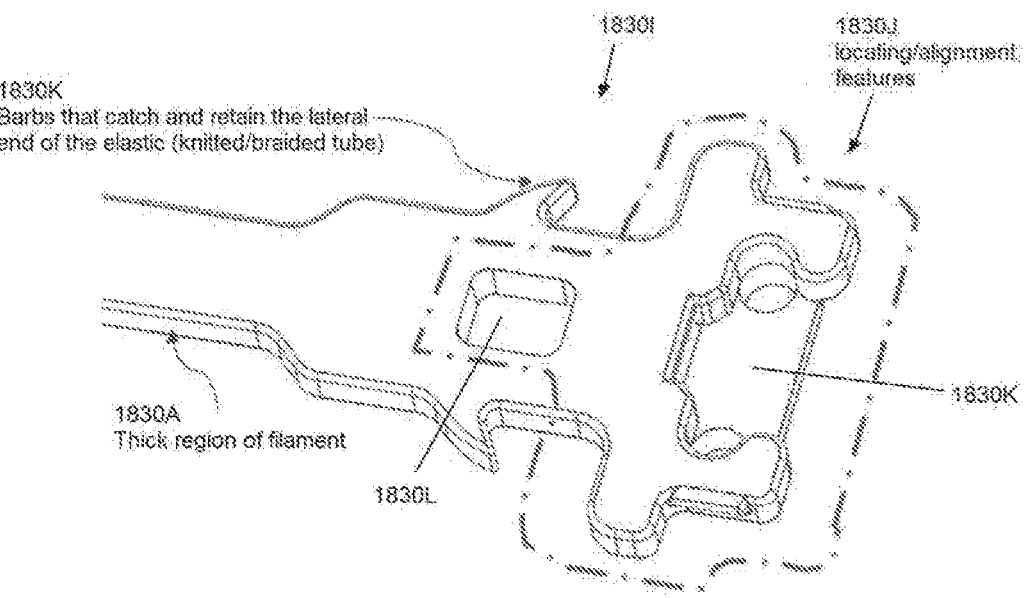
FIG. 55 is a perspective view of a filament anchor at a lateral end of the filament, to secure the filament to headgear.

With reference to FIGS. 30 and 55, the lateral end of filament 1830 comprises a filament anchor or connector or attachment 1830I that is used to attach/anchor the filament 1830 securely onto the headgear 200, and in one example to the headgear crown portion formed by straps 204, 206. These straps 204, 206 form a loop which extends around the rear of the head of the user and is sometimes known in the art as a halo.

The filament anchor 1830I includes a plurality of location and/or alignment features 1830J for locating and/or aligning the filament 1830 with the headgear 200 to enable mating/connection between the filament anchor 1830I and headgear 200 to ensure correct and accurate alignment and orientation of the filament 1830 during manufacturing, and in this example during an overmoulding process where overmoulding secures the filament 1830 to the headgear 200.

The location and/or alignment features 1830J comprise a plurality of lugs, recesses, slots, apertures to provide a plurality of non-aligned edges, walls and surfaces against which the overmould material can flow to provide a strong bond between the filament and headgear. These features 1830J are formed on a widened end of the filament 1830 that forms the filament anchor 1830I. The widened end is substantially planar and extends transversely outwardly from the longitudinal axis of the filament 1830. The lugs and recesses are also generally planar and extend transversely outwardly of the longitudinal axis of the filament 1830. The distal end of the filament anchor 1830I comprises an elongate slot 1830K whose distal margin is open such that the distal end of the filament anchor 1830I is generally 'U' shaped or forked when viewed from above. In this embodiment a single oblong aperture 1830L is provided through which overmould material can flow during manufacturing.

The filament anchor 1830I also comprises, in this embodiment, barbs 1830K located more medially relative to the locating features 1830J to retain the lateral end of an outer sheath or cover, such as an elastic tube, enveloping the filament 1830 and filament support structure 208.

Frictional Adjustment

With the above described directional adjustment units 1800, the amount of frictional force generated is proportional to how far the frictional engagement members 1820 are allowed to tip over (i.e. the angle limits of rotation of the frictional engagement members 1820 relative to the 'free' position). The designs disclosed herein focus on providing a frictional adjustment arrangement being a mechanism, assembly, or configuration of features arranged to vary the angle through which the frictional engagement members 1820 can rotate, using physical engagement formations shaped and positioned to prevent further rotation. The rotatable frictional engagement members 1820 are contained by a housing 1810 which in some examples may be altered to be in contact with the free ends of the frictional engagement members 1820 (when force is generated).

With additional reference to FIGS. 56 to 64, a directional adjustment unit 1800 comprises a frictional adjustment arrangement configured to adjust the degree of frictional engagement of the frictional engagement member 1820 with the filament 1830 when in the engaged configuration.

In the examples of FIGS. 56 to 64, the frictional adjustment arrangement is configured to constrain, or control the degree of movement of the frictional engagement members 1820 relative to the housing 1810 and/or relative to the filament 1830. The degree of relative movement adjusts the effective size of the aperture in the or each frictional engagement member 1820, when viewed along the longitudinal axis of the filament 1830, and therefore the amount of friction between the aperture and the filament 1830.

Figure 56:
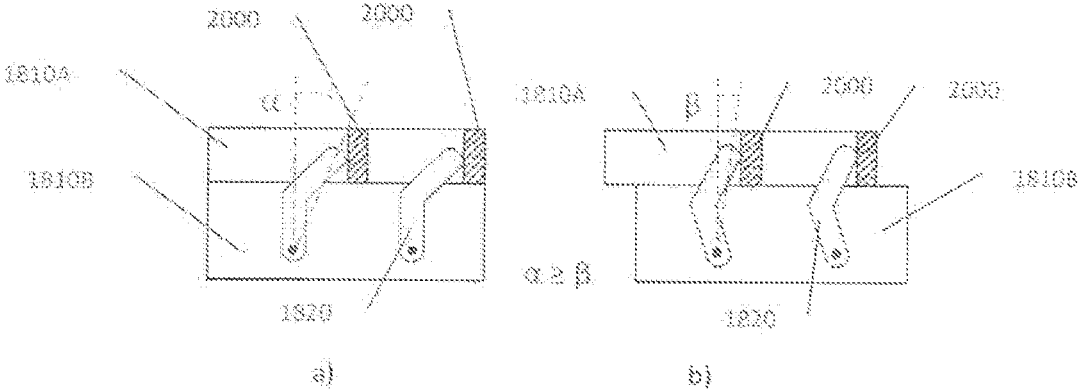
FIGS. 56*a* and 56*b* shows a first embodiment of a frictional adjustment arrangement in accordance with the present disclosure, in first and second conditions.
Figure 57:
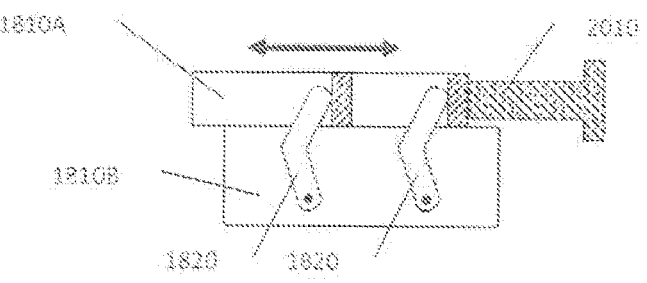
FIG. 57 shows a modification of the first embodiment of FIG. 56.

Referring initially to FIG. 56, the housing 1810 comprises upper and lower sub-housings 1810A, 1810B, that are movably connected together. In this example, the upper sub housing 1810A is slidably mounted on the lower sub-housing 1810B so as to be able to move relative to the lower sub-housing 1810B in a direction parallel with the longitudinal axis of the filament 1830.

The upper sub-housing 1810A comprises a plurality of downwardly directed engagement formations 2000 such as lugs, protrusions, or projections that project down into the housing interior from a top or side wall of the upper sub-housing 1810A, or from any other part of the upper sub-housing 1810A that is spaced from the pivots 1824 of the frictional engagement members 1820. There is an engagement formation 2000 for each frictional engagement member 1820, that is, two of each in this example. Each engagement formation 2000 is positioned to engage with an upper free end of a respective frictional engagement member 1820, that is, a part of the frictional engagement member 1820 distal from the pivot 1824.

The degree of pivotal movement of each frictional engagement member 1820 relative to housing 1810 is governed by the position of the upper sub-housing 1810A relative to the lower sub-housing 1810B.

With reference to FIG. 56a, with the upper and lower sub-housings 1810A, 1810B aligned, the engagement formations 2000 are spaced a relatively large distance from the free ends of frictional engagement members 1820 and thus a relatively large degree of movement of the frictional engagement members 1820 is possible. Thus, when the frictional engagement members 1820 have pivoted to the extent required to abut the engagement formations 2000, the effective size of the apertures 1876 in the frictional engagement members 1820 is relatively small when the frictional engagement members 1820 and thus the maximum frictional or engagement force between the filament 1830 and each frictional engagement member 1820 is relatively high. This provides a relatively high degree of resistance to a user extending the headgear strap.

The user can adjust this maximum frictional or engagement force by moving the protrusions 2000 relative to the frictional engagement member 1820. In this example this can be achieved by sliding the upper sub-housing 1810A relative to the lower sub-housing 1810B. This moves the protrusions 2000 relative to the lower sub-housing 1810B, in a direction parallel with the longitudinal axis of the filament 1830, and thus reduces the degree or range of movement possible by each frictional engagement member 1820 relative to the housing 1810, as can be seen from FIGS. 56a and 56b. Thus the effective size of the apertures 1876 in the frictional engagement members 1820 is relatively large when the frictional engagement members 1820 abut or engage with the protrusions 2000 and thus the maximum frictional or engagement force between the filament 1830 and each frictional engagement member 1820 is relatively low. This provides a relatively low degree of resistance to a user extending the headgear strap.

In this example the frictional adjustment arrangement comprises a combination of the upper and lower sub-housings 1810A, 1810B and the protrusions 2000. This leads to the movement of the top half of the housing which features hard stops/barriers in contact with the free ends of the individual frictional engagement members (when in the configuration in which friction force is generated, angles α and β are more than 0°—see FIG. 56). This in turn changes the maximum tilt angle of the frictional engagement members 1820.

Such a frictional adjustment arrangement can be used with any number of frictional engagement members 1820, including one, two, or more than two.

With reference to FIG. 56, the frictional adjustment arrangement in this example comprises an actuator configured to control the frictional adjustment arrangement. In this example, the actuator comprises a user actuator 2010, configured to be moved or gripped by a user's hand or finger, and is in the form of an adjustment or set screw, the end of which engages or at least abuts the upper sub-housing 1810A. The screw or user actuator 2010 is shown schematically in FIG. 57, but is mounted on lower sub-housing 1810B, such that rotation of the screw or user actuator 2010, extends or retracts the screw relative to both sub-housings, and consequently moves the upper sub-housing 1810A relative to the lower housing 1810B.

With reference to FIG. 58, altering the maximum rotation angle of the frictional engagement members 1820 affects the force profile of the directional adjustment unit 1800 for example as shown in the second profile of FIG. 58b. The original force profile of a directional adjustment unit without a frictional adjustment arrangement is shown in the example force profile of FIG. 58a.

The maximum force produced by the tilting of the frictional engagement members 1820 (i.e. friction/slip force) is increased or decreased depending on the tilt angle limit provided by the said hard stops/barriers. This alteration of the force profile applies to all embodiments described herein, as all alter the friction force generated. The overall shape of the force profile is not altered.

Figure 59:
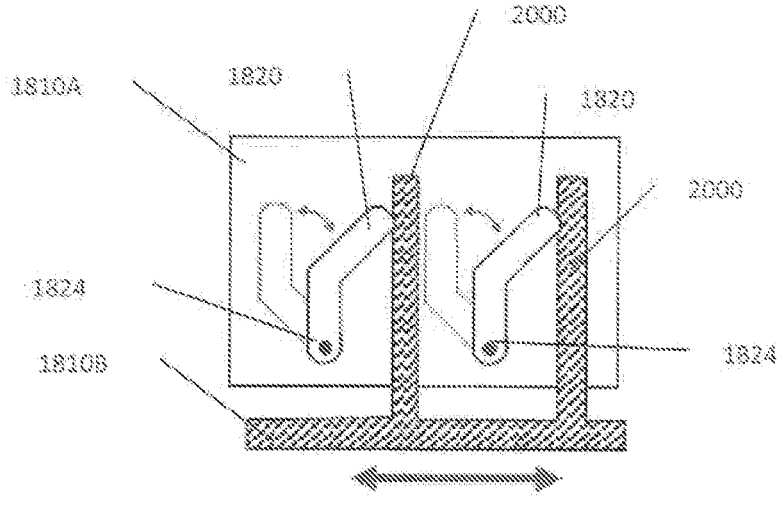
FIG. 59 shows a second embodiment of a frictional adjustment arrangement in accordance with the present disclosure.

With reference to FIG. 59, another embodiment of the frictional adjustment arrangement again comprises a split housing 1810 comprising upper and lower sub-housings 1810a, 1810b. In this embodiment the engagement formations 2000 are upstanding from the lower sub-housing 1810b, the lower sub-housing 1810b comprising the base of the housing 1810.

Figure 60:
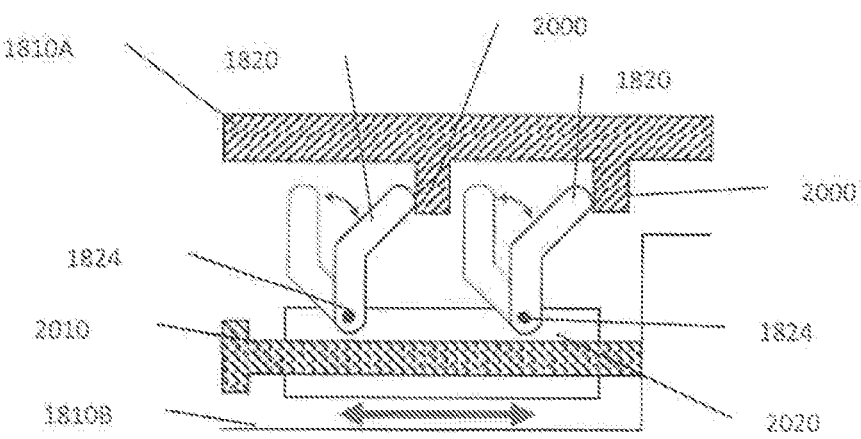
FIG. 60 shows a third embodiment of a frictional adjustment arrangement in accordance with the present disclosure.

With reference to FIG. 60, another embodiment of the frictional adjustment arrangement comprises a housing 1810, with engagement formations 2000 projecting downwardly into the housing 1810 from the underside of the top of the housing 1810.

In this embodiment the frictional engagement members 1820 are mounted on a carriage 2020 movably mounted in the housing 1810. The carriage 2020 can move relative to the housing 1810 in a direction parallel to the longitudinal axis of the filament 1830. Movement of the carriage 2020 adjusts the position of the pivoted lower end 1824 of each frictional engagement member 1820 relative to the engagement formations 2000 and the housing 1810. Movement of the carriage 2020 adjust the degree or range of movement of the frictional engagement members 1820 and thus the effective size of the aperture 1876 in each through which the filament 1830 extends.

In this embodiment a user actuator 2010 is provided to move the carriage 2020 relative to the housing 1810. In this example the user actuator 2010 comprises a threaded shaft, threadably mounted in the carriage 2020, rotation of which threaded shaft adjusts the amount by which the threaded shaft projects from the carriage 2020.

Figure 61:
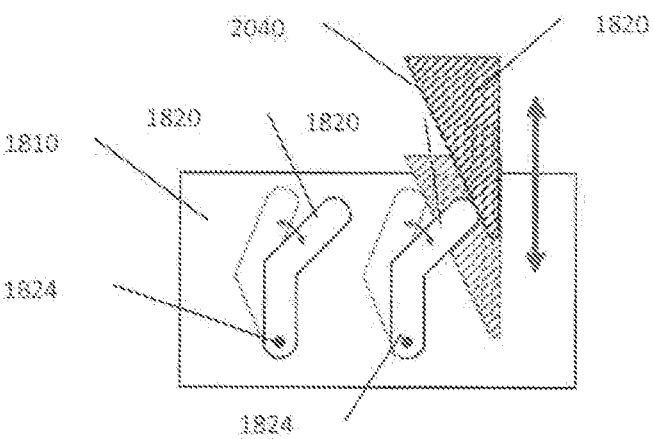
FIG. 61 shows a fourth embodiment of a frictional adjustment arrangement in accordance with the present disclosure.

With reference to FIG. 61, another frictional adjustment arrangement comprises a movable engagement formation 2030 which is movably mounted in the housing 1810. The formation 2030 comprises a cam, wedge shaped in this example, comprising a camming surface or face 2040 which engages the upper or free end of the frictional engagement member 1820, when the frictional engagement member 1820 has pivoted to its maximum degree of movement. The maximum degree of movement is determined by the position of the formation 2030 in the housing 1810. By adjusting the position of the formation 2030 in the housing 1810, a different part of the camming surface 2040 engages with the frictional engagement member 1820 to limit its movement. This adjusts the maximum degree of movement of the frictional engagement member 1820 and thus the effective size of the aperture 1876 through which the filament 1830 extends.

In this embodiment, the formation 2030 is movable substantially vertically within the housing 1810, in a direction orthogonal to the longitudinal axis of the filament 1830, the camming surface 2040 being inclined relative to that longitudinal axis. In this example the camming surface 2040 is substantially planar, the plane of which is at a constant angle of inclination. The camming surface 2040 could be multi-faceted and comprise multiple portions, for example multiple planar portions, each, or some of which, have different angles of inclination. The camming surface 2040 could comprise a curved surface, or comprise multiple curved surfaces. By varying the angle of inclination, and or the planar portions, and/or any curved portions, the force profile generated by movement of the cam 2040 can be varied.

Figure 62:
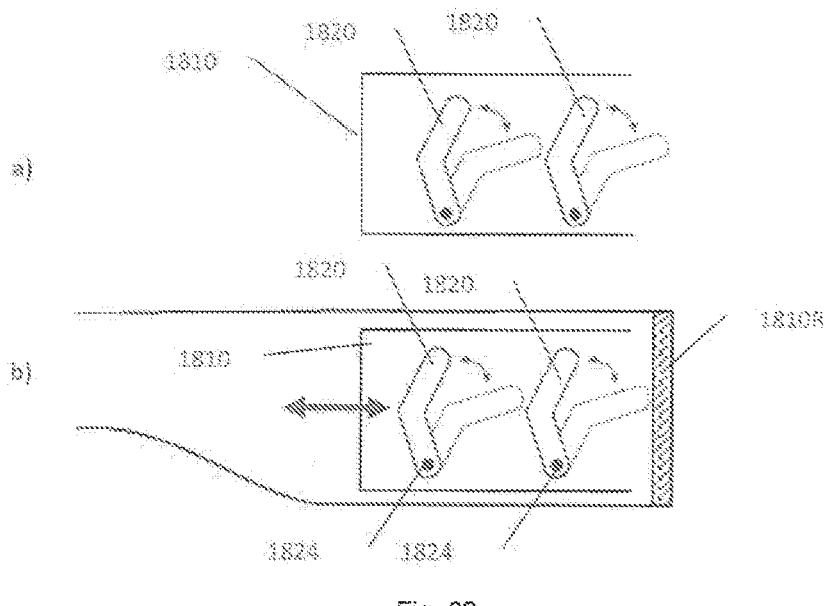
FIG. 62*a* is schematic view of a directional adjustment unit with a housing having an open end.
FIG. 62*b* is schematic view of a directional adjustment unit with a fifth embodiment of a frictional adjustment arrangement including a housing having an open end.

With reference to FIG. 62, another frictional adjustment arrangement is provided in which the degree or range of movement of only one frictional engagement member 1820 is limited. The movement of the or each other frictional engagement member 1820 is not limited, or is less limited, in this embodiment. This embodiment introduces the concept of being able to vary the resistance to headgear extension provided by the directional adjustment unit 1800 by selecting the number of frictional engagement members 1820 whose movement can be limited, or by varying the degree or range of one frictional engagement member 1820 differently to another frictional engagement member 1820.

In this embodiment, a split housing arrangement is provided similar to that of the embodiment described above in respect of FIG. 59, where the lower sub-housing 1810B can move relative to the upper sub-housing 1810B, and thus adjust the position of the pivot axes 1824 of the frictional engagement members 1820. In this example, engagement formation 2000 is provided by an end wall 1810R of the upper sub-housing 1810A, which engages or abuts the free end of the frictional engagement member 1820 that is nearest that end wall 1810R, limiting its movement.

It will be appreciated that any number of frictional engagement members 1820 could be provided, and the movement of any one or more of these could be limited by respective engagement formations 2000. For example the movement of only one frictional engagement member 1820 could be limited by a respective engagement formation 2000, or the movement of only one frictional engagement member 1820 not to be limited by an engagement formation 2000.

Figure 63A:
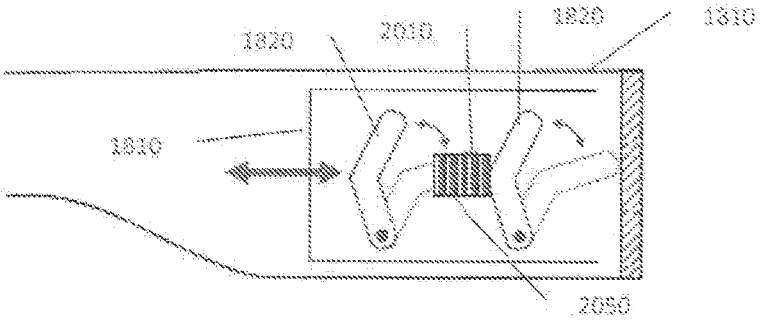
FIGS. 63*a*) and *b*) are schematic views of actuators of the frictional adjustment arrangement of FIG. 62.
Figure 63B:
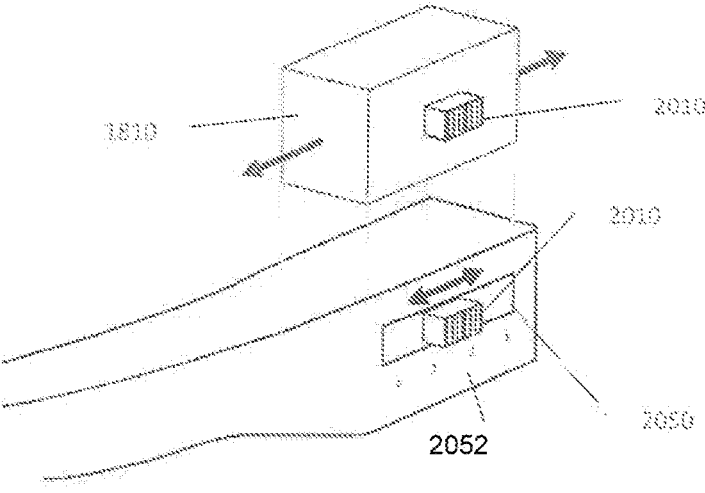

Referring to FIG. 63, an example user actuator 2010 is provided, for use with any of the above described embodiments, comprising a button or slider, slidably mounted in the upper or lower sub-housing 1810a, 1810b, for sliding movement in a slot 2050 in the housing parallel to the longitudinal axis of the filament 1830. The user actuator in the form of the button or slider protrudes from the side wall of the housing 1810 and may be configured to move:

a) the upper sub-housing 1810a relative to the lower sub-housing 1810b or vice versa;

b) one or more of the engagement formations 2000 relative to one or more of the frictional engagement members 1820;

c) The pivot axis 1824 of the frictional engagement members 1820 relative to the engagement formations 2000.

The user actuator 2010 may be provided with indicia 2052 indicative of differing maximum degrees or ranges of movement of the frictional engagement members 1820, and therefore the differing levels of resistance to extension of the headgear.

The user actuator 2010 may comprise frictional features, or be configured such that the user actuator 2010 cannot move freely, such that there is no unwanted movement of the button or slider. This could be achieved by way of control of the tolerances of the user actuator 2010 in the form of the button or slider and the slot 2050 in the housing 1810.

The user actuator 2010 may be directly connected to, or integral with, the upper sub-housing 1810a, the lower sub-housing 1810b, or the carriage 2020 on which the frictional engagement members 1820 are mounted. The user actuator 2010 may comprise a connector or connector mechanism which connects the user actuator 2010 to the upper sub-housing 1810a, the lower sub-housing 1810b, or the carriage 2020, and configured to transmit movement of the user actuator 2010 into movement of the upper sub-housing 1810a, the lower sub-housing 1810b, or the carriage 2020. The ratio of movement of the user actuator to the movement of the upper sub-housing 1810a, the lower sub-housing 1810b, or the carriage 2020 may be 1:1. Alternatively, the connector mechanism can be configured to be geared such that an amount of movement of the user actuator 2010 results in a different amount of movement of the upper sub-housing 1810a, the lower sub-housing 1810b, or the carriage 2020.

Figure 64A:
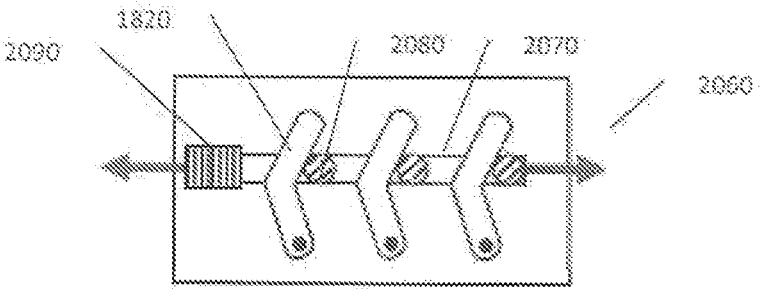
FIGS. 64*a*) and *b*) show a sixth embodiment of a frictional adjustment arrangement in accordance with the present disclosure.
Figure 64B:
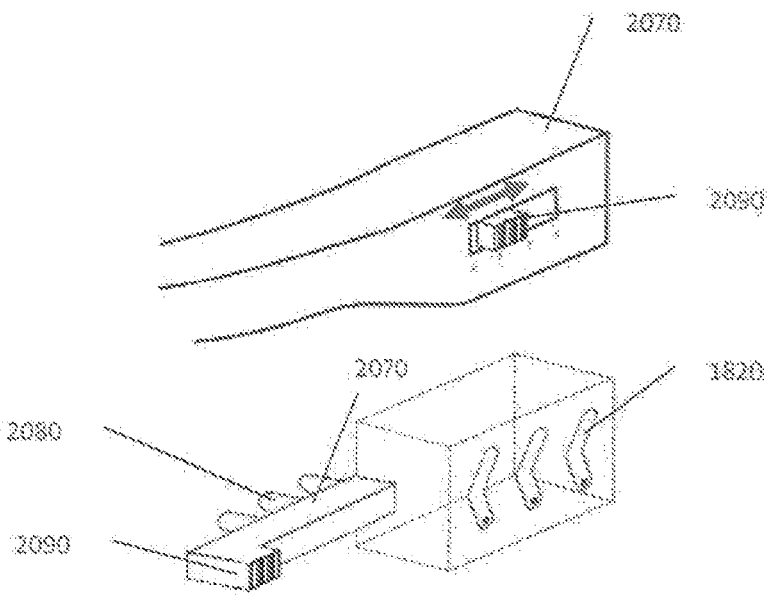

Referring now to FIG. 64, the frictional adjustment arrangement can comprise a selector mechanism 2060 configured to enable the user to select how many of the frictional engagement members 1820 have their movement limited, and therefore by how much the frictional force generated by the frictional engagement members 1820 in total can vary.

An example selector mechanism 2060 comprises an elongate selector body 2070 having a plurality of protrusions 2080 projecting from one side thereof. A button 2090 projects from an opposite side, through an elongate slot in the housing 1810. Each protrusion 2080 projects into the housing 1810 adjacent a respective frictional engagement member 1820, and in particular into the space in which the frictional engagement members 1820 move. Movement of the slider body 2070 using button 2090 adjusts the position of protrusions 2080 relative to housing 1810 and frictional engagement members 1820, and thus controls the degree or range of movement of some of the frictional engagement members 1820. In this example selector mechanism 2060 comprises three protrusions 2080 and therefore controls the movement of three of the frictional engagement members 1820. When moved to one end of the available movement of the slider body 2070, the protrusions 2080 prevent all or substantially all movement of the respective frictional engagement members 1820, thus holding the frictional engagement members 1820 in a fully upright position in which their frictional engagement with the filament 1830 is at a minimum. Thus, the amount of friction by which the frictional engagement members 1820 engage the filament 1830 is substantially controlled by, in this example, the remaining one frictional engagement member 1820, that is, the frictional engagement member 1820 that is not engaged by the selector mechanism 2060.

Friction Adjustment—Rack & Pinion

FIG. 65 illustrates a directional adjustment unit 2800 incorporating a rack and pinion mechanism as described in our earlier application WO2017/158544, the entire contents of which are hereby incorporated by reference.

Unit 2800 may be incorporated in a headgear or headgear and patient interface, such as the headgear and any of the interfaces of FIGS. 2-3.

Unit 2800 comprises a rack 2810 and pinion 2820, where the pinion 2820 is contained in housing 1810. As shown in FIG. 65, the pinion 2820 comprises a centrally located gear 2830 which is flanked on each side by a circular flange 2840 that has a larger diameter than the outer diameter of the gear teeth 2850. A cylindrical shaft 2860 extends axially through the pinion 2820, protruding from the outer walls of the pinion 2820 and provides a rotational linkage between the pinion 2820 and the housing 1810. The shaft 2860 and pinion 2820 are configured such that there is no relative rotational movement therebetween.

The rack 2810 can be functionally similar to the above-described filament 1830. The rack 2810 is elongate and comprises a plurality of teeth 2880 along one side that are configured to mesh with the teeth 2850 of the gear 2830, such that linear movement of the rack 2810 is translated into rotational movement of the pinion 2820. The rack 2810 has a free end 2810A and a fixed end 2810B. When assembled with the housing 1810, the fixed end 2810B is proximal to a brake 3000 and the free end 2810A is proximal to the pinion 2820. The fixed end 2810B is configured to be integrally formed with or permanently joined to another mask component such as a frame or headgear arrangement. The free end 2810A is configured to remain unattached such that it may move relative to other mask components.

In some embodiments the fixed end 2810B of the rack 2810 is integrally formed or permanently joined with a headgear strap. This arrangement provides a strap element for the headgear that can be lengthened or shortened, relative to a frame or other mask component that includes the housing, thus allowing the headgear size to be adjusted. Alternatively, the fixed end of the rack 2810 may be integral with or permanently joined to a mask frame or other mask component and the housing 1810 may be fixed to a headgear strap.

The brake 3000 comprises an extrusion that is substantially rectangular in cross-section but includes one side wall 3010 that is concave. The concave side wall 3010 has a diameter that substantially matches the outer diameter of the flanges 2840 of the pinion 2820. The concave side wall 3010 of the brake 3000 protrudes from the internal surface of the right wall 1810R of the housing 1810. The brake 3000 can be made of a soft and compressible material such as an elastomeric plastic or rubber.

In a retraction movement of the rack 2810, as shown in FIGS. 65b, 65c, the fixed end 2810B of the rack 2810 is moved towards the housing 1810 and thus the free end 2810A moves away from the housing 1810. This movement would result in the reduction of the length of the headgear when combined in such an arrangement as described earlier.

During this retraction movement the linear movement of the rack 2810 causes the teeth 2880 of the rack 2810 to mesh with the teeth 2850 of the gear 2830 and rotate the pinion 2820 in a clockwise direction (relative to the page). This rotation also pushes the pinion 2820 towards the left side wall 1810L of the housing 1810, and keeps the shaft 2860 at the left end of an elongate shaft aperture 2870 in the housing 1810. The internal surface of the left side wall 1810L is curved to substantially match the outer diameter of the pinion 2820. This reduces friction between the pinion 2820 and the housing 1810 and allows the rack 2810 to move freely through the housing 1810. In this position, there is clearance between the pinion 2820 and the concave side wall 3010 of the brake 3000.

In some embodiments the rack and pinion mechanism 2810, 2820 can be combined with a biasing means such as an elastic strap that provides a retraction force that biases the rack 2810 to move in the retraction direction without the user applying an external force.

Figure 65D:
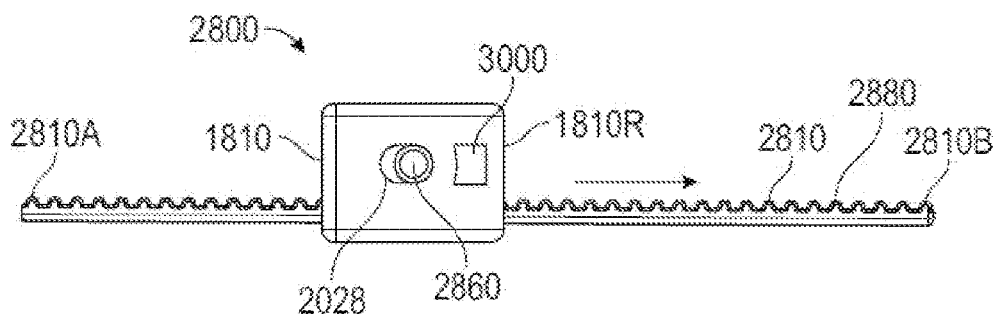
Figure 65E:
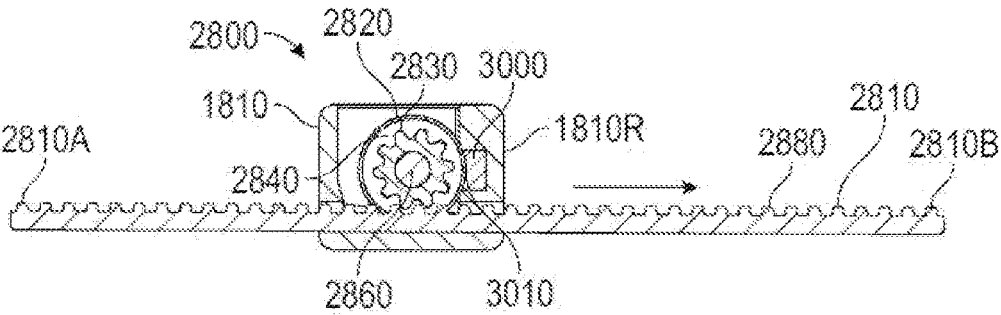

In an extension movement of the rack 2810, as shown in FIGS. 65d, 65e, the fixed end 2810B of the rack 2810 is moved away from the housing 1810 and thus the free end 2810A moves towards the housing 1810. This movement would result in an extension in the length of the headgear when combined in such an arrangement as described earlier.

During this extension movement the linear movement of the rack 2810 causes the teeth 2880 of the rack 2810 to mesh with the teeth 2850 of the gear 2830 and rotate the pinion 2820 in an anticlockwise direction (when viewed along the axis of rotation of the pinion 2820 in FIG. 65). This rotation also pushes the pinion 2820 towards the right side wall 1810R of the housing 1810 and the brake 3000. The shaft 2860 slides towards the right side of the shaft aperture 2028 such that the flanges 2840 of the pinion 2820 contact the concave side wall 3010 of the brake 3000 and compress the brake 3000. This provides friction between the pinion 2820 and the brake 3000 which prevents the rack 2810 from moving freely through the housing 1810. The concave side wall 3010 of the brake 3000 allows the pinion 2820 to continue to rotate in response to the linear movement of the rack 2810, but a higher force is required to induce this.

When combined within a respiratory interface arrangement this results in a resistance to elongation of the headgear, which requires the user to intentionally apply a large enough force to overcome the friction between the pinion and brake, in order to increase the size of the headgear.

With additional reference to FIGS. 66 to 68, a directional adjustment unit 2800 comprises a frictional adjustment arrangement configured to adjust the degree of frictional engagement of the brake 3000 with the flanges 2840 when in the engaged configuration. This is similar to the embodiment of FIG. 65 except that brake 3000 is adjustable. The position of the pinion 2820 is togglable from one side of the slot to the other. This provides two different levels of friction (i.e. no contact with brake 3000 and contact with brake 3000). The slip force can be further adjusted by adjusting the horizontal position of the brake 3000. Rotating the dial 4010 leads to movement of the brake 3000 in the horizontal direction towards or away from the pinion 2820. In the high-friction configuration pictured in (a), which corresponds to the configuration pictured in FIG. 65*d*, the engagement between the pinion 2820 and a brake 3000 moved to the left side will be greater, therefore leading to a greater friction force.

In the FIG. 66*a* arrangement, a user actuator 4010 is provided on the housing in the form of a dial whose rotational axis is parallel to that of pinion 2820. Rotation of the dial moves the brake 3000 within the housing 1810 as will be described in more detail with reference to FIG. 67 below.

In the FIG. 66*b* arrangement, a user actuator 4010 comprises a set screw 4030 threadably mounted in the housing 1810, for rotation about a set screw axis perpendicular to the axis of rotation of the pinion 2820. The set screw 4030 has a brake engaging end 4040 which abuts against the brake 3000. Rotation of the set screw 4030, moves the brake 3000 toward or away from the pinion 2820, in a direction parallel to the longitudinal axis of the rack 2810. The relative position of the brake 3000 relative to the pinion 2820 serves to adjust the friction between the two components when the pinion 2820 is driven into contact with the brake 3000.

With reference to FIG. 67, dial 4020 is mounted on a shaft 4070 which is itself rotatably mounted on the brake 3000. A gear wheel 4050 is also mounted on the shaft and engages with a matching gear profile 4060 in a slot 4070 in the side wall 1810S of the housing 1810. Rotation of the dial 4020 drives gear wheel 4050 along gear profile 4060 and thus moves the brake 3000 toward or away from the pinion 2820, to adjust the frictional force between the pinion 2820 and the brake 3000.

With reference to FIG. 68 a further frictional adjustment arrangement for a directional adjustment unit 2800 is similar to the embodiments of FIGS. 65 to 67 except that brake 3000, which comprised a drum type brake pad or block configured to engage flanges 2840 in a radial direction that is perpendicular to the axis of rotation of the pinion 2820, is replaced with a brake disc 5000 and brake calliper 5010 having axially opposed brake pads configured to receive brake disc 5000 therebetween and to frictionally engage the brake disc 5000 in an axial direction, that is, parallel to the axis of rotation of the pinion 2820. In this embodiment, the brake disc 5000 comprises the flanges 2840 of pinion 2820, but could alternatively comprise a separate or further component additional to flanges 2840.

A user actuator (not shown) may be provided to vary the frictional force applied by the opposed brake pads to the disc 5000. The user actuator may be configured to move one or each brake pad in an axial direction toward or away from the disc 5000, for example via an adjustment screw or cam. Alternatively or additionally, the brake calliper 5010 may comprise calliper halves movably mounted together, whereby the user actuator is configured to move one or both of the calliper halves towards or away from the other.

The brake disc 5000 and pinion 2820 are mounted together via a selective engagement unit (not shown) which is configured such that the brake disc 5000 and pinion 2820 engage and rotate together when rotated in a first direction, but disengage and allow relative rotation between the brake disc 5000 and pinion 2820 when the pinion 2820 is rotated in the opposite direction. The selective engagement unit 5020 thus allows the frictional force generated by the brake pads and brake disc 5000 to resist movement of the rack 2810 in one direction (being a direction which extends the headgear), but does not resist, or at least reduces the resistance, of movement of the rack 2810 in the opposite direction (being a direction which retracts the headgear. As with all of the directional adjustment units 1800, 2800 described herein, the amount of force generated to resist extension of the headgear can be adjusted.

The selective engagement unit could comprise any one or more of:
   a) a ratchet mechanism;
   b) a slipper or one way clutch.

FIGS. 68*b*) to 68*d*) show different configurations of the brake disc 5000 and the brake calliper 5010. FIG. 68*b*) is an end view of the arrangement of FIG. 68*a*). However, in this example, the calliper 5010 or at least the brake pads may be moved in a vertical direction towards the axis of rotation of the pinion wheel, to adjust engagement of the brake pads with the disc 5000. FIG. 68*c*) uses two brake discs 5000 and a pair of brake pads each configured to engage a respective disc 5000. Each brake pad engages a radially outer surface of the discs 5000. Again the brake pads may be moved vertically to adjust engagement. FIG. 68*d*) comprise a single brake pad or block configured to be positioned between a spaced apart pair of brake discs 5000 so that the single brake pad engages both discs 5000. Again the brake pads may be moved vertically to adjust engagement. In these examples, the or each brake pad or block may therefore comprise opposed inclined faces that increase their engagement with the brake discs 5000 as the disc is moved up and down in a direction perpendicular to the axis of rotation of the discs 5000.

Honeycomb Front Straps

Figure 69:
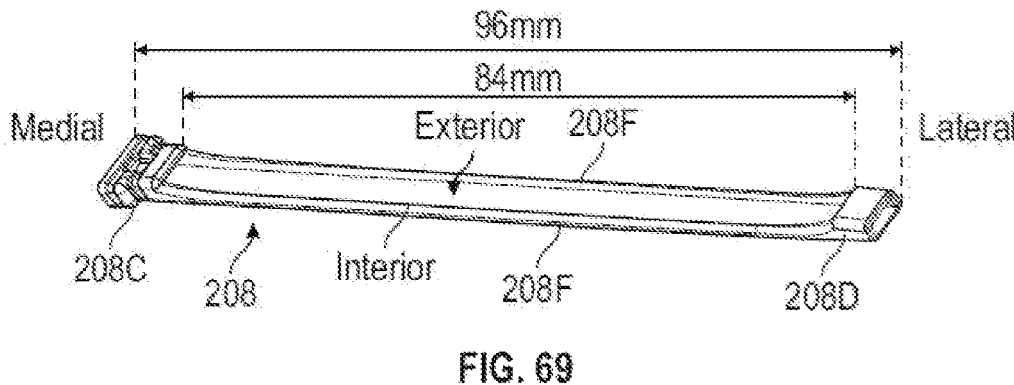
FIG. 69 is a perspective view of an elongate support body comprising part of a directional adjustment unit.
Figure 70:
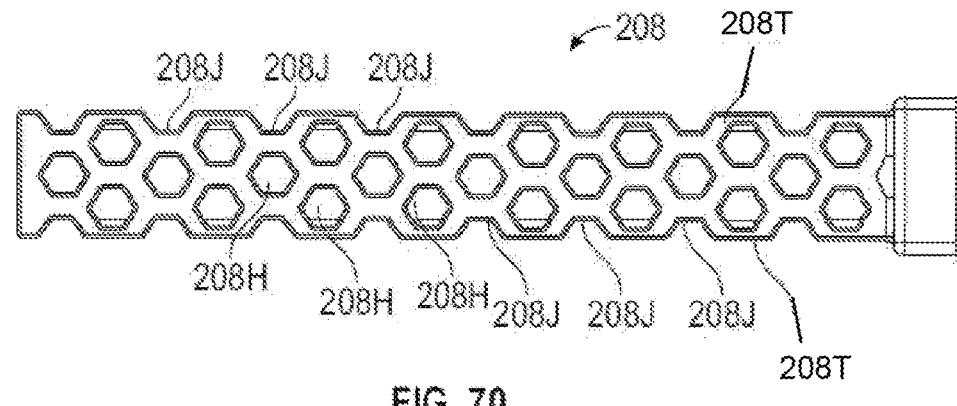
FIG. 70 is a view from one side of a modified elongate support body in accordance with aspects of this disclosure.
Figure 71:
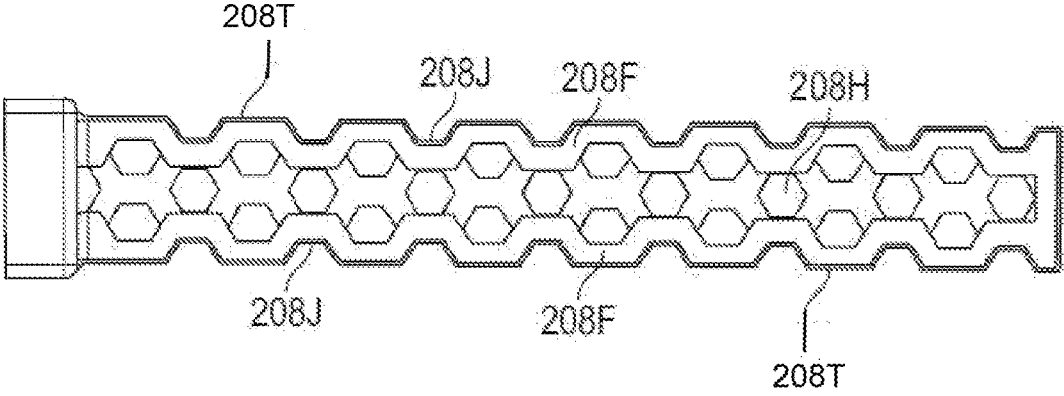
FIG. 71 is a view from the other side of the modified elongate support body of FIG. 70.

In accordance with this disclosure, and with reference to FIGS. 70 to 74, modifications to the pair of front straps or filament support structures 208 are provided. The filament support structures 208 as described above have features as shown in FIG. 69. The filament 1830 is thus supported by a filament support structure 208 in the form of a sheath of a slightly wider width than the larger region 1830B of filament 1830 and with collars 208C, 208D that hold the filament 1830 close to it. The modified filament 1830 feeds through both collars 208C, 208D while being supported by the support structure 208. The support structure 208, with collars 208C, 208D on both ends, otherwise comprises, in this example, an elongate support body being a rectangular length of rigid material (e.g. plastic) in the form of a side wall, which supports the filament 1830 on one side only. In terms of orientation, the support structure 208 lays behind the filament 1830 and provides an interface, or intermediate layer, between the user's skin and the filament 1830. The collars 208C, 208D face outwards, away from the user's face.

Figure 72:
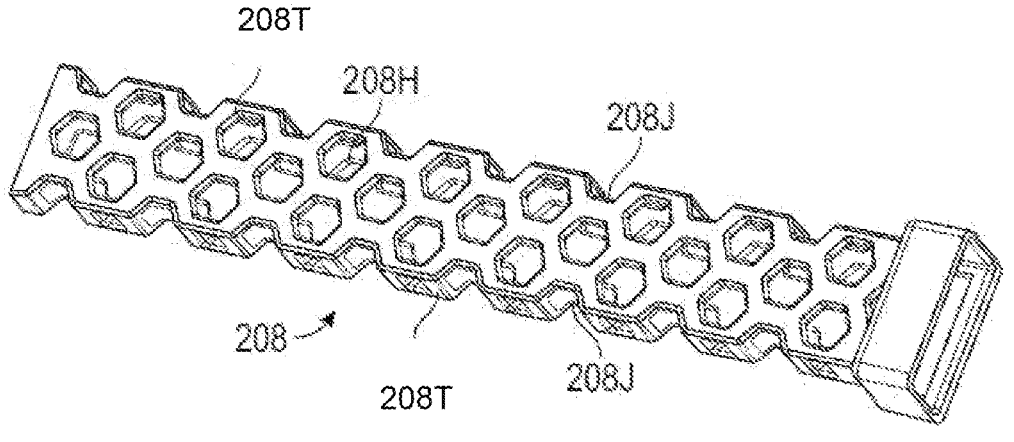
FIGS. 72 and 73 are perspective views of the modified elongate support body of FIGS. 70 and 71.
Figure 73:
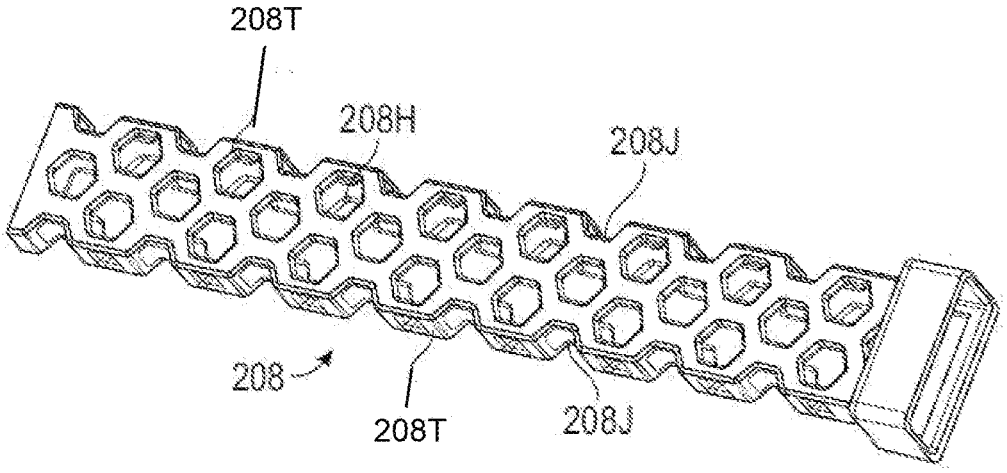
Figure 74:
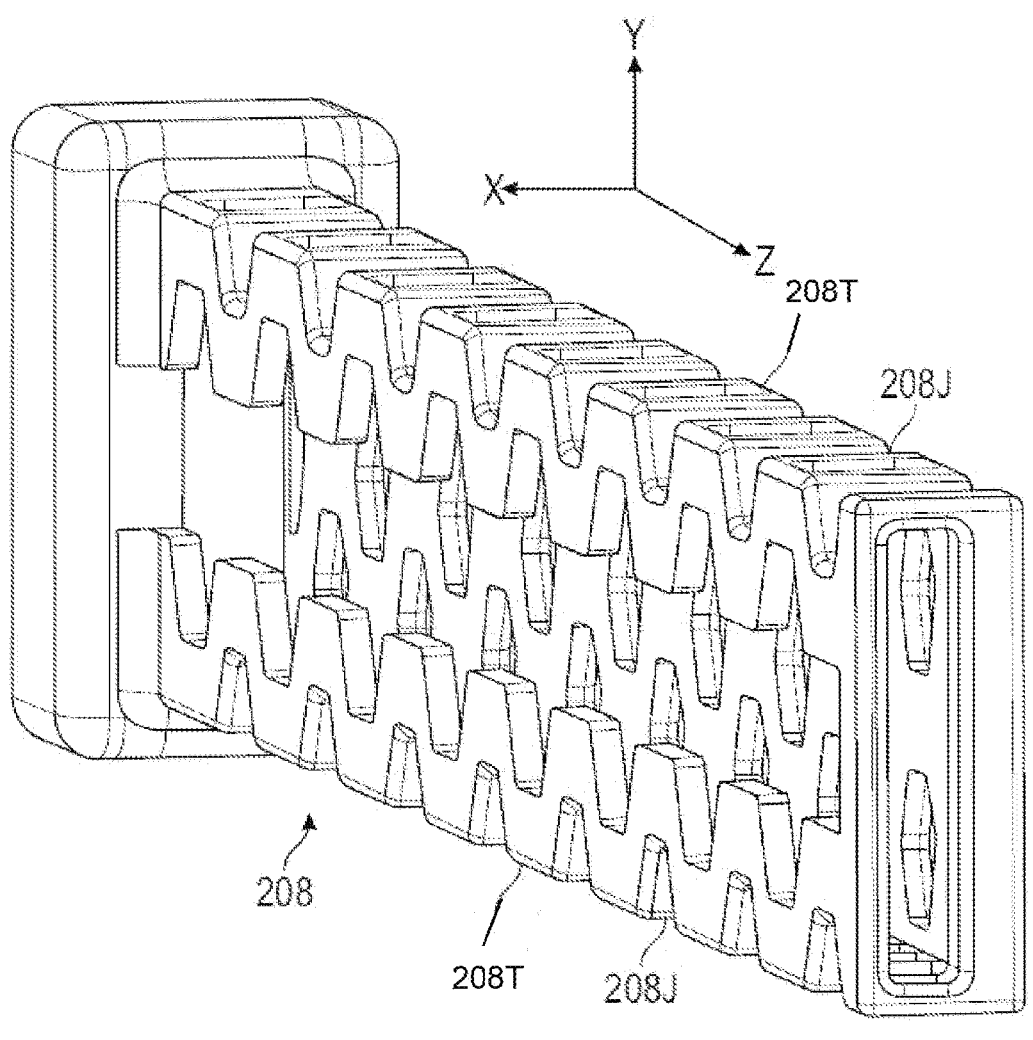
FIG. 74 is a perspective view from a lateral end of the modified elongate support body of FIGS. 70 to 73.

With reference to FIGS. 70 to 74 the filament support structure 208 is modified such that at least a portion of the elongate support body has a bending stiffness which is greater in a direction along the transverse axis (x-axis using the reference system of FIG. 74) extending across the elongate support body than in a direction along the vertical axis (y-axis using the reference system of FIG. 74). The filament support structure is therefore configured to flex more easily vertically (i.e. up and down the user's face) than in the transverse direction (i.e. horizontally towards and away from the user's face). As can be seen with reference to the x-y-z coordinate system shown in FIG. 74, the modified filament support structure 208 has a structure configured such that the bending stiffness is higher about the transverse y-axis than about the vertical x-axis; allowing the honeycomb support structure to bend/curve transversely to conform to the shape of the user's cheeks, while being stiff enough to support and maintain vertical stability of the seal provided by the mask. Compared to a filament support structure design with solid walls, the entire structure is more flexible in both the x and y directions. In the x-axis, this allows the structure to conform more easily to the shape of the user's face, but the effects of the modifications in this disclosure are more significant in the y-axis—the filament support structure can flex up and down much more easily to allow easier adjustment of the mask seal angle and position of the mask seal.

The elongate support body is provided with a bending control structure having one or more bending control formations, configured to control bending of the elongate support body in the manner described above. In this example the bending control formations comprise a plurality of apertures 208H, cut-outs 208J and castellations 208T spaced apart along the length of the elongate support body.

In this example, the apertures 208H are each of hexagonal shape, and are arranged in a regularly array in which the spacing between the apertures 208H is regular, and the pattern/arrangement of apertures 208H is regular. In this example the regular array is such that the elongate support body has a honeycomb type structure.

The elongate support body may comprises at least one such aperture 208H, and the, each, or any one of, the apertures 208H may be of any one of the following shapes:
a. circular;
b. elliptical;
c. triangular;
d. quadrilateral;
e. pentagonal;
f. hexagonal;
g. any other shape having multiple sides, where the sides may be straight or arcuate.

Figure 22:
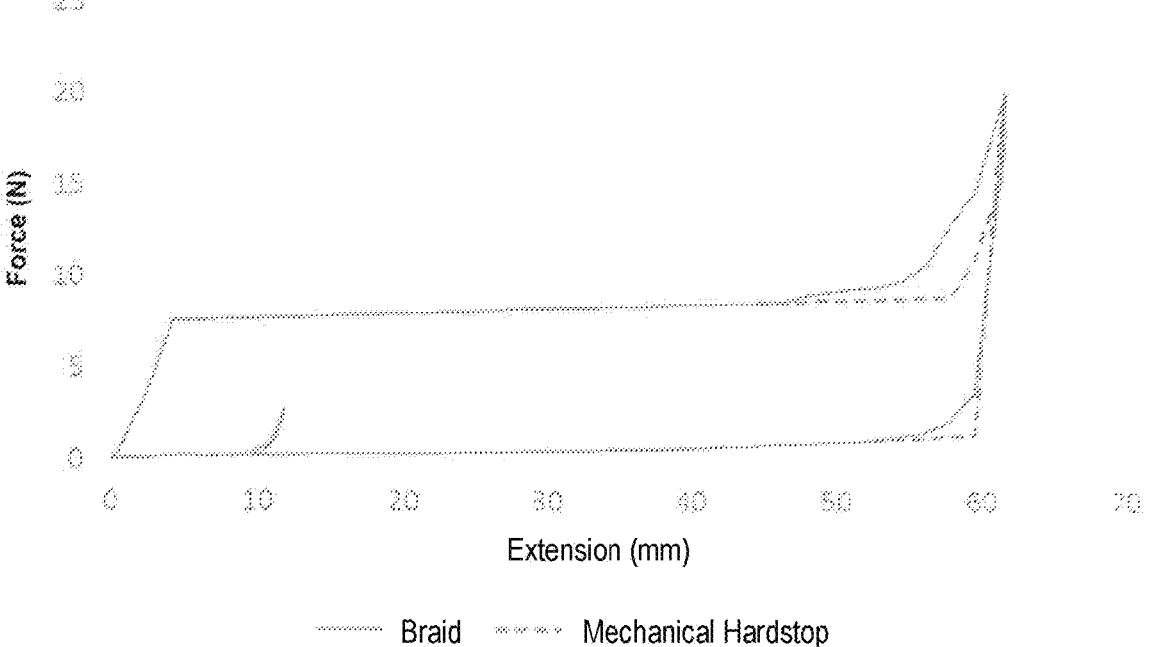
FIG. 22 shows a force comparison between our prior directional adjustment unit and a directional adjustment according to an embodiment.

The filament support structure 208 comprises a pair of elongate guide surfaces 208F that extend along the filament support structure 208 parallel to the longitudinal axis of the filament support structure 208, and which constrains the filament relative to the filament support structure in a direction perpendicular to the longitudinal axis. In this example, both elongate guide surfaces 208F are also provided with bending control formations in the form of at least one cut-out 208J being a portion of the elongate guide surfaces 208F where there is no wall material or where there is reduced wall material. The elongate support body is also provided with such cut-outs 208J, when the filament support structure 208 is viewed in a direction perpendicular to its longitudinal axis, that is, when viewed along the x-axis of FIG. 22.

In this embodiment a plurality of cut-outs 208J are provided. Each cut-out 208J in this example is of geometric shape, comprising regular lines and shapes, and in this case is a half hexagon. Any other multi-faceted shape is envisaged, including where the cut-out comprises one or more straight portions and/or one or more curved portions. The cut-outs 208J are arranged such that the elongate guide surfaces 208F and elongate support body is castellated or toothed and comprises a plurality of castellations or teeth 208T each pair of which is separated by a respective cut-out 208J.

In this embodiment, the upper and lower margins of each elongate guide surface 208F are each provided with cut-outs 208J. Each elongate guide surface 208F is therefore of an undulating or zig-zag profile when viewed from the side along the x-axis, the profile being formed by the combination of cut-outs 208J and castellations 208T.

As can best be seen in FIGS. 72 and 73, the apertures 208H are arranged along the length of the elongate support body in a repeating pattern or array of a single aperture, then a pair of vertically stacked apertures, then another single aperture and so on. The portion of the elongate support body in which each single aperture 208H is formed is aligned, with respect to the longitudinal axis of the elongate support body, with the cut-outs 208J on the elongate guide surfaces 208F. Thus each single aperture 208H is longitudinally aligned with a pair of cut-outs 208J, whilst each portion of the elongate support body having a pair of apertures 208H, has no cut-out.

In this embodiment, the apertures 208H and cut-outs 208J are provided along substantially the entire length of the filament support structure 208. However, it is envisaged that the apertures 208H and cut-outs 208J may be provided along only a portion or portions of the length of the filament support structure 208. The apertures 208H and cut-outs 208J may extend over 50% of the length of the elongate support body, preferably over 75% of the length, and more preferably over 90% of the length.

The side with elongate guide surfaces with no wall material or reduced wall material is designed to face away from the user's face so that the inner components (filament) do not contact the skin.

The modified filament support structure 208 may be used with any of the directional adjustment units 1800, 2800 described above.

With reference to FIGS. 75 to 78, a further example of a respiratory interface system or respiratory mask system 2100 is shown for the delivery of respiratory therapy to a patient according to another embodiment. This mask system 2100 is similar to the mask system 100 of FIGS. 2 and 3, with some differences as described below. The mask system 2100 may comprise an interface, such as a mask 2102. In the illustrated arrangement, the mask 2102 comprises a seal 2104 and a frame 2106, as described in further detail herein. The illustrated mask system 2100 also includes a headgear 2200 (which may also be referred to as a "headgear assembly" herein). The mask 2102 and headgear 2200 may comprise a connection system to attach the headgear 2200 to the mask 2102. Various forms of connection systems may be used to attach the headgear 2200 to the mask 2102. Similarly, the mask 2102 may be coupled to at least one and possibly multiple different types of headgear.

The seal 2104 can be configured for sealing around and/or underneath a patient's mouth and/or nose. In the illustrated arrangement, the seal 2104 is a nasal seal configured to deliver the flow of breathing gases only to the user's nose. In particular, the illustrated seal 2104 includes a pair of nasal pillows configured to create a seal with the user's nares and a secondary sealing portion that surrounds the nasal pillows and is configured to create a secondary seal with one or more of an underside of the user's nose, side portions of the user's nose and the user's upper lip.

However, features of the present disclosure can be implemented with other mask systems having other types of mask seals, such as full-face seals, for example and without limitation.

The frame 2106 is configured for supporting the seal 2104 and attaching the seal 2104 to the headgear 2200. The frame 2106 may also comprise a gas inlet 2108 configured to attach to a gas conduit 2110 for delivering a flow of breathing gas to the patient via the mask 2102.

Headgear 2200 comprises at least one strap, which can include a side strap comprising, or being connected to a filament support structure 2208, at least one yoke assembly 2021, and at least one filament 1830 which extends within the at least one filament support structure 2208 and enters the yoke assembly 2021. The headgear 2200 also comprises the directional adjustment unit 1800 according to any of the embodiments disclosed herein.

Figures 82, 83:
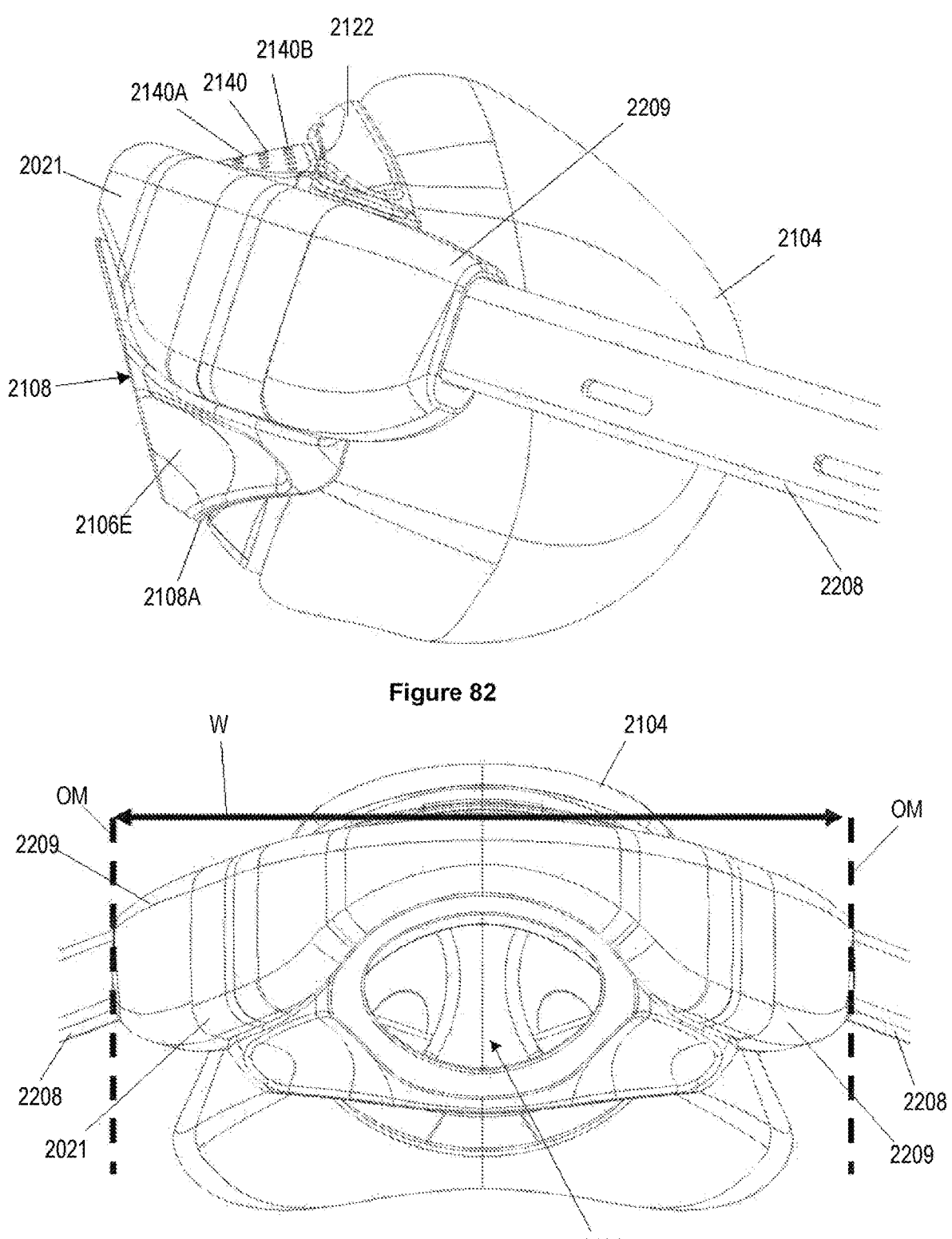
FIG. 82 is an enlarged side view of the seal assembly and filament support structure of FIG. 80.
FIG. 83 is an enlarged front view of the seal assembly and filament support structure of FIG. 80.
Figure 84:
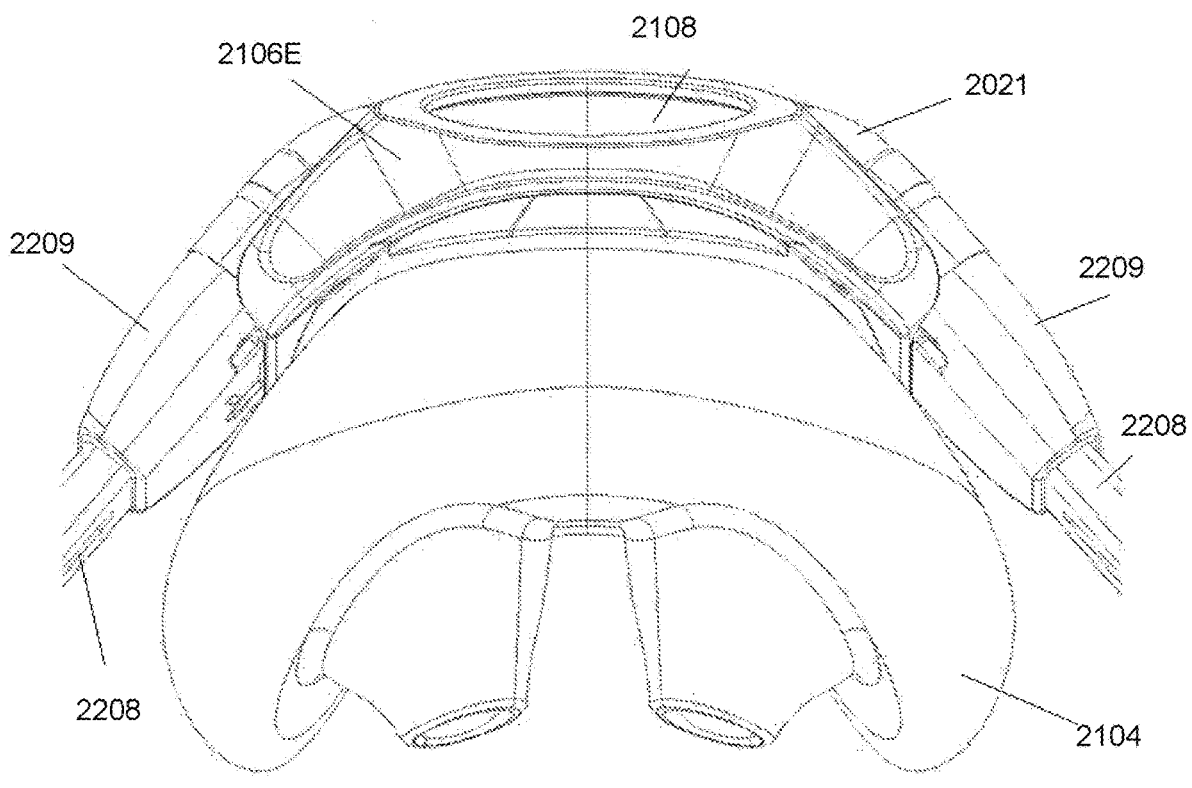
FIG. 84 is an enlarged bottom view of the seal assembly and filament support structure of FIG. 80.

In system 2100, the yoke assembly 2021 is narrower than yoke assembly 20, when viewed from the front along the central axis of mask inlet 2108. The yoke assembly 2021 is narrower across a dimension W which extends between the two laterally outermost margins OM of the yoke assembly 2021, as can best be seen in FIG. 83. As with yoke assembly 20, the ends of the opposed filaments 1830 enter the yoke 2021 from the respective filament support structures 2208. However, in this embodiment, the ends of the opposed filaments are not contained within yoke 2021, but instead pass through the yoke 2021 and into the opposite filament support structure 2208. Thus each filament support structure 2208 is provided with two longitudinal extending filament passages, to simultaneously accommodate both the first filament 1830 passing into yoke assembly 2021, and also the end of the other filament passing out of yoke assembly 2021. This modification means that the width of yoke assembly 2021 can be smaller than the width of yoke assembly 20, because the yoke assembly does not need to contain the filament 1830. Consequently, the yoke assembly 2021 extends laterally across a smaller portion of the user's face. This results in a general increase in comfort of the user, and in particular, when the user is lying down, enables the user to roll their head further before the yoke assembly 2021 contacts a pillow. This can best be seen from FIG. 117, where the dashed lines linking the yoke assembly to the user's face illustrate the additional angle by which the user's head can rotate, before the yoke assembly 2021 contacts the bed or pillow P. A horizontally narrower yoke assembly (i.e. shorter length) increases the ease of side-sleeping when the mask is in use. The yoke assembly 2021 extends horizontally beyond the most lateral points of the mask frame 2106, and therefore forms the widest points of the mask assembly that is rigid. A narrower yoke assembly therefore brings the lateral most points of the mask 102 as a whole, further from the surface of the pillow P when the user is sleeping on their side. This allows a greater angle range of rotation of the head before the end of the yoke comes into contact with the pillow. Contact with the pillow P may lead to the yoke assembly 2021 and therefore the mask 2102 being pushed away from the pillow and becoming dislodged. This may lead to leaks and affect the delivery of CPAP therapy to the user, as well as causing user discomfort.

In system 2100, the yoke assembly 2021 is a two piece assembly comprising a front member 2021*a* and a rear member 2021*b* which in this example are joined together with a snap-fit engagement provided by interengaging formations on each member 2021*a/b*.

As can most clearly be seen in FIG. 106 onwards, the front member 2021*a* and rear member 2021*b* are provided with guide formations on their internal surfaces. These guide formations, when the front member 2021*a* and rear member 2021*b* are secured together, define filament guide passages through the yoke assembly 2021. Yoke assembly 2021 therefore does not require the divider insert 22 of yoke assembly 20. The guide passages are configured such that the filaments 1830 are guided past each other, through the yoke assembly 2021, without interfering with one another. In the described example, the guide passages are configured such that the filaments 1830 cross over one another at the centre of the yoke assembly 2021, with each filament 1830 entering the yoke assembly 2021 at a first position, being guided downwardly into the yoke assembly 2021 before exiting the yoke assembly 2021 at a second, higher position.

Further, one of the front member 2021*a* and rear member 2021*b* is provided with a guide formation that spaces one of the filaments 1830 away from the front of the yoke assembly 2021. This enables one of the filaments 1830 to take a path through the yoke assembly 2021 that is further from the front of the yoke assembly 2021 than the other, thus enabling the filaments 1830 to cross over, inside the yoke assembly 2021, without interfering with one another.

In system 2100, the housing 1810 of each directional adjustment unit 1800 is received, or at least partially received, in a respect recess formed in the lateral ends of yoke assembly 2021. Each unit 1800 is held in place by a respective end cap 2209 which, in this example, retains the unit 1800 on the yoke assembly 2021 via a snap fit connection. End cap 2209 further engages the end of the elongate support member 2208, to retain member 2208 on the yoke assembly 2021.

In system 2100, headgear 2200 is of a similar configuration to headgear 200, but comprises knitted tubes into which semi-rigid plastic is injected to form the core of the rear portion of the headgear. The side straps of the headgear are formed by elongate support bodies or elongate support structures 2208, and now contain the ends of the filaments 1830, as described above.

With reference to FIGS. 79 to 101, mask 2102 is similar to mask 102 but has some differences. Mask 2102 comprises a flexible seal or cushion 2104, a more rigid mask frame 2106, and an intermediate clip 2122. Clip 2122 comprises a first clip portion 2122*a* and a second clip portion 2122*b* that capture a rim of the seal 2104 between them. The clip 2122 is configured to selectively connect to the frame 2106, such as by a snap-fit, friction fit or other suitable arrangement. The frame 2106 can include a vent 2140, which is configured to exhaust gases from an interior of the seal 104. Optionally, the mask 2102 can include a vent insert or diffuser 2152 that covers the vent 2140 to control the exhaust flow. In mask 2102, the shape or aspects of the seal 2014 and frame 2106 have changed, the shape and position of the vent 2140 has changed, and the mounting of the yoke assembly 2021 on the mask frame 2106 has changed.

Frame 2106 comprises a gas inlet 2108 for connection to gas conduit 110, optionally via a conduit connection portion 2108B which comprises an inlet 2103D. Gas inlet 2108 in this embodiment, is provided on a lower portion of the frame 2106, when viewed from the front, and is provided in a protruding boss 2108A which projects outwardly from the front of the mask frame 2106 in a direction along the central axis of the gas inlet 2108. In this example, the boss 2108A is substantially elliptical, with inlet 2108 also being elliptical. In particular both the boss 2108A and inlet 2108 are wider than they are high, such that each extend further laterally outwardly from the axis of the inlet 2108, than they extend vertically. This configuration reduces the visibility of the mask 2102 on the user's face, by minimising any interference with the user's line of sight, and can also minimise interference with the user's mouth, as the reduced height spaces the mask 2102 away from the mouth.

The upper part of the boss 2108A comprises a flat but arcuate surface 2106A which extends across the front of the frame 2106 and defines the lower part of a yoke mount in the form of a recess 2106B which receives the yoke assembly 2021. The upper part of the recess 2106B is defined by a pair of outwardly extending upper protrusions 2106C that overhang the recess 2106B. The yoke assembly 2021 is retained in the recess 2106B via snap fit formations 2106D at the lateral ends of the recess 2106B, which engage with the first member 2021A of yoke assembly 2021.

Figure 85:
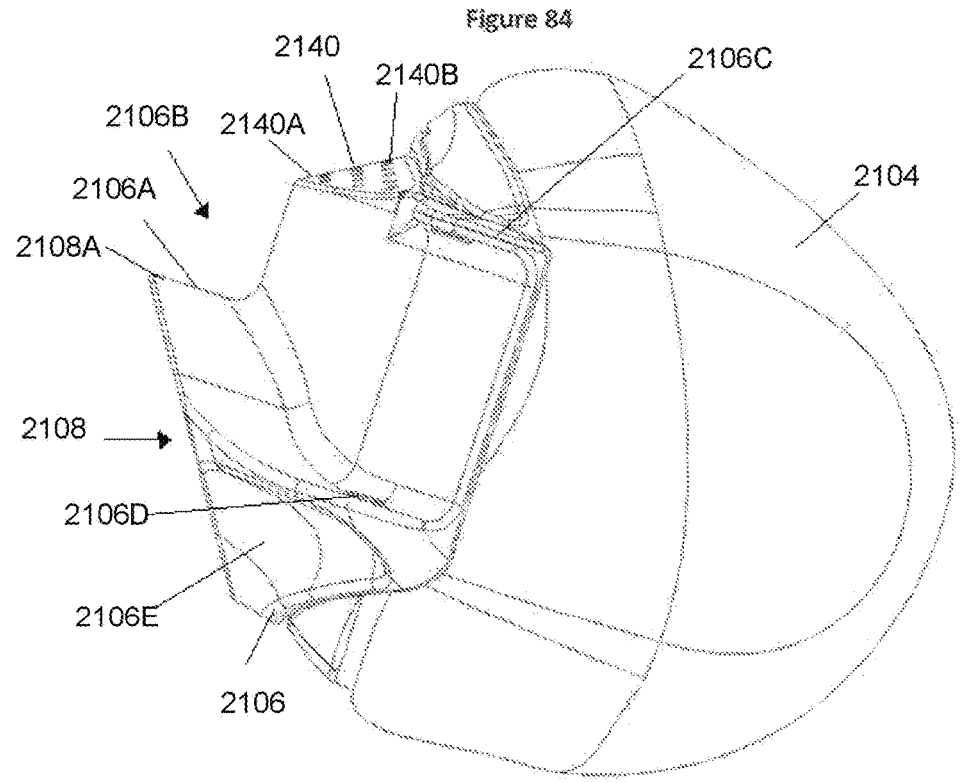
FIG. 85 is an enlarged side view of the seal assembly of FIG. 80.
Figure 86:
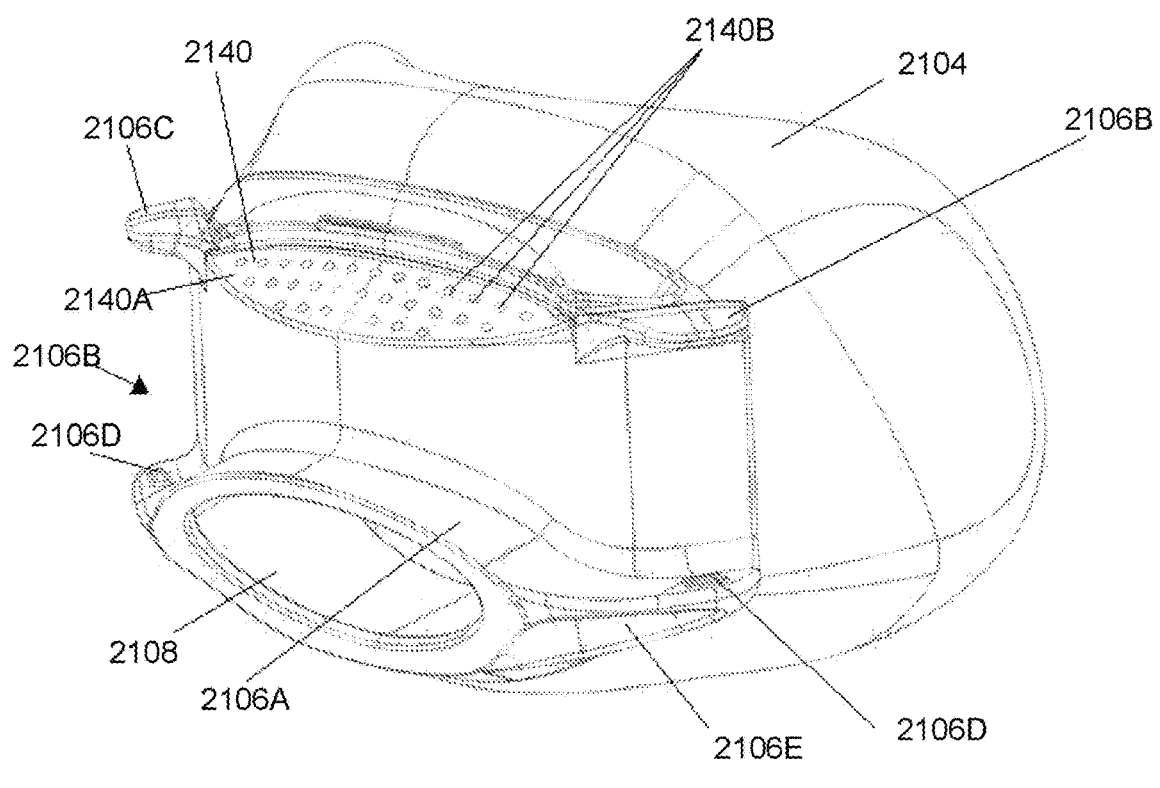
FIG. 86 is an enlarged perspective view of the seal assembly of FIG. 80.
Figure 87:
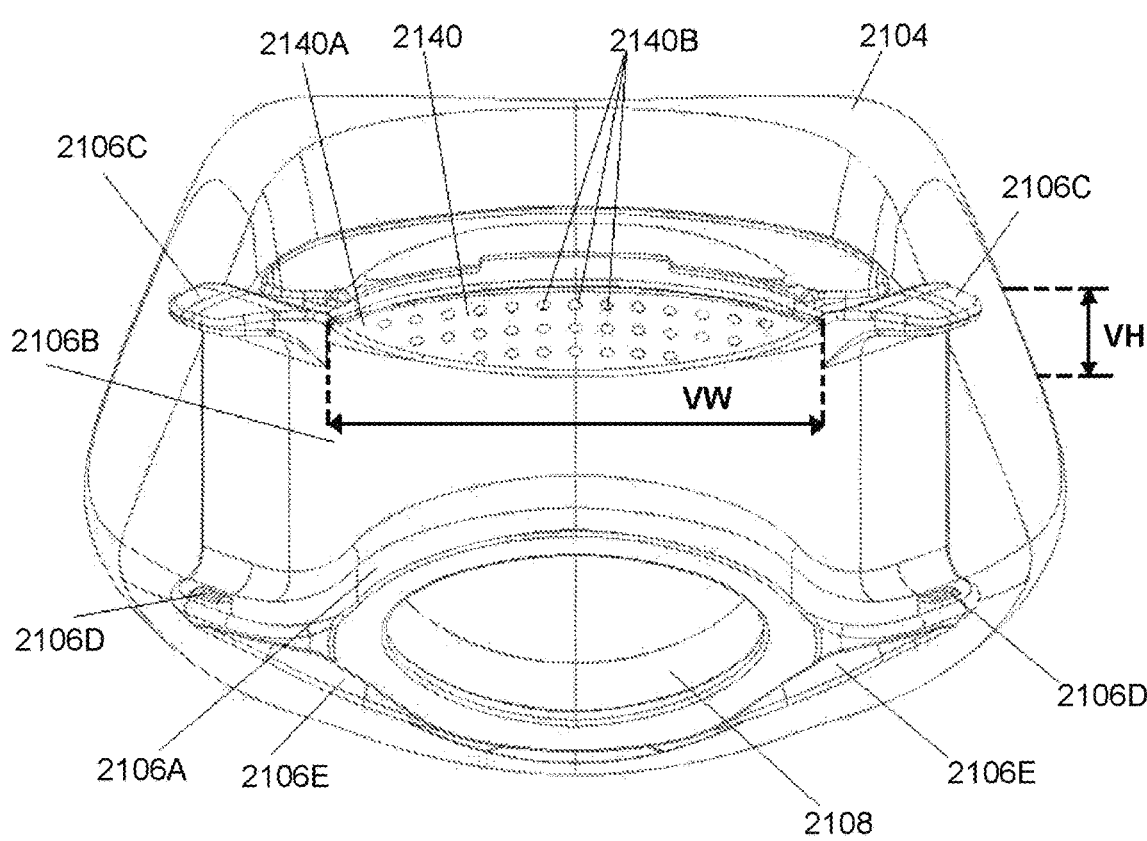
FIG. 87 is an enlarged front view of the seal assembly of FIG. 80.
Figure 88:
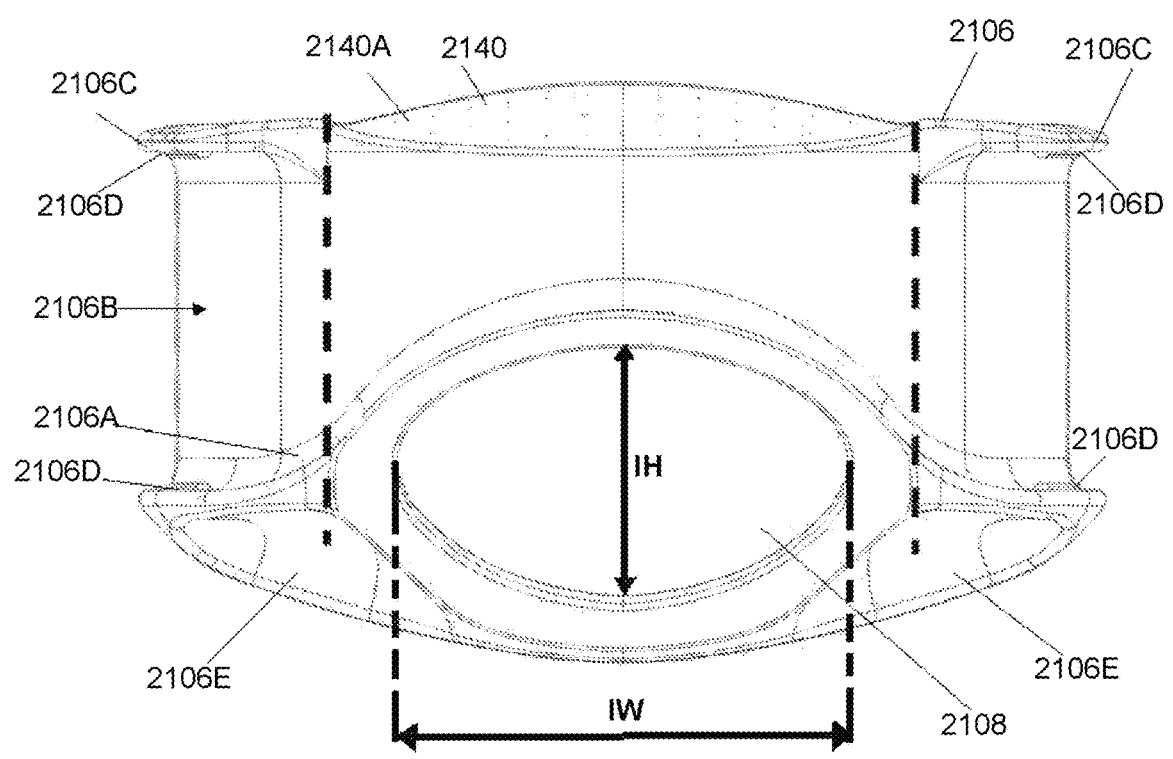
FIG. 88 is an enlarged front view of the frame assembly of FIG. 75.
Figure 89:
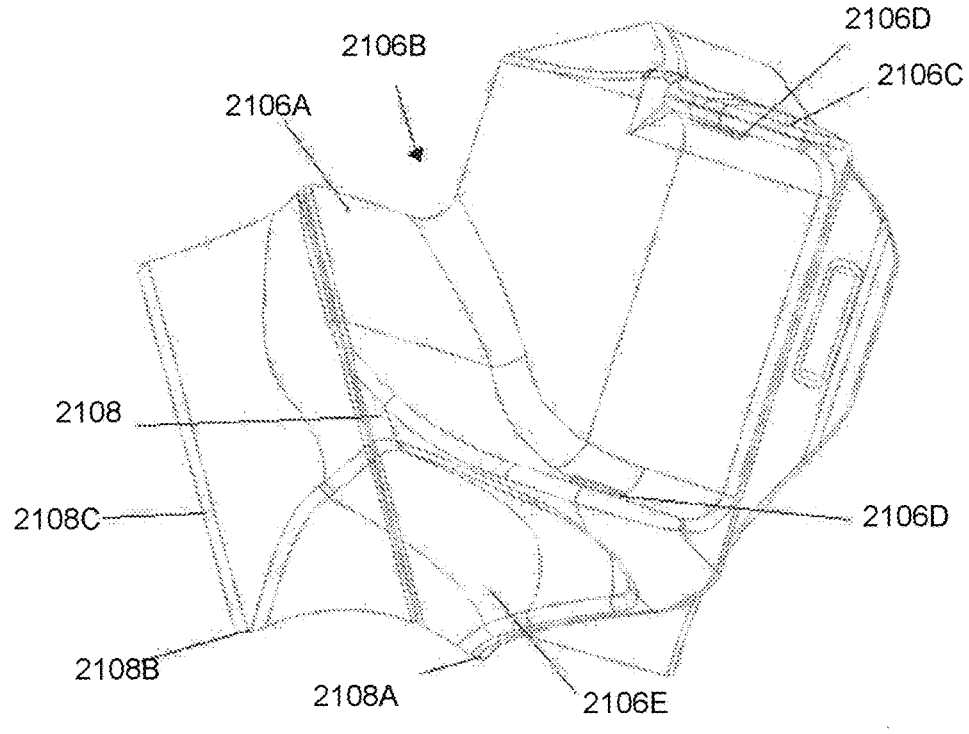
FIG. 89 is an enlarged side view of the frame assembly of FIG. 75.
Figure 90:
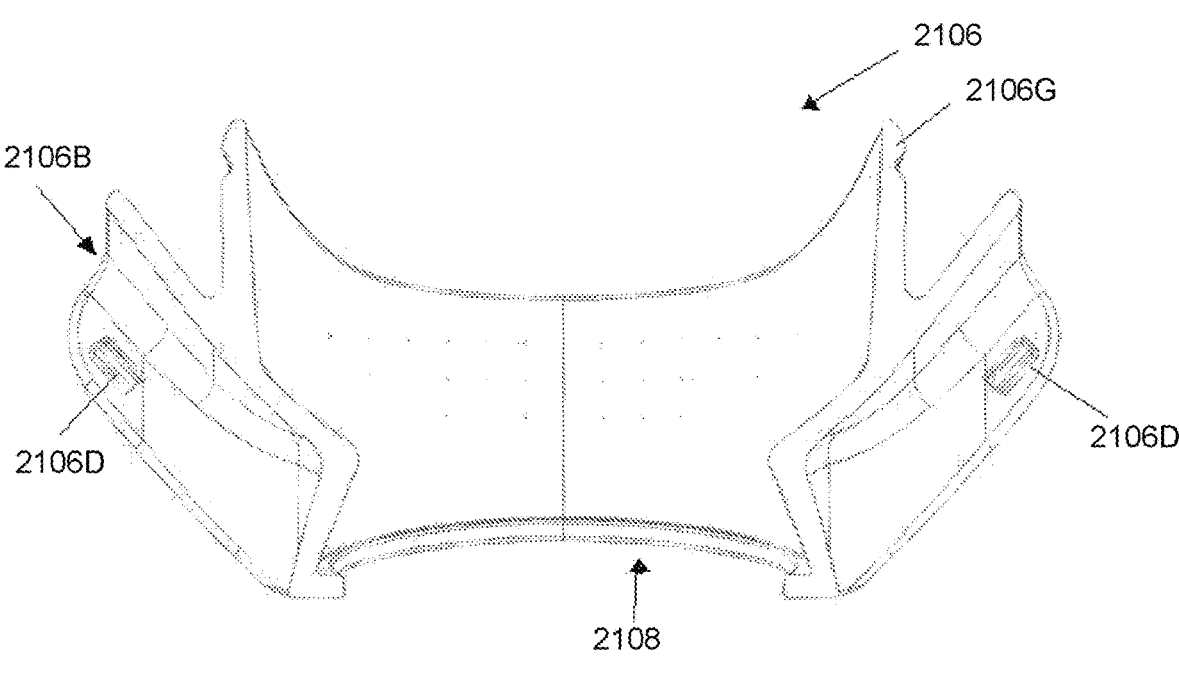
FIG. 90 is an enlarged rear view of the frame assembly of FIG. 75.
Figure 91:
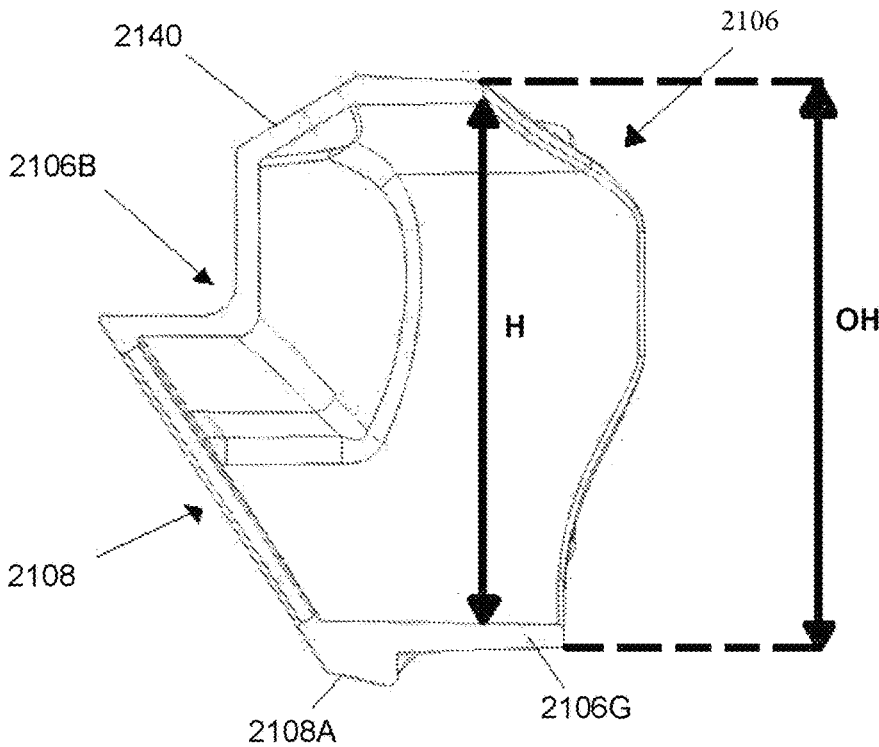
Figure 92:
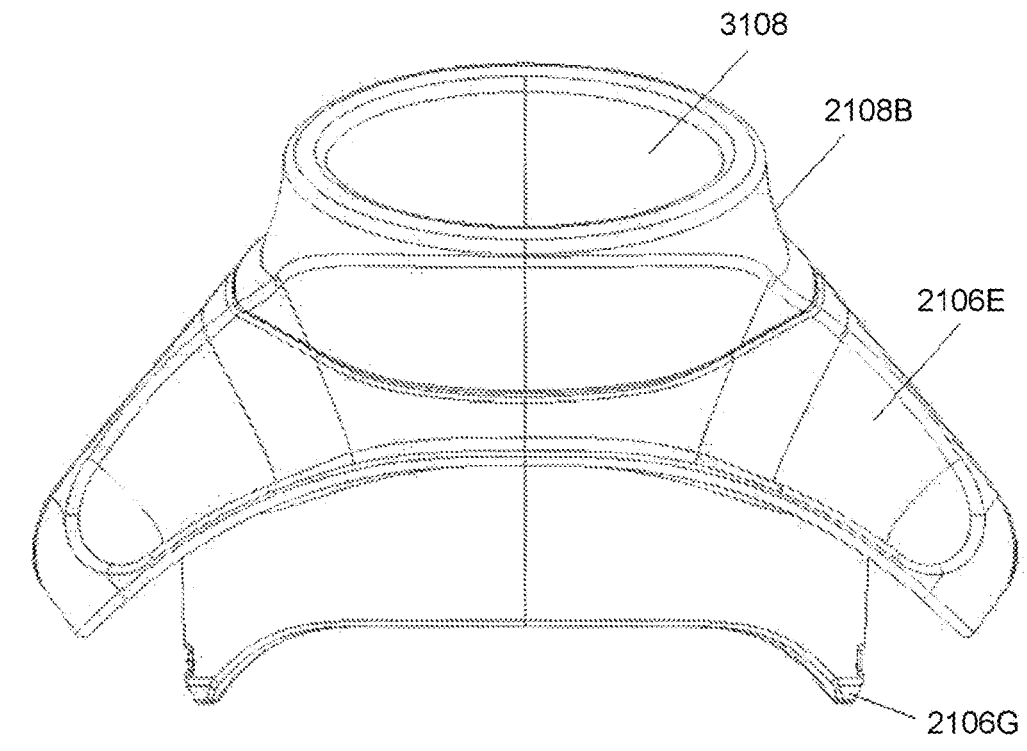
Figure 93:
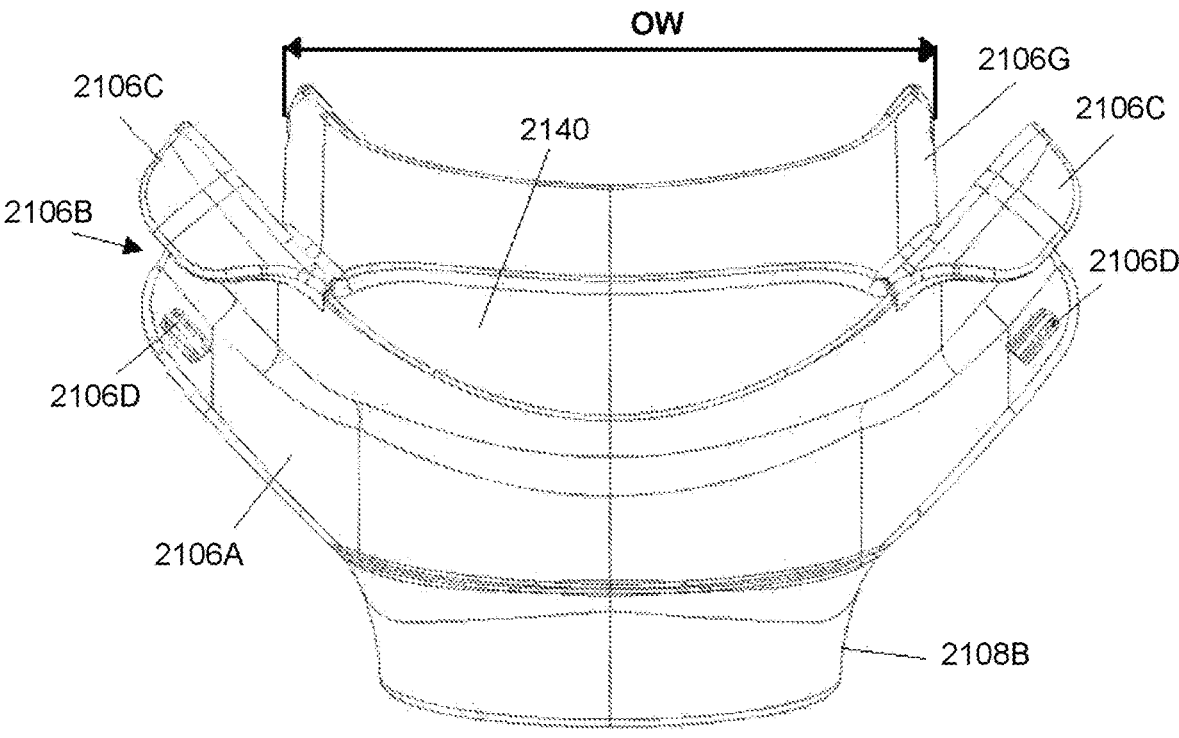

With reference to FIGS. 85, 86 and 89 in particular, the front of the frame 2106 is comprises a laterally spaced pair of finger grip portions 2106E defined by recessed portions, one either side of the inlet 2108, below the recess in which the yoke assembly 2021 is mounted. These recessed portions provide increase surface area for better grip and a tactile indicator for the grip location when adjusting the position of the seal 2104. These grip concavities may be only on the front surface of the mask frame 2106 or may also extend to the lower region of the inlet boss 2108A or a conduit connector portion 2108B extending from inlet boss 2018A.

In this embodiment, the vent 2140 comprises a substantially convex, elliptical vent surface 2140A provided above recess 2106B, between the pair of outwardly extending upper protrusions 2106C. The vent 2140 comprises an array of vent apertures 2140B on the vent surface 2140A, which may be laser drilled for example. The vent surface 2140A is inclined upwardly relative to the axis of the inlet 2108 such that the axis of each vent aperture 2140B is directed upwardly and forwardly away from the frame 2106. This configuration directs exhaled gas upwardly and forwardly away from the frame 2106, and away from the user. The vent surface 2140A is an integral part of the front of the frame 2106. The vent surface 2140A is positioned behind and above the yoke assembly 2021. The vent 2140 is configured such that the yoke assembly 2021 does not interfere with the path of the exhaust gas flowing through the vent 2140.

Figures 94, 95:
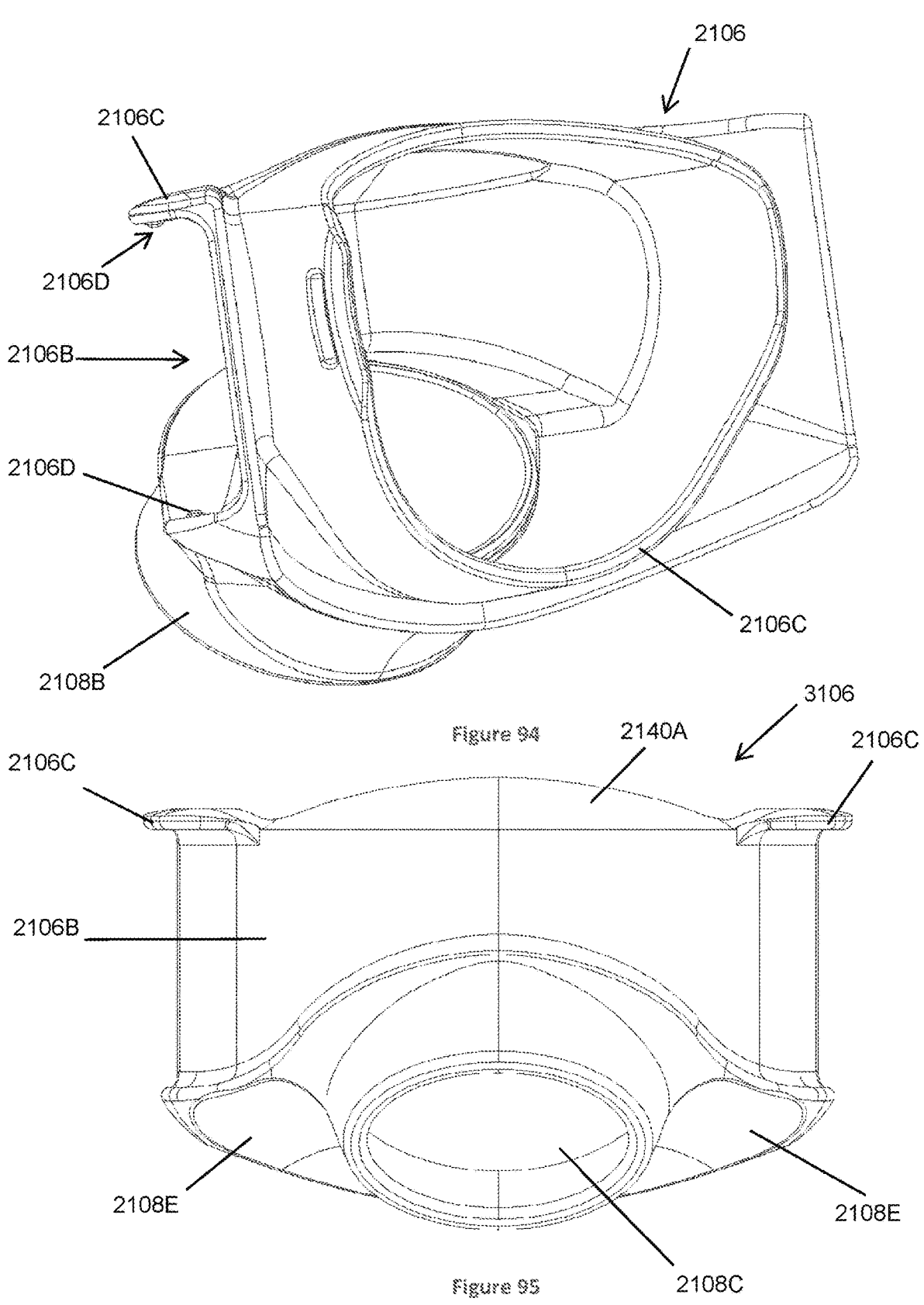

With reference to FIG. 94, the rear of the frame 2106 comprises an outlet collar 2106C which engages with clip 2122 to mount the seal 2104 to the frame 2106. The outlet collar 2106C is D-shaped in the sense that an upper portion of the outlet collar 2106C is wider than a lower portion of the outlet collar 2106C. The outlet collar 2106C thus tapers inwardly, when viewed along the axis of the outlet collar 2106C. The outlet collar 2106C thus comprises an inverse trapezoid, albeit with a generally arcuate top, sides and base, in this example. In this example the top, sides and base margin are arcuate and each bow outwardly away from the axis of the outlet collar 2106C. Having an outlet collar 2106C of this shape, allows more surface area at the top of the frame 2106, on which to locate the vent 2140, and on which to shape and configure the vent 2140 to achieve the desired direction of flow of the exhaled gases from the mask 2102.

The frame 2106 is shorter in a vertical dimension when viewed along the axis of inlet 2108, than frame 106, but also wider, so as to still achieve the desired cross-sectional area for the gases flow.

In this embodiment, there is no vent on the inlet boss 2108A, meaning that the length of the boss 2108A can be minimised, whilst still being long enough (in a direction along the axis of the inlet 2108) to allow the yoke assembly 2021 to be mounted on the frame 2106.

The mask frame inlet 2108 in this embodiment does not have vent apertures distributed radially around it like the embodiment of FIG. 3c. Mask frame inlet 2108 has the vent apertures located on a vent surface 2140A above the recess 2106B and between the two outwardly extending upper protrusions 2106C. The lower margin of the vent surface 2140A is generally in line with the upper margin of the outwardly extending upper protrusions 2106C, and the upper margin of the vent surface 2140A extends upwardly beyond the upper margin of the outwardly extending upper protrusions 2106C. As noted above, the vent surface 2140A is sloped in a way which directs the gas upwards and forwards, away from the face and away from the lower region of the mask 2102, this lower region typically being where user's may tend to place their hands to adjust the mask position. This design change addresses the possible production of noise when exhaled gas hits the user's hands, causing noise. The vent surface 2140A is around the same width as the width of the outer surface of the mask frame inlet boss 2108A as can best be seen by dashed lines A in FIGS. 87 and 88. The vent surface 2140A requires fluid connection between the mask frame outlet collar 2106C. The upper region of the outlet collar 2106C therefore has a width that is at least the width of the vent surface 2140A.

With reference to FIG. 89, the inlet boss 2108A extends into a conduit connection portion 2108B, which may be a separate component mounted on inlet boss 2108A via snap fit connection for example, or may be integral therewith. Conduit connection portion 2108B comprises a gases inlet 2108C.

Figures 96, 97:
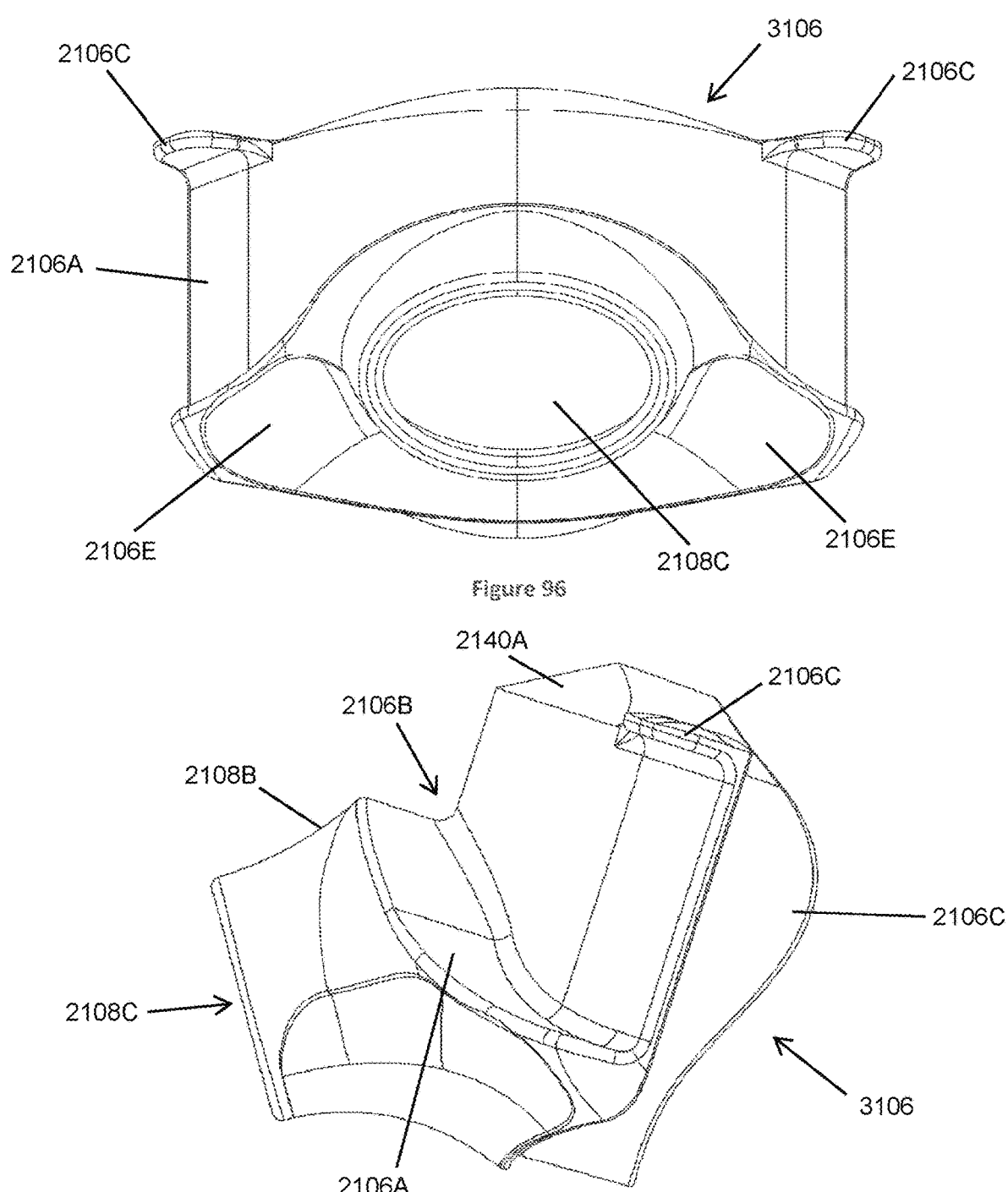

With reference to FIGS. 95 to 97, further detail changes to mask frame 2106 are shown in modified mask frame 3106. Frame 3106, comprises an inlet boss 2108A which projects less than that of frame 2106, but has a longer, and integral, conduit connector 2108B, with larger finger grip portions 2106E that extend from below the recess 2106A and along most of the length of the conduit connector 2108B, almost to the distal end of the conduit connector 2108B, when the frame 3106 is viewed from the side.

Figures 98, 99:
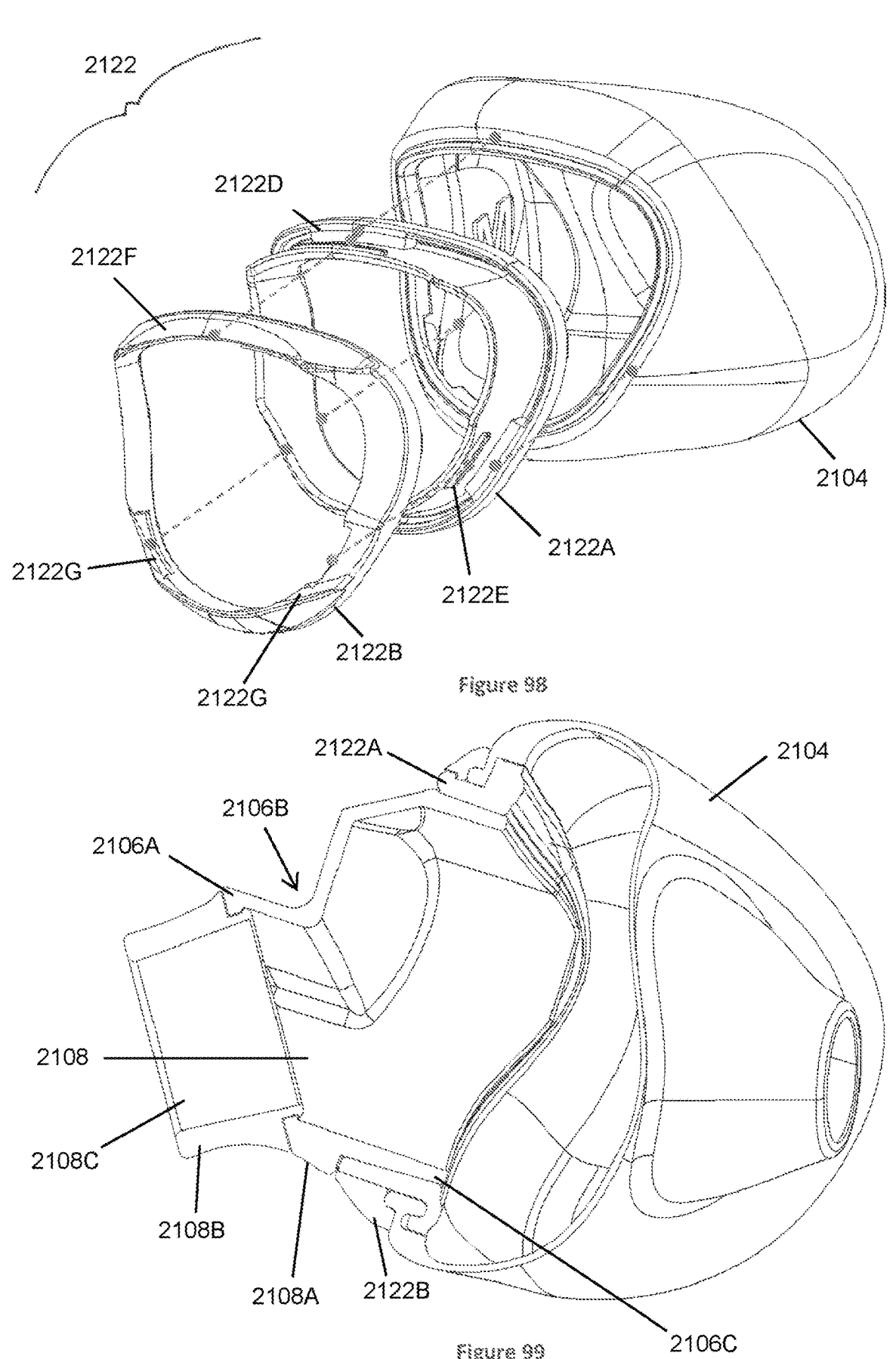
Figures 100, 101:
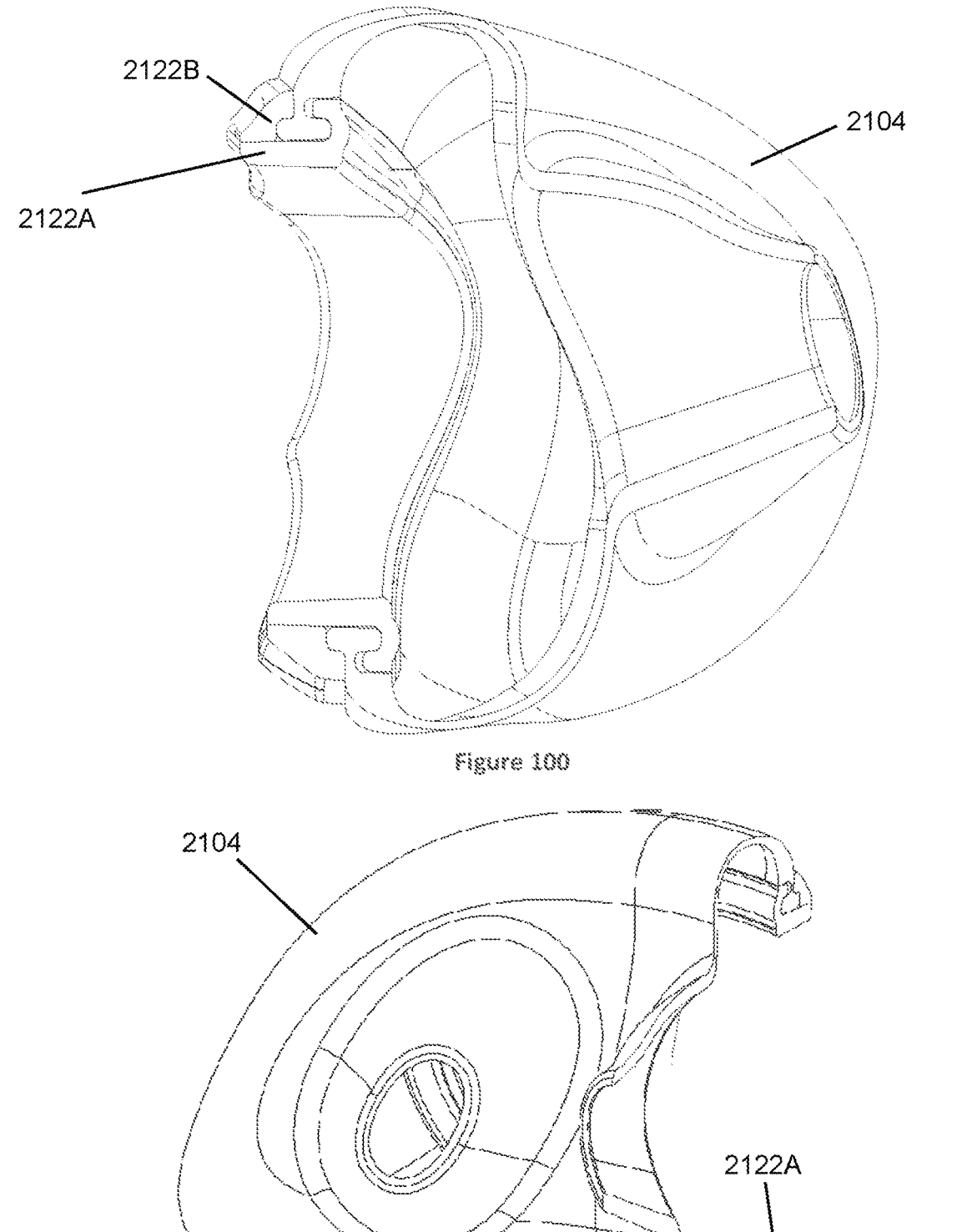

With reference to FIGS. 98 to 101, the shape of the clip 2122 can be seen more clearly. The clip 2122 defines a gas flow aperture 2122C which is similar inverse trapezoidal shape to the shape of the outlet collar in the frame 2106. Further, the first clip portion 2122a comprises connection features 2122D/E in a triangular arrangement with one connection feature 2122D at the top of the clip 2122, and a pair of laterally opposed connection features 2122E on each side of the clip 2122 in the lower portion of the clip 2122. The second clip portion 2122b comprises connection features 2122F/G also in a triangular arrangement with one connection feature 2122F at the top of the clip 2122, and a pair of laterally opposed connection features 2122G on each side of the clip 2122 in the lower portion of the clip 2122. The seal 2104 comprises correspondingly arranged connection features 2104D/E. The dashed lines in FIG. 98 show the pairing of connection features between the clip 122 and seal 104. The connection features can comprise any suitable combination of protrusions, recesses and/or snap fingers configured to inter-engage and mount one component to the adjacent component. The connection features may comprise snap-fit features. The snap-fit may in part be achieved via deformation of the clip 2122 and/or the seal 2104, as the components are mounted together. The connection features may be configured to align the components as they are assembled together, as well as ultimately connecting the components together.

Figure 102:
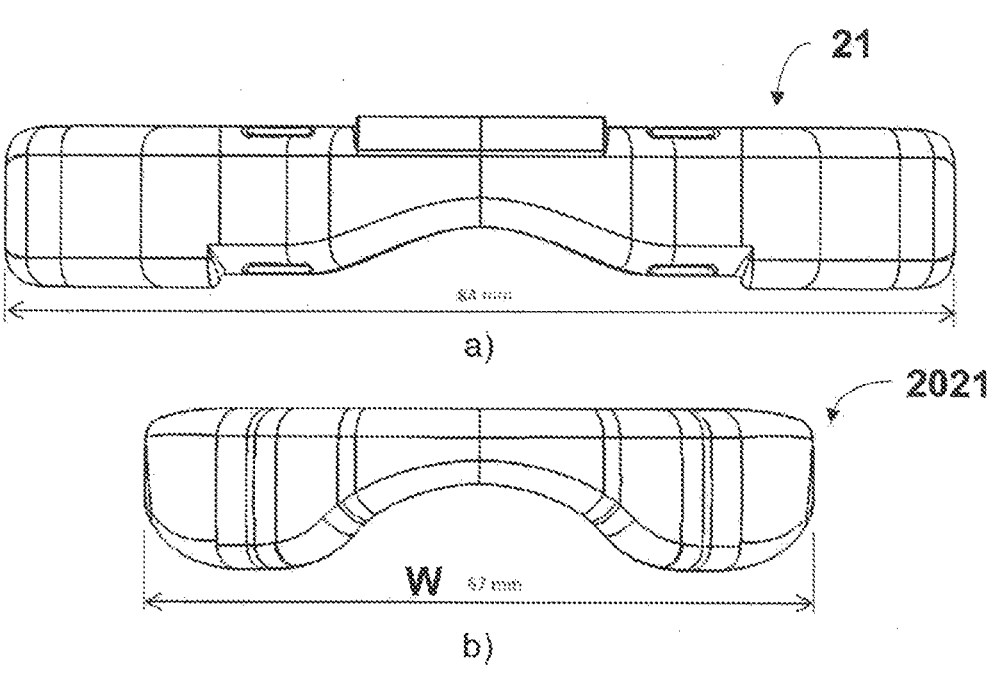

Referring now to FIGS. 102 and 103, a comparison is made of the shape and exterior dimensions of the yoke assemblies 21 and 2021. As can clearly be seen, the yoke 2021 is narrower than yoke 21, providing the advantages outlined above of reducing impact on the user's vision, and allowing the user to turn their head further before the yoke 2021 contacts the user's bed or pillow. This may allow better side sleeping.

As an example only, yoke 2021 has reduced horizontal width (measured between the furthest lateral points of the yoke), and reduced thickness, when viewed from above and measured between the front and rear yoke members, when compare with the yoke 21. This can be seen with reference to FIG. 103. The horizontal distance between the interior surface of the ends of the yoke is wider than the nasal breadth of most of the typical users requiring OSA treatment, and therefore will fit most of those users. This allows the yoke assembly to be used with various seal sizes without requiring a different sized yoke for each seal size. Example approximate dimensions, of one example embodiment, for comparison are:

|  | Yoke 21 | Yoke 2021 |
| --- | --- | --- |
| Width, mm | 84 | 67 |
| Depth, mm | 39 | 29 |
| Thickness, mm | 7.5 | 6.7 |

Further example approximate dimensions of the yoke 2021 include:

Horizontal distance along the interior surface between the lateral ends of yoke assembly: 58.5 mm Depth of filament path from the front yoke member 2021A at the centre of the yoke assembly: 24.1 mm Distance between the centre (i.e. forwardmost part) of the front surface of yoke assembly and rearmost point of the yoke assembly (at the rear surface of the yoke assembly at each lateral end): 29.15 mm Distance between the centre of the rear surface of the yoke assembly and the rearmost point of yoke assembly (at the rear surface of the yoke assembly at each lateral end): 22.45 mm With reference to FIGS. 104 and 105, the yoke rear member 2021A is provided with engagement features 2021H, in the form of indents, for engagement with the frame 2106, to retain the yoke assembly 2021 on the frame 2106. No engagement features are provided on the yoke front member 2021A, enabling the front of the yoke front member 2021A to have a smooth, uninterrupted outer surface.

Referring to FIG. 106, the mounting of the yoke assembly 2021 on the frame 2106 can be more clearly seen. The lower surface of the frame recess 2106B, and the upper outwardly extending frame protrusions are provided with yoke engaging lugs 2106C that are received in the indents 2021H of yoke rear member 2021B. These lugs 2106C, and the indents 2021H, may together form a snap-fit connection between the yoke assembly 2021 and the frame 2106.

FIGS. 107 to 110 show the engagement of end caps 2209 with the lateral ends of the yoke assembly 2021. Each end cap 2209 is hollow, and clips onto a male part 2021K of the lateral end of the yoke assembly, that projects from the lateral end. The interior of each end cap 2209 comprises one part of a snap fit connection being a slot 2209A which receives a ramped projection 2021J on the male part of the lateral end of the yoke assembly 2021. Ramped projection 2021J deforms the end cap 2209 as the end cap 2209 is pushed onto yoke assembly 2021 before snapping back once projection 2021J is received in slot 2209A. These connection features facilitate the alignment and engagement of the two parts. After assembly, the yoke end cap 2209 may be permanently attached through welding or other similar methods.

As can be seen from FIG. 111, each end cap 2209 also mounts each filament support structure 2208 onto yoke assembly 2021 by way of collar 2208C/D of filament support structure 2208 being received inside end cap 2209 and being clamped between end cap 2209 and yoke assembly 2021 once end cap 2209 is mounted on yoke assembly 2021. This also serves to retain the housing 1810 of frictional adjustment unit 1800 on the yoke assembly 2021, with the housing 1810 being partially retained inside the lateral end of the yoke assembly 2021, and partially retained inside the end cap 2209.

As noted above, there are two filaments 1830, each filament 1830 extending from a first filament support structure 2208, through the yoke assembly 2021, where the filaments 1830 cross over, and on to the other filament support structure 2208. Thus one end of each filament 1830 is fixedly mounted in one filament support structure 2208, and therefore connected to the headgear 200. The opposite end of each filament 1830 is movably mounted in the other filament support structure 2208. Thus each filament support structure 2208, and the yoke assembly 2021, comprises a pair of filament guide passages, one for each filament 1830.

As can be seen from FIGS. 110 to 112, and FIGS. 116 and 119, each filament support structure 2208 comprises a pair of vertically stacked filament guide passages 2208F/G. These passages 2208F/G can vary in cross section along the length of the filament support structure 2208, and each passage can be of different sizes so as to correspond to the size of the portion of the length of the filament 1830 that is contained within the passage 2208A/B. In this embodiment, the lower guide passage 2208G guides a filament 1830 into a lower portion of the yoke assembly 2021, through a frictional adjustment unit 1800. Inside the yoke assembly 2021, the filament 1830 is guided upwardly through the yoke assembly 2021 and out of an upper part of the opposite lateral end of the yoke assembly 2021 and into an upper guide passage 2208F of the other filament support structure 2208, without passing through a directional adjustment unit 1800. The filament 1830 can move freely within the upper guide passage 2208F of that other filament support structure 2208.

Referring to FIGS. 110 and 111, the entry and exit paths to and from the yoke assembly 2021 can be seen. The projecting male part 2021K of each lateral end of the yoke assembly is hollow, and comprises a ceiling and a base. Intermediate the ceiling and the base is an upper guide surface 2021L over which a filament 1830 passes before exiting the yoke assembly 2021 and entering the upper passage 2208F of the filament support structure 2208. Also intermediate the ceiling and the base is a lower guide surface 2021M which projects part way into the male part 2021K. This lower guide surface 2021M is at the same height as the lower guide passage 2208G of the filament support structure 2208 and thus receives the incoming filament 1830 from the filament support structure 2208. This lower guide surface also provides an abutment against which the housing 1810 of the directional adjustment unit 1800 abuts, the unit 1800 this being held in position between the lower guide surface 2021M and the end collar 2208C/D of the filament support structure 2208.

It is to be noted that the above is configured such that the two filaments 1830 enter the lateral ends of the yoke assembly 2021 at the same height. This helps ensure that the filaments 1830 are subject to the same forces, such that the filaments 1830 are force balanced across the yoke assembly 2021. The left and right housings 1810 are therefore oriented the same way to ensure that the interaction between the frictional engagement members 1824 and filament 1830 on both sides are the same. This leads to equal force characteristics when extending and reducing the length of the side straps of the headgear 200.

Referring to FIGS. 112, 113, 115, and 116, the path of each filament 1830 is shown by reference to lines P1, P2. In FIG. 116, one filament 1830 is shown as a dark circle, with the other as a white circle. The interior features of the yoke front and rear members 2021A/B are constructed to separate the paths of the filaments 1830 and prevent obstruction between the two components which both pass through the yoke assembly 2021. The front yoke member 2021A comprises a pair of guide surfaces 2021L/M as described above. Each filament 1830, at entry to the yoke assembly 2021, is guided along a path defined between the pair of guide surfaces 2021L/M. As the filament 1830 reaches the centre of the yoke assembly 2021, it is guided upwardly and along an exit path defined between the upper guide surface 2021L and the ceiling of the yoke assembly 2021 so as to exit the yoke assembly 2021 at a position higher than the point of entry into the yoke assembly 2021. The front yoke member 2021A also comprises a raised guide surface 2021N on one side of the yoke member only. This projects up from the page, in FIGS. 113 and 115. This guide surface 2021N spaces one filament 1830 from the other, in a direction generally aligned with the axis of the inlet 108 (into and out of the page in FIGS. 113 and 115), to allow one filament 1830 to pass underneath the other, without interfering with one another.

Figure 114:
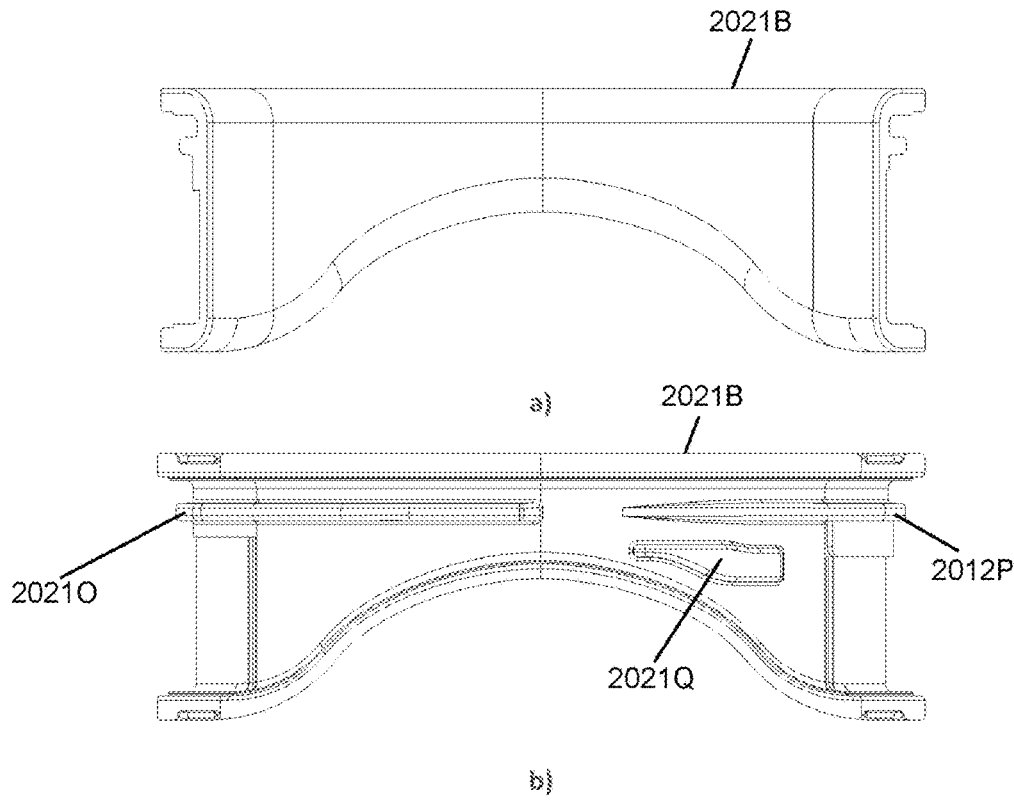

Referring to FIG. 114, the rear yoke member 2021B comprises three elongate ramp formations 20210/P/Q. Elongate ramp formation 20210 presses one filament into an exit path defined between the upper guide surface 2021L and the ceiling of the yoke assembly 2021. Elongate ramp formation 2021P presses the other filament into the exit path defined between the upper guide surface 2021L and the ceiling of the yoke assembly 2021. Intermediate guide ramp formation 2021Q helps guide one of the filaments 1830 from the entry path up to the exit path inside the yoke assembly 2021. For clarity these ramp formations are also shown in FIG. 115. The dashed lines in FIG. 115, show where the filaments 1830 are closer to the front of the yoke assembly 2021 than the rear.

The combination of the interior features of the front and rear yoke members 2021A/B are therefore configured to guide each filament 1830 from a lower entry point to a higher exit point, when the yoke assembly 2021 is viewed from the front. The combination of features are also configured to guide each filament 1830 toward or away from the front yoke member 2021A/B. This combination of guiding of the filaments 1830 up and down, and also toward and away from one or other yoke member, causes each filament 1830 to take a 3D path through the yoke assembly 2021, thus allowing the filaments 1830 to cross over inside the yoke assembly 2021, without interference. The filament cross over can be seen in FIG. 115, reference X.

With reference to FIG. 116, it can be seen, for example with reference to the filament shown in black circle, that the filament 1830 enters one side of the yoke assembly 2021 approximately aligned with the centre axis of the yoke assembly 2021, then gradually moves towards the front yoke member 2021A towards the centre of the yoke assembly 2021, before moving upwardly and back towards, but spaced above, the yoke assembly centre axis before exiting the other side of the yoke assembly 2021. The other filament 1830, in white circle, takes an opposite path.

Yoke assembly 2021 thus provides a filament guide path from one lateral end of the yoke assembly 2021 to the other. The filament 1830 passes from inside one filament support structure 2208 through the yoke assembly 2021, with the free end of that filament 1830 exiting the yoke assembly 2021 and being contained within the other opposite filament support structure 2208. The filament 1830, when assembled into yoke assembly 2021, filament support structures 2208 and directional adjustment units 1800 (with a directional adjustment unit 1800 being provided for each filament 1830), has an operative length which is the distance by which the filament 1830 can be pulled through a directional adjustment unit 1800, before the hard stop 1830 of the filament 1830 prevents any further movement of the filament 1830. This filament operative length is configured to be longer than the filament guide path through the yoke assembly 2021. This helps ensure that the free end of the filament 1830 remains contained in the opposite filament support structure 2208. In one example, the guide path length through the yoke assembly 2021 is around 80 mm, and so the filament operative length is greater than 80 mm.

Referring now to FIGS. 118 to 121, an embodiment of a filament support structure 2208 is similar to previously described filament support structure 208, but with some different features. The first of these is that the medial end collar 208C/D of previously described filament support structure 208 has been modified such that the modified collar 2208C/D is primarily downwardly directed, with the remainder of the collar 2208C/D being substantially flush with the filament support structure 2208. Previous embodiment 208 had a collar 208C/D that is taller (upper and lower walls) and wider (interior and exterior walls) than the distal opening of the end cap 209 that has the same dimensions as the main portion of the filament support structure 208. The updated filament support structure 2208 also has a collar 2208C/D that is taller and wider. Its upper wall is continuous with the main portion of the elongate support body (interior side wall) 2208A, while the lower wall protrudes downwardly. The shape of the downwardly protruding collar 2208C/D corresponds to the space provided in the yoke end cap 2209 to retain the filament support structure 2208 to the yoke assembly 2021.

Previously described filament support structure 208 has an exterior side that lacked a wall to fully enclose both filaments 1830. The absence of one wall can decrease rigidity.

We propose an alternative embodiment which includes an exterior wall 2208B as well as interior wall 2208A. Both exterior and interior walls of the filament support structure 2208 comprise apertures 2208E that are spaced along the longitudinal length of the filament support structure 2208 on the main portion. The apertures 2208E have the purpose of reducing the stiffness of the filament support structure 2208. This increased flexibility allows the component to curve around the patient's cheeks and increase comfort. There is sufficient stiffness to support the position of the seal 2104 on the user's face. The apertures 2208E on the interior wall 2208B and exterior wall 2208A are not directly opposite each other, rather, the locations alternate along the length of the filament support structure 2208. This arrangement, as opposed to an identical aperture arrangement, on both walls 2208A/B leads to maintenance of some rigidity throughout the length of the filament support structure 2208 without creating any significant weak points that may break or become compromised in structure and support. The alternate spacing of the apertures 2208E is shown most clearly in FIG. 118.

Referring to FIGS. 122 and 123, the previously described filament 1830 component may be modified to produce an upper edge that is continuous (same level with) between the thin and thick regions 1830B, 1830A. The thin region 1830B is the section of the filament 1830 that passes through the frictional engagement members 1824 and housing 1810. The thick region 1830A provides the filament 1830 with some rigidity and stability. The previously described filament 1830 comprises a taper on both upper and lower sides of the filament 1830, as can best be seen in FIG. 23*a*. In the modified embodiment, the lower edge alone tapers upwards to form the lower edge of the thin region 1830B—this single sided taper increases tooling accuracy, which can be important especially for the thin region 1830B which requires relatively high accuracy to achieve the desired interaction with the frictional engagement members 1824.

The lateral (distal) side of the mechanical hard stop 1830E contacts the medial side of the hard stop wall on the lateral end of the filament support structure 2208 when the thin region 1830B of the filament 1830 is retracted out of the yoke assembly 2021 to a maximum extent. This determines the maximum length of the side strap of the headgear 200.

The following are example dimensions of the filament:

The thin region has a length of 107 mm and the thick region has a length of 103 mm.

The thin region has a thickness of 0.86 mm and the thick region has a thickness of 1.22 mm.

The thin region has a width of 1.00 mm and the thick region has a width of 3.50 mm.

The length between the medial end of the filament component and the locating features is 214 mm. This gives a length of 4 mm for the width tapering region between the thin and thick regions.

The hard stop has a length (longitudinal direction) of 1.74 mm and a height of 0.66 mm.

For the avoidance of doubt, it is intended that features of any of the mask systems 100 and 2100 can be combined as required. It is not intended that the features of mask system 100 be exclusive only to mask system 100. In particular mask system 100 can include any of the features of any one or more of mask frame 2106, yoke assembly 2021, filament support structures 2208, and end caps 2209. Likewise mask system 2100 can include any of the features of any one or more of mask frame 106, yoke assembly 20, filament support structures 208, and end caps 209. Likewise either mask system 100, 2100 can be used with any of the filaments 1830 described herein. Further, either mask system 100, 2100 may use any of the masks 104, 2104 described herein.

It will be appreciated that the yoke assembly 20, 2021 may comprise a separate assembly mounted on the mask frame, or may be integral with the frame 106, 2106. For example, with reference to FIGS. 113 to 115, the filament guide paths P1, P2, and any or some of the guide formations may be provided partially or fully by the frame 106, 2106. It is envisaged that the yoke assembly 20, 2021 could be partially formed by the frame 106, 2106. For example, the rear yoke member 21B, 2021B could be formed by the frame 106, 2106, with the front yoke member 21A, 2021A being mounted directly on the frame 106, 2106.

In the described embodiments, the directional adjustment unit 1800 is a separate assembly, that is mounted in, and retained by, either the yoke assembly fully, or the yoke assembly and end cap in combination. However, other configurations are possible. It will therefore be appreciated that for example the housing 1810 of the directional adjustment unit 1800 may be integral with, or comprise a component that is integral with, the yoke assembly 20, 2021, and/or the mask frame 106, 2106.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

Any discussion of the prior art throughout the specification should in no way be considered as an admission that such prior art is widely known or forms part of common general knowledge in the field.

The invention claimed is:

1. A headgear for a respiratory mask, the headgear comprising:

a strap;

a filament located at least partially within the strap; and a directional adjustment unit comprising:

at least one frictional engagement member having an aperture forming a cavity extending through the at least one frictional engagement member, wherein:

the aperture is arranged to receive the filament therethrough, wherein the cavity forms an upper rounded edge and a lower sharp edge on a single side of the frictional engagement member, the at least one frictional engagement member in a first configuration provides a disengaged configuration with respect to the filament, in a second configuration the at least one frictional engagement member provides an engaged configuration with respect to the filament, and the at least one frictional engagement member is movable between the engaged configuration and the disengaged configuration, and wherein the filament comprises a filament body having a rectangular shape in a cross-section taken perpendicular to a longitudinal axis thereof, and the filament body having a substantially flat exterior surface portion extending along the longitudinal axis, so that, in the engaged configuration, the substantially flat exterior surface portion of the filament body is brought into contact with the at least one frictional engagement member.

2. The headgear of claim 1, wherein the at least one frictional engagement member is movable around a pivot axis, and wherein the first configuration comprises a first pivoted configuration and the second configuration comprises a second pivoted configuration.

3. The headgear of claim 2, wherein the cavity forms an engagement surface region that is linear or substantially linear along a lateral axis parallel or substantially parallel to the pivot axis.

4. The headgear of claim 3, wherein the engagement surface region forms part of or comprises at least one interior cavity wall surface of the at least one frictional engagement member.

5. The headgear of claim 2, wherein the aperture is provided offset to the pivot axis and extends through the at least one frictional engagement member along an axis that is perpendicular to the pivot axis.

6. The headgear of claim 2, further comprising one or more of:

wherein the cavity comprises a side which is parallel or substantially parallel to the pivot axis;

wherein the cavity comprises a quadrilateral cross section in a plane parallel to the pivot axis and an axis normal to the pivot axis;

wherein the cavity extends through the at least one frictional engagement member perpendicular or substantially perpendicular to the pivot axis; or wherein the cavity extends through the at least one frictional engagement member symmetrically around a central axis.

7. The headgear of claim 2, wherein the at least one frictional engagement member comprises:

a base member through which the pivot axis extends;

at least a first section extending from the base member in a direction perpendicular to the pivot axis; and a second section extending from an end of the first section in a direction away from the pivot axis, wherein the second section is arranged at an angle in relation to the first section.

8. The headgear of claim 7, wherein the at least first section comprises a rectangular cross section in plane perpendicular to the pivot axis.

9. The headgear of claim 2, wherein the upper rounded edge comprises a curvature with reference to an axis parallel to the pivot axis.

10. The headgear of claim 1, wherein the aperture, at a face of the at least one frictional engagement member, is:

non-round, non-circular, non-elliptic, or non-oval; or quadrilateral, or rectangular.

11. The headgear of claim 1, wherein a shape of the cavity comprises a rectangular elongated body or prism.

12. The headgear of claim 1, wherein at least one interior cavity sidewall surface comprises a flat or substantially flat profile in one or more frontal planes, wherein each frontal plane intersects a central axis at a distinct position and comprises a normal vector of the central plane said distinct position.

13. The headgear of claim 1, wherein at least one interior cavity sidewall surface comprises a flat or substantially flat profile along one or more central plane normal vectors, each intersecting a central axis at different longitudinal positions thereof.

14. The headgear of claim 1, wherein at least one interior cavity sidewall surface maintains a flat or substantially flat profile along a portion of a central axis.

15. The headgear of claim 1, wherein the cavity forms an engagement surface region, wherein the engagement surface region provides, in the engaged configuration, a frictional engagement against the filament, in use.

16. A respiratory mask or interface comprising the headgear of claim 1.

17. A respiratory therapy system comprising the respiratory mask or interface of claim 16, the respiratory therapy system further comprising one or more of:

a flow generator;

a humidifier;

a breathing gas delivery conduit; or an expiratory circuit.

18. The headgear of claim 1, wherein movement of the filament in a first direction changes the configuration of the at least one frictional engagement member from the disengaged configuration to the engaged configuration and wherein the single side of the frictional engagement member faces the first direction.

19. A directional adjustment unit for a headgear for a respiratory mask, the directional adjustment unit comprising:

a housing;

at least one frictional engagement member arranged to be movable with respect to the housing, the at least one frictional engagement member having a rectangular aperture extending therethrough for receiving a filament of a strap of the headgear therethrough, wherein the at least one frictional engagement member, in a first movable configuration, provides a disengaged configuration with respect to the filament, and in a second movable configuration, provides an engaged configuration with respect to the filament; and the filament comprises a filament body having a substantially flat exterior surface portion extending along a longitudinal axis thereof, so that in the engaged configuration the substantially flat exterior surface portion of the filament body is brought into contact with the at least one frictional engagement member, and wherein the rectangular aperture forms a cavity that forms an upper rounded edge and a lower sharp edge on a single side of the frictional engagement member.

20. The directional adjustment unit of claim 19, wherein the housing comprises an external opening for slidably receiving and/or accommodating the filament and/or part of the strap, in use.

21. The directional adjustment unit of claim 19, wherein movement of the filament in a first direction changes the configuration of the at least one frictional engagement member from the disengaged configuration to the engaged configuration and wherein the single side of the frictional engagement member faces the first direction.

* * * * *